US010076414B2

(12) United States Patent
Rourke et al.

(10) Patent No.: US 10,076,414 B2
(45) Date of Patent: Sep. 18, 2018

(54) METHOD AND APPARATUS FOR REPAIRING A MITRAL VALVE

(71) Applicant: MitraSpan, Inc., Woburn, MA (US)

(72) Inventors: Jonathan M. Rourke, Belmont, MA (US); Stanley B. Kyi, Andover, MA (US); Robert B. Fishman, North Reading, MA (US); Shownа H. Chang, Arlington, MA (US)

(*) Notice: Subject to any disclaimer, the term of this patent is extended or adjusted under 35 U.S.C. 154(b) by 0 days.

(21) Appl. No.: 15/216,880

(22) Filed: Jul. 22, 2016

(65) Prior Publication Data

US 2016/0324636 A1 Nov. 10, 2016

Related U.S. Application Data

(63) Continuation-in-part of application No. 14/599,124, filed on Jan. 16, 2015, now abandoned, which is a
(Continued)

(51) Int. Cl.
*A61F 2/24* (2006.01)
*A61B 17/04* (2006.01)
(Continued)

(52) U.S. Cl.
CPC ........ *A61F 2/2442* (2013.01); *A61B 17/0401* (2013.01); *A61B 17/0467* (2013.01);
(Continued)

(58) Field of Classification Search
CPC ................................. A61F 2/24; A61F 2/2418
(Continued)

(56) References Cited

U.S. PATENT DOCUMENTS 5,450,860 A 9/1995 O'Connor
5,593,424 A 1/1997 Northrup, III
(Continued)

FOREIGN PATENT DOCUMENTS

WO WO 97/30659 8/1997
WO WO 01/070116 9/2001
(Continued)

OTHER PUBLICATIONS

Tomasz A. Timek et al., Septal-lateral Annular Cinching Abolishes Acute Ischemic Mitral Regurgitation, The Journal of Thoracic and Cardiovascular Surgery, May 2002, vol. 123. No. 5, pp. 881-888.
(Continued)

*Primary Examiner* — Suzette J Gherbi
(74) *Attorney, Agent, or Firm* — Pandiscio & Pandiscio

(57) ABSTRACT

A method for beneficially displacing a papillary muscle, the method comprising: anchoring one end of an implant suture to a trigone or central fibrous body of the mitral valve; passing another end of the implant suture through a papillary muscle so that the implant suture extends between a trigone or central fibrous body of the mitral valve and the papillary muscle; tensioning the implant suture while displacing the papillary muscle toward the trigone or central fibrous body of the mitral valve; and securing the tensioned implant suture to the displaced papillary muscle so as to maintain the displaced papillary muscle in position relative to the trigone or central fibrous body of the mitral valve; wherein the foregoing steps of anchoring, passing, tensioning and securing are all effected while the heart is beating.

13 Claims, 90 Drawing Sheets

Related U.S. Application Data continuation-in-part of application No. 13/766,521, filed on Feb. 13, 2013, now Pat. No. 9,011,531.

(60) Provisional application No. 61/598,047, filed on Feb. 13, 2012, provisional application No. 61/740,901, filed on Dec. 21, 2012, provisional application No. 61/928,293, filed on Jan. 16, 2014, provisional application No. 62/195,492, filed on Jul. 22, 2015.

(51) Int. Cl.
| | |
|---|---|
| A61B 17/132 | (2006.01) |
| A61B 17/00 | (2006.01) |
| A61B 17/06 | (2006.01) |
| A61B 17/064 | (2006.01) |
| A61B 17/12 | (2006.01) |
| A61B 17/22 | (2006.01) |
| A61B 17/34 | (2006.01) |

(52) U.S. Cl.
CPC ........ *A61B 17/0485* (2013.01); *A61F 2/2457* (2013.01); *A61F 2/2487* (2013.01); *A61B 17/132* (2013.01); *A61B 2017/00243* (2013.01); *A61B 2017/00349* (2013.01); *A61B 2017/00477* (2013.01); *A61B 2017/00557* (2013.01); *A61B 2017/00783* (2013.01); *A61B 2017/045* (2013.01); *A61B 2017/0406* (2013.01); *A61B 2017/0409* (2013.01); *A61B 2017/0417* (2013.01); *A61B 2017/0441* (2013.01); *A61B 2017/0464* (2013.01); *A61B 2017/0477* (2013.01); *A61B 2017/0649* (2013.01); *A61B 2017/06104* (2013.01); *A61B 2017/12004* (2013.01); *A61B 2017/22038* (2013.01); *A61B 2017/22044* (2013.01); *A61B 2017/3425* (2013.01)

(58) Field of Classification Search
USPC ........................................ 623/2.1–2.19, 2.36
See application file for complete search history.

(56) References Cited

U.S. PATENT DOCUMENTS

| | | | |
|---|---|---|---|
| 5,709,695 A | 1/1998 | Northrup, III | |
| 5,860,992 A | 1/1999 | Daniel et al. | |
| 5,961,440 A | 10/1999 | Schweich, Jr. et al. | |
| 5,961,539 A | 10/1999 | Northrup, III et al. | |
| 5,972,030 A | 10/1999 | Garrison et al. | |
| 6,210,432 B1 | 4/2001 | Solem et al. | |
| 6,406,420 B1 | 6/2002 | McCarthy et al. | |
| 6,514,194 B2 | 2/2003 | Schweich, Jr. et al. | |
| 6,537,198 B1 | 3/2003 | Vidlund et al. | |
| 6,562,052 B2 | 5/2003 | Nobles et al. | |
| 6,676,702 B2 | 1/2004 | Mathis | |
| 6,695,866 B1 | 2/2004 | Kuehn et al. | |
| 6,752,813 B2 | 6/2004 | Goldfarb et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,893,459 B1 | 5/2005 | Macoviak | |
| 6,908,478 B2 | 6/2005 | Alferness et al. | |
| 6,949,122 B2 | 9/2005 | Adams et al. | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 6,989,028 B2 | 1/2006 | Lashinski et al. | |
| 7,004,958 B2 | 2/2006 | Adams et al. | |
| 7,011,682 B2 | 3/2006 | Lashinski et al. | |
| 7,037,334 B1 | 5/2006 | Hlavka et al. | |
| 7,044,967 B1 | 5/2006 | Solem et al. | |
| 7,083,628 B2 | 8/2006 | Bachman | |
| 7,087,064 B1 | 8/2006 | Hyde | |
| 7,090,695 B2 | 8/2006 | Solem et al. | |
| 7,112,207 B2 | 9/2006 | Allen et al. | |
| 7,112,219 B2 | 9/2006 | Vidlund et al. | |
| 7,125,420 B2 * | 10/2006 | Rourke | A61F 2/2451 623/2.36 |
| 7,125,421 B2 | 10/2006 | Tremulis et al. | |
| 7,179,282 B2 | 2/2007 | Alfemess et al. | |
| 7,189,201 B2 | 3/2007 | Borst et al. | |
| 7,241,310 B2 * | 7/2007 | Taylor | A61B 17/3478 623/2.11 |
| 7,270,676 B2 | 9/2007 | Alferness et al. | |
| 7,296,577 B2 | 11/2007 | Lashinski et al. | |
| 7,300,462 B2 | 11/2007 | Swinford et al. | |
| 7,311,728 B2 | 12/2007 | Solem et al. | |
| 7,351,259 B2 | 4/2008 | Swinford et al. | |
| 7,364,588 B2 | 4/2008 | Mathis et al. | |
| 7,381,210 B2 | 6/2008 | Zarbatany et al. | |
| 7,431,726 B2 | 10/2008 | Spence et al. | |
| 7,503,932 B2 | 3/2009 | Mathis et al. | |
| 7,563,273 B2 | 7/2009 | Goldfarb et al. | |
| 7,588,582 B2 | 9/2009 | Starksen et al. | |
| 7,591,826 B2 | 9/2009 | Alferness et al. | |
| 7,608,091 B2 | 10/2009 | Goldfarb et al. | |
| 7,608,102 B2 | 10/2009 | Adams et al. | |
| 7,618,449 B2 | 11/2009 | Tremulis et al. | |
| 7,635,386 B1 | 12/2009 | Gammie | |
| 7,637,946 B2 | 12/2009 | Solem et al. | |
| 7,655,015 B2 | 2/2010 | Goldfarb et al. | |
| 7,655,040 B2 | 2/2010 | Douk et al. | |
| 7,665,040 B2 | 2/2010 | Nakamura | |
| 7,666,193 B2 | 2/2010 | Starksen et al. | |
| 7,666,224 B2 | 2/2010 | Vidiund et al. | |
| 7,682,360 B2 | 3/2010 | Séguin | |
| 7,736,388 B2 | 6/2010 | Goldfarb et al. | |
| 7,740,638 B2 | 6/2010 | Hyde | |
| 7,753,923 B2 | 7/2010 | St. Goar et al. | |
| 7,758,595 B2 | 7/2010 | Allen et al. | |
| 7,758,637 B2 | 7/2010 | Starksen et al. | |
| 7,799,073 B2 | 9/2010 | Khalapyan | |
| 7,803,167 B2 | 9/2010 | Nobles et al. | |
| 7,811,296 B2 | 10/2010 | Goldfarb et al. | |
| 7,846,179 B2 | 12/2010 | Belef et al. | |
| 7,860,555 B2 | 12/2010 | Saadat | |
| 7,871,368 B2 | 1/2011 | Zollinger et al. | |
| 7,871,433 B2 | 1/2011 | Lattouf | |
| 7,887,552 B2 | 2/2011 | Bachman | |
| 7,905,892 B2 | 3/2011 | Nobles et al. | |
| 7,930,016 B1 | 4/2011 | Saadat | |
| 7,935,145 B2 | 5/2011 | Alfieri et al. | |
| 7,935,146 B2 | 5/2011 | Langberg et al. | |
| 7,967,833 B2 | 6/2011 | Sterman et al. | |
| 7,998,151 B2 | 8/2011 | St. Goar et al. | |
| 8,029,518 B2 | 10/2011 | Goldfarb et al. | |
| 8,029,565 B2 | 10/2011 | Lattouf | |
| 8,043,368 B2 | 10/2011 | Crabtree | |
| 8,052,592 B2 | 11/2011 | Goldfarb et al. | |
| 8,066,766 B2 | 11/2011 | To et al. | |
| 8,070,805 B2 | 12/2011 | Vidlund et al. | |
| 8,127,323 B2 | 2/2012 | Ando et al. | |
| 8,133,272 B2 | 3/2012 | Hyde | |
| 8,142,493 B2 | 3/2012 | Spence et al. | |
| 8,163,010 B1 | 4/2012 | Hausen et al. | |
| 8,187,207 B2 | 5/2012 | Machold et al. | |
| 8,187,299 B2 | 5/2012 | Goldfarb et al. | |
| 8,262,725 B2 | 9/2012 | Subramanian | |
| 8,382,829 B1 | 2/2013 | Call et al. | |
| 8,454,656 B2 | 6/2013 | Tuval | |
| 8,470,028 B2 | 6/2013 | Thornton et al. | |
| 9,011,531 B2 * | 4/2015 | Rourke | A61F 2/2466 606/139 |
| 2002/0013571 A1 | 1/2002 | Goldfarb et al. | |
| 2002/0087173 A1 | 7/2002 | Alferness et al. | |
| 2003/0069636 A1 | 4/2003 | Solem et al. | |
| 2003/0083538 A1 | 5/2003 | Adams et al. | |
| 2003/0105520 A1 | 6/2003 | Alferness et al. | |
| 2003/0120264 A1 | 6/2003 | Lattouf | |
| 2003/0120340 A1 | 6/2003 | Liska et al. | |
| 2003/0130731 A1 | 7/2003 | Vidlund et al. | |
| 2003/0144697 A1 | 7/2003 | Mathis et al. | |

(56) References Cited

U.S. PATENT DOCUMENTS

| | | |
|---|---|---|
| 2003/0171776 A1 | 9/2003 | Adams et al. |
| 2003/0171806 A1 | 9/2003 | Mathis et al. |
| 2003/0191497 A1 | 10/2003 | Cope |
| 2004/0039443 A1 | 2/2004 | Solem et al. |
| 2004/0102840 A1 | 5/2004 | Solem et al. |
| 2004/0127983 A1 | 7/2004 | Mortier et al. |
| 2004/0153147 A1 | 8/2004 | Mathis |
| 2004/0158321 A1 | 8/2004 | Reuter et al. |
| 2004/0181238 A1 | 9/2004 | Zarbatany et al. |
| 2004/0225300 A1 | 11/2004 | Goldfarb et al. |
| 2004/0243227 A1 | 12/2004 | Starksen et al. |
| 2005/0004667 A1 | 1/2005 | Swinford et al. |
| 2005/0027351 A1 | 2/2005 | Reuter et al. |
| 2005/0038507 A1 | 2/2005 | Alferness et al. |
| 2005/0075723 A1 | 4/2005 | Schroeder et al. |
| 2005/0080483 A1 | 4/2005 | Solem et al. |
| 2005/0137685 A1 | 6/2005 | Nieminen et al. |
| 2005/0137700 A1 | 6/2005 | Spence et al. |
| 2005/0149182 A1 | 7/2005 | Alferness et al. |
| 2005/0209690 A1 | 9/2005 | Mathis et al. |
| 2005/0216078 A1 | 9/2005 | Starksen et al. |
| 2005/0222678 A1 | 10/2005 | Lashinski et al. |
| 2005/0261704 A1 | 11/2005 | Mathis |
| 2006/0004443 A1 | 1/2006 | Liddicoat et al. |
| 2006/0020335 A1 | 1/2006 | Kowalsky et al. |
| 2006/0020336 A1* | 1/2006 | Liddicoat ............ A61B 17/0644 623/2.37 |
| 2006/0025750 A1 | 2/2006 | Starksen et al. |
| 2006/0025784 A1 | 2/2006 | Starksen et al. |
| 2006/0030885 A1 | 2/2006 | Hyde |
| 2006/0058817 A1 | 3/2006 | Starksen et al. |
| 2006/0116757 A1 | 6/2006 | Lashinski et al. |
| 2006/0116758 A1 | 6/2006 | Swinford et al. |
| 2006/0241340 A1 | 10/2006 | Schroeder et al. |
| 2006/0271174 A1 | 11/2006 | Nieminen et al. |
| 2006/0276890 A1 | 12/2006 | Solem et al. |
| 2007/0038293 A1 | 2/2007 | St. Goar et al. |
| 2007/0038297 A1 | 2/2007 | Bobo, Jr. et al. |
| 2007/0061010 A1 | 3/2007 | Hauser et al. |
| 2007/0066879 A1 | 3/2007 | Mathis et al. |
| 2007/0073391 A1 | 3/2007 | Bourang et al. |
| 2007/0080188 A1 | 4/2007 | Spence et al. |
| 2007/0093857 A1 | 4/2007 | Rogers et al. |
| 2007/0112424 A1 | 5/2007 | Spence et al. |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0135912 A1 | 6/2007 | Mathis |
| 2007/0173926 A1 | 7/2007 | Bobo, Jr. et al. |
| 2007/0185572 A1 | 8/2007 | Solem et al. |
| 2007/0276414 A1 | 11/2007 | Nobles |
| 2007/0276437 A1 | 11/2007 | Call et al. |
| 2008/0058839 A1 | 3/2008 | Nobles et al. |
| 2008/0091264 A1 | 4/2008 | Machold et al. |
| 2008/0109037 A1 | 5/2008 | Steiner et al. |
| 2008/0140191 A1 | 6/2008 | Mathis et al. |
| 2008/0167714 A1 | 7/2008 | St. Goar et al. |
| 2008/0183194 A1 | 7/2008 | Goldfarb et al. |
| 2008/0228165 A1 | 9/2008 | Spence et al. |
| 2008/0228266 A1 | 9/2008 | McNamara et al. |
| 2008/0228267 A1 | 9/2008 | Spence et al. |
| 2008/0234704 A1 | 9/2008 | Starksen et al. |
| 2008/0243150 A1 | 10/2008 | Starksen et al. |
| 2008/0243245 A1 | 10/2008 | Thambar et al. |
| 2008/0262609 A1 | 10/2008 | Gross |
| 2008/0269786 A1 | 10/2008 | Nobles et al. |
| 2008/0275503 A1 | 11/2008 | Spence et al. |
| 2009/0082619 A1 | 3/2009 | De Marchena |
| 2009/0137863 A1 | 5/2009 | Schweich, Jr. et al. |
| 2009/0259307 A1 | 10/2009 | Gross et al. |
| 2010/0016958 A1 | 1/2010 | St. Goar et al. |
| 2010/0022823 A1 | 1/2010 | Goldfarb et al. |
| 2010/0023118 A1 | 1/2010 | Medlock et al. |
| 2010/0030242 A1 | 2/2010 | Nobles et al. |
| 2010/0030330 A1 | 2/2010 | Bobo et al. |
| 2010/0042147 A1 | 2/2010 | Janovsky et al. |
| 2010/0049212 A1 | 2/2010 | Caborn et al. |
| 2010/0070028 A1 | 3/2010 | Sugimoto |
| 2010/0094317 A1 | 4/2010 | Goldfarb et al. |
| 2010/0100108 A1 | 4/2010 | Goldfarb et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0174297 A1 | 7/2010 | Speziali |
| 2010/0185278 A1 | 7/2010 | Schankereli |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286767 A1 | 11/2010 | Zipory et al. |
| 2010/0318184 A1 | 12/2010 | Spence |
| 2010/0324669 A1 | 12/2010 | Hlavka et al. |
| 2011/0004227 A1 | 1/2011 | Goldfarb et al. |
| 2011/0009957 A1 | 1/2011 | Langberg et al. |
| 2011/0015655 A1 | 1/2011 | Nobles et al. |
| 2011/0015722 A1 | 1/2011 | Hauser et al. |
| 2011/0022166 A1 | 1/2011 | Dahlgren et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0112632 A1 | 5/2011 | Chau et al. |
| 2011/0125189 A1 | 5/2011 | Stoll, Jr. et al. |
| 2011/0137397 A1 | 6/2011 | Chau et al. |
| 2011/0190793 A1 | 8/2011 | Nobles et al. |
| 2011/0238165 A1 | 9/2011 | Seguin |
| 2011/0257728 A1 | 10/2011 | Kuehn |
| 2011/0270276 A1 | 11/2011 | Rothstein et al. |
| 2011/0288637 A1 | 11/2011 | De Marchena |
| 2011/0313434 A1 | 12/2011 | Kocaturk |
| 2012/0022639 A1 | 1/2012 | Hacochen et al. |
| 2012/0029628 A1 | 2/2012 | Rowe |
| 2012/0078358 A1 | 3/2012 | Vidlund et al. |
| 2012/0083806 A1 | 4/2012 | Goertzen |
| 2012/0095552 A1 | 4/2012 | Spence et al. |
| 2012/0109155 A1 | 5/2012 | Robinson et al. |
| 2012/0123531 A1 | 5/2012 | Tsukashima et al. |
| 2012/0130405 A1 | 5/2012 | Cohn et al. |
| 2012/0143323 A1 | 6/2012 | Hasenkam et al. |
| 2012/0209376 A1 | 8/2012 | Hauser et al. |
| 2013/0103055 A1 | 4/2013 | Schaller et al. |
| 2013/0103140 A1 | 4/2013 | Subramanian et al. |
| 2013/0110230 A1 | 5/2013 | Solem |
| 2013/0116780 A1 | 5/2013 | Miller et al. |
| 2013/0190863 A1 | 7/2013 | Call et al. |
| 2013/0190864 A1* | 7/2013 | Smolinsky ............ A61F 2/2445 623/2.36 |
| 2013/0211513 A1 | 8/2013 | Rourke et al. |
| 2013/0282059 A1 | 10/2013 | Ketai et al. |
| 2013/0282112 A1 | 10/2013 | Oba et al. |
| 2013/0338764 A1 | 12/2013 | Thornton et al. |
| 2014/0100420 A1 | 4/2014 | Mortier et al. |
| 2014/0148825 A1 | 5/2014 | Nobles et al. |
| 2014/0222138 A1 | 8/2014 | Machold et al. |
| 2015/0012087 A1* | 1/2015 | Miller .................. A61F 2/2445 623/2.37 |
| 2015/0119981 A1* | 4/2015 | Khairkhahan ........ A61F 2/2442 623/2.36 |

FOREIGN PATENT DOCUMENTS

| | | |
|---|---|---|
| WO | WO 2004/082523 | 9/2004 |
| WO | WO 2005/097002 | 10/2005 |
| WO | WO 2009/081396 | 7/2009 |
| WO | WO 2010/093837 | 8/2010 |
| WO | WO 2011/047168 | 4/2011 |
| WO | WO 2011/047201 | 4/2011 |
| WO | WO 2012/036798 | 3/2012 |
| WO | WO 2012/106422 | 8/2012 |
| WO | WO 2012/004679 | 10/2012 |

OTHER PUBLICATIONS

Frederick A. Tibayan et al.; Does Septal-lateral Annular Cinching Work for Chronic Ischernic Mitral Regurgitation?, The Journal of

(56) References Cited

OTHER PUBLICATIONS

Thoracic and Cardiovascular Surgery, Mar. 2004, vol. 127, No. 3, pp. 654-663.

* cited by examiner

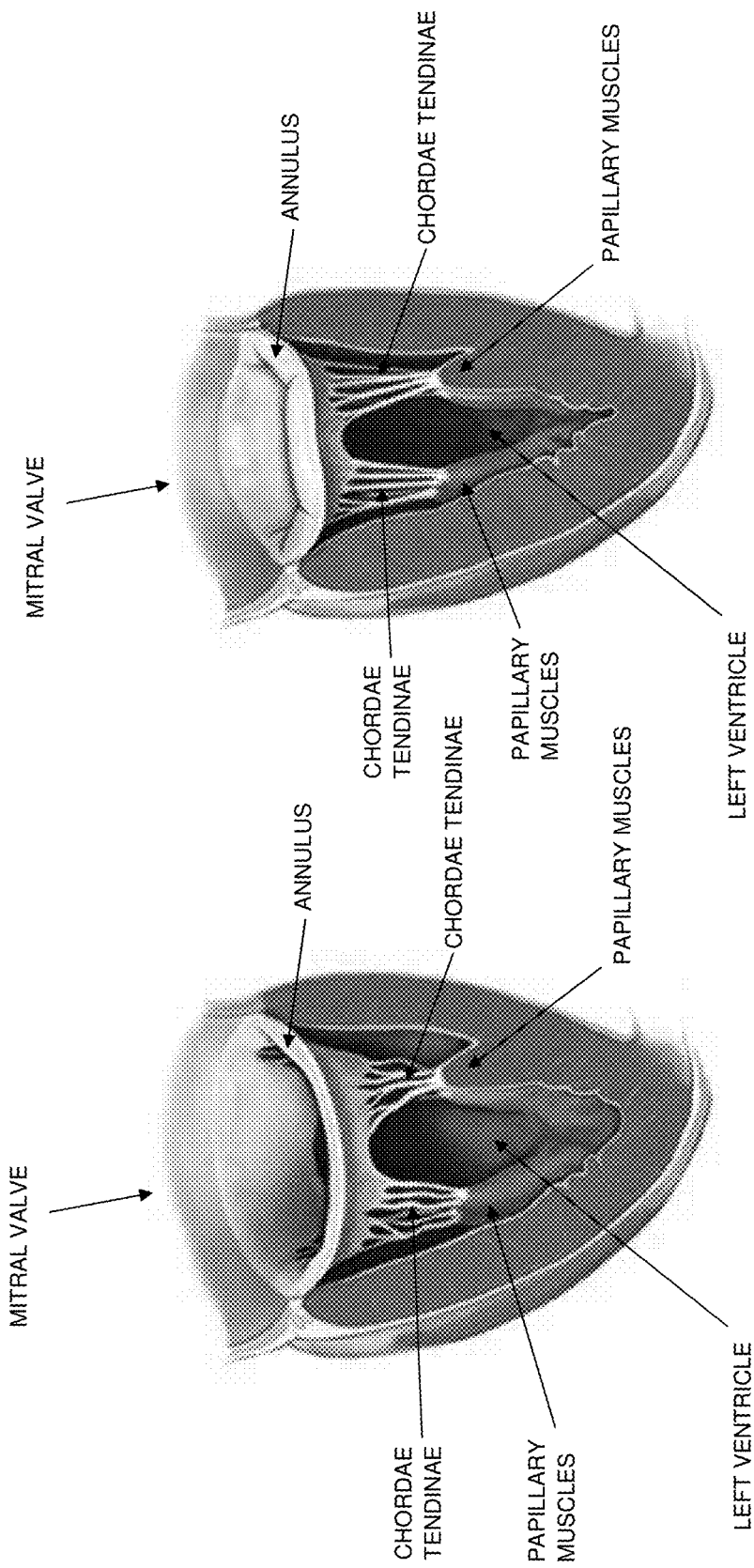

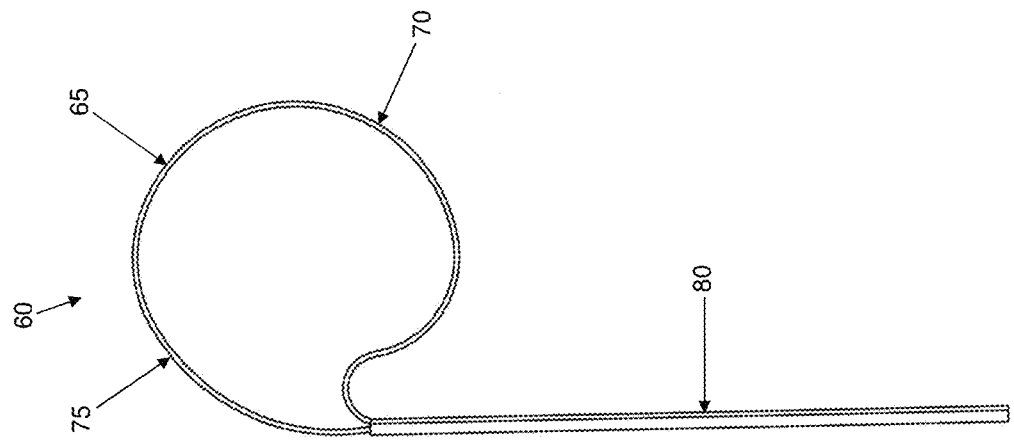
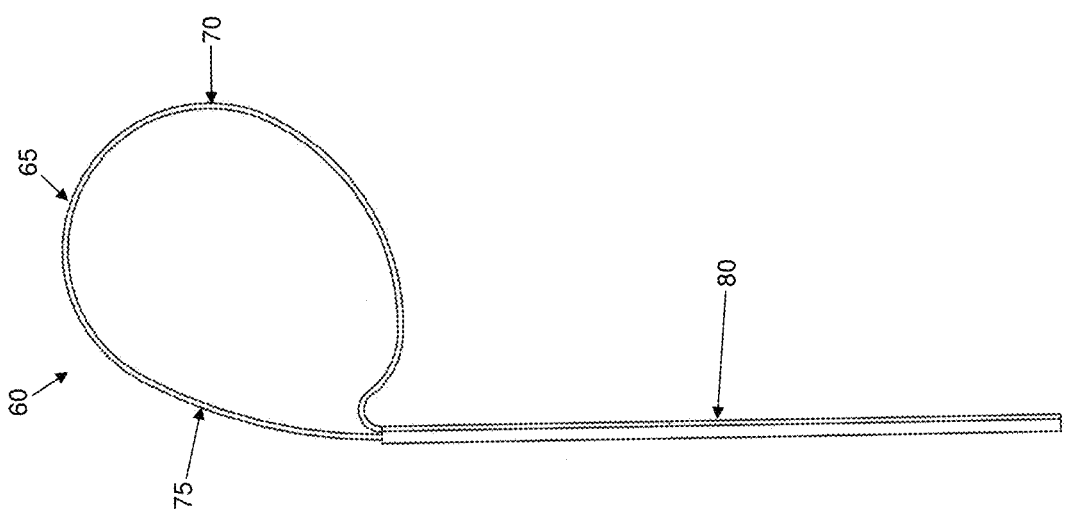
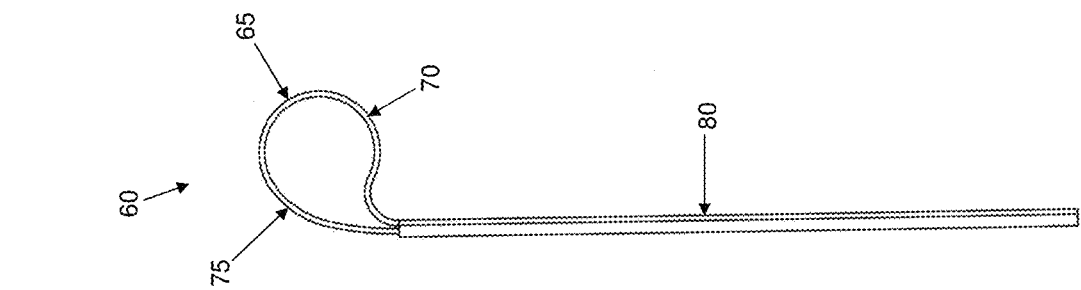
FIG. 42

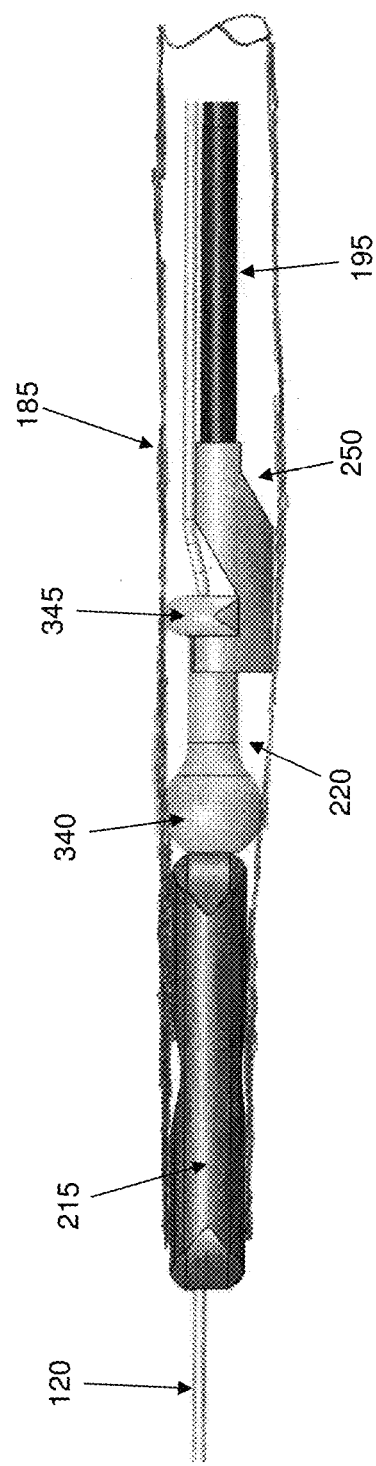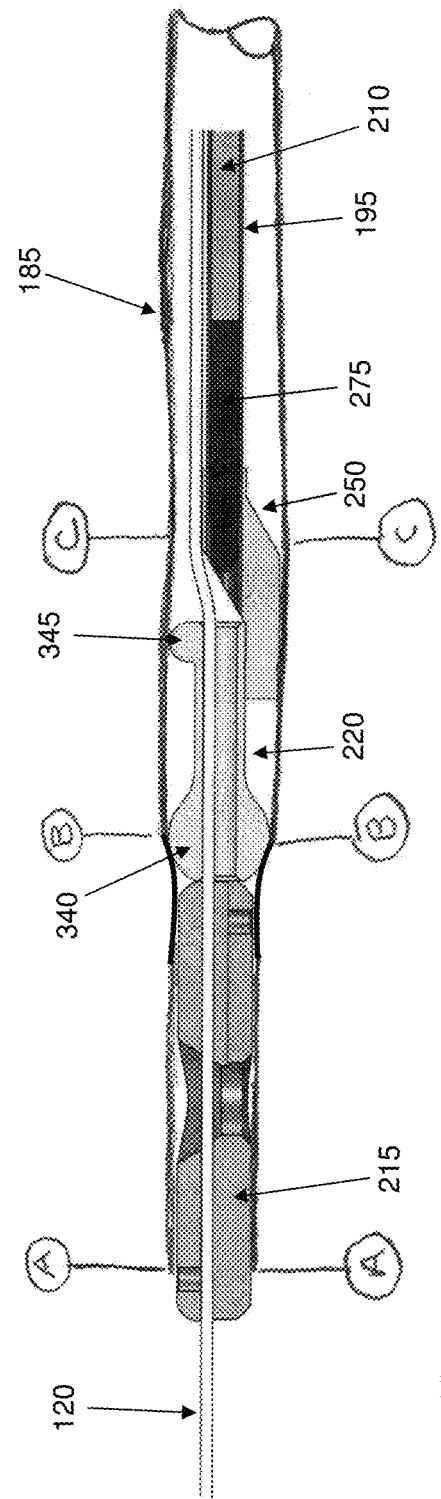

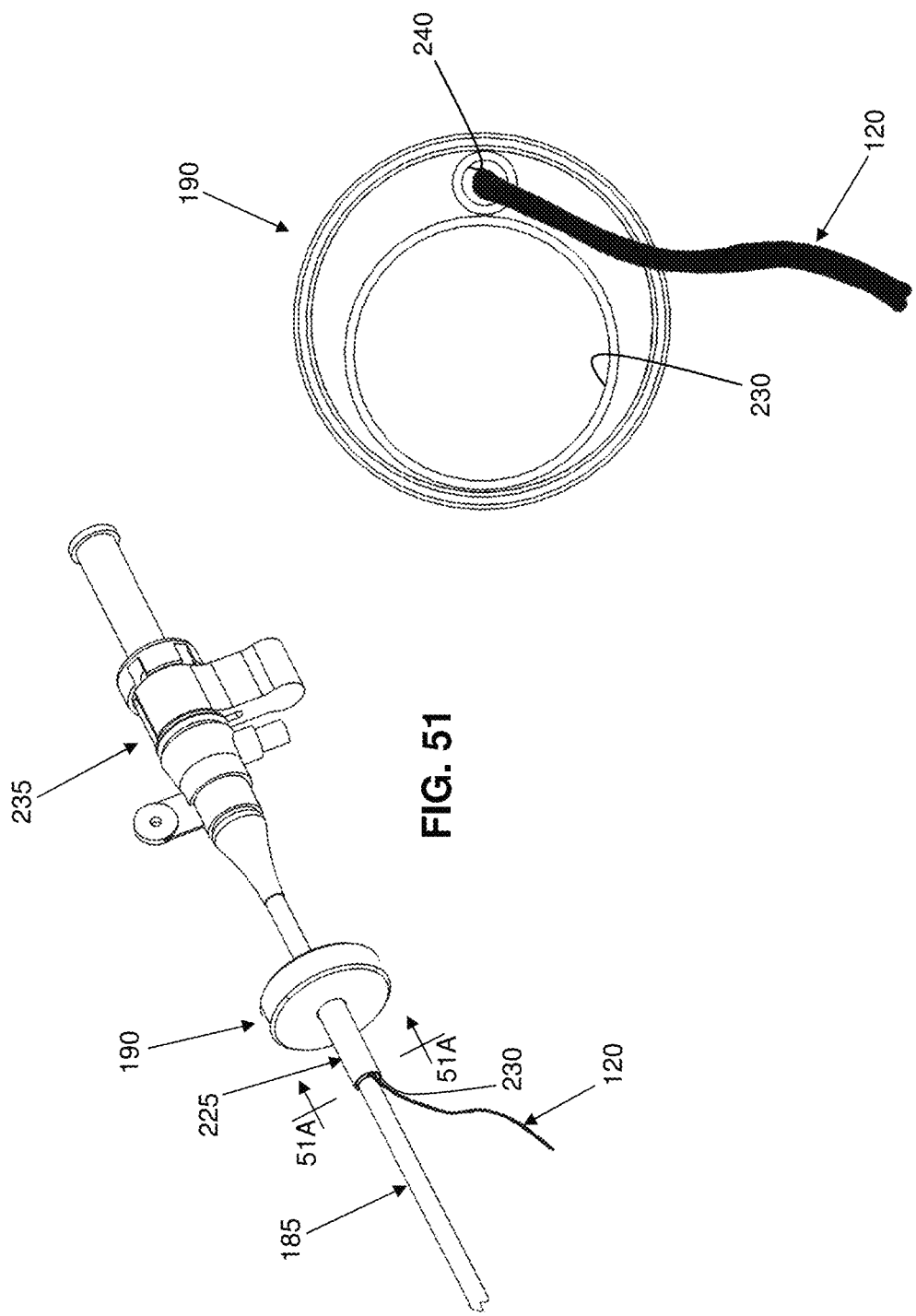

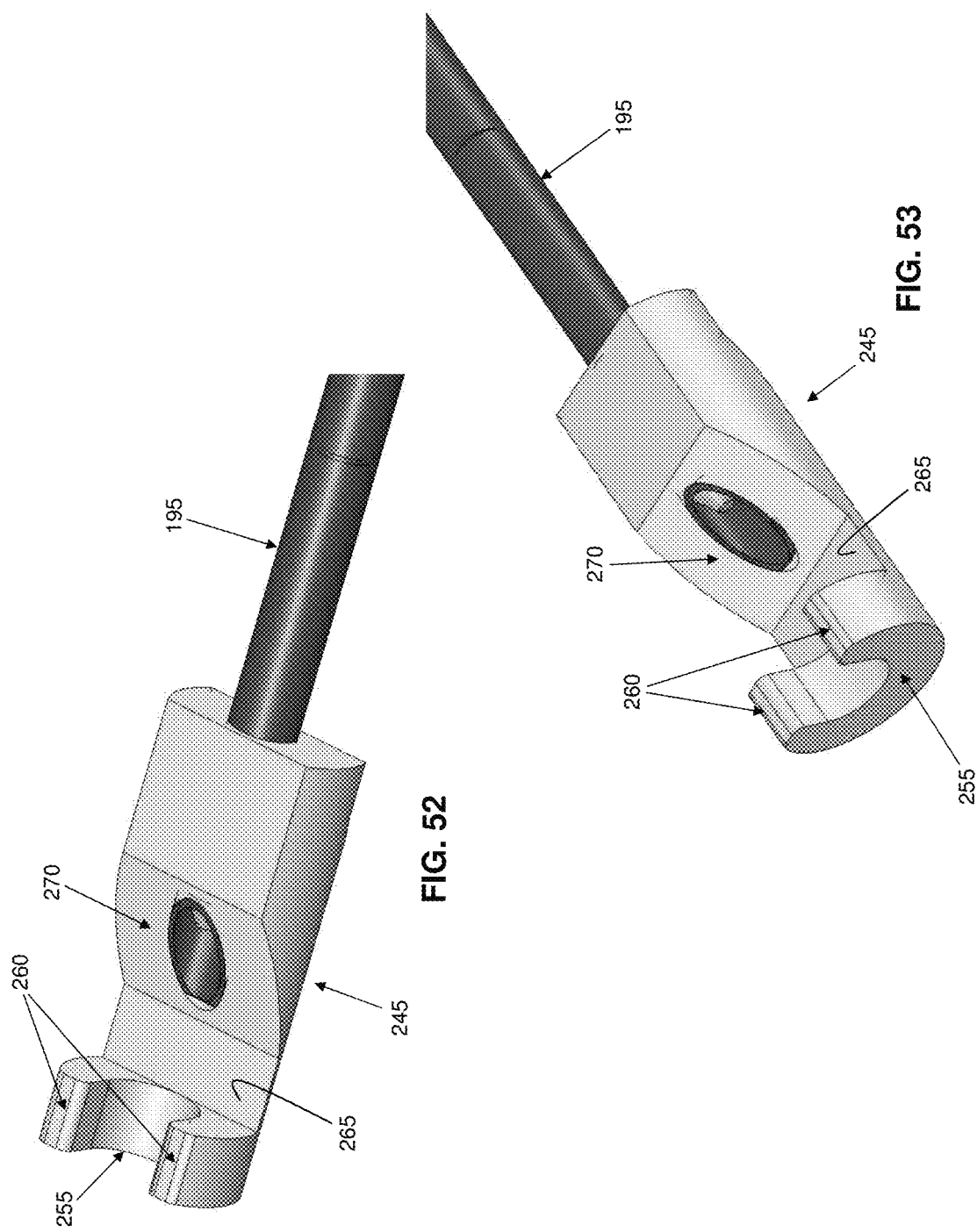

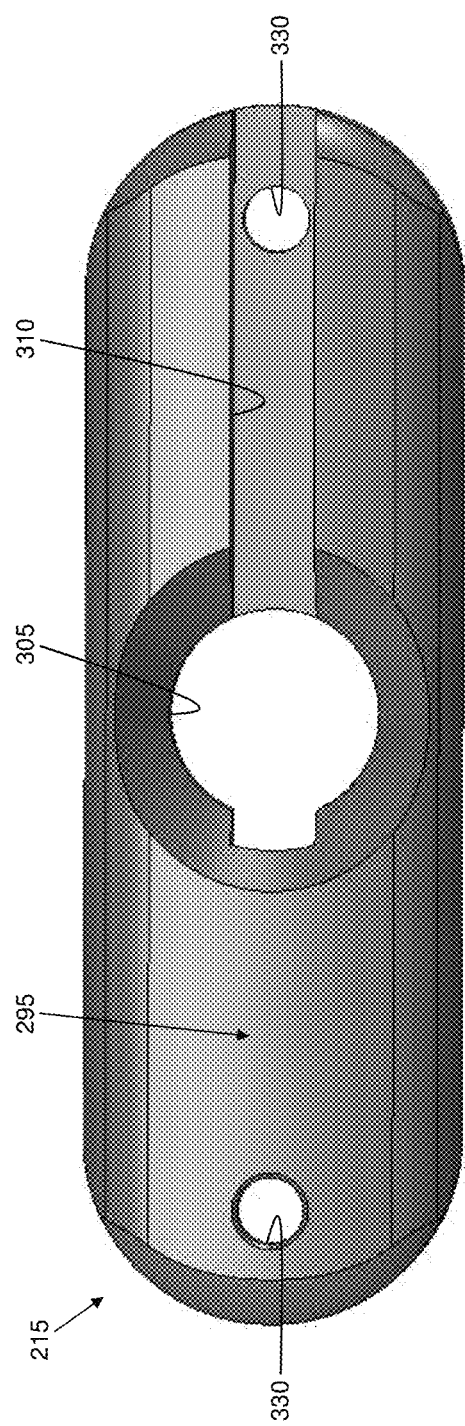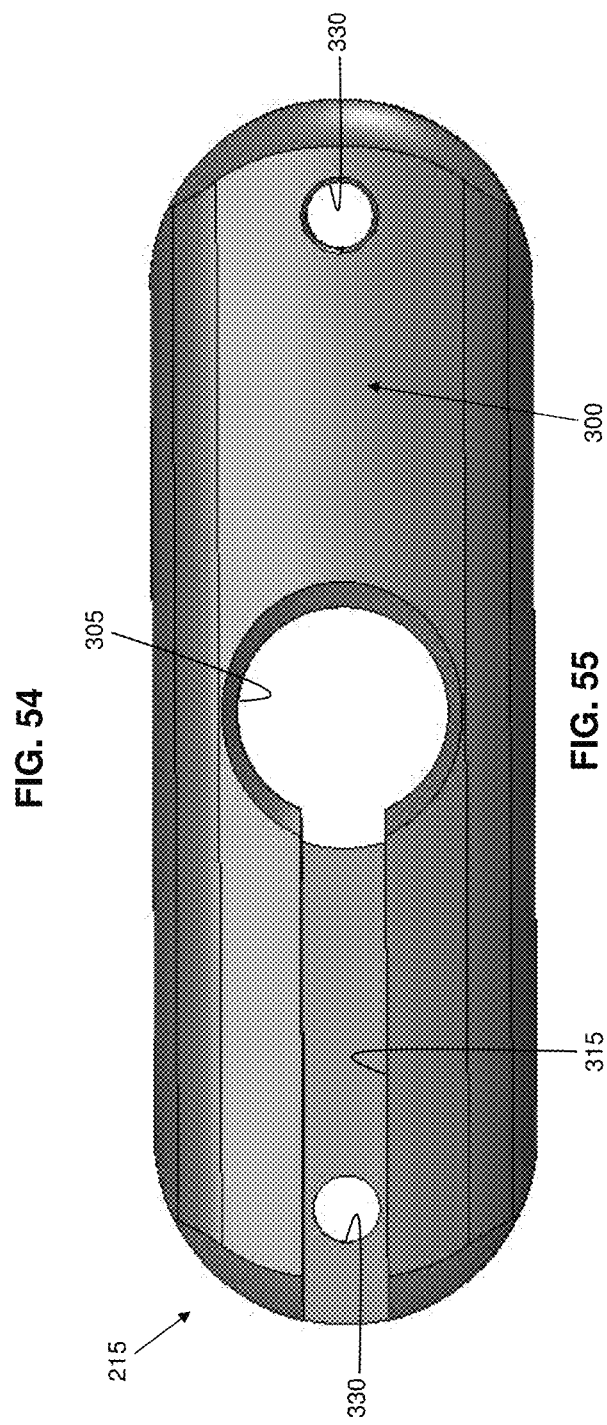

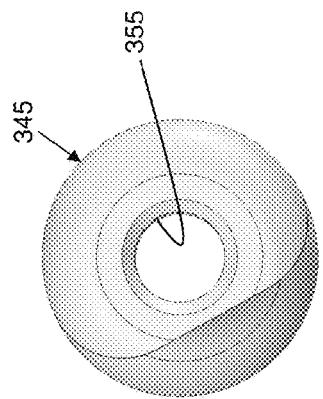
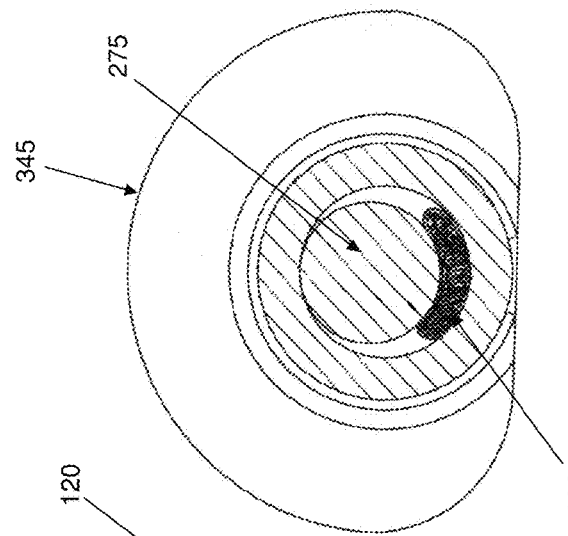
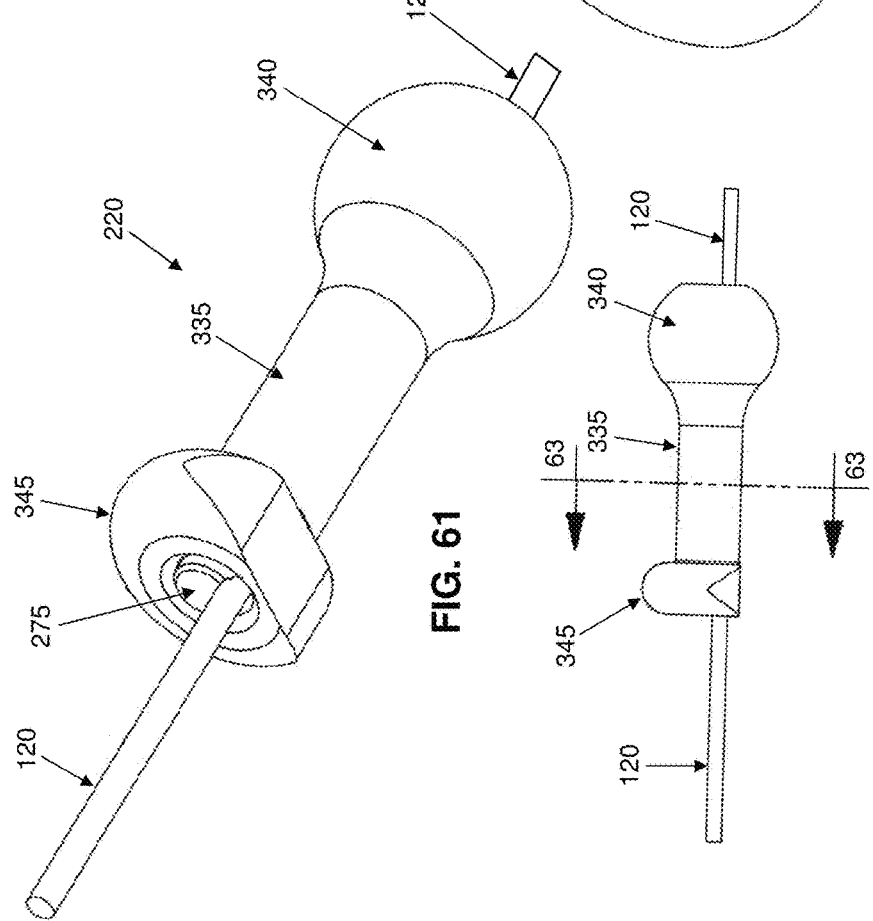
FIG. 60
FIG. 63
FIG. 61
FIG. 62

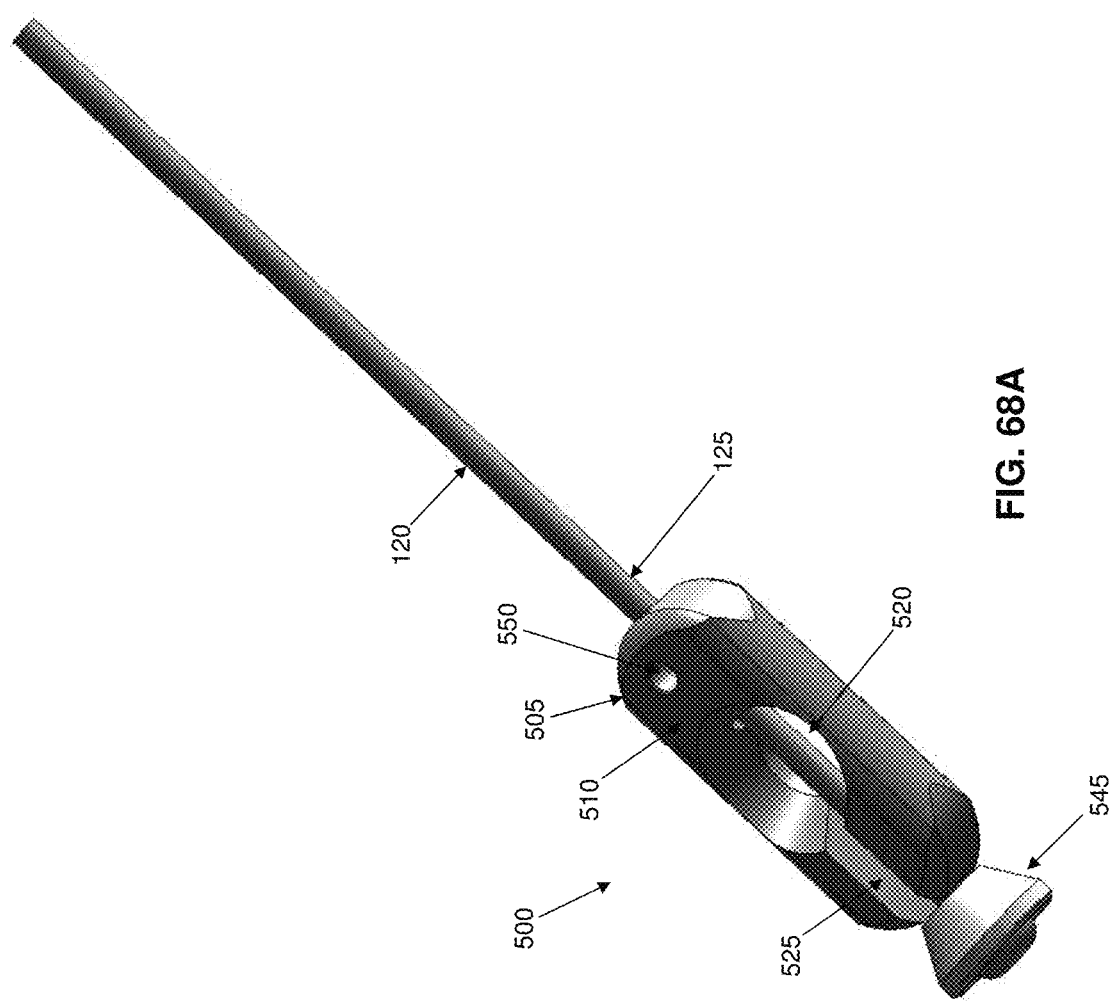

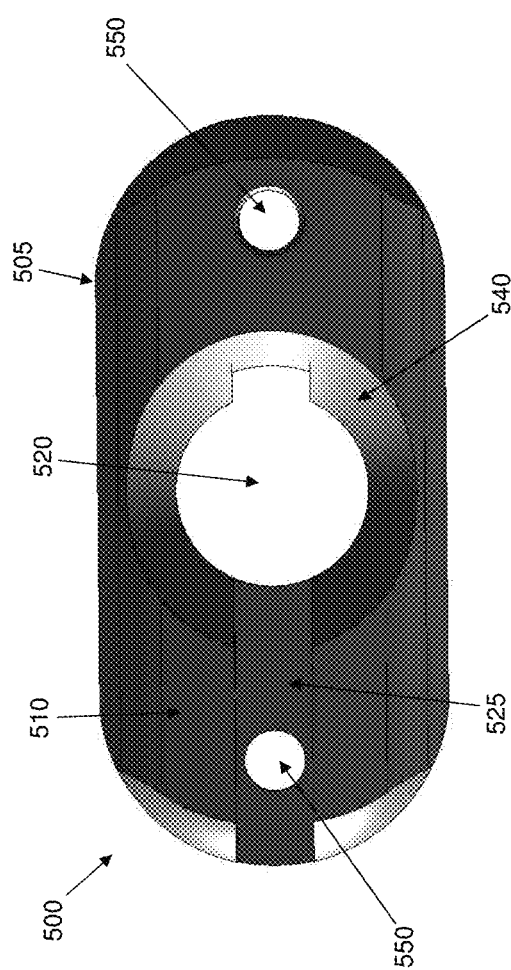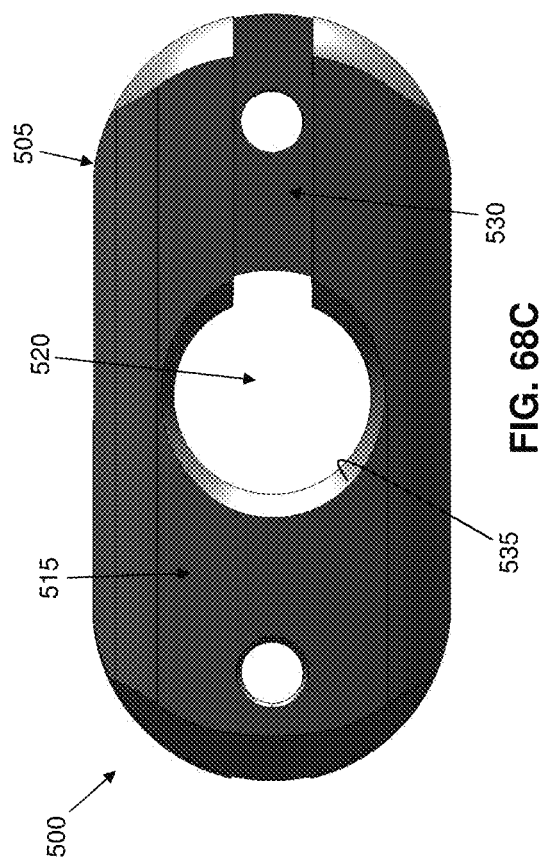

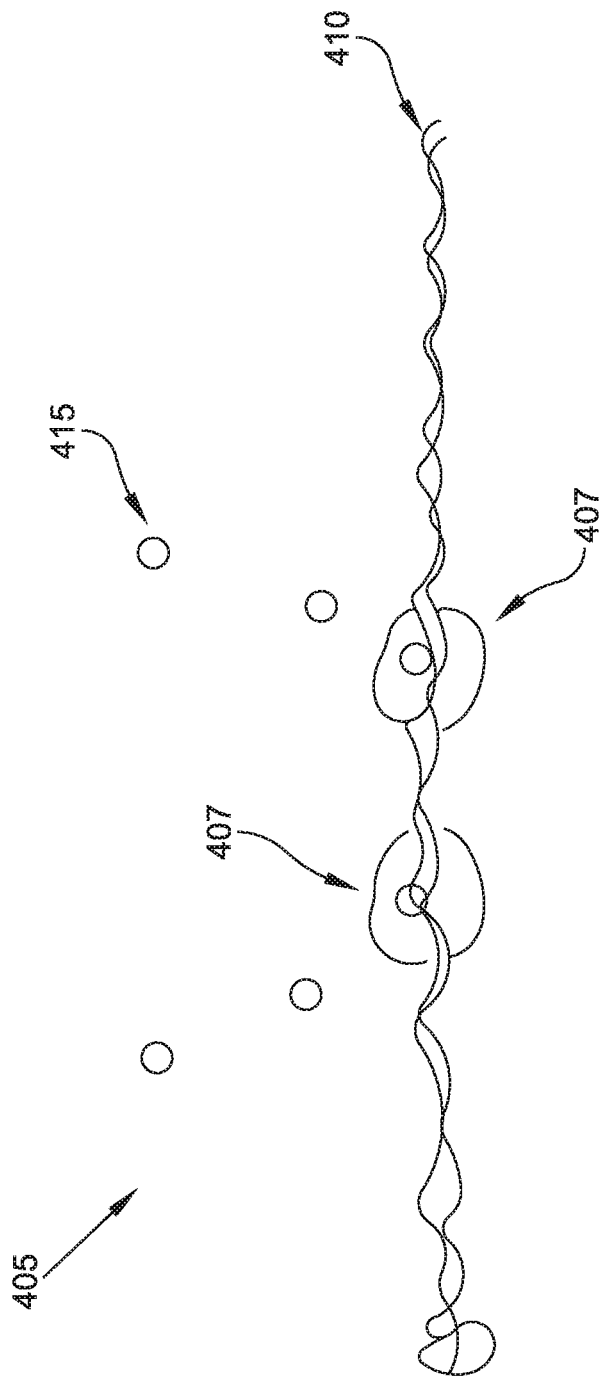

PLACEMENT OF ACCESS SHEATH AND USE OF TARGET CROSS TOOL AND SNARE TO ROUTE SUTURE THROUGH THE ANTERIOR FIBROUS ANNULUS

SUTURE ROUTED THROUGH THE ANTERIOR ANNULUS

SUTURE ROUTED THROUGH TIP OF THE PAPILLARY MUSCLE AND SNARED OUT THROUGH PORT #1

FIG. 78 — FINAL SPAN PATH OF SUTURE IN PLACE READY TO BE TENSIONED

SPAN-TENSION TOOL IN PLACE TO REDUCE
SPAN DIMENSION BETWEEN PAPILLARIES
AND FIBROUS BASE OF THE HEART

FINAL SPAN TENSIONED AND LOCKED. EITHER PROCEDURE COMPLETE AND SHEATH REMOVED, OR THE SHEATH USED TO GO FORWARD AND PLACE OTHER PAPILLARY OR ANNULAR SPANS.

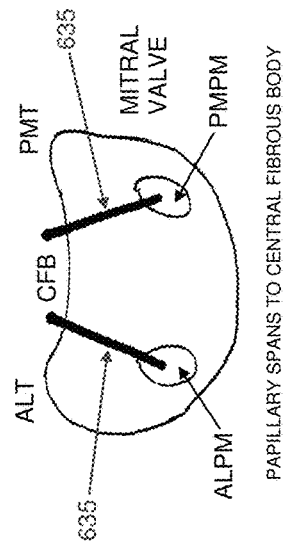
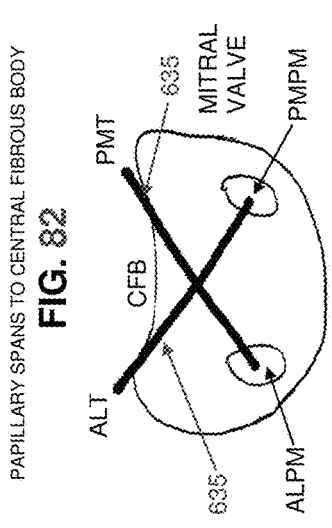
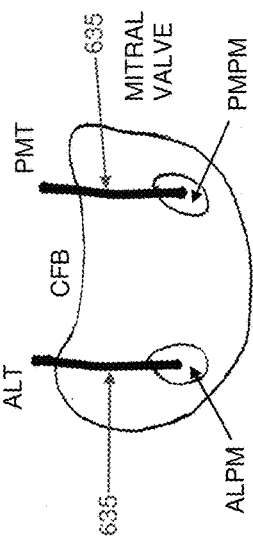
FIG. 82 PAPILLARY SPANS TO CENTRAL FIBROUS BODY
FIG. 83 PAPILLARY SPANS TO DIAGONALLY OPPOSED TRIGONE
FIG. 84 PAPILLARY SPANS TO NEARBY TRIGONE
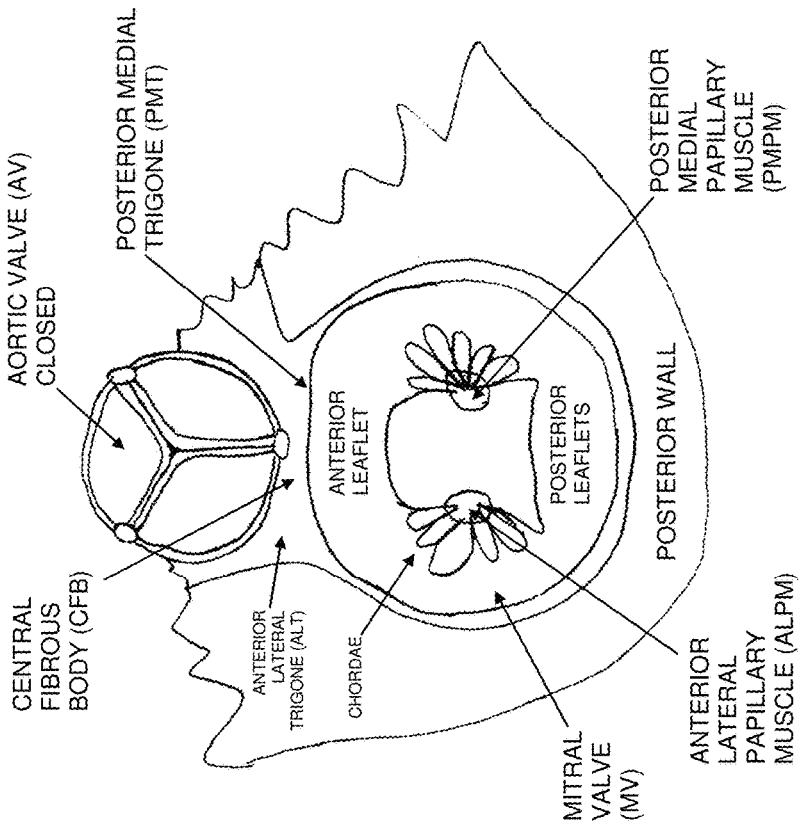
FIG. 81 TRANSVERSE SECTION OF LEFT SIDE OF HEART, SUPERIOR VIEW, ATRIUM AND VESSELS REMOVED

METHOD AND APPARATUS FOR REPAIRING A MITRAL VALVE

REFERENCE TO PENDING PRIOR PATENT APPLICATIONS

This patent application:
(1) is a continuation-in-part of pending prior U.S. patent application Ser. No. 14/599,124, filed Jan. 16, 2015 by MitraSpan, Inc. and Jonathan M. Rourke et al. for METHOD AND APPARATUS FOR REPAIRING A MITRAL VALVE, which patent application:
  (i) is a continuation-in-part of prior U.S. patent application Ser. No. 13/766,521, filed Feb. 13, 2013 by MitraSpan, Inc. and Jonathan M. Rourke et al. for METHOD AND APPARATUS FOR REPAIRING A MITRAL VALVE, which patent application claims benefit of:
    (a) prior U.S. Provisional Patent Application Ser. No. 61/598,047, filed Feb. 13, 2012 by Jonathan M. Rourke et al. for METHODS AND DEVICES FOR MITRAL VALVE REPAIR; and
    (b) prior U.S. Provisional Patent Application Ser. No. 61/740,901, filed Dec. 21, 2012 by Jonathan M. Rourke et al. for METHODS AND DEVICES FOR MITRAL VALVE REPAIR; and
  (ii) claims benefit of prior U.S. Provisional Patent Application Ser. No. 61/928,293, filed Jan. 16, 2014 by MitraSpan, Inc. and Jonathan M. Rourke et al. for METHODS AND DEVICES FOR MITRAL VALVE REPAIR; and
(2) claims benefit of prior U.S. Provisional Patent Application Ser. No. 62/195,492, filed Jul. 22, 2015 by MitraSpan, Inc. and Jonathan M. Rourke et al. for METHODS AND APPARATUS FOR REPAIRING A MITRAL VALVE.

The six (6) above-identified patent applications are hereby incorporated herein by reference.

FIELD OF THE INVENTION

This invention relates to methods and apparatus for performing cardiac structural repairs in general, and more particularly to methods and apparatus for performing mitral valve repairs and beneficial left ventricular structural repairs.

BACKGROUND OF THE INVENTION

The mitral valve is located in the heart between the left atrium and the left ventricle. See FIG. 1. A properly functioning mitral valve permits blood to flow from the left atrium to the left ventricle when the left ventricle expands (i.e., during diastole), and prevents the regurgitation of blood from the left ventricle back into the left atrium when the left ventricle contracts (i.e., during systole). FIG. 2 shows a properly functioning mitral valve during diastole, and FIG. 3 shows a properly functioning mitral valve during systole.

In some circumstances the mitral valve may fail to function properly, such that regurgitation may occur. By way of example but not limitation, mitral regurgitation is a common occurrence in patients with heart failure. Mitral regurgitation in patients with heart failure is caused by changes in the geometric configurations of the left ventricle, papillary muscles, chordae tendinae and mitral annulus. These geometric alterations result in incomplete coaptation of the mitral leaflets at systole. In this situation, mitral regurgitation is generally corrected by plicating the mitral valve annulus so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to draw the annulus, in a purse-string-like fashion, to a smaller radius, thereby improving leaflet coaptation and reducing mitral regurgitation.

This method of mitral valve repair, generally referred to as "annuloplasty", effectively reduces mitral regurgitation in heart failure patients. This, in turn, reduces symptoms of heart failure, improves quality of life and increases longevity. Unfortunately, however, the invasive nature of such mitral valve surgery (i.e., general anesthesia, chest wall incision, cardiopulmonary bypass, cardiac and pulmonary arrest, incision on the heart itself so as to gain access to the mitral valve, etc.), and the risks associated therewith, render most heart failure patients poor surgical candidates for an annuloplasty. Thus, a less invasive means to increase leaflet coaptation and thereby reduce mitral regurgitation in heart failure patients would make mitral valve repair available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for other medical, interventional or surgical therapy.

SUMMARY OF THE INVENTION

As a result, one object of the present invention is to provide an improved method for reducing mitral regurgitation.

Another object of the present invention is to provide improved apparatus for reducing mitral regurgitation.

Another object of the present invention is to provide a method and apparatus for cardiac valve repair, and particularly mitral valve repair, that avoid certain disadvantages of the prior art.

Another object of the present invention is to enable mitral valve repair in a minimally invasive manner without the need for cardiopulmonary bypass or significant surgical intervention.

Another object of the present invention is to provide a means for placing one or more spanning sutures across the mitral valve, and anchoring those spanning sutures to the mitral annulus and nearby cardiac structures, in such a manner as to effect a beneficial reduction in the dilation and distortion of the mitral annulus which causes mitral regurgitation.

A further object of the present invention is to provide a method and apparatus for favorably remodeling the left ventricle.

Another object of the present invention is to provide a method and apparatus for mitral valve repair, either via transapical access with a small exposure incision to the skin in the vicinity of the apex of the left ventricle, complete percutaneous access to the left ventricle, or a combination of transapical and percutaneous access including trans-septal puncture or retrograde access through the aorta and aortic valve. In any case, it is an object of the present invention to provide procedure access through the left ventricular wall to the interior of the left ventricle via a small diameter apical access sheath or access/closure device.

A related object of the present invention is to provide a method and apparatus that do not require a sternotomy when providing procedure access to the mitral valve.

Another related object of the present invention is to provide a method and apparatus that do not require cardiopulmonary bypass or aortic manipulation when reducing mitral regurgitation.

Another object of the present invention is to provide a method and apparatus for mitral valve repair that provides for a controllable anterior/posterior dimension change of the mitral valve while a functional improvement in valve competence is continuously evaluated by real-time cardiac ultrasound or other diagnostic means.

One preferred embodiment of the present invention comprises the provision and use of novel, low-profile devices that are sequentially inserted into the left ventricle of the heart, deploy a spanning suture across the mitral valve on the atrial side, anchor the spanning suture to one side of the annulus with a first anchor, adjust the length of the spanning suture crossing the left atrium while performing real-time ultrasound evaluation of mitral regurgitation, and permanently terminate the spanning suture to a second anchor on the other side of the annulus. The present invention provides novel tools that allow this novel process to be performed quickly, easily and safely, by one of several possible approaches, optionally multiple times on a given valve, until satisfactory correction of the mitral regurgitation has been achieved.

A well-known limitation of prior art devices is that they are not broadly effective because of the high degree of variation in patient anatomies. Significantly, the present invention provides a method and apparatus that provides a high degree of effectiveness across a wide range of patient anatomies, particularly in allowing a clinician to adjust their technique based upon observation of the effectiveness of the initial adjustment of the spanning suture and to increase or decrease the magnitude of the adjustment made on the valve until an acceptable correction has been achieved.

In one preferred embodiment of the present invention, the procedure is generally as follows. External access is established to the left ventricular apex using conventional transapical techniques (e.g., such as those used in the positioning of aortic valves). The left ventricular apex is exposed, either surgically through incision or via direct needle access using the Seldinger technique. An apical access sheath having an internal working diameter of approximately 3-5 mm is passed through the myocardium and directed towards the center of the mitral valve. See FIG. 4.

A first positioning sheath is passed into the left ventricle via the apical access sheath and the distal tip of the first positioning sheath is positioned against the annulus of the valve at a structurally advantageous point. See FIG. 5. Once proper positioning is verified (e.g., by imaging, either via echocardiography or fluoroscopy), a first curved tube is advanced out of the first positioning sheath and through the annulus. See FIG. 6. A first guidewire is passed through the first curved tube (and hence through the annulus) and into the left atrium. See FIG. 7. The first guidewire preferably has an atraumatic tip to avoid damaging the atrial wall and/or surrounding tissues and is visible via ultrasonic or fluoroscopic imaging.

Separately, a center sheath is advanced through the apical access sheath and through the leaflets of the mitral valve so that the distal end of the center sheath is positioned in the left atrium. See FIG. 8. This center sheath may be placed before or after the aforementioned puncture crossing of the mitral annulus via the first positioning sheath, first curved tube and first guidewire. A snare is then advanced through the center sheath. See FIG. 9. Under ultrasonic and/or fluoroscopic guidance, the first guidewire and snare are manipulated so that the first guidewire is captured by the snare, and then the snare is used to bring the first guidewire out to the operative sterile field through the center sheath. See FIG. 10. This leaves the first guidewire extending from the apex, across the left ventricle, through one side of the annulus, into the left atrium, into the center sheath, between the mitral leaflets and then back across the left ventricle. See FIG. 11.

The annulus puncture process is then repeated on the opposite side of the annulus, e.g., using a second positioning sheath and an associated annulus-crossing second curved tube. See FIGS. 12 and 13. Once the second curved tube has been placed across the annulus, a second guidewire is passed through the annulus-crossing second curved tube and advanced into the left atrium. See FIG. 14. Then a snare is advanced through the center sheath and captures the distal end of the second guidewire. See FIG. 15. At this point the snare is retracted so as to bring the second guidewire out to the operative sterile field through the center sheath. See FIG. 16. Once the distal ends of the first and second guidewires have been brought out to the operative sterile field, they are terminated (i.e., connected together) at the operative sterile field. See FIG. 17. Then the termination is sent back up through the center sheath so that the termination resides in the left atrium. See FIG. 18.

Once the first and second guidewires have been passed through opposing sides of the annulus, terminated (i.e., joined) to one another, and their termination advanced back to the left atrium, the termination between the two guidewires is pulled through the second positioning sheath and its annulus-crossing second curved tube, thereby establishing a continuous loop of guidewire extending from the apex, across the left ventricle, through one side of the annulus, across the left atrium, through the other side of the annulus, across the left ventricle, and back down to the apex. See FIG. 19.

At this point, the first positioning sheath (and its annulus crossing first curved tube), the second positioning sheath (and its annulus crossing second curved tube), and the center sheath may all be removed from the operative site, if they have not already been removed.

The aforementioned continuous section of guidewire is sometimes hereinafter referred to as "the crossing guidewire".

And the aforementioned approach for placing the crossing guidewire is sometimes hereinafter referred to as the "cross and snare" approach.

It should be appreciated that the term "crossing guidewire" is intended to be a broad term of art, since in fact the construction of the crossing "guidewire" may be effected with wire, suture, filaments, coils, and/or other materials known in the art capable of establishing a spanning structure able to provide the desired device handling in vivo.

It should be further appreciated that, if desired, a single, dedicated tool could be employed, sequentially, to provide both a positioning sheath and a curved tube, and this single, dedicated tool could be used, sequentially, for both sides of the mitral annulus. Thus, with such a construction, the single, dedicated tool (providing the positioning sheath and the curved tube) would be used first on one side of the mitral annulus to route a guidewire through the annulus; and then the single, dedicated tool (providing the positioning sheath and curved tube) would be removed from the first side of the mitral annulus and then re-positioned on the opposite side of the annulus and used in a similar fashion to pass a second guidewire through the opposite side of the annulus.

In an alternative embodiment of the present invention, the crossing guidewire can be established using a somewhat different approach, which will sometimes hereinafter be referred to as the "cross and catch" approach. More particularly, with the "cross and catch" approach, the first positioning sheath is passed into the left ventricle via the apical access sheath and its distal end is positioned against the annulus at a first location. See FIG. 5. Then the first curved tube is advanced out of the first positioning sheath and through the annulus at that first location. See FIG. 6. Next, the second positioning sheath is passed into the left ventricle via the apical access sheath and its distal end is positioned against the annulus at a second location. See FIG. 20. Then the second curved tube is advanced out of the second positioning sheath and through the annulus at that second location. See FIG. 21.

Next, a funnel-shaped snare is advanced through the second curved tube of the second positioning sheath so that the funnel-shaped snare faces the first curved tube exiting the first positioning sheath. See FIG. 22. Then a guidewire is advanced through the first curved tube of the first positioning sheath, across the left atrium and into the funnel-shaped snare exiting the second curved tube of the second positioning sheath. See FIG. 23. The funnel-shaped snare captures the distal end of the guidewire, and then the funnel-shaped snare is retracted through the second curved tube of the second positioning sheath until the distal end of the guidewire emerges at the operative sterile field. See FIG. 24. Then the distal end of the guidewire is detached from the funnel-shaped snare. See FIG. 25. The first positioning sheath and its associated annulus-crossing first curved tube are withdrawn, and the second positioning sheath and its associated annulus-crossing second curved tube are withdrawn, leaving the guidewire extending from the apex, across the left ventricle, through one side of the annulus, into the left atrium, through the other side of the annulus, across the left ventricle and back down to the apex. See FIG. 26.

In another alternative embodiment of the present invention, the crossing guidewire can be placed using still another approach, which will sometimes hereinafter be referred to as the "cross and receive" approach. More particularly, with the "cross and receive" approach, a first positioning sheath is passed into the left ventricle via the apical access sheath and its distal end is positioned against the annulus at a first location. See FIG. 5. Then a first curved tube is advanced out of the first positioning sheath and through the annulus at that first location. See FIG. 6. Next, a second positioning sheath is passed into the left ventricle via the apical access sheath and its distal end is positioned against the annulus at a second location. See FIG. 20. Then a second curved tube is advanced out of the second positioning sheath and through the annulus at that second location. See FIG. 21.

Next, an inflatable funnel is advanced, in a deflated state, through the second curved tube of the second positioning sheath so that the inflatable funnel faces the first curved tube exiting the first positioning sheath. Then the inflatable funnel is inflated so that the mouth of the inflatable funnel faces the first curved tube exiting the first positioning sheath. See FIG. 27. Next, a guidewire is advanced through the first curved tube of the first positioning sheath, across the left atrium and into the inflatable funnel exiting the second curved tube of the second positioning sheath. See FIGS. 28 and 29. The guidewire is advanced down the second curved tube of the second positioning sheath until the distal end of the guidewire emerges at the operative sterile field. See FIG. 30. The inflatable funnel is deflated and withdrawn from the second curved tube of the second positioning sheath. See FIG. 31. Then the first positioning sheath and its associated annulus-crossing first curved tube are withdrawn, and the second positioning sheath and its associated annulus-crossing second curved tube are withdrawn, leaving the guidewire extending from the apex, across the left ventricle, through one side of the annulus, into the left atrium, through the other side of the annulus, across the left ventricle and back down to the apex. See FIG. 32.

By any of the foregoing approaches, a continuous path of guidewire (or suture or other filamentary element) is established, travelling from the apical access sheath, through the mitral annulus on one side, across the left atrium, back through the mitral annulus and back out through the apical access sheath. It should be noted that by the methods and tools described herein, such a crossing path can be established at a wide range of anatomically-preferred locations and with the establishment of only "small caliber" holes through the annulus, that is, holes approximately the diameter of the intended implant suture.

Once the crossing guidewire has been established, preferably using one of the aforementioned three approaches (i.e., the "cross and snare" approach, the "cross and catch" approach, or the "cross and receive" approach), a spanning implant can be deployed across the annulus of the mitral valve so as to reconfigure the geometry of the mitral valve.

More particularly, the spanning implant comprises a spanning suture having a first end, a second end and a first anchor connected to the first end of the spanning suture. The spanning implant also comprises a second anchor which is fit over the second end of the spanning suture, slid along the spanning suture to an appropriate position and then secured in place, as will hereinafter be discussed. See FIG. 33.

Note that the spanning suture may comprise conventional surgical suture (e.g., braided suture, monofilament suture, etc.), filament, wire, cable and/or substantially any other flexible elongated body consistent with the requirements of the present invention. For the purposes of the present invention, all such constructions are intended to be encompassed by the term "spanning suture".

The spanning implant is preferably deployed in the following manner. First, one end of the crossing guidewire is secured to the second end of the spanning suture. See FIG. 34. Then the crossing guidewire is used to draw the spanning suture from the apex, across the left ventricle, through one side of the annulus, across the left atrium, through the other side of the annulus, across the left ventricle, and back down to the apex. The crossing guidewire is pulled until the first anchor at the first end of the spanning suture is seated against the annulus, generally disposed in the space between the leaflet insertion and the ventricular wall. See FIG. 35. The second anchor is then slid onto the second end of the spanning suture and advanced along the spanning suture toward the annulus. See FIG. 36. The second anchor is advanced until the second anchor seats against the opposite side of the annulus, on the ventricular side of the annulus. See FIG. 37. Thus, as a result of the foregoing, the first anchor is disposed against the ventricular side of the annulus at a first location, the spanning suture extends through the annulus at that first location, across the left atrium, and through the annulus at a second location, and the second anchor seats against the ventricular side of the annulus at the second location.

Finally, an implant tensioning tool, integrally fitted with a coaxial suture lock, is advanced over the second end of the spanning suture so as to engage the second anchor. The implant tensioning tool is then used to progressively tension the spanning suture, which causes the two sides of the annulus to be drawn together along the line of the spanning suture, until the desired anterior/posterior dimension is achieved for the annulus, whereby to provide the desired reduction in mitral regurgitation. Preferably this tensioning of the spanning suture is done under real-time ultrasound observation. Once the desired mitral reconfiguration has been achieved, the implant tensioning tool is used to lock the second anchor in position on the spanning suture with the coaxial suture lock. See FIG. 38. This maintains the mitral valve in its reconfigured state. The implant tensioning tool is then removed, and the excess spanning suture remaining proximal to the coaxial suture lock may then be removed (e.g., with a cutoff tool) or terminated to the left ventricular wall. See FIG. 39.

In a separate preferred embodiment, the implant tensioning tool additionally houses and delivers the second anchor.

This foregoing process may then be repeated as needed with other spanning implants so as to effect a complete, effective and structurally durable reconfiguration of the mitral valve. See FIG. 40. It is anticipated that, in a typical case, two spanning implants will be used to reconfigure the annulus, each anchored in either the anterior or posterior trigone and spanning from the trigone to the posterior annulus, with the anterior trigone connected to the posterior annulus generally in the vicinity of the P1/P2 leaflet intersection, and the posterior trigone connected to a point in the vicinity of the P2/P3 leaflet intersection. It is anticipated that, depending upon the degree of dilation of the mitral annulus, and the specialized anatomical issues of a particular patient, as many as four or five spanning implants may be used to reconfigure the annulus, anchored through the anterior and posterior trigones, or from a more central point along the central fibrous body of the heart, and across and through the posterior annulus.

For the purposes of the present invention, the first anchor may be considered "fixed" (i.e., "the first, fixed anchor"), in the sense that the spanning suture may be tensioned relative to the first anchor when the first anchor is positioned against the mitral annulus. However, the term "first, fixed anchor" is not intended to be construed as requiring that the first anchor be fixedly secured to the spanning suture, since the first anchor may be connected to the spanning suture in a manner which allows the spanning suture to be to tensioned relative to the first anchor when the first anchor is positioned against the mitral annulus, yet which also allows the spanning suture to move relative to the first anchor when the spanning suture is moved in an opposite direction. By way of example but not limitation, the "first, fixed anchor" may comprise a central through-hole, and the spanning suture may comprise an end having an enlargement larger than the central through-hole of the anchor; in this case, the spanning suture may extend through the central through-hole of the anchor and be tensioned by pulling the spanning suture so that the enlargement engages the first, fixed anchor, however, the spanning suture may also be moved relative to the first, fixed anchor by pushing the spanning suture so that the enlargement moves away from the first, fixed anchor.

Furthermore, for purposes of the present invention, the second anchor may be considered "sliding" (i.e., "the second, sliding anchor"), in the sense that the second anchor may be slid along the spanning suture prior to fixation relative to the spanning suture. However, the term "second, sliding anchor" is not intended to be construed as requiring that the second anchor be slidable relative to the spanning suture at all times, since the second, sliding anchor is intended to be fixedly secured to the spanning suture after the spanning suture has been tensioned so as to reconfigure the mitral annulus.

In one preferred form of the invention, the spanning implant may be deployed from anterior to posterior, i.e., the first, fixed anchor is deployed against the anterior annulus and the second, sliding anchor is deployed against the posterior annulus. However, it is also anticipated that the direction of the spanning implant might be reversed, with the first, fixed anchor deployed against the posterior annulus and the second, sliding anchor deployed against the anterior annulus.

It should be appreciated that each anchor (i.e., the aforementioned first, fixed anchor and the aforementioned second, sliding anchor) may be optimized for the anatomical location for which it is deployed, with preferably smaller shapes in the higher-flow, highly fibrous trigone locations and larger shapes in the slower-flow, less fibrous posterior wall locations.

It should be appreciated that the procedure described above has distinct advantages over many alternative approaches. The approach of the present invention can, as described, effect substantial, effectively unlimited reduction of the anterior/posterior dimension of the mitral annulus. Furthermore, the method affords all of the advantages of a minimally invasive procedure.

In one preferred form of the invention, there is provided a method for repairing a mitral valve, the method comprising:

positioning a crossing guidewire across the mitral valve, the crossing guidewire passing through the annulus of the mitral valve at a first location and passing through the annulus of the mitral valve at a second location;

using the crossing guidewire to position a spanning implant across the mitral valve, with the spanning implant extending from the first location to the second location;

anchoring the spanning implant at the first location;

tensioning the spanning implant so as to draw the first location and the second location together; and anchoring the spanning implant at the second location.

In another preferred form of the invention, there is provided apparatus for repairing a mitral valve, the apparatus comprising:

a suture having a first end and a second end, a first anchor secured to the first end of the suture, a second anchor slidably mounted to the second end of the suture, and a coaxial suture lock for locking the second anchor to the suture.

In another preferred form of the invention, there is provided apparatus for repairing a mitral valve, the apparatus comprising:

a crossing guidewire extending from the left ventricle, through the annulus at a first location, into the left atrium, through the annulus at a second location, and into the left ventricle.

In another preferred form of the invention, there is provided apparatus for repairing a mitral valve, the apparatus comprising:

a positioning sheath having a distal end, a proximal end, and a lumen extending therebetween, the positioning sheath being configured to extend across the left ventricle and contact the annulus of the mitral valve at a first location, with the distal end of the positioning sheath set so that the lumen of the positioning sheath is aimed into the left atrium; and a curved tube having a distal end, a proximal end, and a lumen extending therebetween, the curved tube being configured to telescopically extend through the positioning sheath, across the annulus at the first location and present its distal end substantially parallel to the plane of the mitral valve annulus.

In another preferred form of the invention, there is provided apparatus, said apparatus comprising:

an anchor, said anchor comprising:

an elongated body having a distal end and a proximal end, and a first side and a second side;

a through-hole formed in said body intermediate said distal end and said proximal end and extending through said body from said first side to said second side, said through-hole being sized to receive a spanning suture;

a proximal slot formed in said first side of said body and communicating with said through-hole, said proximal slot being sized to receive a spanning suture; and a distal slot formed in said second side of said body and communicating with said through-hole, said distal slot being sized to receive a spanning suture;

at least a portion of said proximal slot being axially aligned with at least a portion of said distal slot so that said proximal slot, said through-hole and said distal slot together form an axial passageway extending from said distal end of said elongated body to said proximal end of said elongated body, with said axial passageway being sized to receive a spanning suture.

In another preferred form of the invention, there is provided apparatus comprising:

a form-fitting, stretchable sheath; and a medical component disposed within said form-fitting, stretchable sheath.

In another preferred form of the invention, there is provided a pledget assembly comprising:

a central ring having a distal end and a proximal end and an opening extending from said distal end to said proximal end;

a surgical pledget mounted to said central ring and extending radially outboard thereof; and a helical coil having a distal end and a proximal end, said helical coil being mounted to said central ring and extending distally thereof, said helical coil being configured for turning into tissue for fixation thereto.

In another preferred form of the invention, there is provided a method for reconfiguring a mitral valve, said method comprising:

positioning a spanning suture across the mitral valve, said spanning suture extending from the left ventricle of the heart, through the annulus of the mitral valve at a first location, across the left atrium of the heart, through the annulus of the mitral valve at a second location, and back to the left ventricle of the heart;

positioning a first anchor connected to said spanning suture against the ventricular side of the mitral valve at the first location and positioning a second anchor connected to said spanning suture against the ventricular side of the mitral valve at the second location and tensioning said spanning suture so as to draw the first location and the second location together, whereby to reconfigure the mitral valve; and fixedly securing said second anchor to the spanning suture so as to maintain the mitral valve in its reconfigured state;

wherein at least one of said first anchor and said second anchor comprises:

an elongated body having a distal end and a proximal end, and a first side and a second side;

a through-hole formed in said body intermediate said distal end and said proximal end and extending through said body from said first side to said second side, said through-hole being sized to receive said spanning suture;

a proximal slot formed in said first side of said body and communicating with said through-hole, said proximal slot being sized to receive said spanning suture; and a distal slot formed in said second side of said body and communicating with said through-hole, said distal slot being sized to receive said spanning suture;

at least a portion of said proximal slot being axially aligned with at least a portion of said distal slot so that said proximal slot, said through-hole and said distal slot together form an axial passageway extending from said distal end of said elongated body to said proximal end of said elongated body, with said axial passageway being sized to receive said spanning suture.

In another preferred form of the invention, there is provided a method for reconfiguring a mitral valve, said method comprising:

positioning a spanning suture across the mitral valve, said spanning suture extending from the left ventricle of the heart, through the annulus of the mitral valve at a first location, across the left atrium of the heart, through the annulus of the mitral valve at a second location, and back to the left ventricle of the heart;

positioning a first anchor connected to said spanning suture against the ventricular side of the mitral valve at the first location and positioning a second anchor connected to said spanning suture against the ventricular side of the mitral valve at the second location and tensioning said spanning suture so as to draw the first location and the second location together, whereby to reconfigure the mitral valve; and fixedly securing said second anchor to the spanning suture so as to maintain the mitral valve in its reconfigured state;

wherein at least one of said first anchor and said second anchor is delivered through a form-fitting, stretchable sheath making an engaging fit with said at least one of said first anchor and said second anchor.

In another preferred form of the invention, there is provided a method for beneficially displacing a papillary muscle, the method comprising:

anchoring one end of an implant suture to a trigone or central fibrous body of the mitral valve;

passing another end of the implant suture through a papillary muscle so that the implant suture extends between a trigone or central fibrous body of the mitral valve and the papillary muscle;

tensioning the implant suture while displacing the papillary muscle toward the trigone or central fibrous body of the mitral valve; and securing the tensioned implant suture to the displaced papillary muscle so as to maintain the displaced papillary muscle in position relative to the trigone or central fibrous body of the mitral valve;

wherein the foregoing steps of anchoring, passing, tensioning and securing are all effected while the heart is beating.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 2 and 3 are schematic views showing the mitral valve, with FIG. 2 showing a properly functioning mitral valve during diastole, and FIG. 3 showing a properly functioning mitral valve during systole;

FIG. 42 is a schematic view showing a novel snare formed in accordance with the present invention;

FIGS. 50C and 50D are schematic views similar to FIGS. 50A and 50B, but with the sheath of the STTT removed;

FIGS. 51, 51A, 52 and 53 are schematic views showing further details of the STTT of FIG. 47;

FIGS. 54-59 are schematic views showing further details of the second, sliding anchor of FIGS. 48 and 49;

FIGS. 60-63 are schematic views showing further details of the coaxial suture lock of FIGS. 48 and 49;

FIGS. 68A-68F are schematic views showing another form of the first, fixed anchor of the present invention; and FIGS. 69, 70, 70A and 71 are schematic views showing a novel surgical felt pledget disposed between the ventricular side of the posterior mitral annulus and the second, sliding anchor;

FIGS. 72-84 are schematic views showing a novel method and apparatus for permanently beneficially displacing one or both of the papillary muscles.

DETAILED DESCRIPTION OF THE PREFERRED EMBODIMENTS

The present invention summarized above may be better understood by reference to the following exemplary description of the preferred embodiments, which should be read in conjunction with the accompanying drawings wherein like reference numbers are used for like parts. The following description of the preferred embodiments, set out below to facilitate the construction and use of an implementation of the present invention, is not intended to limit the present invention, but instead to serve as a particular example thereof so as to facilitate its construction and use. Those skilled in the art should appreciate that they may readily use the conception and specific embodiments disclosed herein as a basis for modifying the method and apparatus disclosed, or designing additional methods and apparatus, for carrying out the same purposes of the present invention. It should be appreciated that such methods and apparatus do not depart from the spirit and scope of the present invention in its broadest form.

Figure 1:
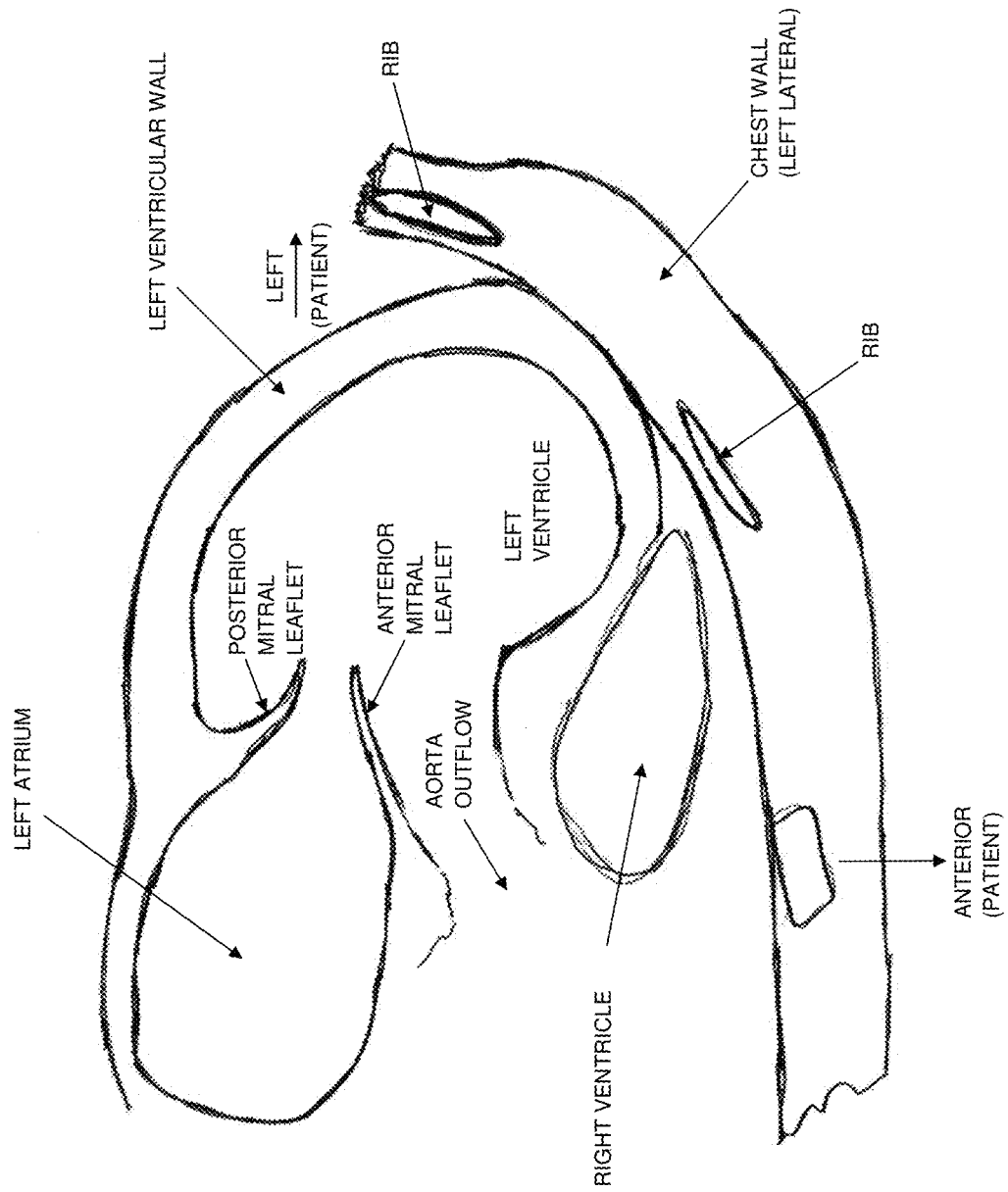
FIG. 1 is a schematic view showing the relevant target anatomy for the method and apparatus of the present invention, with the view being taken along an axial plane through the apex of the left ventricle and the leaflets of the mitral valve.

In accordance with the present invention, the heart may be accessed through one or more openings made by one or more small incisions in a portion of the body proximal to the thoracic cavity, for example, between one or more of the ribs of the rib cage, proximate to the xyphoid appendage, or via the abdomen and diaphragm. This location can be appreciated by viewing the anatomy shown in FIG. 1. Access to the thoracic cavity may be sought so as to allow the insertion and use of one or more thoracoscopic instruments. Additionally, access to the heart may be gained by direct puncture of the heart from the xyphoid region (i.e., via an appropriately sized needle, e.g., an 18 gauge needle). Access may also be achieved using percutaneous means. Accordingly, the one or more incisions should be made in such a manner as to provide an appropriate surgical field and access site to the heart.

Suitable surgical candidates are identified by reviewing available cardiac imaging which may include, but is not limited to, transesophageal echocardiogram (TEE), transthoracic echocardiogram (TTE), magnetic resonance imaging (MRI), computer tomagraphy (CT), fluoroscopy, chest x-rays, etc. Rendered 3D models of the patient's anatomy may be constructed and reviewed, in addition to reviewing previous imaging of the anatomy, in order to plan device access and the mitral valve repair.

The patient is prepped and placed under anesthesia, and appropriate ultrasound imaging (TEE or TTE) is set up so as to provide real-time assessment of the geometry and function of the mitral valve. The procedure is conducted in a standard cardiac operating room or, optionally, in a hybrid operating room which additionally provides for fluoroscopic imaging. A minimally invasive approach is used to access the thoracic cavity. This minimally invasive approach involves a small incision in the skin between the ribs to expose a surgical field suitable for device access and to provide a purse-string suture for the access site if necessary. Such an incision is typically about 1 cm to about 10 cm in length, or about 3 cm to about 7 cm in length, or about 5 cm in length, and should be placed near the pericardium so as to allow ready access to, and visualization of, the heart.

The planned access point and device orientation are generally determined by pre-procedure imaging and anatomical models, and are confirmed by anatomical landmarks and procedural imaging such as ultrasound and fluoroscopy. Access to the left ventricle of the heart may be made at any suitable site of entry, but is preferably made through a point near to, but not at, the apex of the heart, in a region of diffuse vasculature, so as to avoid coronary arteries, papillary muscles and chordae tendineae. The papillary muscles and chordae tendineae of the mitral valve are shown in FIGS. 2 and 3. Apparatus orientation is optimized so as to provide access to the applicable target locations of the mitral valve annulus and to minimize the need to manipulate the access site during device use. The apparatus is advanced into the heart through a small incision stabilized by a purse-string suture, a direct puncture of the heart with the apparatus (with or without a purse-string suture), or by a series of devices of increasing diameter (dilators) until the apparatus with the largest diameter is positioned (with or without a purse-string suture) through the wall of the left ventricle. It is thus expected that the generally preferred axis of alignment of the apparatus will be along a central axis defined by the point of access to the left ventricular apex and the centroid of the mitral valve plane.

Transesophageal echocardiography (TEE) (2D or 3D), transthoracic echocardiography (TTE), intracardiac echo (ICE), or cardio-optic direct visualization (e.g., via infrared vision from the tip of a 7.5 French catheter) may be performed to assess the condition of the heart and its valves. A careful assessment is made of the location and type of cardiac dysfunction via conventional echocardiographic means, e.g., TEE or TTE, so as to facilitate planning of the appropriate structural correction to be performed on the mitral valve annulus, whereby to improve mitral valve function and reduce mitral valve regurgitation. The use of TEE, TTE, ICE or the like can also assist in determining if there is a need for adjunctive procedures to be performed on the leaflets and subvalvular structures, and can indicate whether an adjunctive or alternative minimally invasive approach, or direct surgery, is advisable.

All of the steps and apparatus described below can be best appreciated by reference to the attached figures. The operative method and preferred apparatus characteristics will now be described, including multiple preferred embodiments of the method and apparatus of the present invention.

1. Left Ventricular Access

Access will generally be effected along the left lateral chest wall between the ribs, either with an initial small surgical exposure cut-down, or via direct percutaneous needle puncture. The choice of the specific access method will generally be guided by imaging and considerations such as possible interference with the lobes of the lung.

Apical access is directed by pre-procedural modeling and imaging, and inter-procedural imaging, as previously described. It is expected that the preferred access location and direction will be along an axis directed centrally through the chosen rib space, left ventricle and mitral valve.

Direct percutaneous left ventricular puncture, with or without supplemental dilation, is effected using standard Seldinger techniques well understood in the surgical arts including, in this specific case, the use of an appropriate left ventricular closure device.

Figure 4:
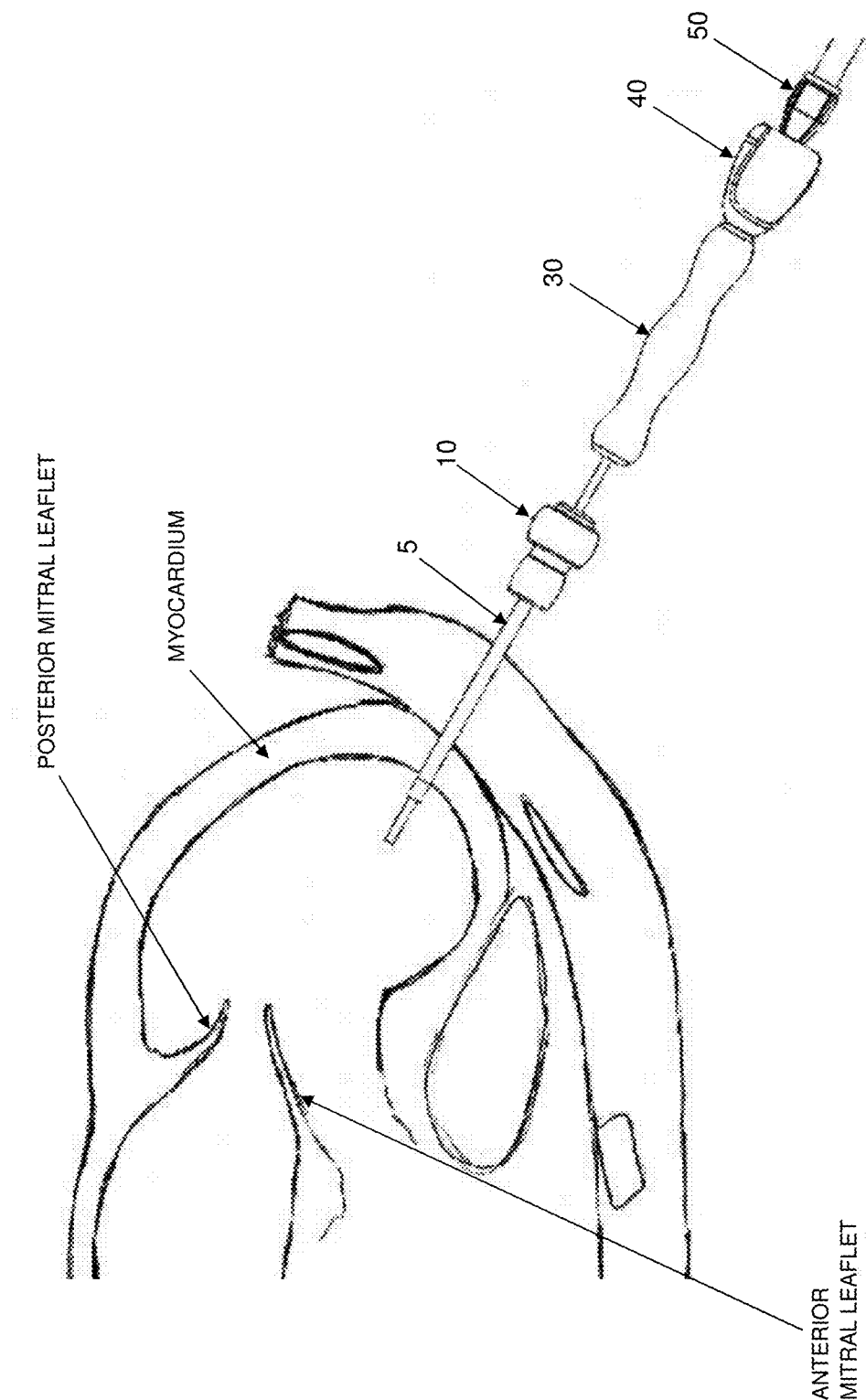
FIG. 4 is a schematic view showing access to the left ventricle having been established with an apical access sheath.

Following the establishment of left ventricular access, an apical access sheath 5 (FIG. 4), preferably between about 3 cm and about 10 cm long, and between about 2.5 mm and about 4 mm internal diameter, typically fitted with an integral, adjustable internal diameter hemostasis valve 10, and with minimal rigid length, is placed into the left ventricle. FIG. 4 shows apical access sheath 5 and hemostasis valve 10 positioned through the chest wall and through the myocardium.

Figure 41:
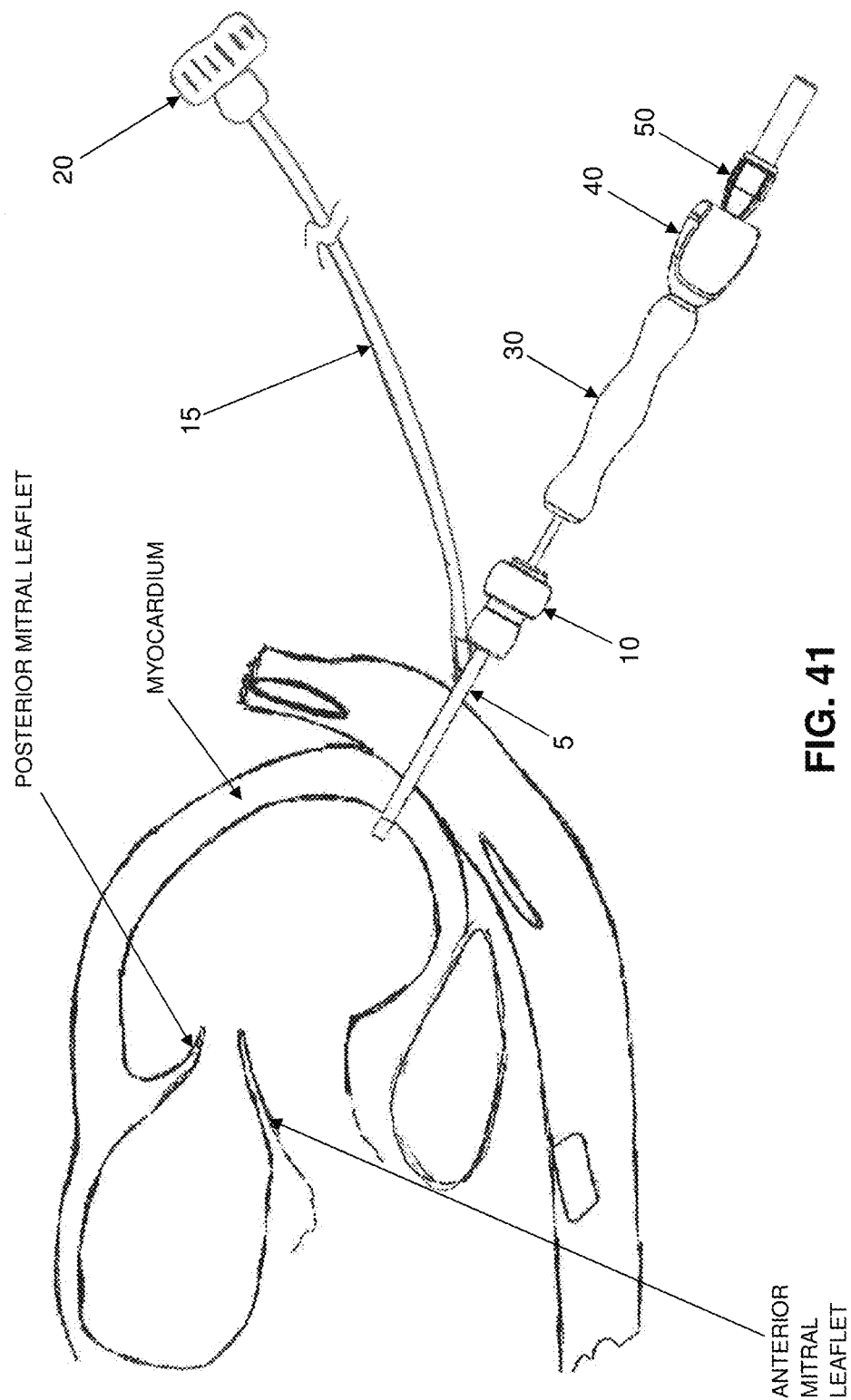
FIG. 41 is a schematic view showing an apical access sheath having a side port access sheath.

Alternatively, FIG. 41 shows another preferred embodiment of apical access sheath 5. As seen in FIG. 41, in addition to the access sheath features described above, a second branch or "Y" leg, constituting a side port access sheath 15, is provided to allow for a second independent access path from the operative sterile field into apical access sheath 5. Side port access sheath 15 is preferably also fitted with an integral, adjustable internal diameter hemostasis valve 20, and joins apical access sheath 5 distal to hemostasis valve 10. The provision of side port access sheath 15 allows for more independent manipulation of multiple clinical tools during the procedure, as will be discussed further below. One preferred design for the joining side port access sheath 15 to apical access sheath 5 is for the "Y" junction of the branches to be formed of a flexible material such as urethane, silicone, etc., to allow for manipulation of the legs and to allow for the insertion of curved tools into apical access sheath 5.

2. Establishing the Crossing Guidewire by the "Cross and Snare" Approach

One preferred approach for beneficially modifying the mitral annulus employs a novel technique, sometimes herein referred to as the "cross and snare" approach, for safely and accurately establishing a desired suture path across the mitral annulus.

The first tool employed in the "cross and snare" procedure is sometimes referred to herein as the "target and cross tool", or "TCT". The TCT can be prepared in various specific variants depending upon the particular preferred embodiment being implemented. More particularly, the TCT may have a multitude of sizes and shapes, e.g., longer or shorter lengths, more or less curves, more or less curvature, etc., depending on the specific patient (e.g., large patient, small patient, etc.) and anatomy to be targeted (e.g., anterior annulus, posterior annulus, a specific trigone, etc.). Thus, the TCT has a preferred shape to allow the clinician to direct the TCT to a desired location on the underside of the posterior mitral annulus in a precise and controlled fashion. Preferably the TCT has a shape which allows the TCT to be directed into a desired position on the ventricular side of the mitral annulus by a direct approach and without requiring significant lateral movement, since such lateral movement can be problematic given the presence of the chordae tendineae on the ventricular side of the mitral valve. Furthermore, the TCT preferably has a shape which allows it to advance to, and directly engage, the ventricular side of the mitral annulus without requiring the deformation or displacement of any intervening cardiac anatomy (e.g., the papillary muscles, chordae tendineae, etc.) when the TCT is advancing to, and engaging, the annulus "crossing" site. Significantly, by providing a method and means which allows the annulus "crossing" site to be accessed without requiring the deformation or displacement of any intervening cardiac anatomy, subsequent steps in the annulus reconfiguration may also be performed without requiring any intervening cardiac anatomy to be deformed or displaced By the methods described herein, once a crossing location has been reached, the TCT tool does not need to be moved laterally within the ventricle, risking entanglement or interference with chordae or other structures. And subsequent steps in the procedure follow the suture path back to the same crossing location, again without requiring lateral motion and the risk of entanglement by either the delivery tools or the deployed implant. This combination of devices and method are a significant advance in the art. The preferred tool characteristics can also be appreciated by reference to the included figures.

Figure 5:
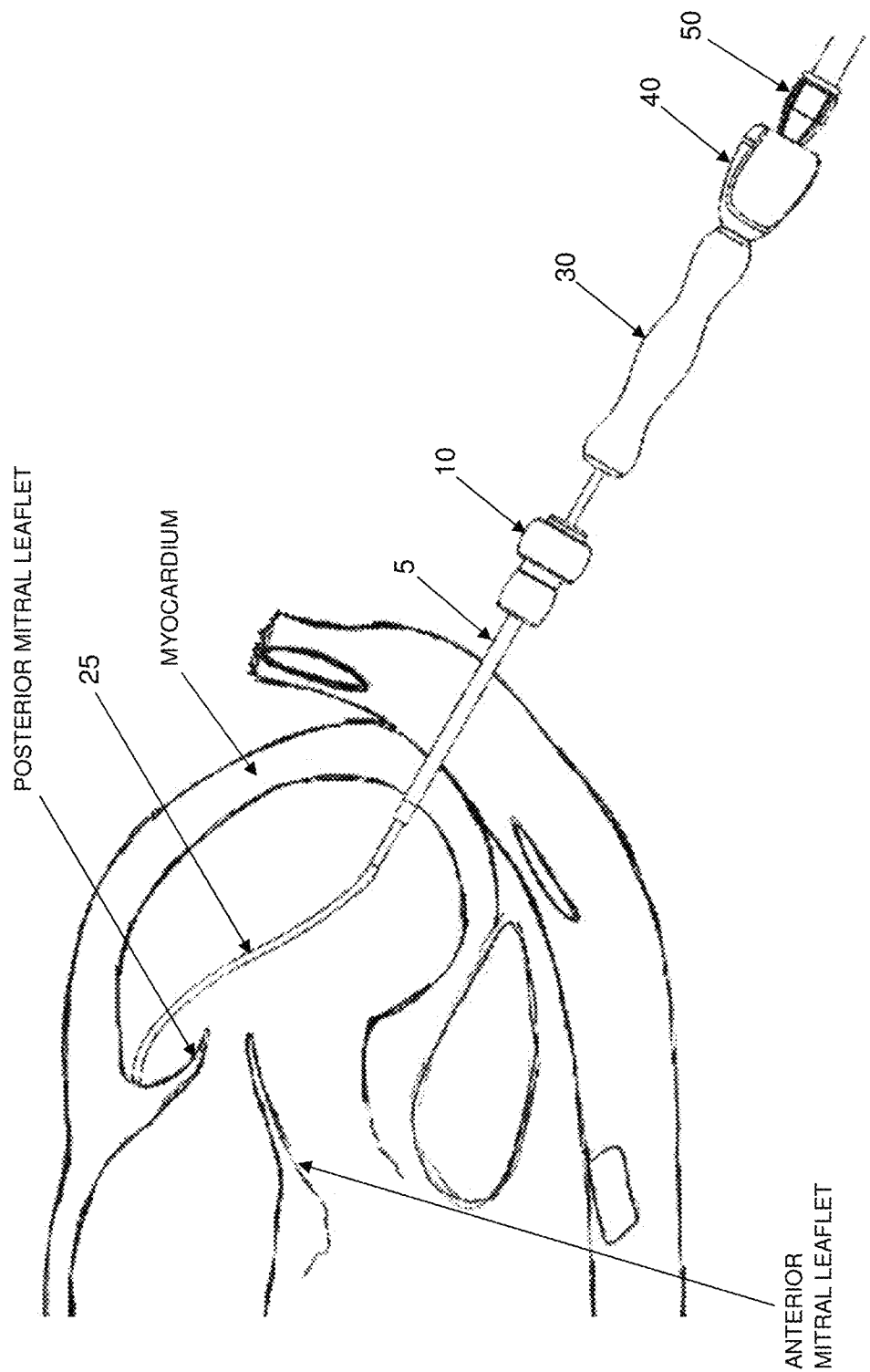
FIGS. 5-19 are schematic views showing establishment of the crossing guidewire using the aforementioned "cross and snare" approach.

FIG. 5 shows a TCT comprising a first positioning sheath 25 and its steering handle 30. First positioning sheath 25 is advanced through apical access sheath 5, through the left ventricle, and into contact with a desired location on the ventricular side of the mitral annulus (e.g., beneath the posterior ventricular side of the mitral annulus). First positioning sheath 25 is generally of low profile, typically 7 French or less. First positioning sheath 25 may include the option for either (i) passive re-shaping by the clinician by careful bending (e.g., in the manner often applied to interventional tools), or (ii) by active tip control (e.g., by providing a "steerable" positioning sheath).

Figure 6:
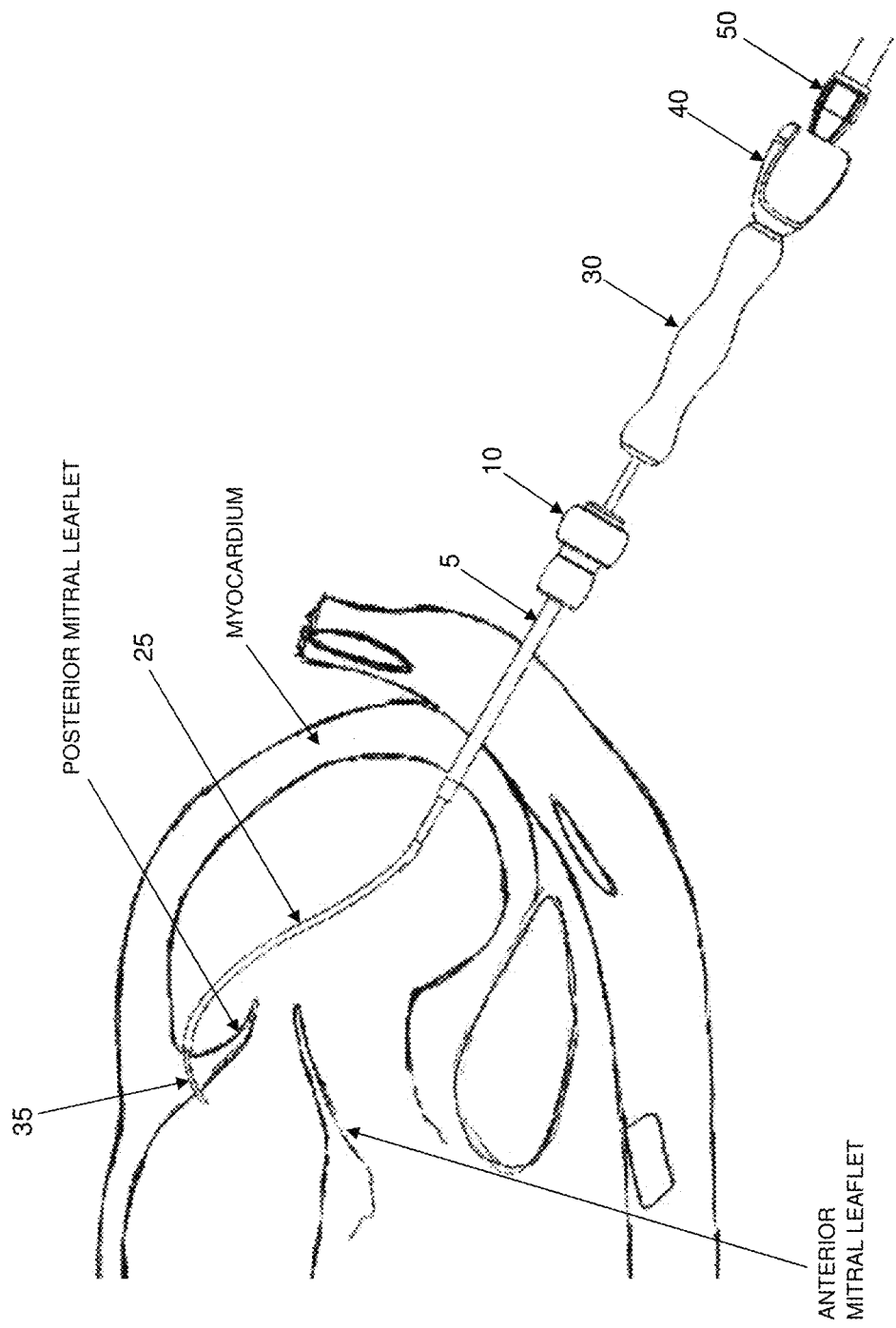

Looking now at FIG. 6, a first curved tube 35 is slidably disposed within first positioning sheath 25. First curved tube 35 includes a handle 40. First curved tube 35 is preferably between about 19 gauge and 23 gauge, and is also pre-shaped in a curvilinear fashion so as to allow it to pass through the annulus and arc towards the central open area of the left atrium. First curved tube 35 may either be sharp, and thus passed through the annular tissue under direct pressure, or it may be smooth-tipped and serve to guide an internally-positioned RF puncture wire (either custom-made or commercially available). If first curved tube 35 is fitted with an internally-positioned RF puncture wire, such wire may be activated with RF energy and advanced through the annulus. First curved tube 35 can then be advanced so as to track along the internally-positioned RF puncture wire in a standard manner while dilating the tissue to achieve passage. Such a configuration has the advantage of stretching the tissue around the internally-positioned RF puncture wire as the first curved tube 35 advances, and thus can be expected to leave a smaller hole upon removal. The advancement of first curved tube 35 and the internally-positioned RF puncture wire may be done simultaneously or, alternatively, the internally-positioned RF puncture wire can be advanced independently of first curved tube 35.

As can be appreciated from the figures, curving first curved tube 35 in the range of a radius of curvature of about 6-20 mm will provide for a crossing path that curves through the fibrous annulus from the left ventricle side into the left atrium while minimizing the possibility of first curved tube 35 puncturing the left atrium. See FIG. 6. The curvature can be readily observed and oriented using fluoroscopy, echocardiography, and pre-planning CT images. First curved tube may be made of Nitinol or other superelastic material, a coiled or braided construction, or a solid hypotube of stainless steel or other similar material with a pattern of openings for flexibility such as holes, slits, or other patterns, to facilitate the retention of a desired, pre-curved shape as first curved tube 35 is advanced out of first positioning sheath 25. Similarly, a curved internally-positioned RF puncture wire fitted to first curved tube 35 may also be fabricated from Nitinol or other superelastic material.

Figure 7:
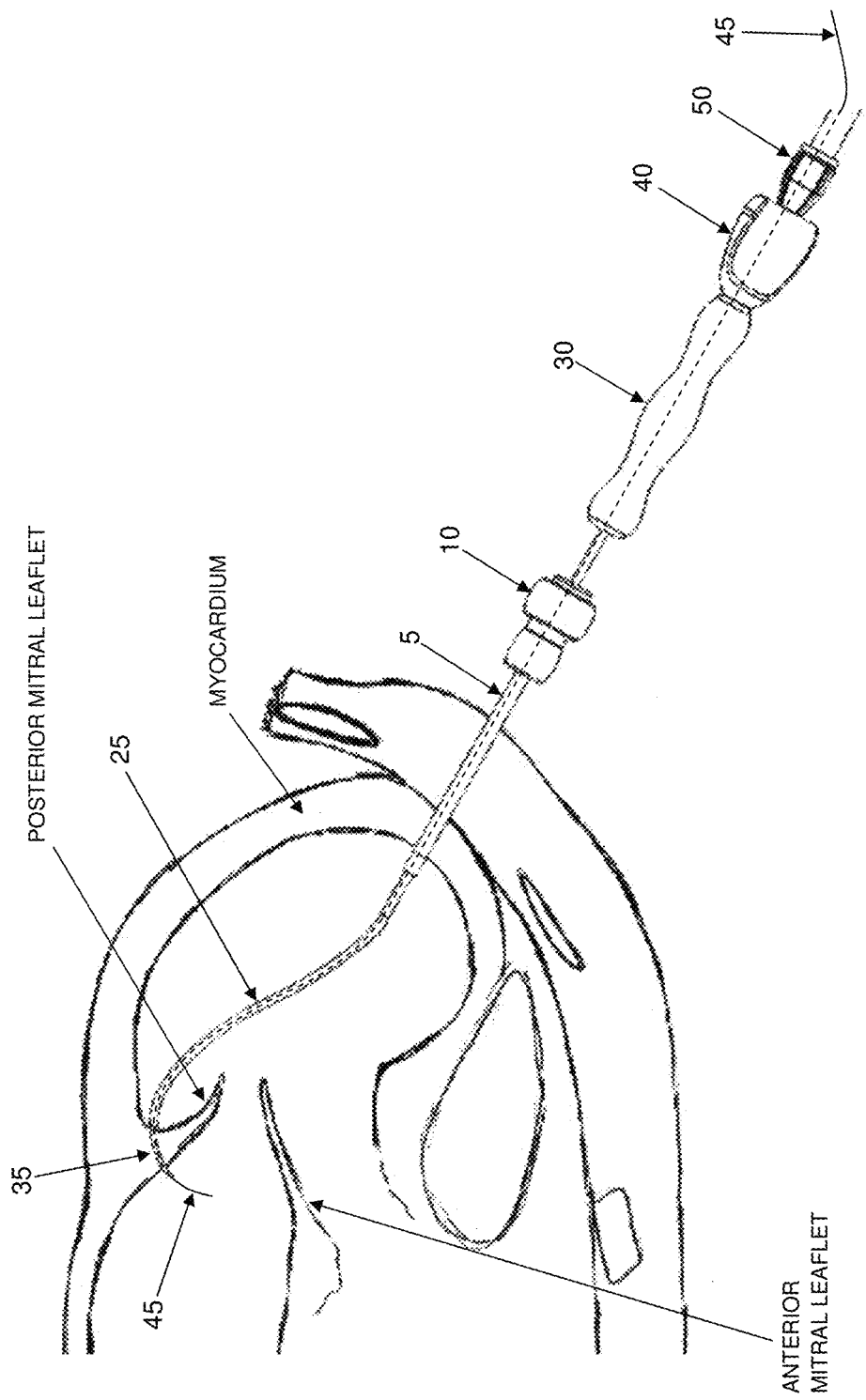

First curved tube 35 includes a guidewire lumen within the tube, which may first carry the aforementioned internally-positioned RF puncture wire, and later carries a first guidewire 45 (see FIG. 7), which may be either a conventional guidewire or a custom-curved guidewire. The lumen in first curved tube 35 is preferably sized to allow passage of conventional coronary guidewires, such as guidewires having diameters of 0.014 inch, 0.025 inch or 0.035 inch.

In accordance with the present invention, first positioning sheath 25 is positioned so as to contact the annulus in the desired location on the left ventricle side of the posterior annulus, and oriented so as to point into the left atrium. The targeting and shaping of first positioning sheath 25 can be readily appreciated with reference to FIG. 5. The orientation of first positioning sheath 25 is facilitated by the orientation of steering handle 30 and also referenced to real-time echocardiography and fluoroscopy, as well as referenced to previously-recorded computed tomography data. The shape of first positioning sheath 25, and the single, low-profile nature of its construction, allows the clinician to safely and controllably direct first positioning sheath 25 to any point beneath the mitral annulus and orient first positioning sheath 25 such that the crossing by first curved tube 35 will occur across the annulus approximately along the intended final line of travel of the spanning implant.

There are various possible approaches to effecting the controlled and safe crossing of first curved tube 35 into the left atrium, the principles of which are generally adapted from well-understood clinical techniques. The simplest approach is to use a sharpened or beveled edge on first curved tube 35, and pressure on the proximal end of handle 40 of first curved tube 35, to cross the annulus and enter the left atrium. In this particular setting, this approach has the disadvantage of causing the release of potential embolic debris, and being less controlled, inasmuch as more pressure might be required to penetrate the annulus and also raises the possibility of damaging surrounding anatomy if first curved tube 35 should plunge forward as it exits the far side of the annulus. Alternatively, first curved tube 35 may be provided with the aforementioned internally-positioned RF puncture wire so as to facilitate passage of first curved tube 35 through the mitral annulus.

In one preferred form of the invention, a crossing wire with preset shape is first advanced out of first positioning sheath 25, across the annulus, and into the left atrium with or without RF energy, and then first curved tube 35 is advanced over the crossing guidewire so as to position first curved tube 35 in the left atrium. Thus, in this form of the invention, the crossing wire essentially acts as a tracking wire for making a preliminary opening in the annulus and then providing a track to be followed by first curved tube 35 as first curved tube 35 is advanced through the annulus. The curved shape of the crossing wire is set so that the crossing wire preferentially emerges back into the left atrium with minimal risk of injury to adjacent structures, and also upon exit into the left atrium is directed generally towards the opposite side of the annulus in the direction of the planned spanning suture. Advancing a crossing wire through the annulus in advance of first curved tube 35 has the advantage that the crossing wire provides a preliminary opening in the annulus which is further dilated by passage of the following first curved tube 35. This sequential opening of the annulus can be less traumatic to the tissue. In addition, using a crossing wire to prepare a track for first curved tube 35 also has the benefit of crossing the annulus with a very small profile element, e.g., one that may be only 0.016" or 0.018". As a result, if the location of the annular cross is not as intended, the crossing wire may be withdrawn with minimal injury to the annulus, and the annular crossing may thereafter be redone, before passing the larger first curved tube 35 through the annulus. Where a crossing wire is used, the handle on the TCT is designed to limit the maximum advance of the crossing wire so as to minimize the possibility of injuring unintended anatomical structures, and also is preferentially fitted with a feature to indicate the rotational or "azimuth" orientation of the crossing wire curvature, conceptually similar to how a periscope is directed.

First curved tube 35 is advanced (either alone, or carrying an internally-positioned RF puncture wire, or over the aforementioned crossing wire) into the left atrium with operator-controlled pressure and forward motion. See FIG. 6. Handle 30 on first positioning sheath 25, and handle 40 on first curved tube 35, are presented and labeled so as to give the operator good indication of the orientation and degree of advancement of first curved tube 35 vis-à-vis first positioning sheath 25. Note that if first curved tube 35 is advanced carrying an internally-positioned RF puncture wire, or over the aforementioned crossing wire, the internally-positioned RF puncture wire or the crossing wire is removed from first curved tube 35 after first curved tube 35 has been advanced through the annulus, thus leaving a hollow conduit extending from the operative field to the left atrium.

After first curved tube 35 has been advanced through the mitral annulus, first guidewire 45 (controlled by a guidewire handle 50) is then advanced through first curved tube 35 and into the left atrium, to be positioned visibly and stably in the left atrium. See FIG. 7. If desired, first guidewire 45 may be a conventional guidewire or, alternatively, first guidewire 45 may be an RF guidewire, in which case the functions of the aforementioned internally-positioned RF puncture wire and first guidewire 45 may be combined. In other words, where first guidewire 45 is an RF guidewire, first guidewire 45 may first be used as the internally-positioned RF puncture wire to facilitate passing first curved tube 35 through the mitral annulus, and thereafter used for establishing the crossing guidewire, as will hereinafter be discussed. A preferred embodiment for a custom "guidewire" is to use a construction based on suture such as braided polyester suture or other braided, porous, or solid material. An atraumatic tapered tip can be formed from the suture or other material by preferential removal of material. The length of the suture can then be modified in stiffness (i.e., to give it adequate column strength for longitudinal advancement) and visual markers may be added, e.g., with layers such as heat-shrink polymers. Such a construction can have the beneficial property of being visible on echocardiography.

Figure 8:
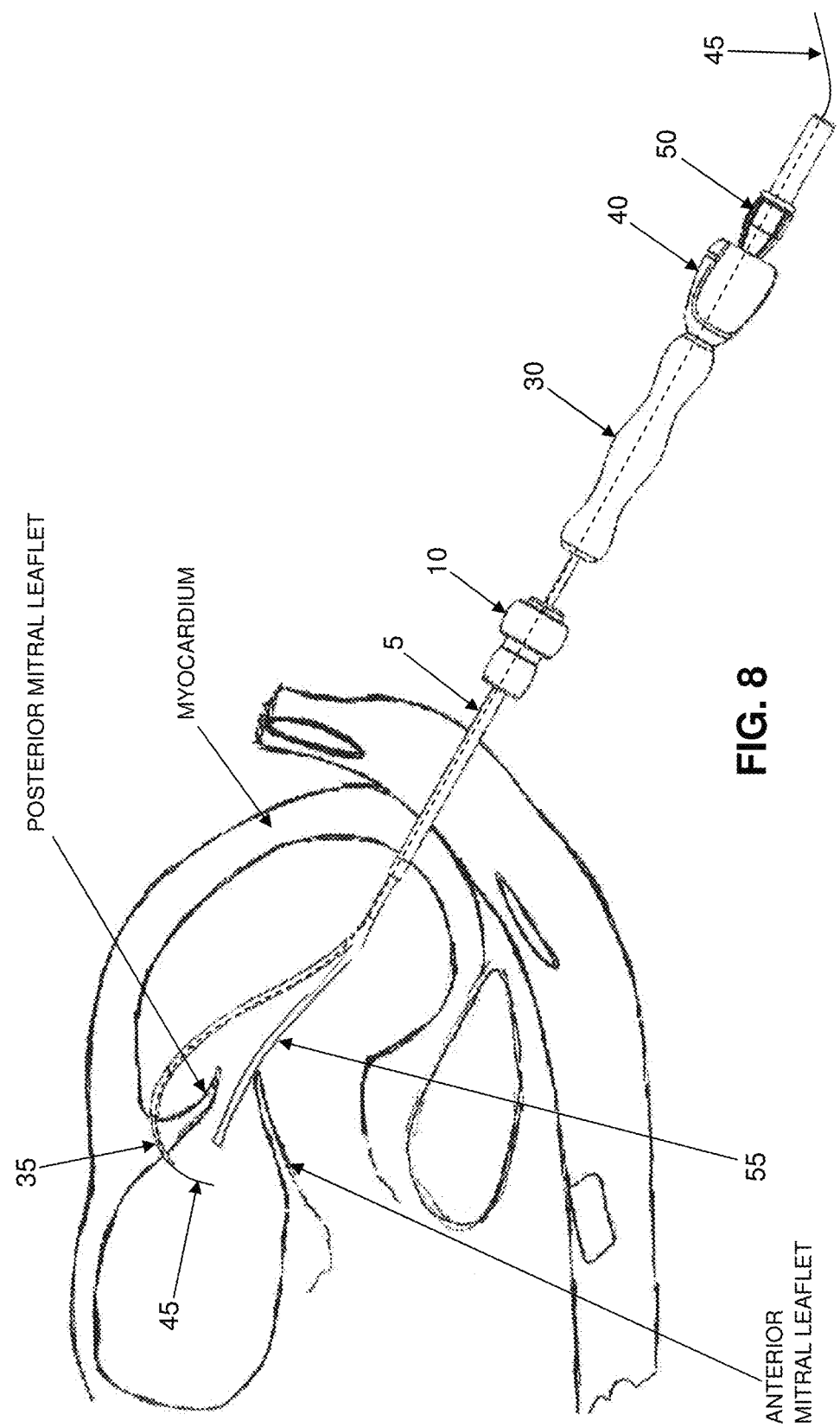
Figure 9:
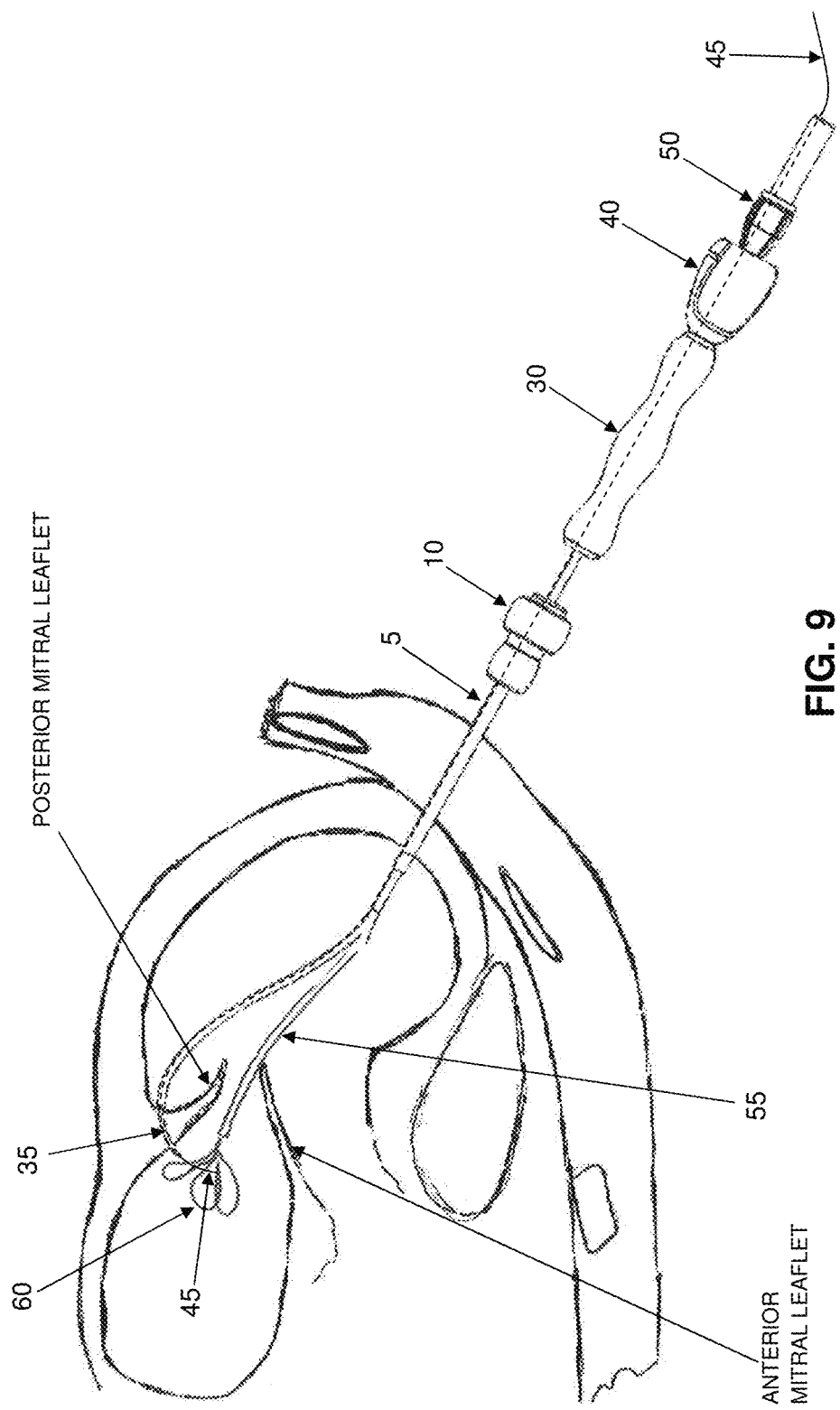

In one preferred form of the invention, and looking now at FIG. 8, a center sheath 55 is advanced through apical access sheath 5, between the mitral valve leaflets and into the left atrium. Then a snare 60 (e.g., a conventional, low-profile interventional snare) is advanced through center sheath 55 and into the left atrium so that it sits in alignment with first guidewire 45. See FIG. 9. Such coronary snares are well-known in the art of interventional cardiology. Where apical access sheath 5 includes a side port access sheath 15, snare 60 may be introduced into apical access sheath 5 by advancing the snare through side port access sheath of apical access sheath 5.

In one preferred form of the invention, snare 60 comprises a conventional, low-profile interventional snare tool of the sort well known in the art of interventional cardiology. In another preferred form of the invention, novel snare 60 may comprise a tool with unique features suitable for the described procedure, and can be constructed in various forms from suture material or other braided/coiled material. By way of example but not limitation, and looking now at FIG. 42, in one preferred embodiment, snare 60 comprises a loop 65 of suture or other material with a flexible distal section 70 and a more rigid proximal section 75. When the loop 65 of suture is advanced from a hypotube or sheath 80, the flexible distal section 70 of loop 65 bends away from the axis of the hypotube or sheath 80 while the more rigid proximal section section 75 of loop 65 tends to remain aligned with the axis of the hypotube or sheath 80. This causes the loop 65 to form a preferential "D" shape that has the benefit of possessing this shape at small and large formed loops and forming a loop that is at least partially eccentric about the axis of the snare tool that may be steered to better align the loop with snaring targets located off of the axis of the loop. The "D" loop can be enlarged in a continuous fashion across a practical size range to best fit the target anatomy and, when rotated, reach to the edges of the atrial anatomy and thus more readily effect cross-suture capture. The suture loop 65 could also be generally circular or oval in shape, or comprise multiple loops in a "tulip" configuration (see FIG. 9), again to better effect suture capture. It should be further noted that constructing the snare loop from a base material of braided suture results in a device with beneficial features of being atraumatic to the adjacent atrial structures, readily visible when viewed via echocardiographic means, and resistant to kinking and damage due to the braided construction of the suture.

Figure 10:
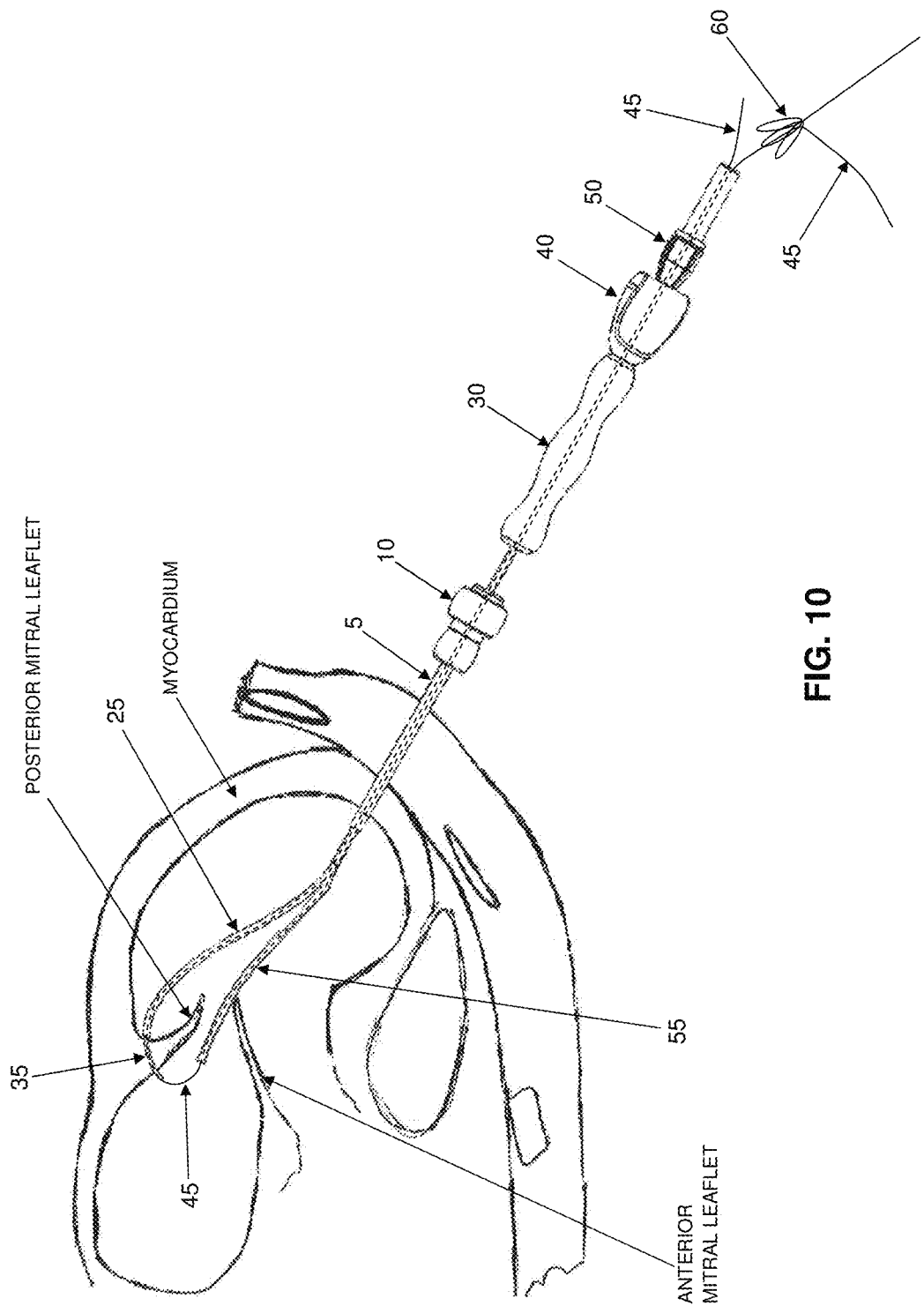
Figure 11:
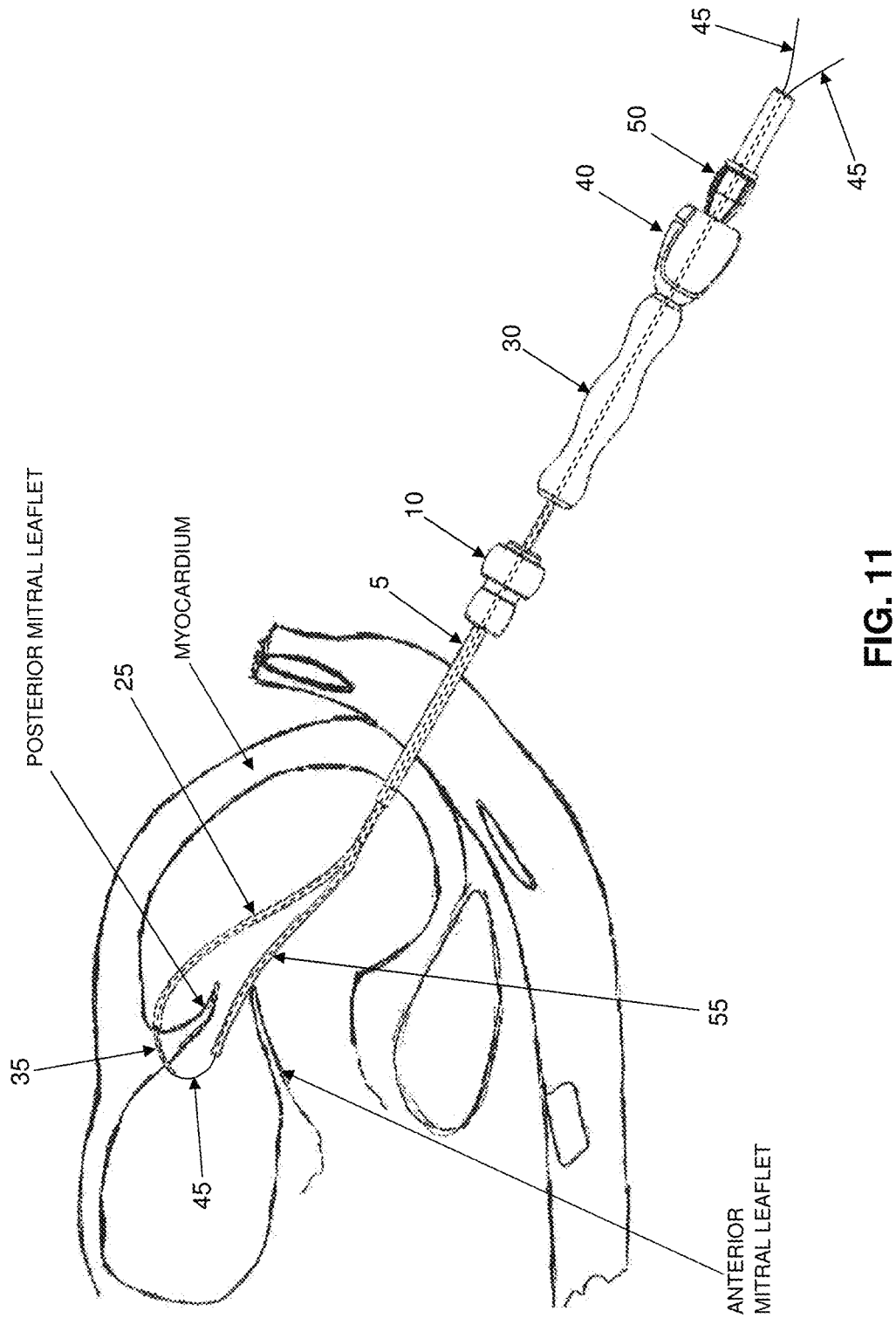

Snare 60 is advanced through center sheath 55 and used to capture first guidewire 45. See FIG. 9. Snare 60 is then fully retracted back through center sheath 55 and apical access sheath 5 until the distal end of first guidewire 45 is drawn through apical access sheath 5 and out into the operative sterile field. See FIG. 10. This leaves the first guidewire extending from the apex, across the left ventricle, through one side of the annulus, into the left atrium, into the center sheath, between the mitral leaflets and then back across the left ventricle. See FIG. 11.

Figure 12:
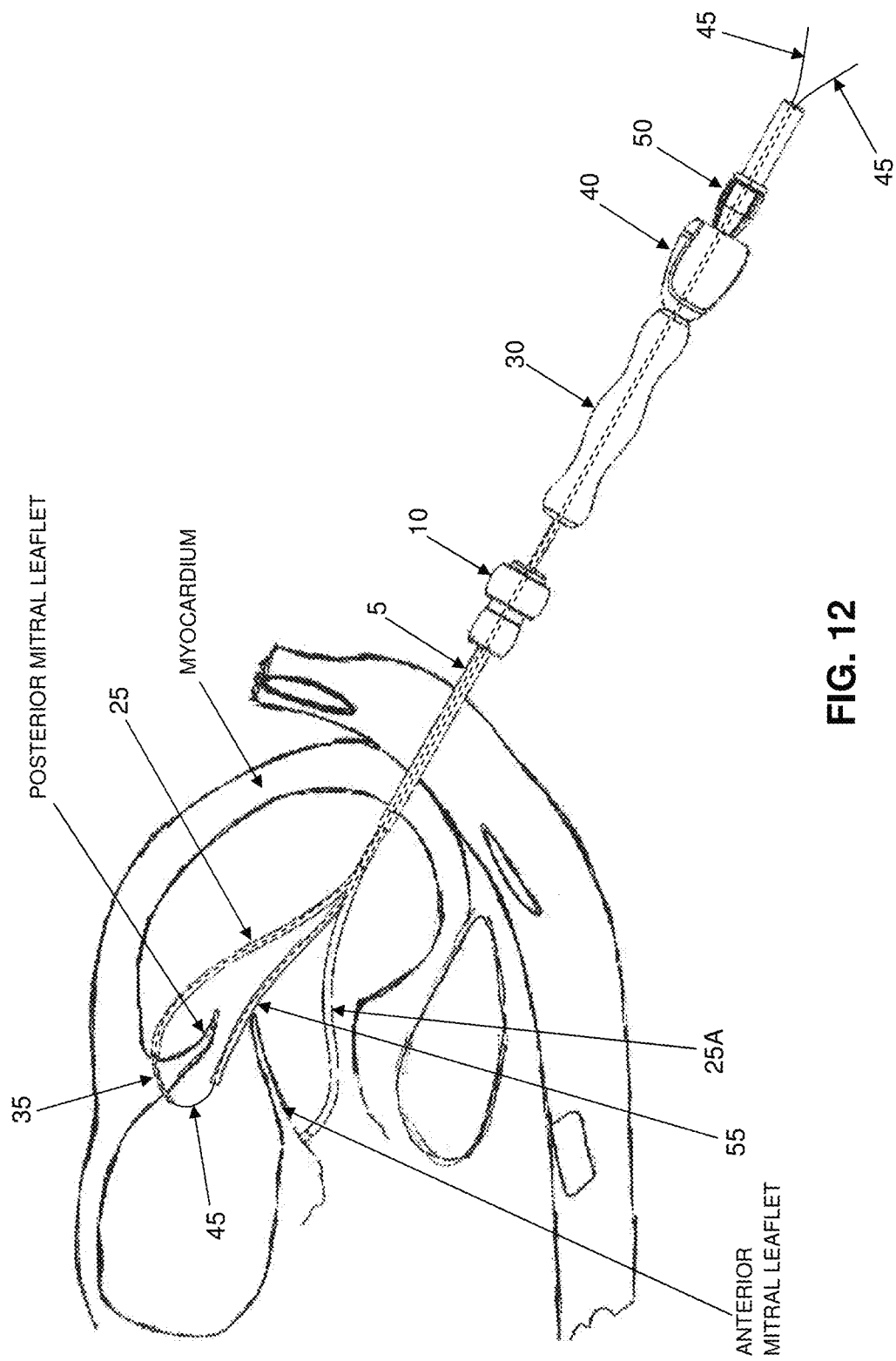
Figure 13:
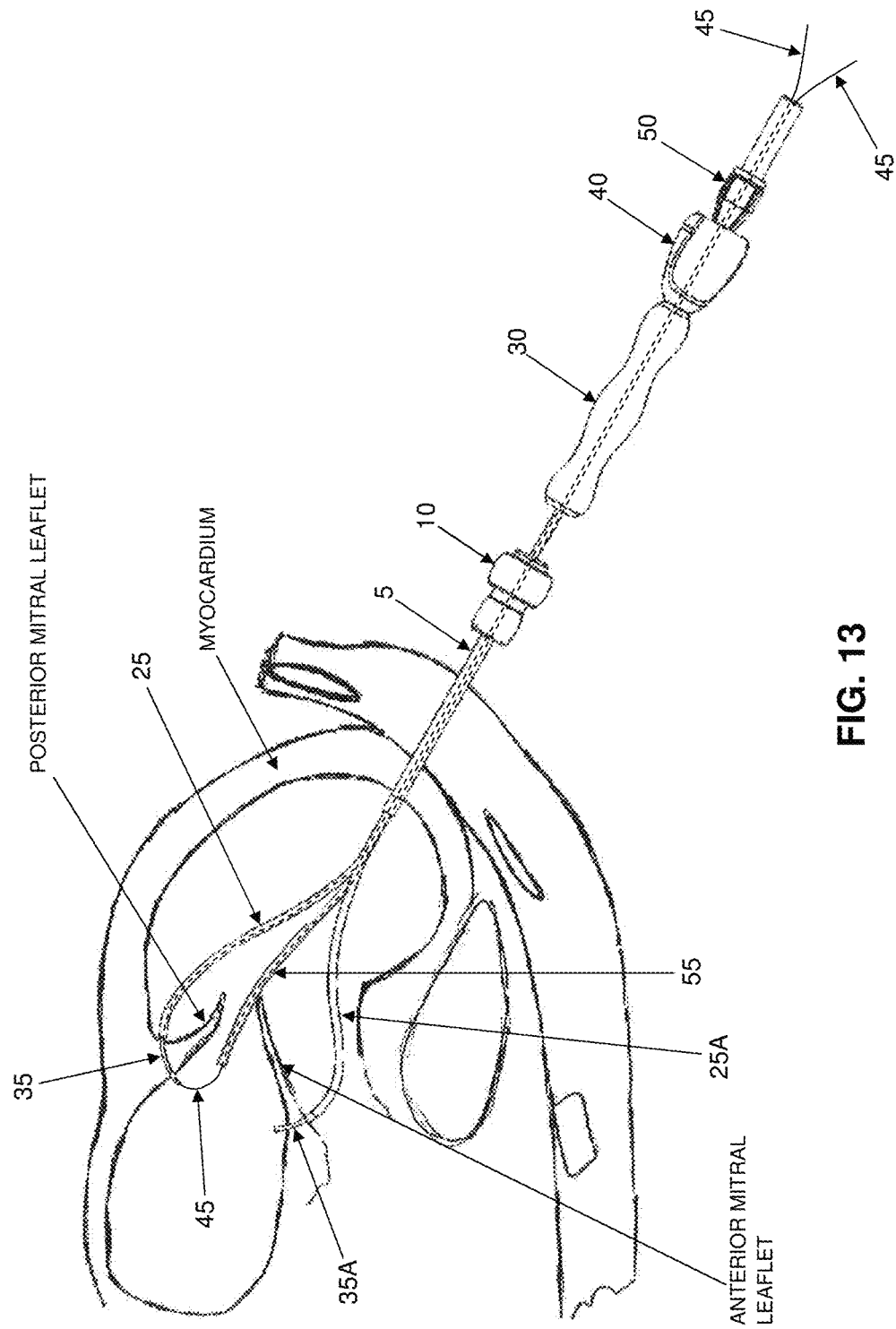
Figure 14:
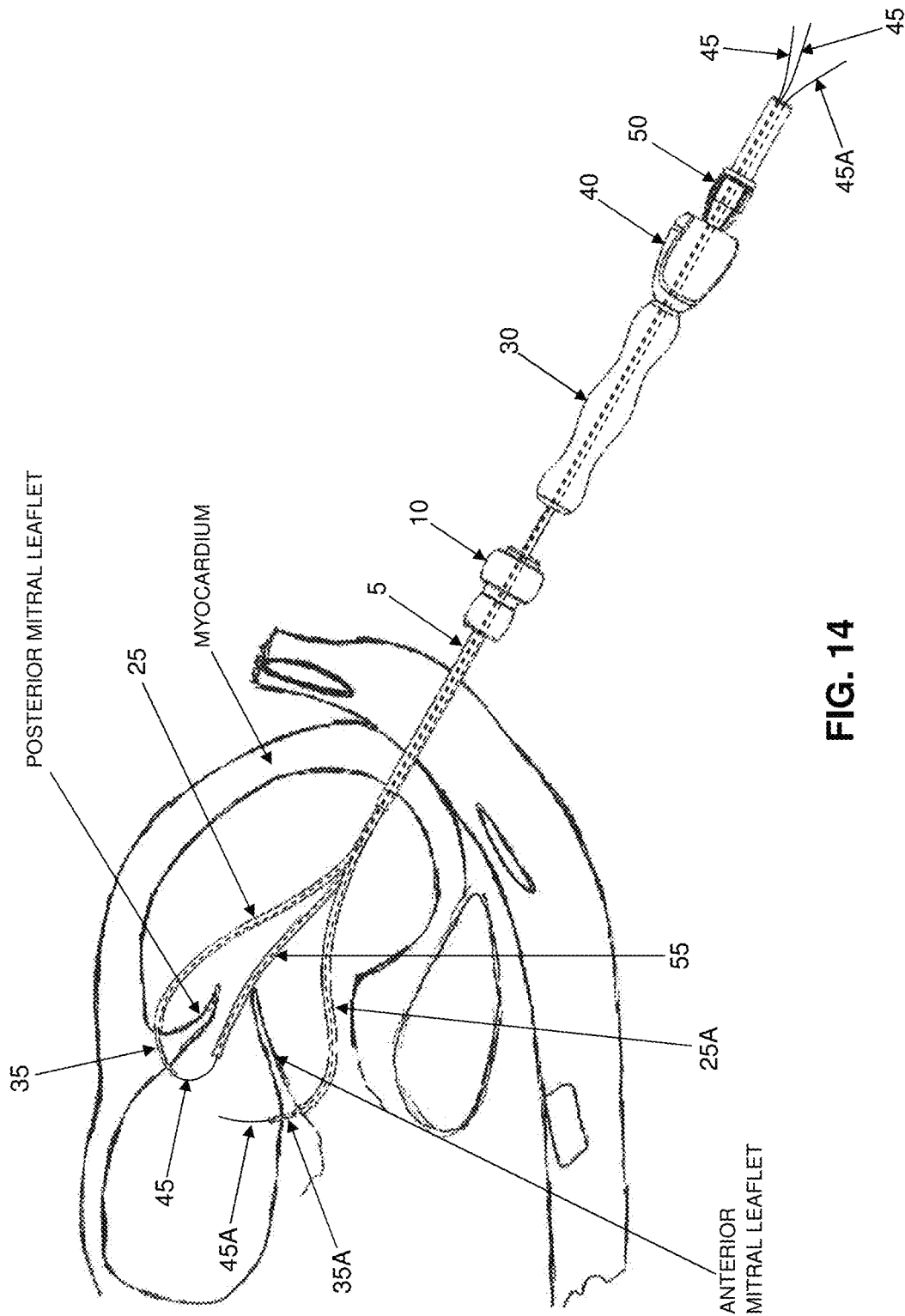

Next, and looking now at FIGS. 12-14, a second TCT, comprising a second positioning sheath 25A, is used to place a second curved tube 35A and a second guidewire 45A through the opposite (i.e., anterior) side of the annulus, using a technique identical to that used to pass first guidewire 45A through the posterior side of the annulus.

Figure 15:
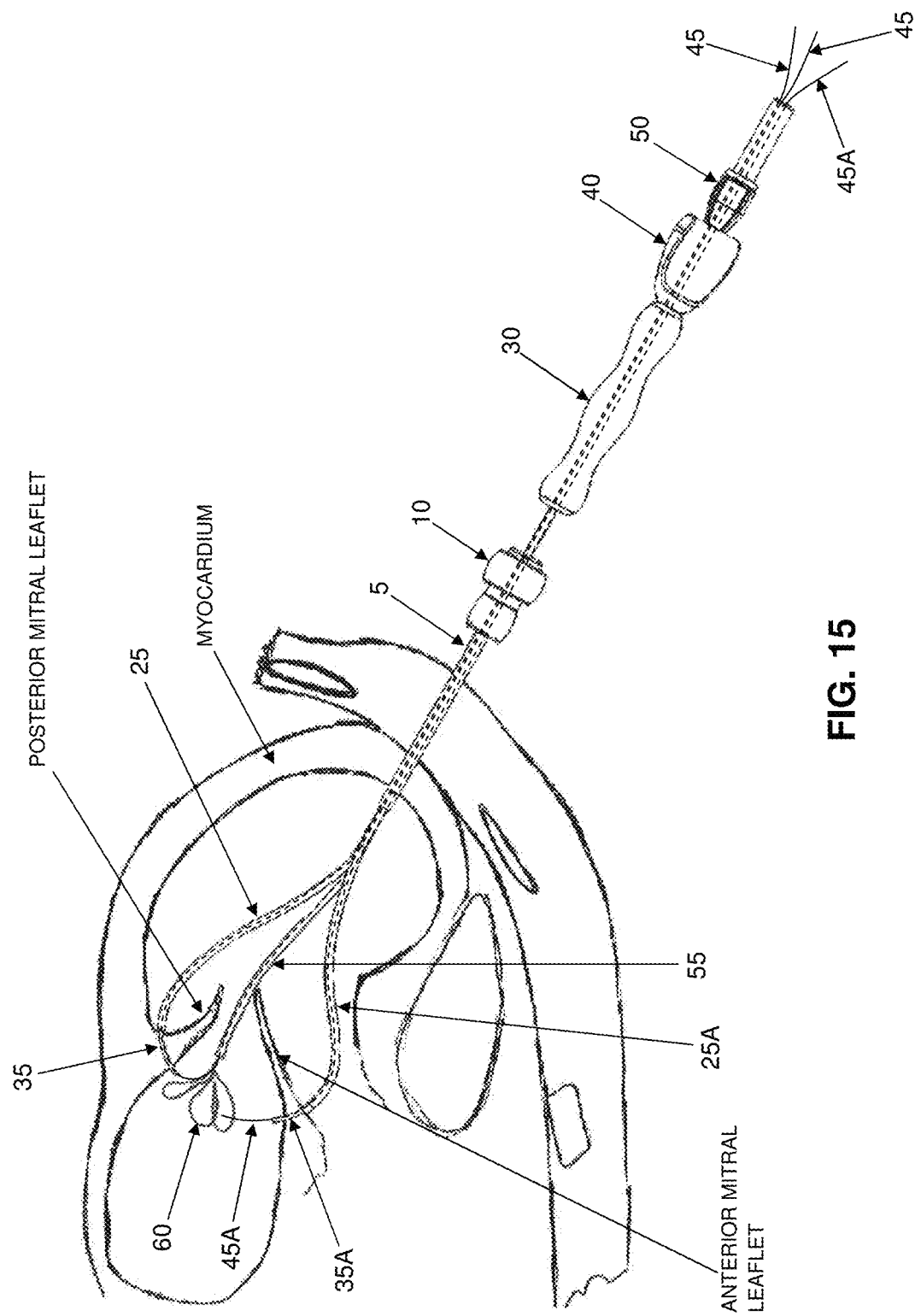
Figure 16:
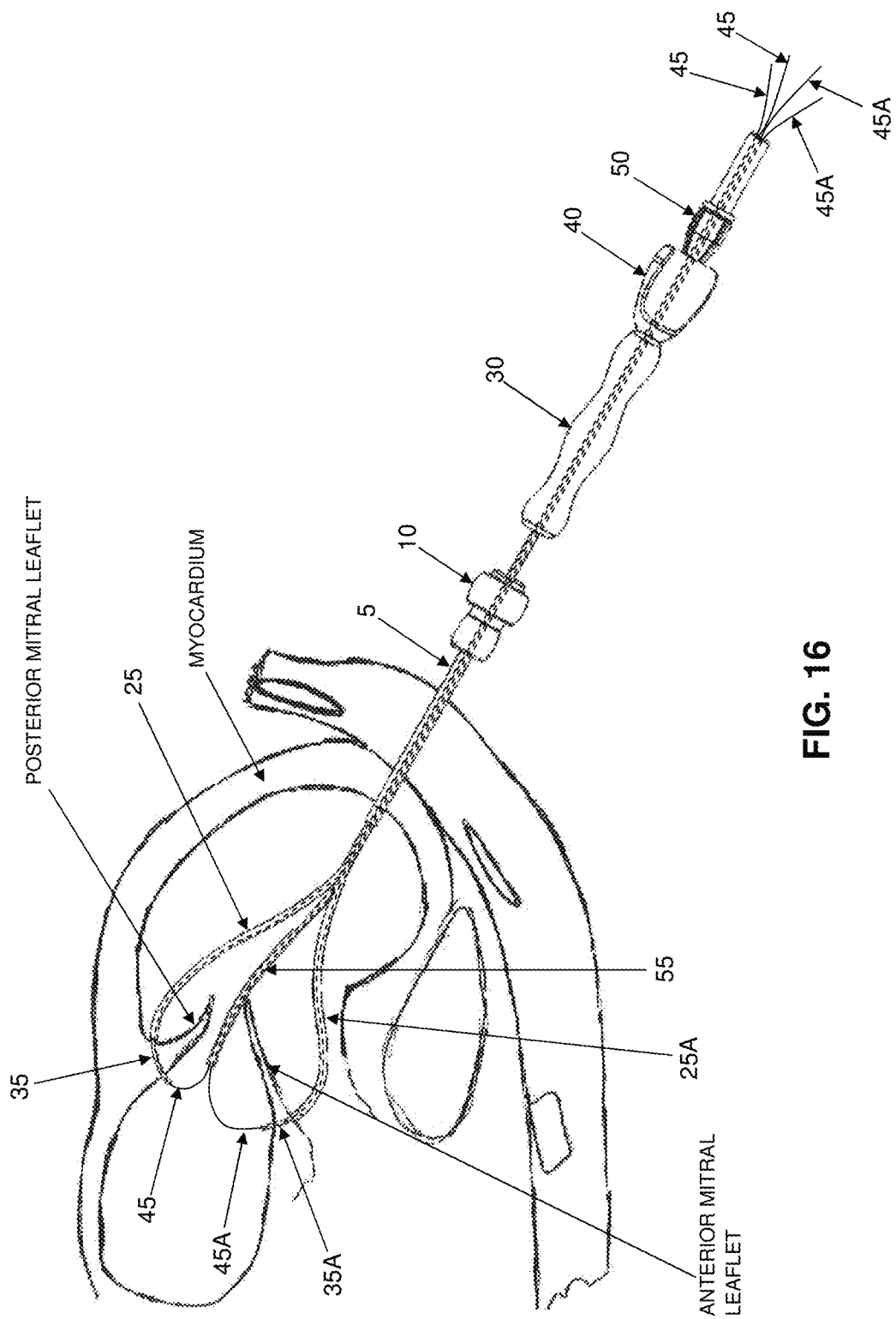

Once second curved tube 35A and second guidewire 45A are positioned through the second (i.e., anterior) side of the mitral annulus, snare 60 is advanced back down apical access sheath 5 and center sheath 55 while first guidewire 45 remains in the lumen of center sheath 55. See FIG. 15. Snare 60 is then used to capture second guidewire 45A and snare 60, carrying the captured second guidewire 45A with it, is fully retracted down center sheath 55 and apical access sheath 5, causing the distal end of second guidewire 45A to be drawn through apical access sheath 5 and out into the operative sterile field. See FIG. 16.

Figure 17:
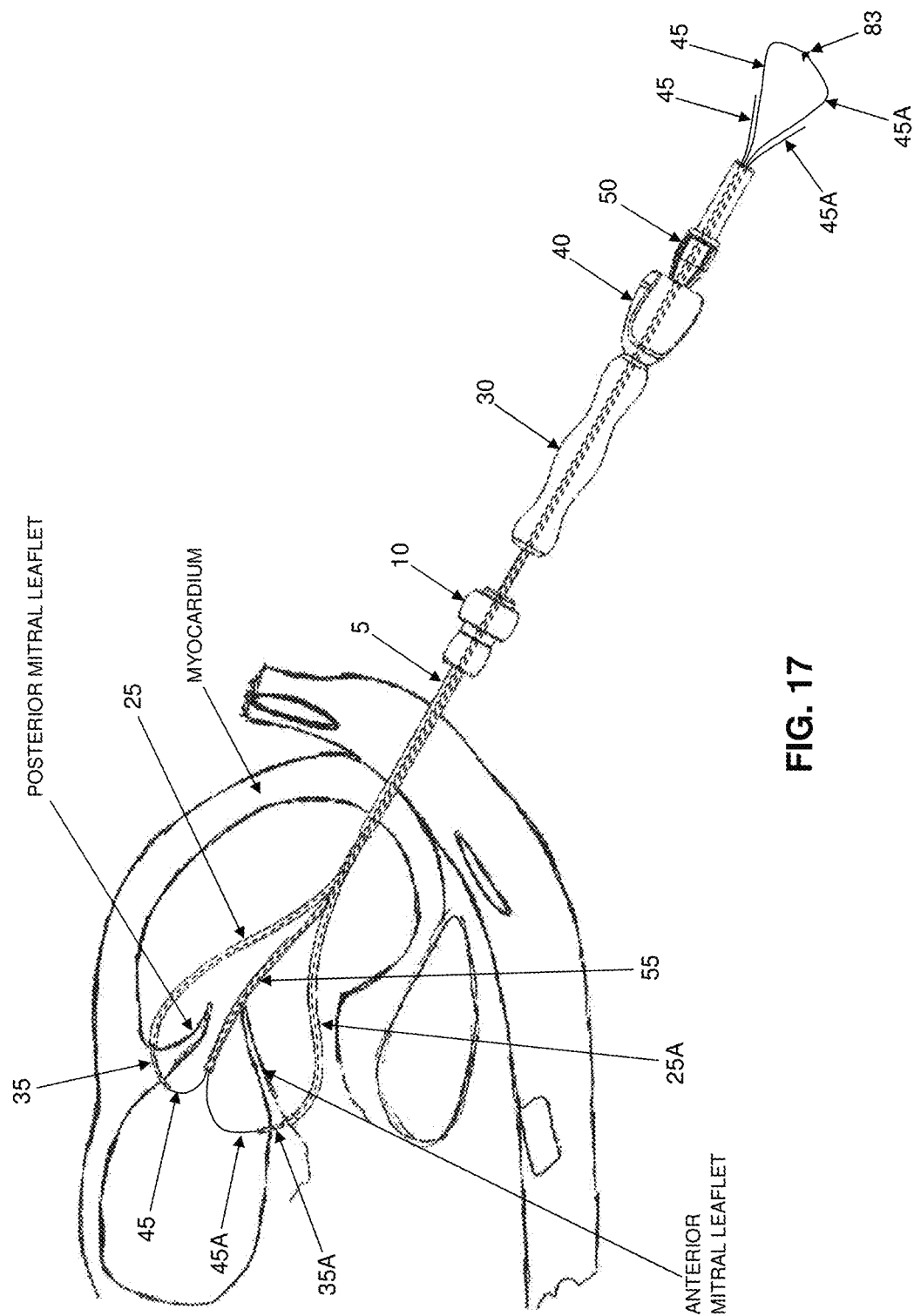

The distal tips of the two guidewires 45, 45A are then joined, or "docked", in the operative sterile field, e.g., at a connection 83. See FIG. 17.

Figure 18:
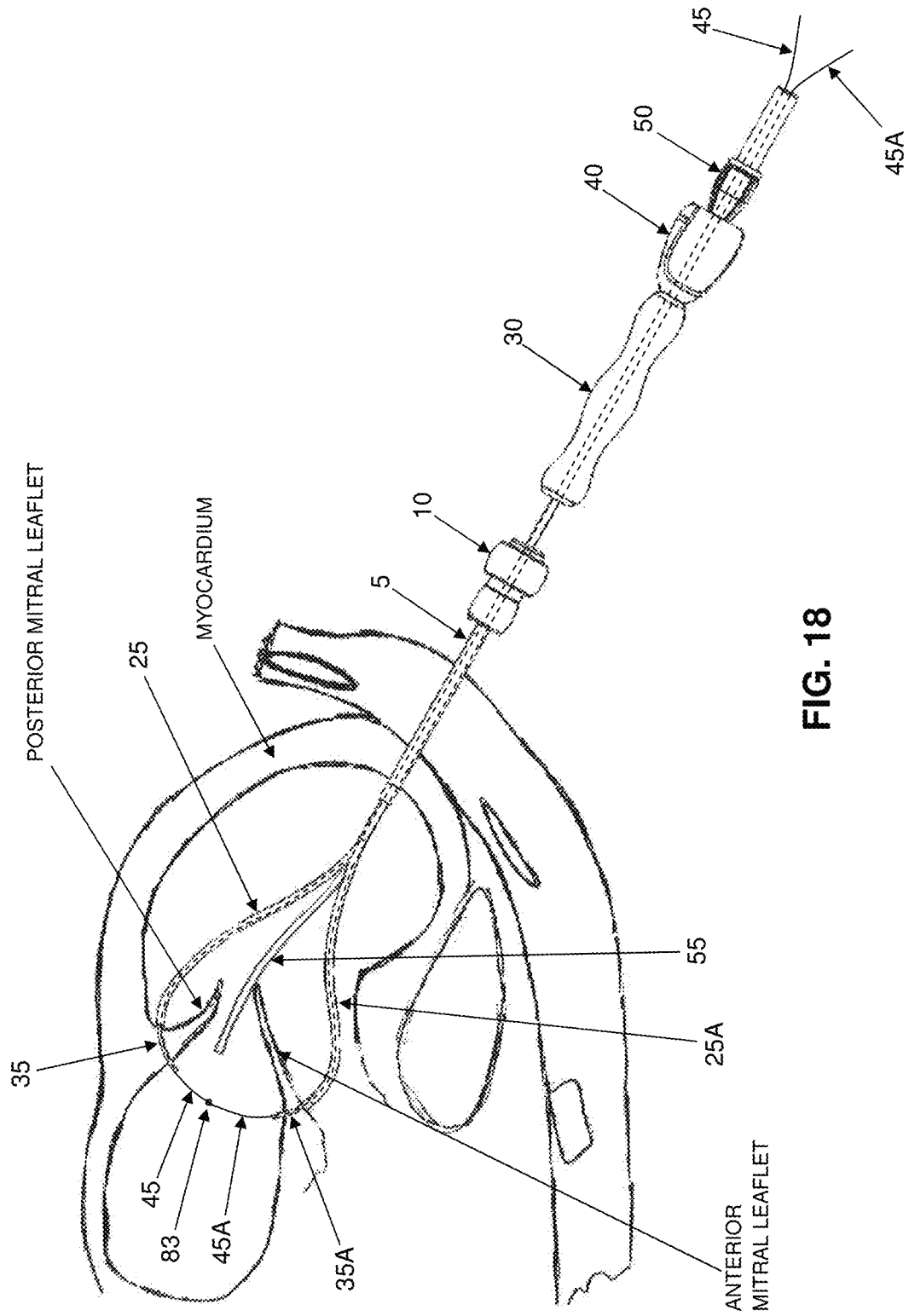

Thereafter, the joined distal ends of guidewires 45, 45A are drawn back through apical access sheath 5 and center sheath 55, crossing the left ventricle, so that the joined distal ends of guidewires 45, 45A are located in the left atrium. See FIG. 18.

Figure 19:
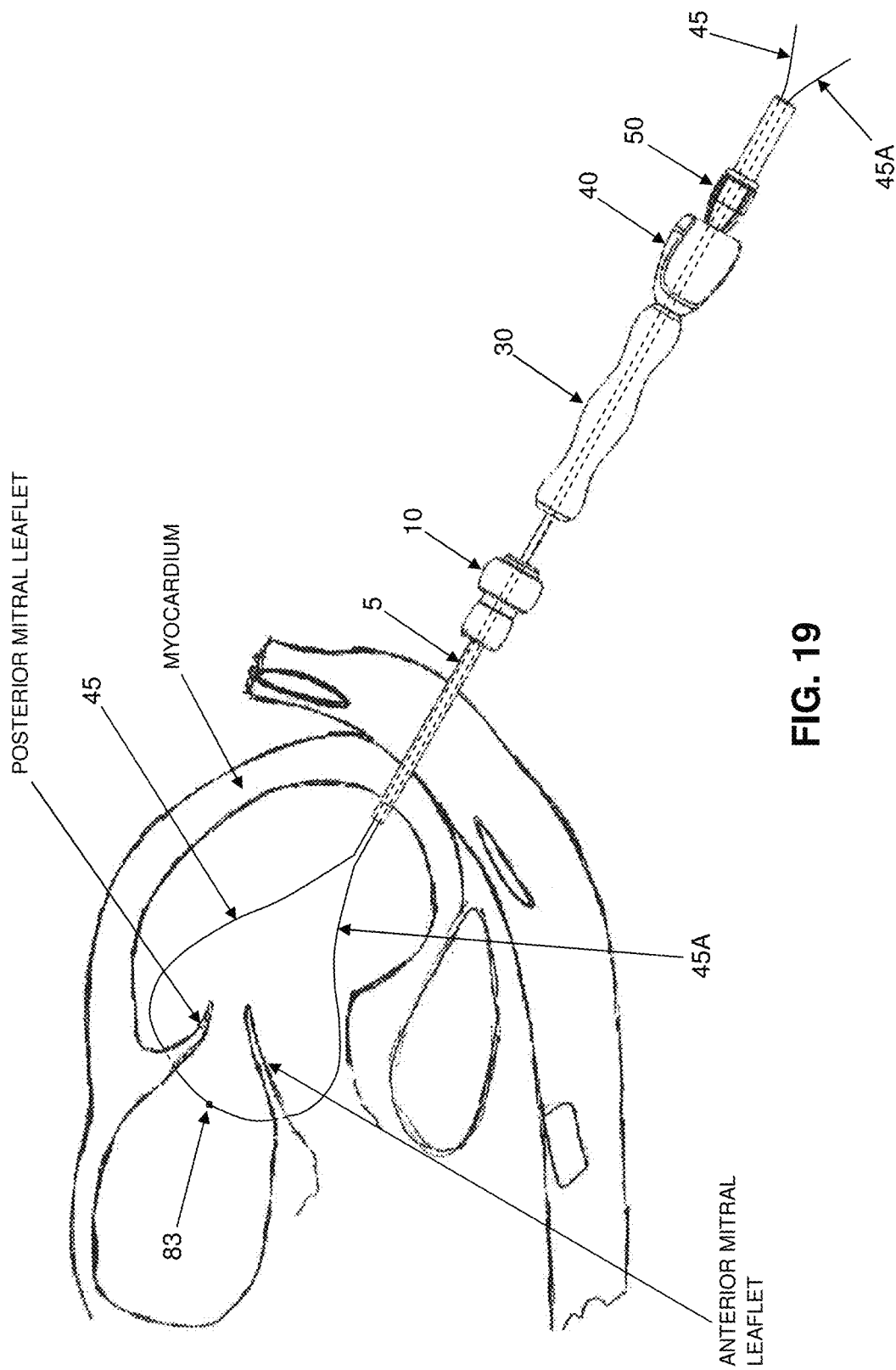
Figure 20:
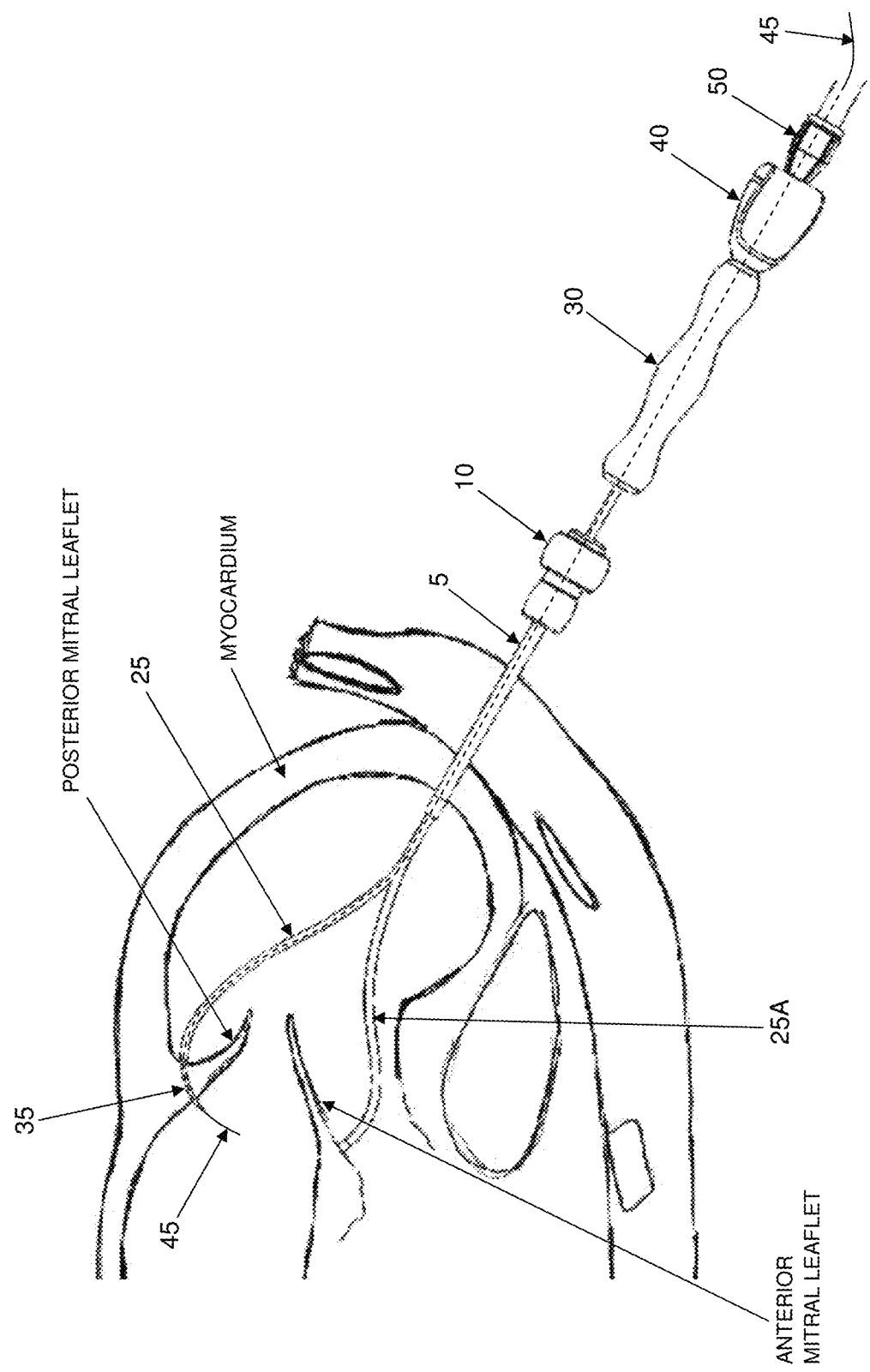
FIGS. 20-26 are schematic views showing selected steps in the establishment of the crossing guidewire using the aforementioned "cross and catch" approach.

At this point, first positioning sheath 25 (and its annulus crossing first curved tube 35), second positioning sheath 25A (and its annulus crossing second curved tube 35A), and center sheath 55 may all be removed from the operative site, if they have not already been removed. See FIG. 19.

As a result of the foregoing, a continuous guidewire path (i.e., a "crossing guidewire") is established, traveling from the left ventricle, through the posterior annulus, across the left atrium, back through the anterior annulus, and then out through the left ventricle, with the continuous guidewire path extending out to the operative sterile field through apical access sheath 5.

3. Establishing the Crossing Guidewire by the "Cross and Catch" Approach

An alternative approach for establishing the crossing guidewire across the mitral annulus (and hence establishing a desired suture path across the mitral annulus) is sometimes hereinafter referred to as the "cross and catch" approach. With this alternative approach, the same operative objective (i.e., the establishment of the crossing guidewire) is achieved using a different combination of steps and apparatus, in particular using a first "target and cross tool", sometimes hereinafter referred to as TCT1, and a second "target and cross tool", sometimes hereinafter referred to as TCT2, as described below.

Preferably TCT1 and TCT2 have a shape which allows them to be directed into a desired position on the ventricular side of the mitral annulus by a direct approach and without requiring significant lateral movement, since such lateral movement can be problematic given the presence of the chordae tendineae on the ventricular side of the mitral valve. Furthermore, the TCT1 and TCT2 preferably have a shape which allows them to advance to, and directly engage, the ventricular side of the mitral annulus without requiring the deformation or displacement of any intervening cardiac anatomy (e.g., the papillary muscles, chordae tendineae, etc.) as the TCTs are advancing to, and engaging, the annulus "crossing" site. Significantly, by providing a method and means which allows the annulus "crossing" site to be accessed without requiring the deformation or displacement of any intervening cardiac anatomy, subsequent steps in the annulus reconfiguration may also be performed without requiring any intervening cardiac anatomy to be deformed or displaced. By the methods described herein, once a crossing location has been reached, the TCT tools do not need to be moved laterally within the ventricle, risking entanglement or interference with chordae or other structures. And subsequent steps in the procedure follow the suture path back to the same crossing location, again without requiring lateral motion and the risk of entanglement by either the delivery tools or the deployed implant. This combination of devices and method is a significant advance in the art.

TCT1 is reinforced for pushability and proximally shapeable, and preferably comprises at least the following two elements, as follows:
 (i) TCT 1 comprises a low-profile, approximately 6 French first positioning sheath 25 (see FIG. 5) having a through lumen and a steering handle 30. First positioning sheath 25 is sufficiently stiff to allow stable placement of the distal tip of first positioning sheath 25 against target locations on the mitral annulus. First positioning sheath 25 may be shaped in various ways to best match the target anatomy, either as supplied or as modified in the field by the clinician.
 (ii) TCT1 also comprises a first curved tube 35 (see FIG. 6), approximately 19-23 gauge in diameter, with handle 40, which is fitted in the lumen of first positioning sheath 25. First curved tube 35 is typically fitted with either a sharpened piercing tip or a smooth tip intended to be used in conjunction with an RF puncture wire of the type discussed above.

In one preferred form of the invention, TCT1 may also comprise a steering tube (not shown) which may be disposed within first curved tube 35 and receive first guidewire 45. This steering tube may be provided to allow the clinician to further control the direction of first guidewire 45 as it passes into the left atrium. The steering tube may be fabricated from Nitinol or another highly elastic material. The steering tube is preferably curved at least as tightly as the distal aspect of first curved tube 35, and is independently rotatable relative to first curved tube 35, so as to provide for more precise manipulation of guidewire 45 (see FIG. 7) into a funnel-shaped snare of TCT2, as will be described below.

Figure 22:
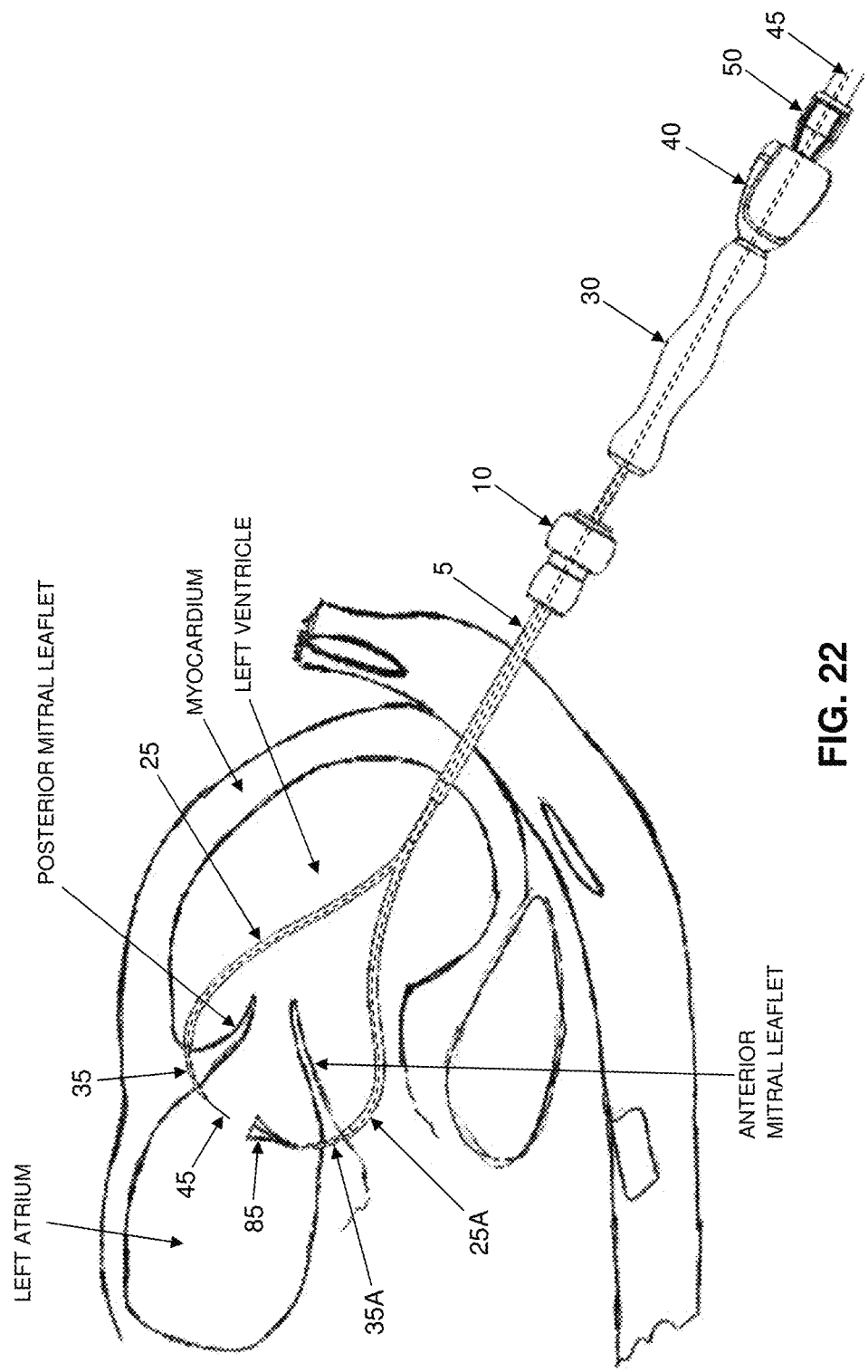
Figure 23:
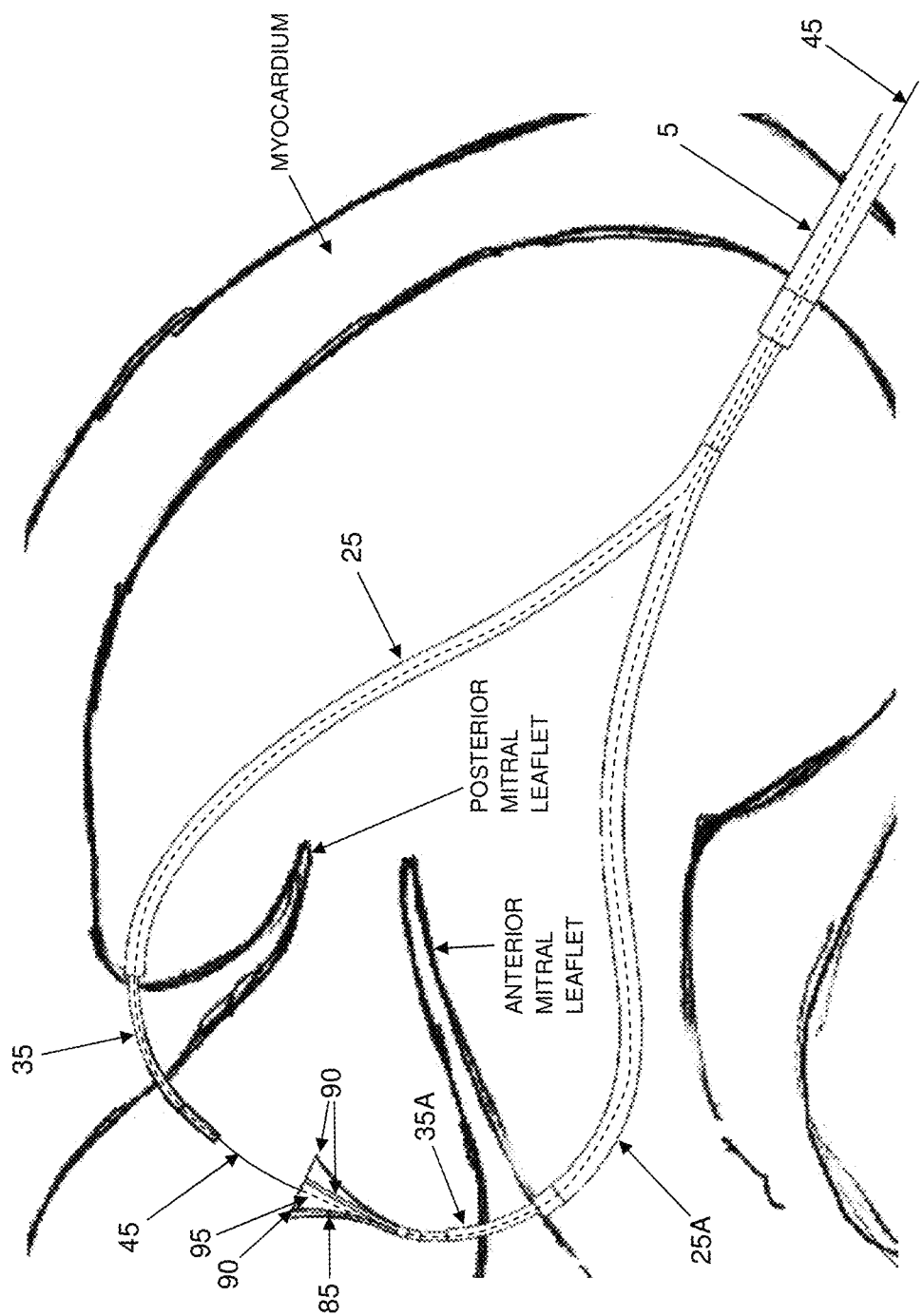

TCT2 is reinforced for pushability and proximally shapeable and steerable. TCT2 preferably comprises three main elements, as follows:
 (i) TCT2 comprises a low-profile, approximately 6 French or approximately 7 French second positioning sheath 25A (see FIG. 20) having a through lumen and a steering handle similar to the aforementioned steering handle of first positioning sheath 25. Second positioning sheath 25A of TCT2 is shaped as shown in FIGS. 20-25 so that it can be readily directed within the left ventricle to positions on the ventricular side of the mitral annulus.
 (ii) TCT2 also comprises a second curved tube 35A (see FIGS. 21-25) of approximately 19 gauge or approximately 20 gauge, with a steering handle similar to the aforementioned steering handle 40 of first curved tube 35. Second curved tube 35A is slidably disposed in the lumen of second positioning sheath 25A and can be controllably advanced through the annular tissue under the control of its steering handle 40.
 (iii) TCT2 also comprises a funnel-shaped snare 85 (FIGS. 22-24) of approximately 0.035 inch outer diameter in a collapsed, undeployed state and fitted within the lumen of second curved tube 35A. Funnel-shaped snare 85 passively collapses when travelling through the 0.035 inch lumen of second curved tube 35A and then, when advanced into the left atrium, passively expands into an outwardly directed funnel as shown in FIGS. 22 and 23. In one preferred embodiment, the funnel-shaped snare is fabricated from elastic stiffening ribs 90 such as might be fabricated from Nitinol or another highly elastic material, and an elastomer web 95 which fills out the spaces between stiffening ribs 90 of funnel-shaped snare 85.

To effect the "cross and catch" approach, TCT1 is positioned so as to contact one side of the annulus in a desired location and oriented so as to point into, and across, the left atrium as described previously and shown in the figures. More particularly, as seen in FIGS. 5 and 6, first positioning sheath 25 is advanced against the ventricular side of the posterior annulus, and then first curved tube 35 is advanced (with RF assistance if necessary, or with the aforementioned crossing wire) into the left atrium so that the outlet of first curved tube 35 is oriented generally parallel to the mitral annulus plane and oriented by rotation so as to point at the opposite planned anchor point (see below).

A guidewire 45 (see FIG. 7) is advanced through first curved tube 35 and into the left atrium. If desired, a steering tube may also, optionally, be positioned between first curved tube 35 and guidewire 45 so as to further guide the advance of guidewire 45 into the desired position in the left atrium.

TCT2 is then used to position second curved tube 35A and funnel-shaped snare 85 through the opposite side of the annulus and into the left atrium, oriented to point generally in the direction of the opposite anchor point established by TCT1. More particularly, second positioning sheath 25A is advanced against the ventricular side of the anterior annulus (see FIG. 20), and then second curved tube 35A of TCT2 is advanced (with RF assistance if necessary, or with the aforementioned crossing wire) into the left atrium so that the outlet of second curved tube 35A is generally parallel to the mitral annulus plane and oriented by rotation so as to point at the opposite anchor point established by TCT1. See FIG. 21. Then funnel-shaped snare 85 is advanced through second curved tube 35A so that the mouth of funnel-shaped snare 85 enters the left atrium and is directed toward guidewire 45. See FIG. 22.

Guidewire 45 is then advanced into funnel-shaped snare 85. See FIG. 23. Then funnel-shaped snare 85 is retracted into second curved tube 35A so that funnel-shaped snare 85 collapses inwardly on guidewire 45, thereby establishing a positive grip on guidewire 45 (i.e., as the funnel-shaped snare is compressed upon recapture within second curved tube 35A).

It will be appreciated that the orientations of TCT1 and TCT2, the first and second curved tubes 35 and 35A, guidewire 45, and funnel-shaped snare 85 can be manipulated by advancing or rotating, using techniques familiar to those skilled in the art of interventional cardiology, so as to ensure proper docking of guidewire 45 with funnel-shaped snare 85.

Figure 24:
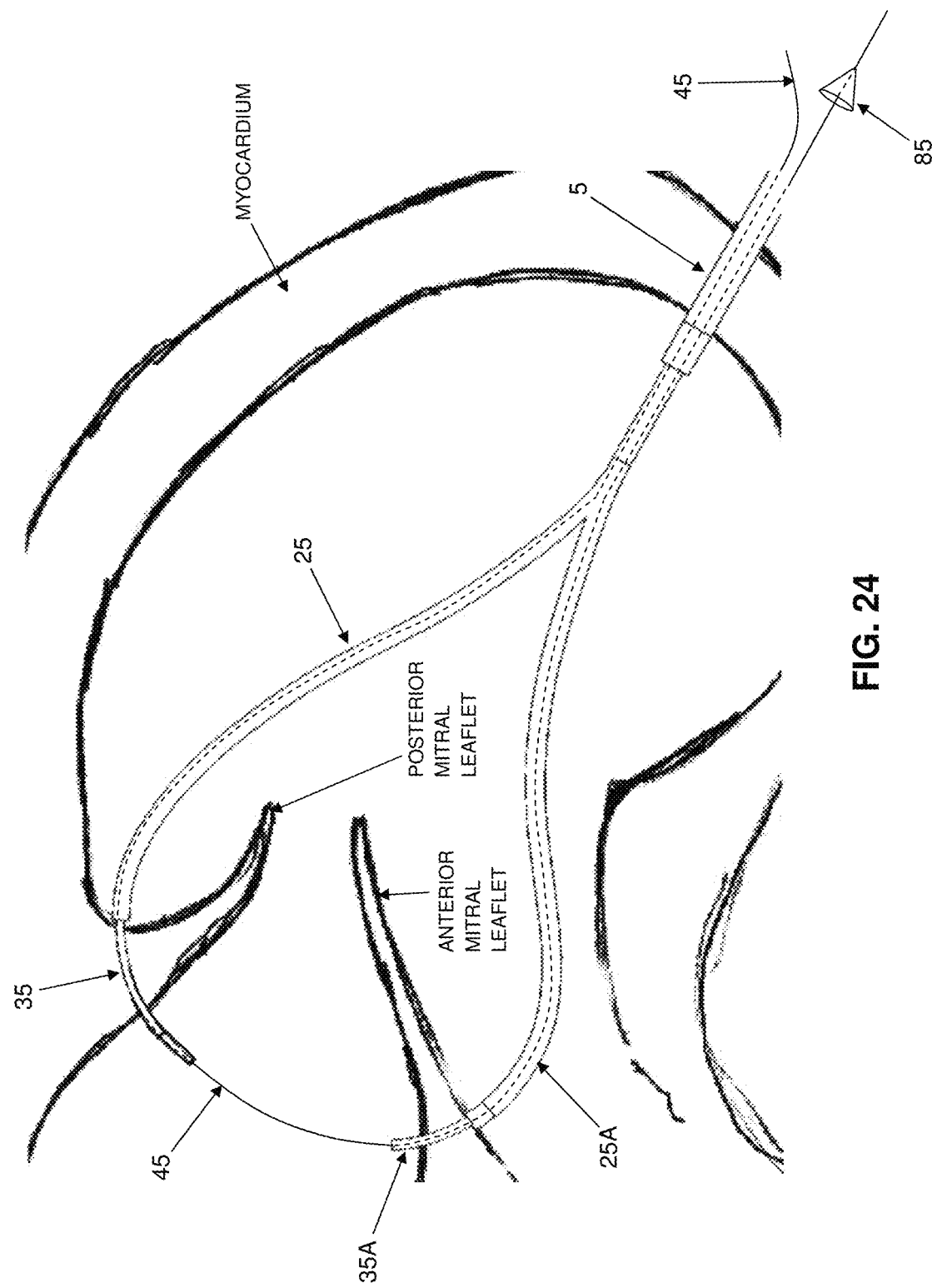
Figure 25:
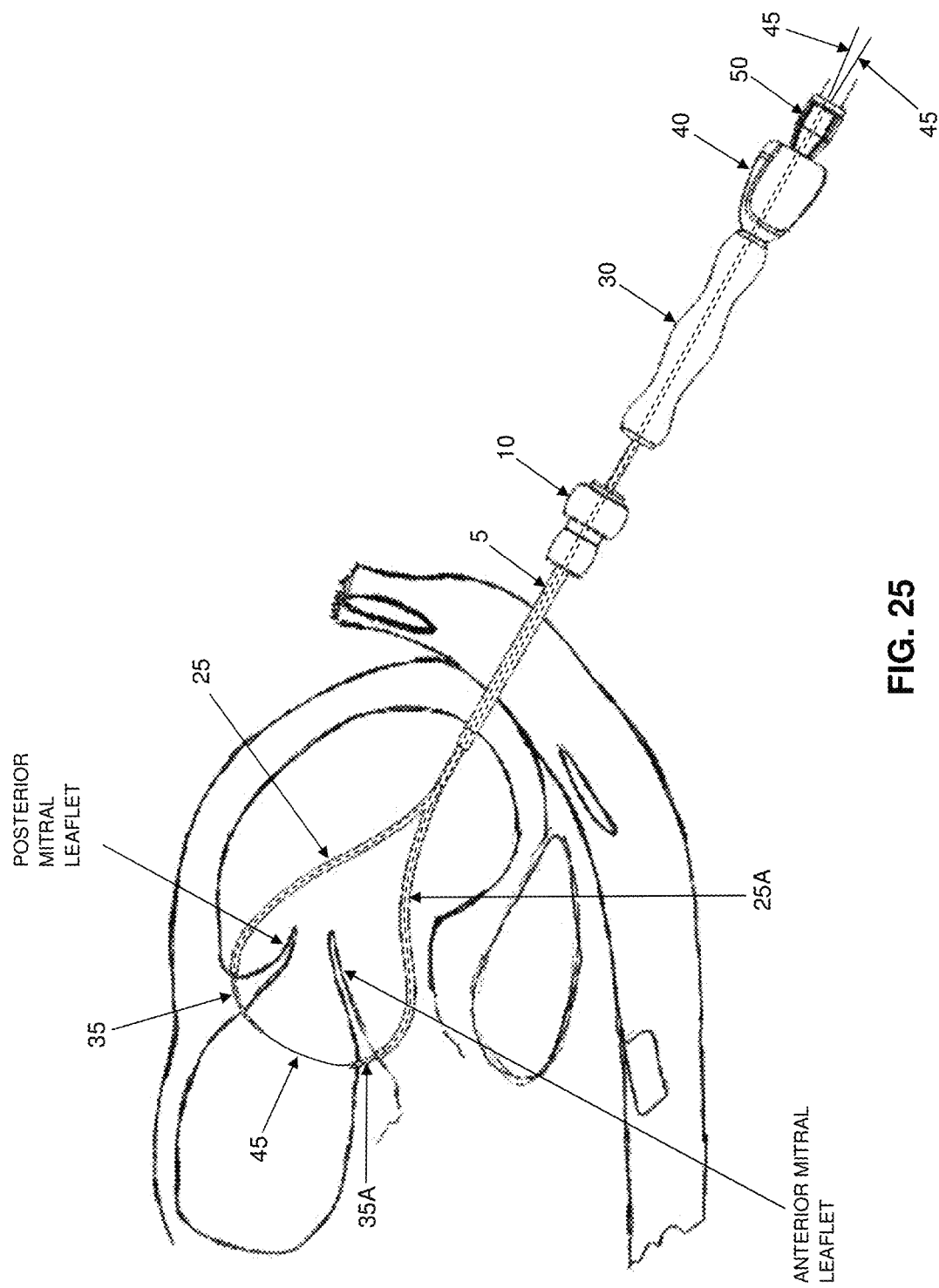
Figure 26:
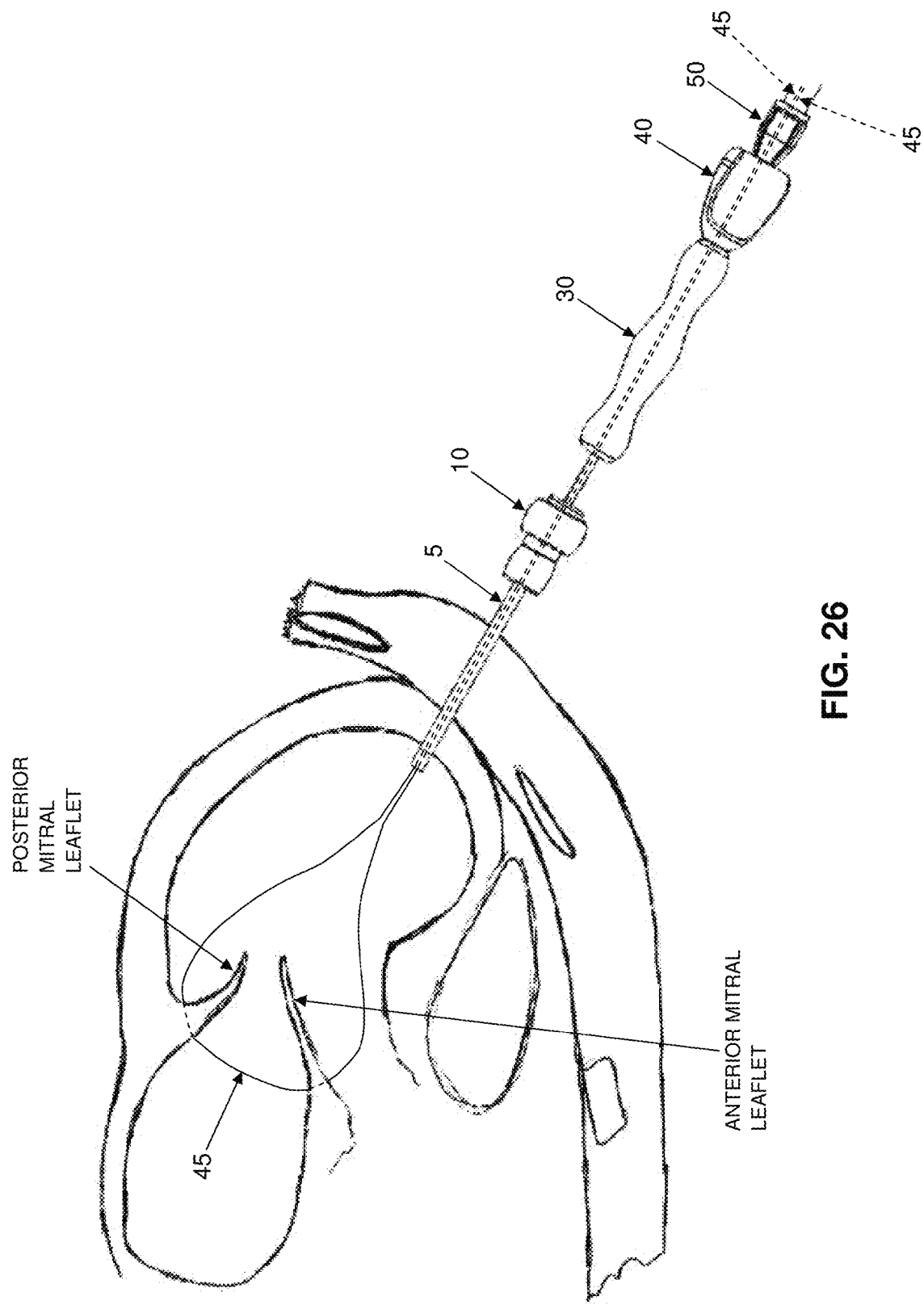

Using funnel-shaped snare 85, the distal end of captured guidewire 45 is retracted by pulling funnel-shaped snare 85 proximally along second curved tube 35A until the assembly has been withdrawn out of the anatomy into the operative sterile field (see FIG. 24). At this point, guidewire 45 is detached from funnel-shaped snare 85 (see FIG. 25), whereby to complete deployment of the crossing guidewire via the "cross and catch" approach. At this point, first positioning sheath 25 (and its annulus crossing first curved tube 35) and second positioning sheath 25A (and its annulus crossing second curved tube 35A) may be removed from the operative site, if they have not already been removed. See FIG. 26.

4. Establishing the Crossing Guidewire by the "Cross and Receive" Approach

Another alternative approach for establishing a crossing guidewire across the mitral annulus is sometimes hereinafter referred to as the "cross and receive" approach. This alternative approach is effected using a first "target and cross tool", sometimes referred to herein as TCT3, and a second "target and cross tool", sometimes referred to herein as TCT4, as described below.

Preferably TCT3 and TCT4 have a shape which allows them to be directed into a desired position on the ventricular side of the mitral annulus by a direct approach and without requiring significant lateral movement, since such lateral movement can be problematic given the presence of the chordae tendineae on the ventricular side of the mitral valve. Furthermore, the TCT3 and TCT4 preferably have a shape which allows them to advance to, and directly engage, the ventricular side of the mitral annulus without requiring the deformation or displacement of any intervening cardiac anatomy (e.g., the papillary muscles, chordae tendineae, etc.) as the TCTs are advancing to, and engaging, the annulus "crossing" site. Significantly, by providing a method and means which allows the annulus "crossing" site to be accessed without requiring the deformation or displacement of any intervening cardiac anatomy, subsequent steps in the annulus reconfiguration may also be performed without requiring any intervening cardiac anatomy to be deformed or displaced. By the methods described herein, once a crossing location has been reached, the TCT tools do not need to be moved laterally within the ventricle, risking entanglement or interference with chordae or other structures. And subsequent steps in the procedure follow the suture path back to the same crossing location, again without requiring lateral motion and the risk of entanglement by either the delivery tools or the deployed implant. This combination of devices and method is a significant advance in the art.

The key features of TCT3 and TCT4 will first be described, and then their sequence of use will be addressed.

TCT3 preferably comprises at least the two following elements, as follows:
(i) TCT3 comprises a 6 French reinforced first positioning sheath (see FIG. 5) with a lumen extending therethrough, curved distal and middle sections, and a steering handle 30. First positioning sheath 25 is shaped so as to reach from the entry point of apical access sheath 5 near the apex of the left ventricle to locations on the mitral annulus; the distal section of first positioning sheath 25 is curved so that the line of action of the exit of the sheath is oriented into the left atrium over a wide range of apical access locations and left ventricular anatomies.
(ii) TCT3 also includes an advanceable first curved tube 35 (see FIG. 6) made of Nitinol and having a curved distal section, generally about 19 gauge to 20 gauge in diameter, with a 0.035 inch lumen, and a proximal handle 40. First curved tube 35 is slidably disposed within first positioning sheath 25. The distal section of first curved tube 35 is curved so that, as it is advanced out of first positioning sheath 25, its exit may be controllably oriented towards the opposite side of the annulus. Nitinol tubing is generally preferred for this application because the curvature of the distal tip may not otherwise be maintained as it is manipulated through the shaped sections of first positioning sheath 25. First curved tube 35 is intended to provide a crossing lumen through the mitral annulus, as will hereinafter be discussed.

In one preferred form of the invention, TCT3 may also comprise an innermost steering tube (not shown) which may be disposed within first curved tube 35 and receive first guidewire 45. This steering tube is also preferably made of Nitinol, with a curved distal section, a <0.035 inch outside diameter, an internal 0.014 inch lumen, and a proximal handle. The distal section of this steering tube is curved (differentially from the first curved tube 35) so that as the steering tube is advanced out of first curved tube 35, its exit may be oriented toward the opposite side of the annulus. Nitinol tubing is generally preferred for this application due to its superelastic properties, which will help ensure that the curvature of the distal tip will be maintained as it is manipulated through the shaped sections of first curved tube 35. Alternatively, other potentially desirable constructions for forming the steering tube include coils, braids, or a solid tube with slots or hole patterns to provide flexibility to the steering tube.

Figure 27:
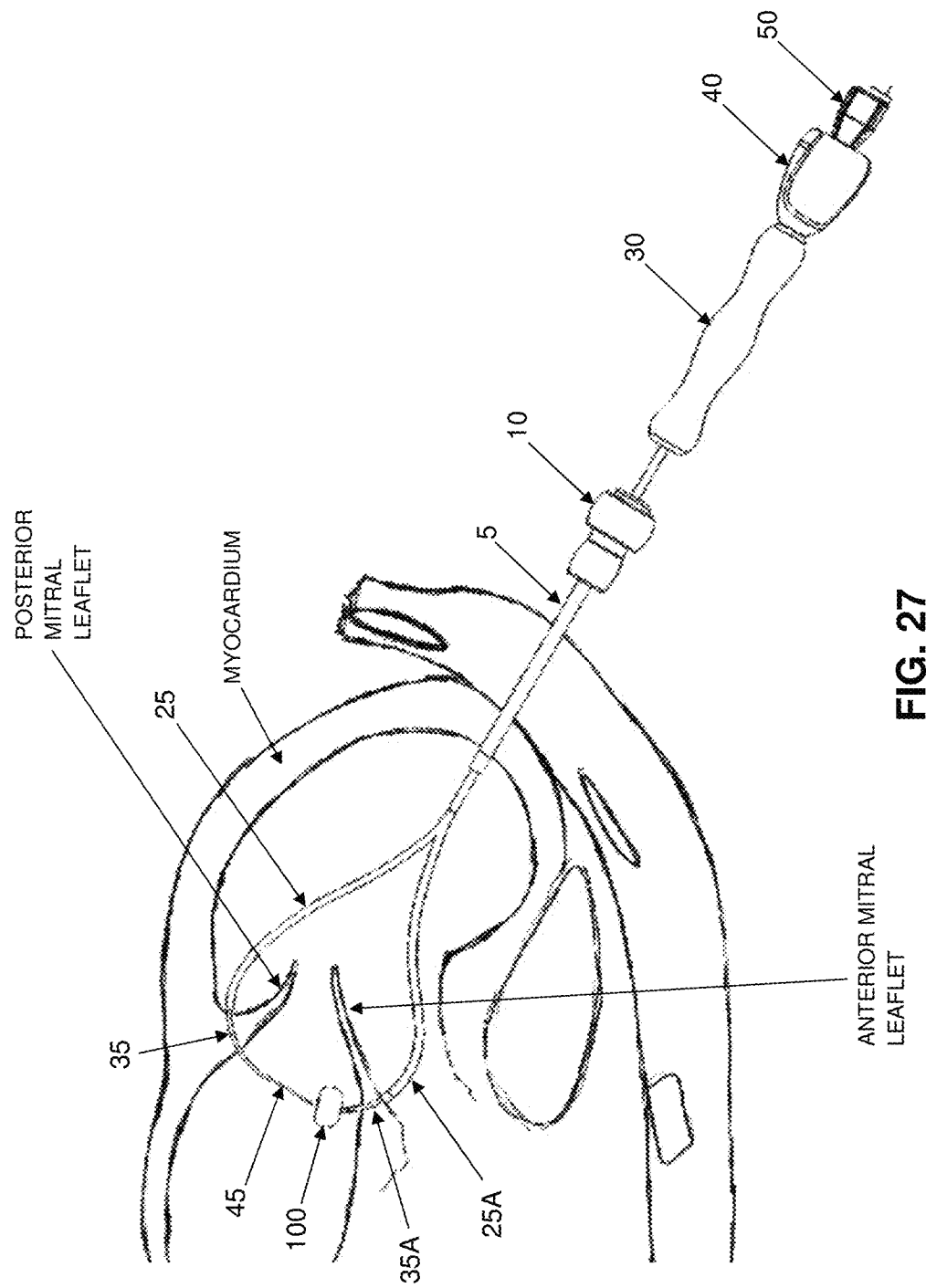
FIGS. 27-32 are schematic views showing selected steps in the establishment of the crossing guidewire using the aforementioned "cross and receive" approach.
Figure 28:
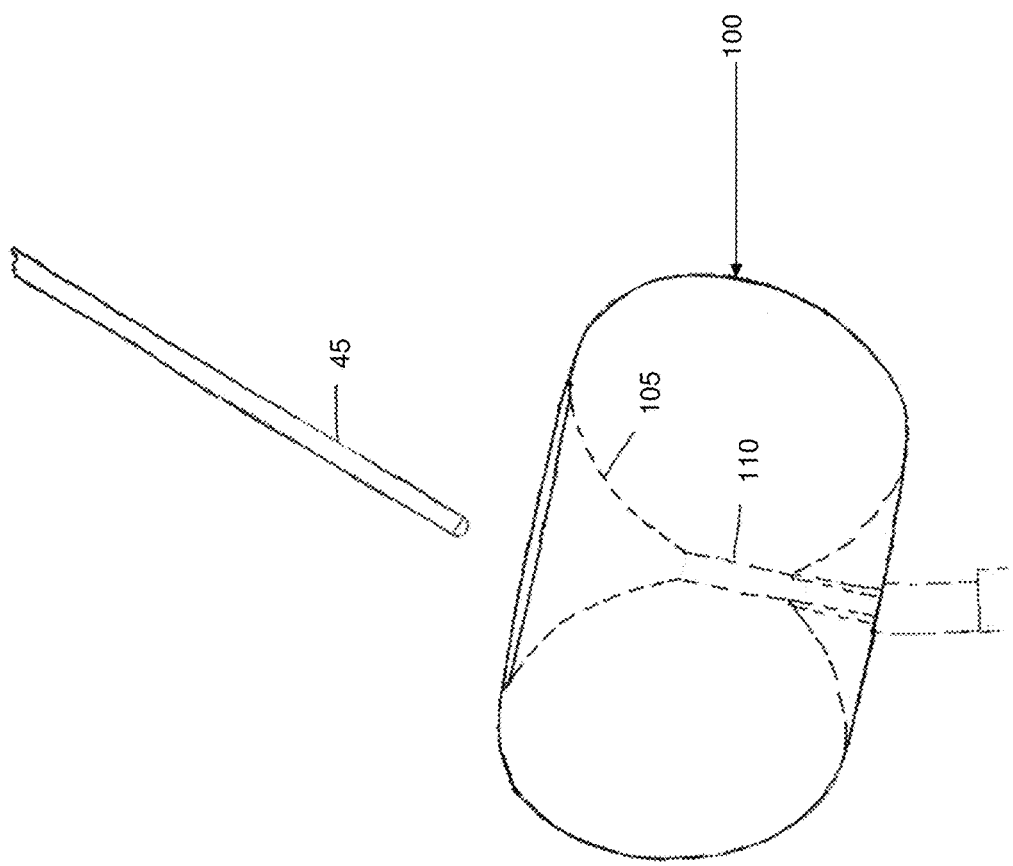
Figure 29:
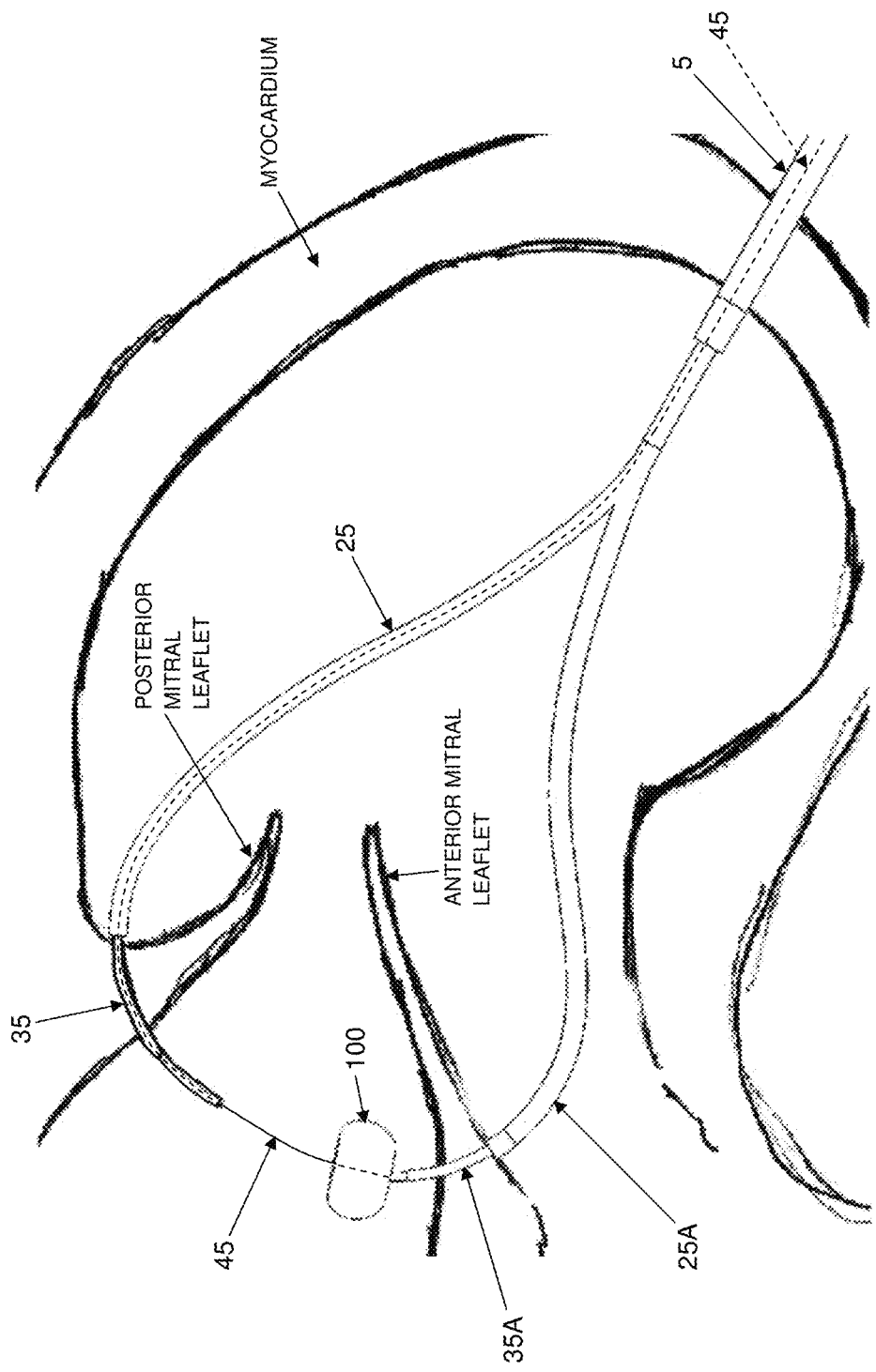
Figure 30:
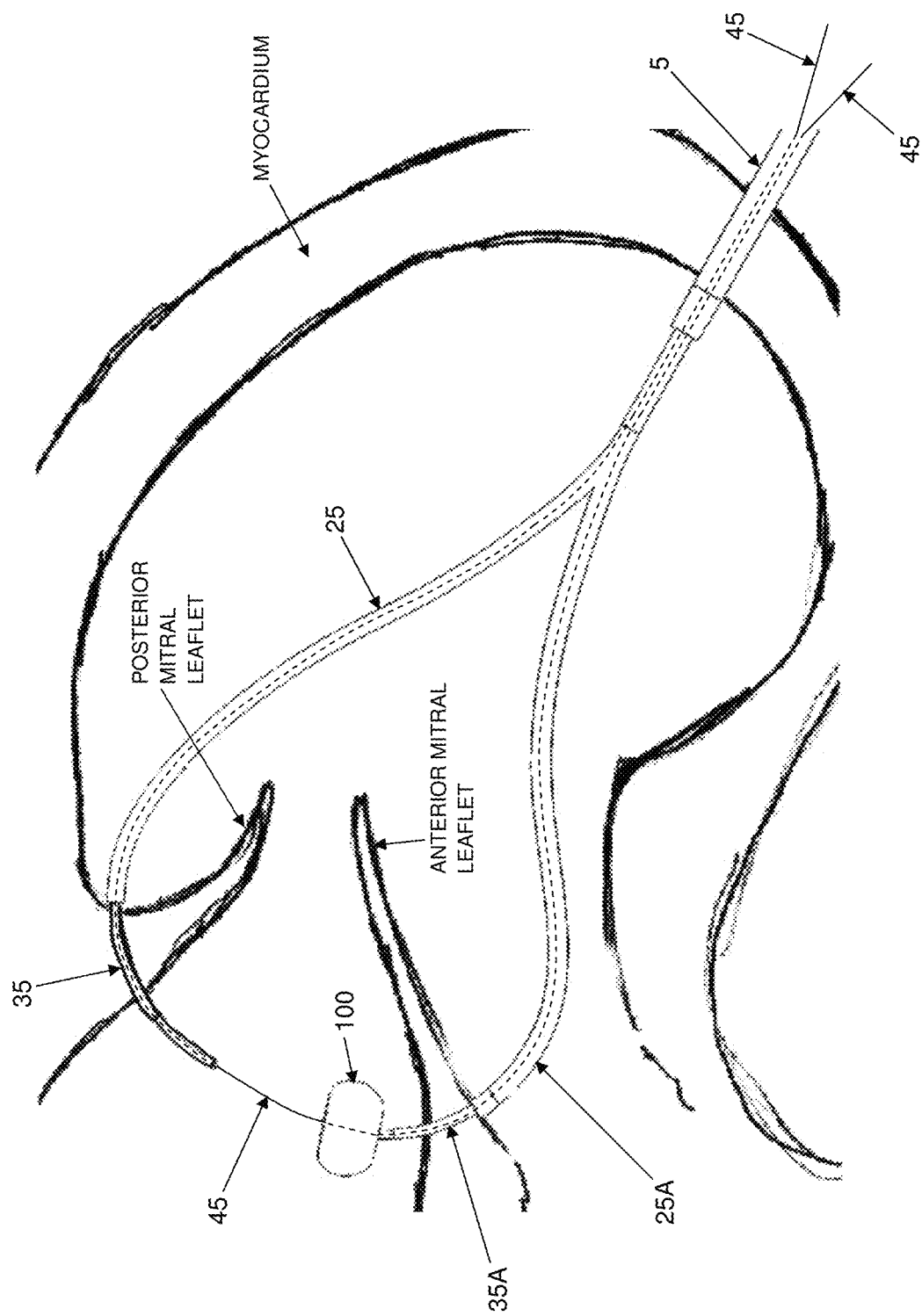
Figure 31:
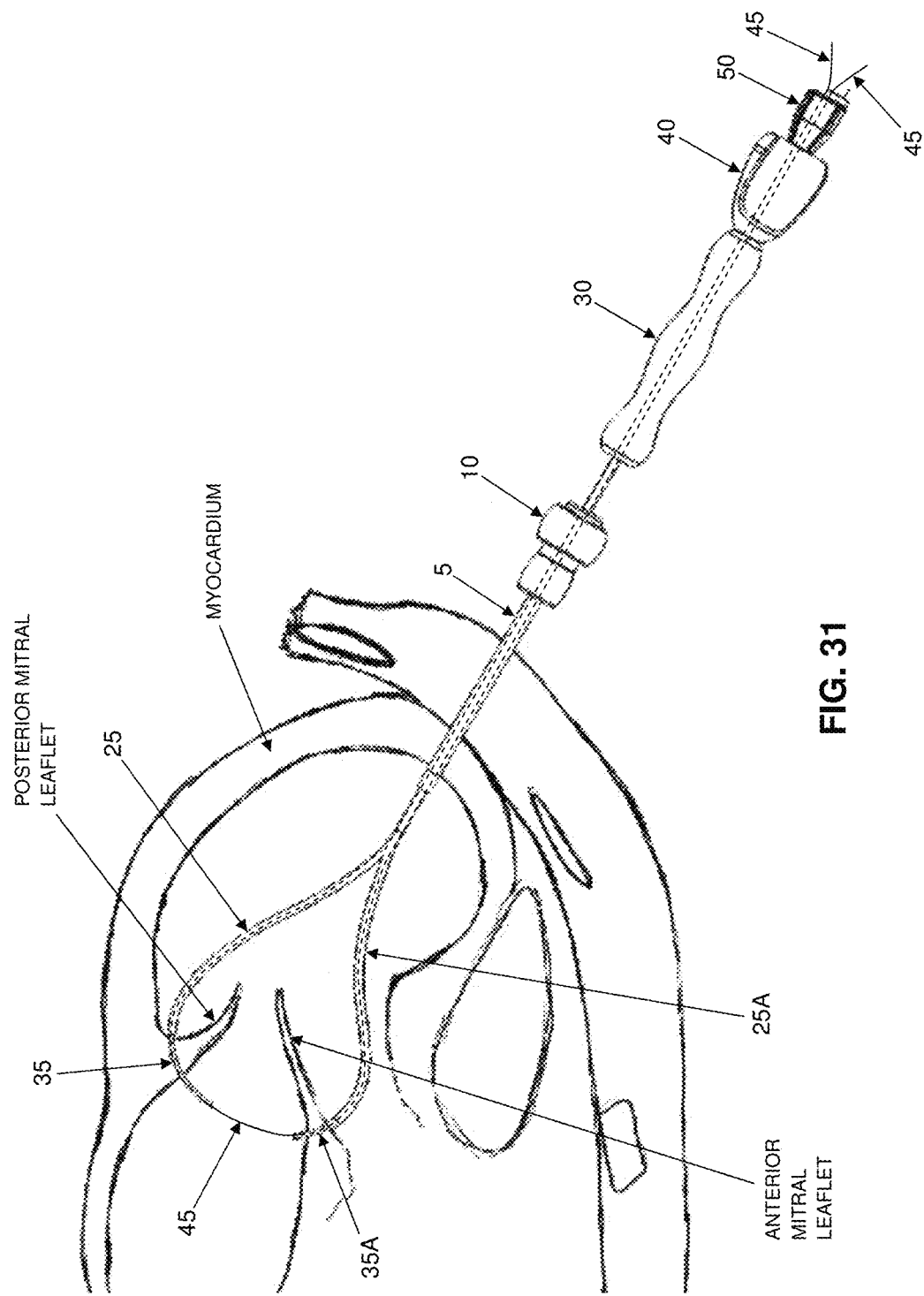

TCT4 comprises three major elements as follows:

(i) TCT4 comprises an approximately 6 French second positioning sheath 25A (see FIG. 27) having an interior lumen extending therethrough, curved distal and middle sections, and a handle similar to the aforementioned steering handle 30. Second positioning sheath 25A is shaped so as to extend through apical access sheath 5 (placed in the apex of the left ventricle) and from there to reach locations on the mitral annulus. In the preferred embodiment, the distal section of second positioning sheath 25A is curved so that the exit of the second positioning sheath is oriented into the left atrium over a wide range of apical access locations and left ventricular anatomies. Second positioning sheath 25A may be re-shapeable by various means including bending, and/or several alternative shapes may be provided so as to account for varying patient size and anatomy.

(ii) TCT4 also comprises a second curved tube 35A (see FIG. 27) which is disposed within second positioning sheath 25A. Second curved tube 35A is preferably made of Nitinol and, in a preferred embodiment, fitted with a progressively curved distal section, of 19 gauge or 20 gauge diameter, with an inner lumen of approximately 0.035 inch, and a handle similar to the aforementioned handle 40. The distal section of the second curved tube 35A is curved so that, as it is advanced out of second positioning sheath 25A, its exit may be oriented toward the opposite side of the mitral annulus, and also afford control of the elevation angle of the most distally-advanced aspect of second curved tube 35A. Nitinol is generally preferred for this application inasmuch as the range of preferred curvatures of the distal tip may not be maintained as it is manipulated and advanced through the curved sections of second positioning sheath 25A. The distal aspect of second curved tube 35A may be finished to a conventional needle-sharp condition, thus facilitating controlled advance of second curved tube 35A through annular tissue by pushing. Alternatively, the distal aspect of second curved tube 35A may be finished square and smooth, and employed in combination with a conventional, flexible RF-assisted puncture wire or a custom RF-assisted puncture wire of matched-curve construction. In the case of a RF assisted puncture wire, the RF puncture wire may be independently advanced through the annulus and then second curved tube 35A advanced over the RF puncture wire, thus allowing second curved tube 35A to be guided (or "track") over the RF puncture wire along the preferred path. Alternatively, second curved tube 35A may be employed in combination with a crossing wire of the type described above.

(iii) TCT4 also comprises an inflatable funnel 100 (see FIGS. 27-30). Inflatable funnel 100 is configured with novel features beneficial to the performance of the "cross and receive" approach. Inflatable funnel 100 could, alternatively, be replaced by a non-inflatable, but still self-expanding, Nitinol (or other superelastic material) funnel-shaped element, i.e., a funnel-shaped element with a self-expanding mesh structure, either with/without a polymer covering, depending upon the fineness of the Nitinol mesh and the desired mating guidewire. The key features of inflatable funnel 100 are as follows:

(a) In the anticipated preferred embodiment, inflatable funnel 100 can be advanced and retracted through an approximately 0.035 inch lumen, with inflatable funnel 100 deflated during advancement and removal. Inflatable funnel 100 is equipped with a 0.014 inch lumen.

(b) The main shaft of inflatable funnel 100 is preferably reinforced with either steel or Nitinol tubing, or a braided composite tube, so as to provide for positive torsional and advance/retraction control during positioning.

(c) In a preferred embodiment, inflatable funnel 100 comprises a unique elastomeric distal balloon with several important properties. The inflated shape of the distal balloon is such that when inflated, it projects distally beyond the end of second curved tube 35A with an overall diameter of approximately 10 mm. Viewed on end, the distal face of the balloon forms a funnel-like mouth 105 (see FIG. 28) with diameter of approximately 6 mm of maximum acceptance diameter, to thereby create a fluoroscopically-visible target for a conventional 0.014 inch guidewire. The interior of the funnel transitions continuously and smoothly into the through lumen 110 of inflatable funnel 100.

The funnel-like mouth 105 of inflatable funnel 100, and through-passing 0.014 inch inner lumen 110 of the inflatable funnel, are designed so that there is a smooth transition between the two, whereby to readily guide an advancing guidewire into the lumen of inflatable funnel 100 and then out to the sterile operative field (via second curved tube 35A).

A crossing guidewire 45 (FIGS. 27-31) is also utilized in the "cross and receive" approach. Crossing guidewire 45 can preferably exhibit properties of a conventional coronary guidewire with several desirable characteristics, in particular, a 0.014 inch maximum diameter throughout, excellent distal radio-opacity to facilitate fluoroscopic visualization and/or distal ultrasonic visibility to facilitate echocardiographic visualization, and a flexible, atraumatic tip with adequate "crossability" to allow crossing guidewire 45 to be readily guided and tracked into mouth 105 of inflatable funnel 100. The proximal end of guidewire may have features such as a reduced diameter (e.g., to allow it to readily dock with the spanning suture of the spanning implant in a manner which maintains a maximum crossing profile of 0.014 inch after docking).

The key steps of the "cross and receive" approach, using the apparatus just described, will now be presented.

First, the first positioning sheath 25 of TCT3 is advanced through apical access sheath 5 and its distal end positioned adjacent to the posterior annulus (FIG. 5). Then first curved tube 35 is advanced through the annulus and into the left atrium (see FIG. 6). As noted above, first curved tube 35 may be advanced through the annulus either alone, or carrying an internally-positioned RF puncture wire, or over an aforementioned crossing wire. Once first curved tube 35 is advanced through the annulus and into left atrium, guidewire 45 is projected out the distal end of first curved tube 35 and into the left atrium. See FIG. 7. In one preferred form of the invention, guidewire 45 is an RF puncture guidewire, and first curved tube 35 and guidewire 45 are inserted into first positioning sheath 25 and positioned and affixed so that the tip of guidewire 45 emerges from the tip of first curved tube 35 by approximately 1 mm or 2 mm, i.e., a distance sufficient to allow the RF action to "lead" the advancement of first curved tube 35 through the annulus on the posterior side of the mitral valve. The RF guidewire 45 is connected to the RF generator and RF guidewire 45 and first curved tube 35 are passed through the posterior annulus.

Next, second positioning sheath 25A of TCT4 is inserted through apical access sheath 5 and positioned against the anterior annulus in the desired anchor location, with the line of action of the distal curved section being oriented so as to point into the left atrium and towards the opposite planned annular anchor point. See FIG. 20. This is done under ultrasound and/or fluoroscopic guidance. The target anatomical locations will, in normal practice, be selected in advance based upon echocardiogram, computer tomography and fluoroscopic data.

Figure 21:
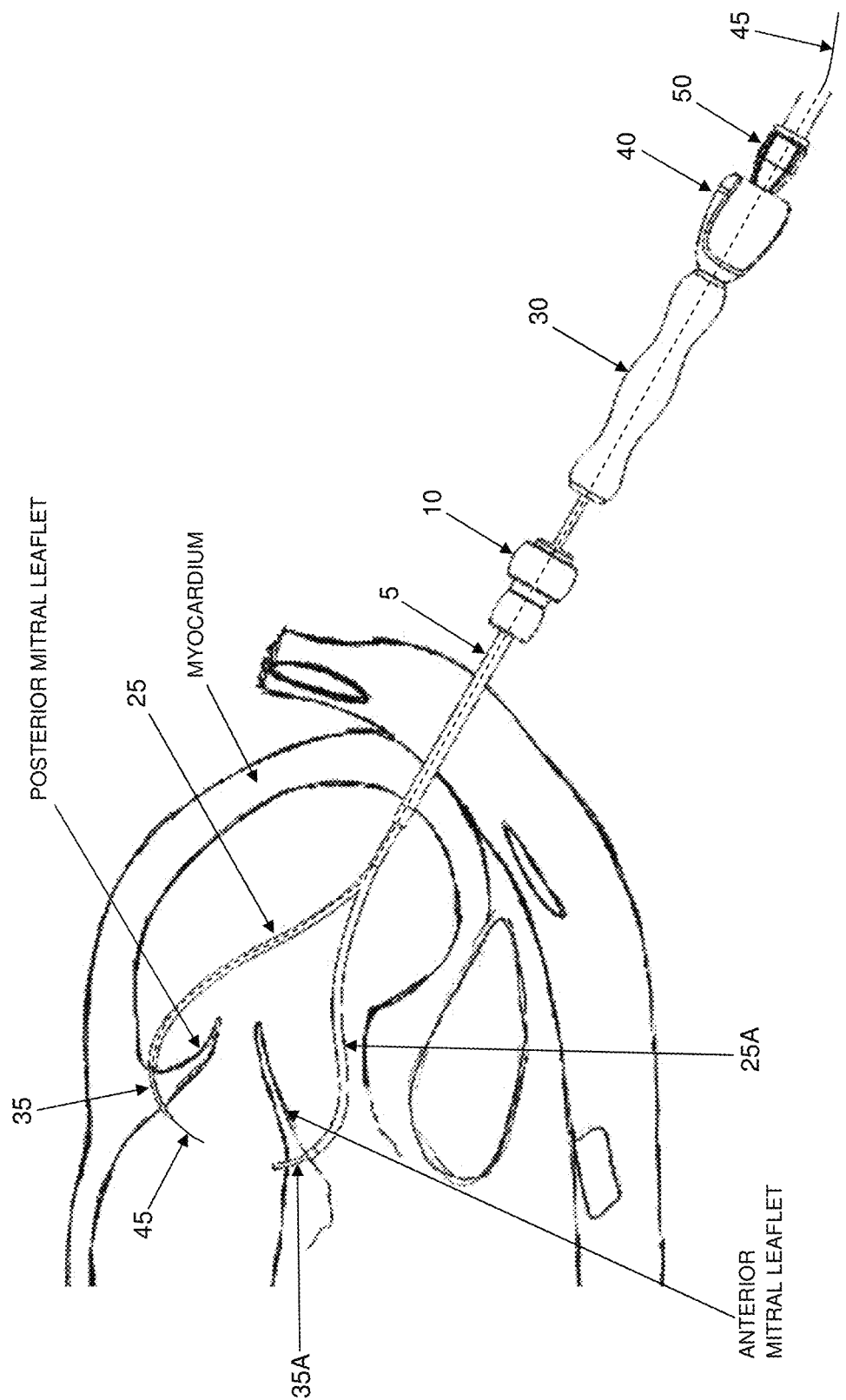

Then, second curved tube 35A is advanced through the annulus and into the left atrium (see FIG. 21). As noted above, second curved tube 35A may be advanced through the annulus either alone, or carrying an internally-positioned RF puncture wire, or over an aforementioned crossing wire. In one preferred form of the invention, an RF puncture wire is inserted into second positioning sheath 25A and positioned and affixed so that the tip of the RF puncture wire emerges from the tip of second curved tube 35A by approximately 1 mm or 2 mm, i.e., a distance sufficient to allow the RF action to "lead" the advancement of second curved tube 35A through the annulus on the anterior side of the mitral valve. The RF generator is turned on, and second curved tube 35A and the RF puncture wire are simultaneously advanced, as an assembly, along a curved path through the anterior annulus as defined by the pre-curve of the devices. Advancement continues until second curved tube 35A and the RF puncture wire emerge into the left atrium sufficiently far that second curved tube 35A is generally parallel with respect to the mitral annulus plane, and oriented by rotation so as to point at the opposite planned anchor point.

After second curved tube 35A has been passed through the mitral annulus (and any RF puncture wire or crossing wire has been withdrawn from the lumen of second curved tube 35A), inflatable funnel 100 is advanced through second curved tube 35A and into the left atrium. If desired, a 0.014 inch guidewire may first be tracked through second curved tube 35A and into the left atrium so as to assist advancement of inflatable funnel 100 and so as to maintain proper positioning of inflatable funnel 100 in the left atrium.

With inflatable funnel 100 positioned in the left atrium, the proximal end of inflatable funnel 100 is locked to second curved tube 35A for stability. Then the inflatable funnel 100 is inflated, preferably with contrast agent.

First curved tube 35 of TCT3 is then adjusted under both echocariodogram and multi-view fluoroscopic guidance so that first curved tube 35 (and hence crossing guidewire 45) are pointed towards the center of inflatable funnel 100. See FIGS. 27 and 28. Note that a steering tube of the sort discussed above may be employed within first curved tube 35 so as to facilitate steering first curved tube (and hence crossing guidewire 45) are pointed towards the center of inflatable funnel 100.

Figure 32:
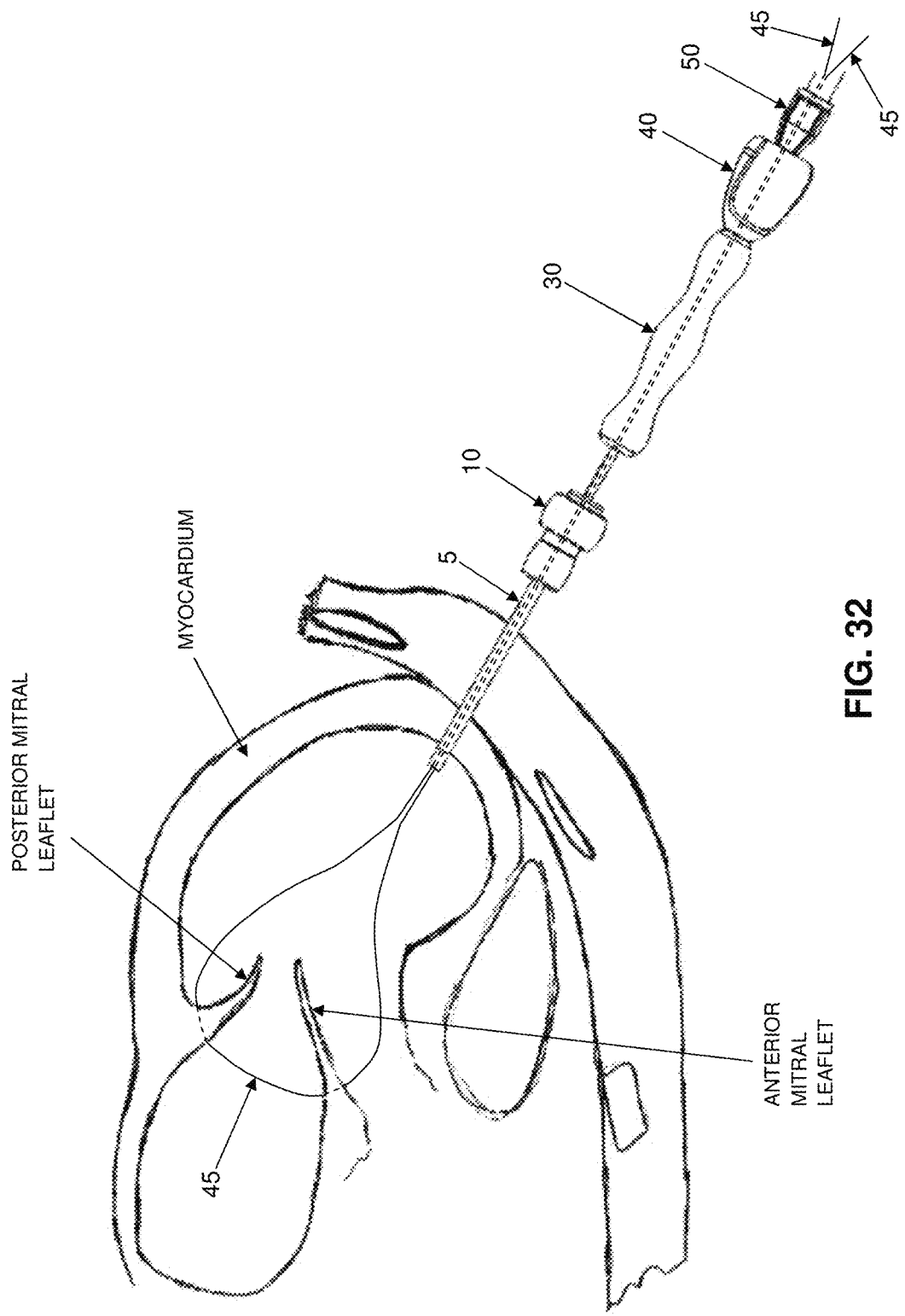

Crossing guidewire 45 is then advanced into the lumen of inflatable funnel 100 and then into the lumen of second curved tube 35A. See FIG. 29. Crossing guidewire 45 is advanced until it exits from the proximal end of apical access sheath 5 in the operative sterile field. See FIG. 30. Then inflatable funnel 100 is deflated and removed from second curved tube 35A. See FIG. 31. At this point, first positioning sheath 25 (and its annulus crossing first curved tube 35) and second positioning sheath 25A (and its annulus crossing second curved tube 35A) may be removed from the operative site, if they have not already been removed. See FIG. 32.

This completes positioning of the crossing guidewire via the "cross and receive" approach.

The three approaches discussed above (i.e., the "cross and snare" approach, the "cross and catch" approach and the "cross and receive" approach), provide highly accurate and controllable means for routing a crossing guidewire (and, subsequently, a spanning implant) along a structurally preferred path from the ventricular side of the mitral annulus, through the mitral annulus to the left atrium, across the mouth of the valve along a desired path, and then back through the annulus on the opposite side of the valve so as to extend into the left ventricle.

In this novel fashion, the method of the present invention allows for targeting a wide range of structural landmarks while avoiding the possibility of entanglement or interference with ventricular structures such as the chordae tendinae and papillary muscles. See FIGS. 2 and 3. Furthermore, the procedure can be performed through a single, low-profile apical access sheath, using a limited set of operative procedures well within the skill of the average interventional clinician. Additionally, and as will hereinafter be discussed, successive, additional spanning passes can be made to effect progressive change to the valve shape in response to observed shape and functional regurgitation on real-time continuous echocardiography.

Other features may be added to the aforementioned apparatus to effect more preferred embodiments. One such feature may be the addition of a compliant balloon on the outer distal tip of the positioning sheath (e.g., first positioning sheath 25, second positioning sheath 25A, etc.). This compliant balloon may be inflated once the distal end of a positioning sheath is nearly in place against the target location on the ventricular side of the annulus. This compliant balloon would serve at least two purposes. First, when filled with a contrast agent, the compliant balloon would provide both an echocardiogram- and fluoroscopically-visible target on the tip of the positioning sheath so as to improve clinical confidence when navigating the positioning sheath against the mitral annulus. Second, the compliant balloon tip would provide a more stable and atraumatic contact of the positioning sheath against the ventricular side of the annulus. An additional possible refinement of a positioning sheath is the addition, by various means, of either echo-attenuating or echo-genic structures and surfaces to the tip of a positioning sheath. A positioning sheath might, in an unmodified state, be fabricated from a material such as stainless steel or Nitinol tubing that would, in the as-manufactured state, create strong, directional echo reflections. The addition of diffusing and attenuating coatings on the distal end of a positioning sheath could render the positioning sheath more readily visible by echocardiographic means. In addition, by attenuating highly directional reflections along the shaft of a positioning sheath, the additional option exists to add echogenic features (such as grooves) or discrete echogenic structures (such as air-entrapping coils), such that specific points on the positioning sheath, preferably the distal tip, are rendered more echogenic.

5. Positioning of the Spanning Implant Across the Mitral Annulus

Once the crossing guidewire is in place, preferably using one of the procedures discussed above (e.g., the "cross and snare" approach, the "cross and catch" approach and the "cross and receive" approach), it is a relatively straightforward matter to effect the implantation and controlled adjustment of the spanning implant. These devices and steps will be described below and can be further appreciated by reference to the figures.

Significantly, inasmuch as the present invention provides a method and means for positioning the crossing guidewire across the mitral valve without requiring the deformation or displacement of any intervening left ventricle anatomy (e.g., the papillary muscles, chordae tendineae, etc.), the spanning implant may also be positioned across the mitral valve without requiring the deformation or displacement of any intervening left ventricle anatomy.

Implantation of the spanning implant can be conducted proceeding from either the anterior side or the posterior side of the crossing guidewire. The crossing guidewire may be constructed of conventional metallic guidewire elements, including combinations of coil, tube and solid elements, to vary the properties of the crossing guidewire from distal end to proximal end. Furthermore, a preferred embodiment of the crossing guidewire includes a pre-prepared continuous transition to the spanning suture of the spanning implant so that, when the spanning implant is to be positioned across the mitral valve, there is already a continuous length of spanning suture routed through the annulus, extending from the operative sterile field, through one side of the annulus from left ventricle to left atrium, across the left atrium, back down through the annulus from left atrium to left ventricle, and then back out into the operative sterile field.

The spanning implant preferably comprises conventional cardiovascular suture, in combination with pre-mounted and procedure-mounted anchoring and covering elements, as discussed below. More particularly, and looking now at FIG. 33, in one form of the present invention, a spanning implant 115 comprises a spanning suture 120 having a first end 125, a second end 130 and a first anchor 135 connected to first end 125 of spanning suture 120. The spanning implant also comprises a second anchor 140 which is fit over second end 130 of spanning suture 120, slid along spanning suture 120 to an appropriate position and then secured in place, preferably using a coaxial suture lock 145, as will hereinafter be discussed.

The spanning suture of the spanning implant is, in one preferred embodiment, a section of suitable permanent, non-bioabsorbable, hemocompatible suture, preferably either PTFE- or ePTFE-covered braided polyester suture. The size of the spanning suture is preferably in the range of 2-0 or larger, given the tensile load expected in this particular application, while presenting a PTFE surface to the blood so as to provide for hemocompatible surface properties. Preferably the spanning suture has a starting length of 25-40 cm to facilitate handling, routing and tensioning. However, only a much smaller portion of this length will ultimately become part of the spanning implant, as discussed below.

Figure 43:
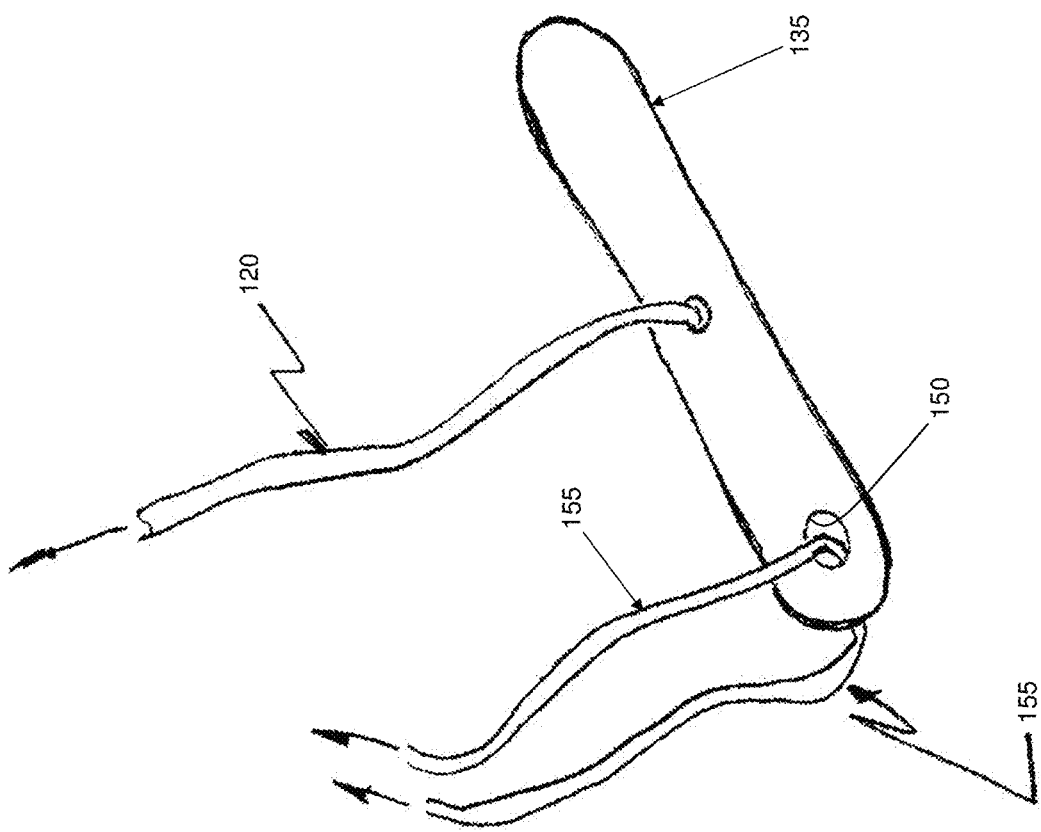
FIG. 43 is a schematic view showing one preferred form of a first, fixed anchor formed in accordance with the present invention.

In one preferred form of the invention, one end of spanning suture 120 (i.e., first end 125) is pre-fitted with a T-bar anchor (i.e., the aforementioned first, fixed anchor 135), preferably made out of 316 stainless steel, titanium, PTFE or other material well known for durable permanent implantation, and also preferable fitted with one or several radiopaque markers, typically tantalum, and optionally coated and buffered with pledgets or a polyester cover. Spanning suture 120 is terminated at first, fixed anchor 135 by a knot, thermal deformation, thermal bonding, adhesive bonding, or a combination of the foregoing. In one preferred form of the invention, first, fixed anchor 135 comprises a concave seat for receiving the termination of spanning suture 120. One preferred configuration of first, fixed anchor 135 is shown in FIG. 43.

In one preferred embodiment, the first, fixed anchor 135 is provided with a through-hole 150 to allow a control line 155 to be passed through the anchor on one end, or possibly on both ends of the anchor. As will be described further below, such a control line 155 will, in conjunction with spanning suture 120, allow the first, fixed anchor 135 to be re-positioned once the first, fixed anchor is in place, particularly if a stiffening sleeve is fitted over control line 155 to provide for both tension and lateral steering of first, fixed anchor 135. Also, control line 155 can be used to positively retain the first, fixed anchor 135 in the delivery tool (see below) during routing into position. Furthermore, control line 155 can allow for elective retrieval of first, fixed anchor 135 subsequent to deployment.

Figure 33:
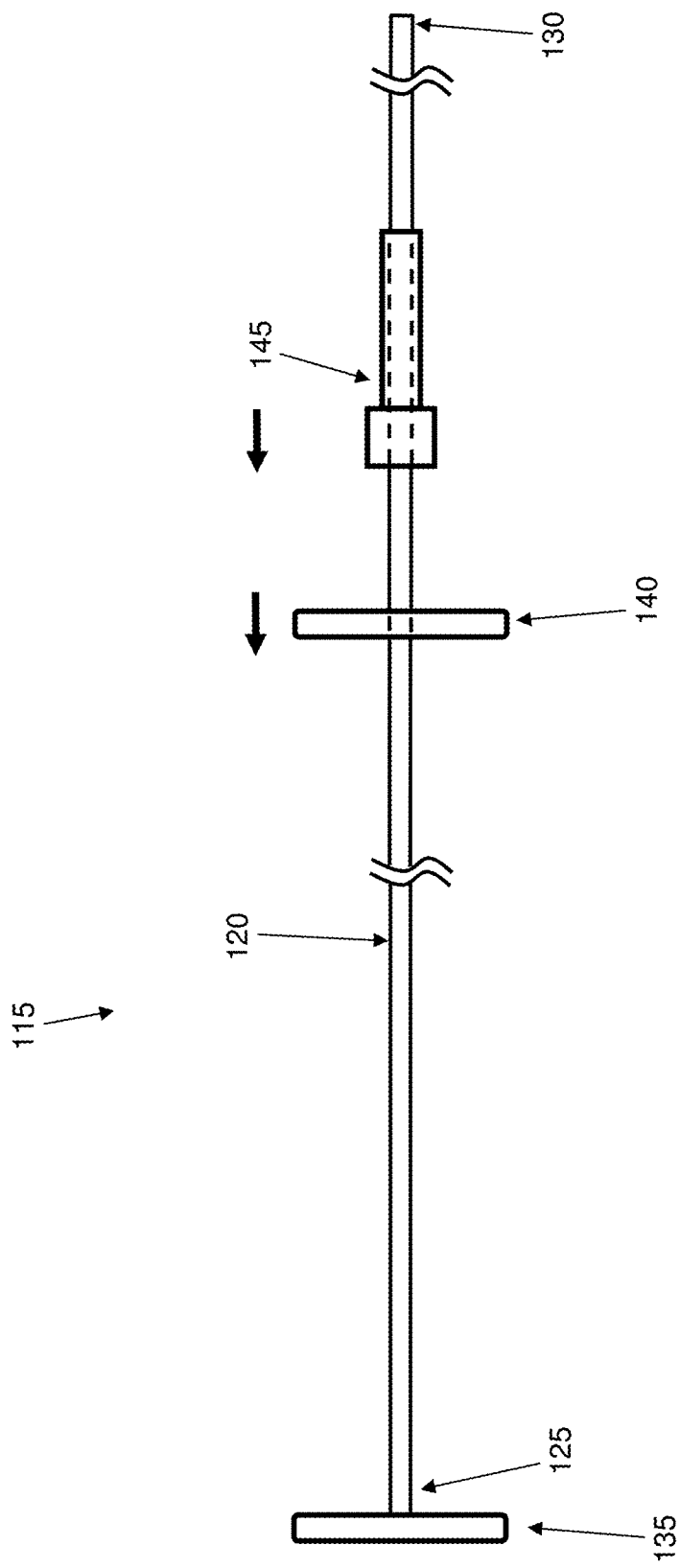
FIG. 33 is a schematic view showing one preferred form of a spanning implant formed in accordance with the present invention.
Figure 34:
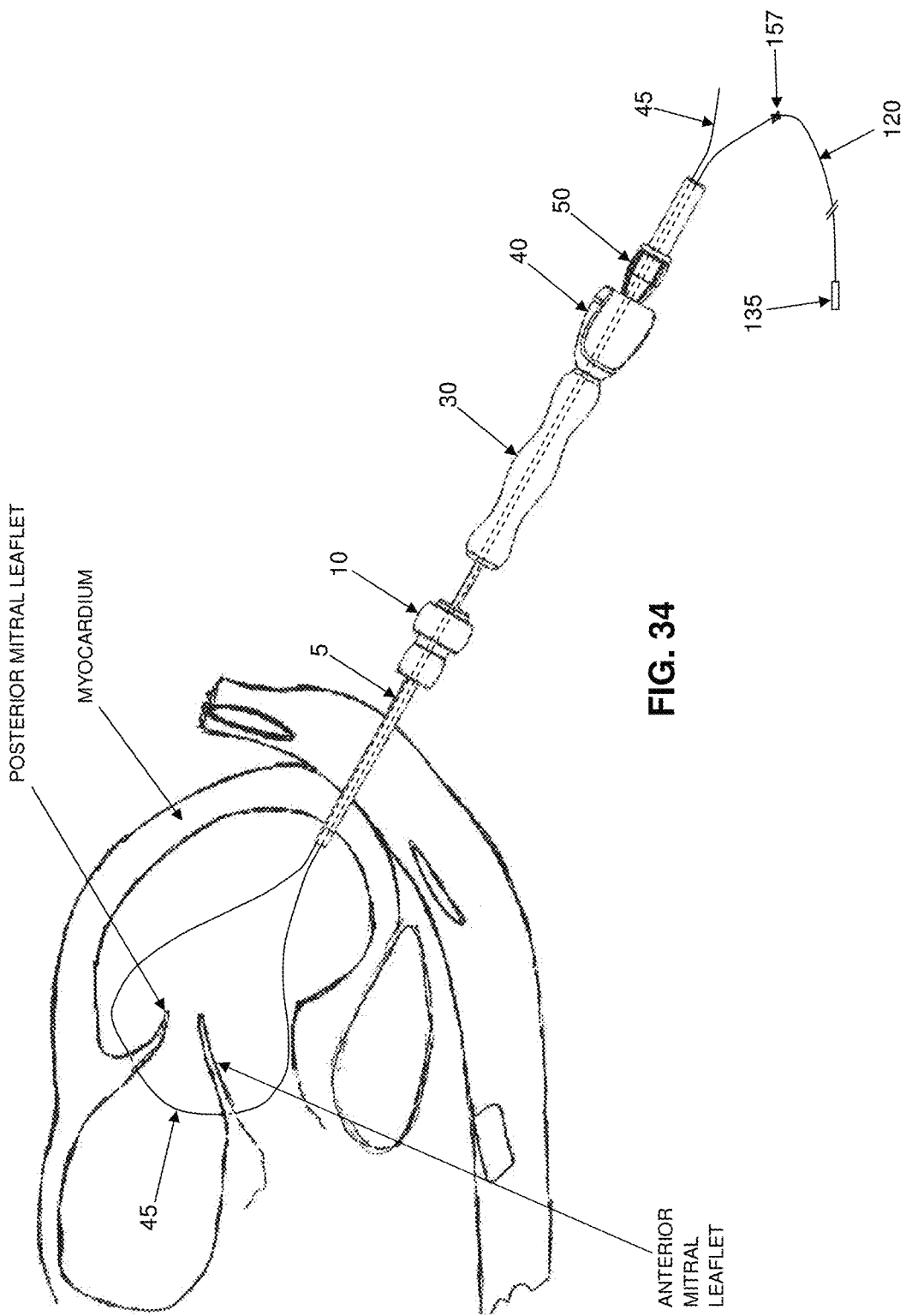
FIGS. 34, 34A and 35-39 are schematic views showing the spanning implant being deployed across the mitral valve, whereby to reconfigure the mitral annulus and thereby reduce mitral regurgitation.

In one preferred embodiment, the opposing end of spanning suture 120 (i.e., second end 130, as seen in FIG. 33) is further fitted with a "docking" feature so that the spanning suture can be attached to the crossing guidewire in a conventional, coaxial manner, e.g., at connection 157 (see FIG. 34). Such docking feature may be effected by various constructions. By way of example but not limitation, a simple approach is to tie a knot of suitable configuration between the spanning suture, factory-terminated, onto the back of the crossing guidewire as previously described. Alternatively, the docking feature may be provided with a coaxial screw lock feature as is conventionally found on docking guidewires employed to facilitate "over the wire" catheter exchanges. In another approach, the free end of spanning suture 120 may be temporarily fused, using thermal or adhesive means, so as to form an attachment with the crossing guidewire. Or the free end of spanning suture 120 may be connected with a tubular mechanical crimped, fused or bonded lock, whereby to secure the spanning suture to the crossing guidewire.

Figure 44:
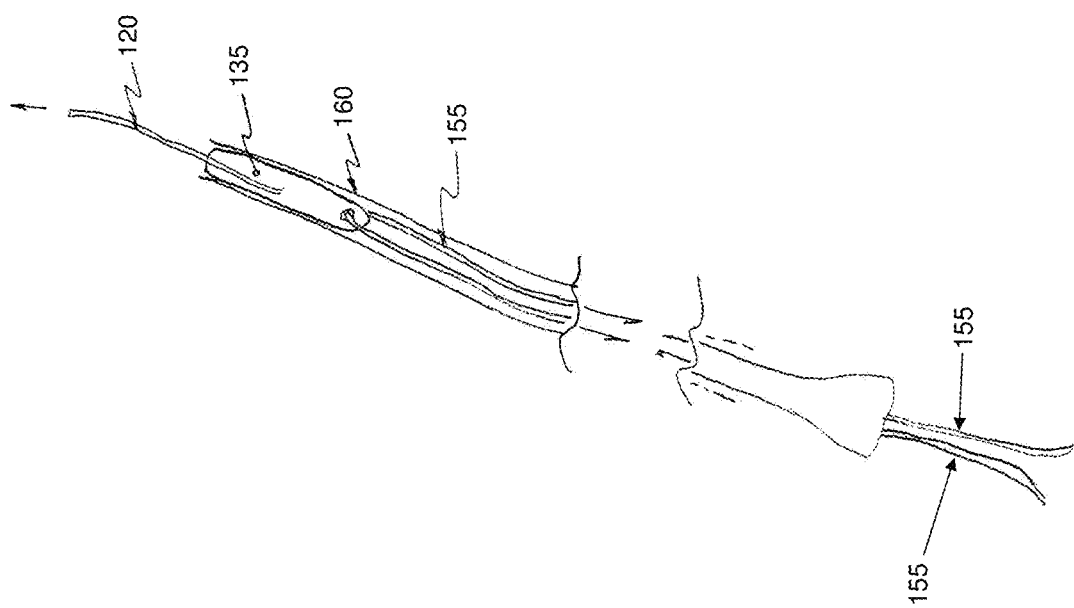
FIG. 44 is a schematic view showing one preferred form of implant-advancing sheath formed in accordance with the present invention.

An implant-advancing sheath 160 (see FIG. 44) is preferably provided to allow for ready advancement of first, fixed anchor 135 into position under the annulus. Implant-advancing sheath 160 preferably comprises an approximately 6 French to approximately 9 French tubular construction with a central through-lumen suitable to accommodate first, fixed anchor 135. In a preferred embodiment, the distal end of implant advancing sheath 160 may be shaped to accommodate first, fixed anchor 135, with control line 155 exiting the proximal end of implant-advancing sheath 160 and with spanning suture 120 exiting the distal end of implant-advancing sheath 160.

Positioning of spanning implant 115 across the mitral annulus will now be described. For purposes of example but not limitation, the implantation sequence will be described beginning from the anterior (trigone) side of the annulus, although it could also be conducted beginning from the posterior side of the annulus.

Figure 34A:
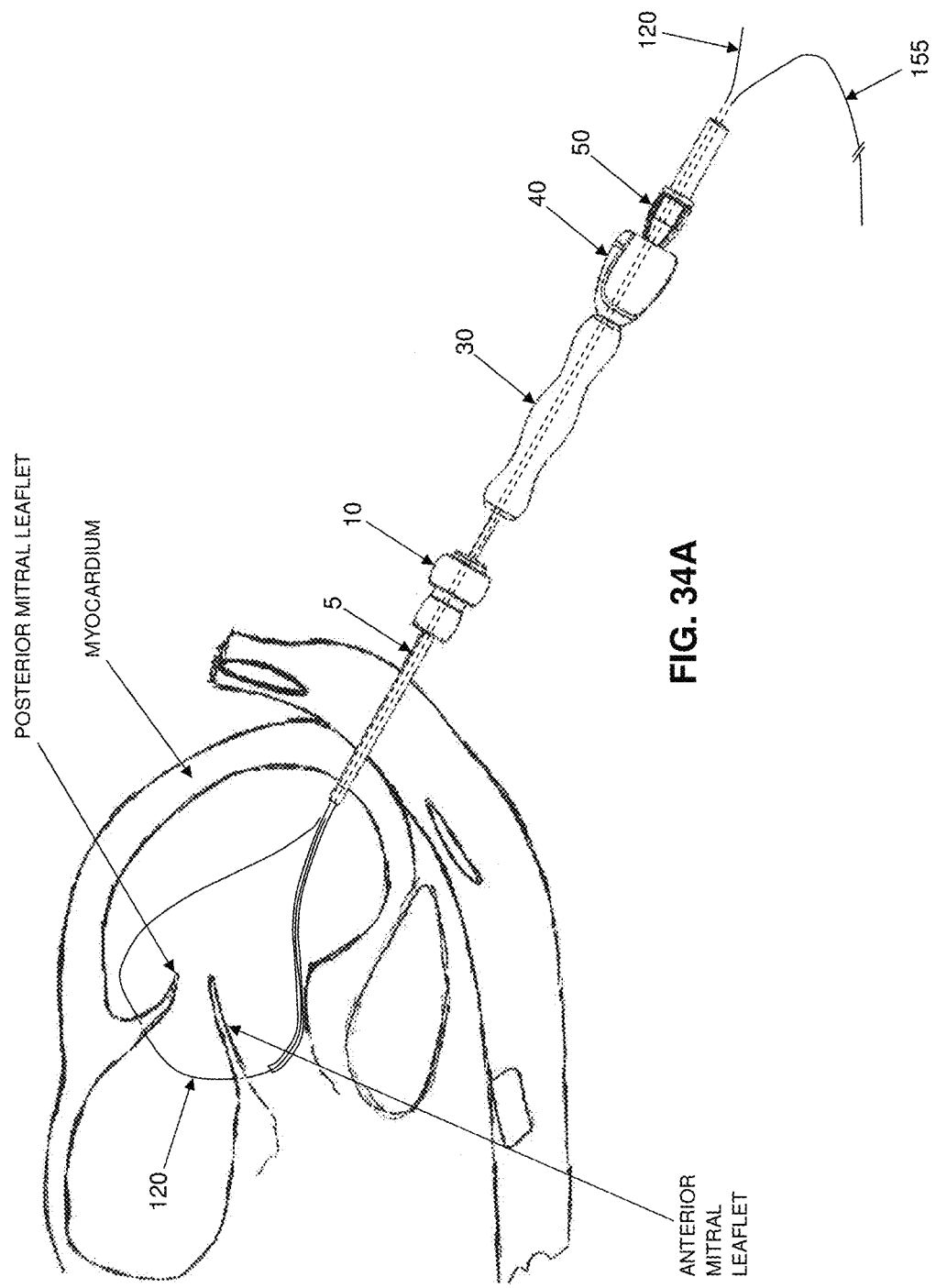

With crossing guidewire 45 in place, the proximal end (i.e., the anterior side) of crossing guidewire 45 is then, as described above, terminated (by one of several means) to the free end (i.e., second end 130) of spanning suture 120, with spanning implant 115 loaded into the implant-advancing sheath 160. See FIG. 34. In a preferred embodiment, spanning implant 115 and implant-advancing sheath 160 are provided, already-assembled, for use in the clinical setting. Then implant-advancing sheath 160 is advanced through apical access sheath 5 and across the left ventricle until it sits near the ventricular side of the anterior annulus. See FIG. 34A.

Figure 35:
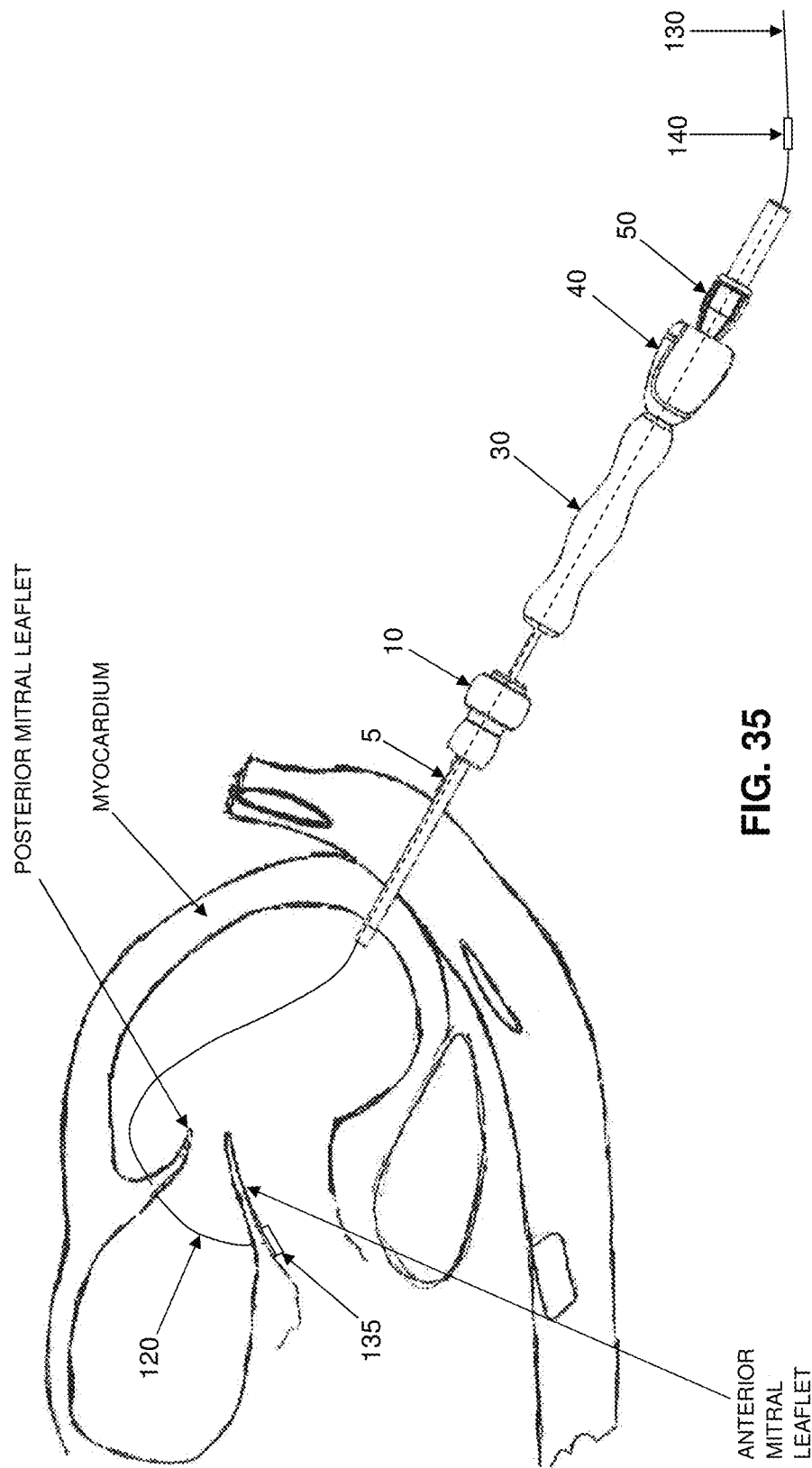

Crossing guidewire 45 is then used to draw spanning suture 120 through the annulus so that the spanning suture extends through the anterior annulus, across the left atrium, through the posterior annulus and extends into the left ventricle, with first, fixed anchor 135 seated against the ventricular side of the anterior annulus. More particularly, with free end 130 of spanning suture 120 attached to crossing guidewire 45, the crossing guidewire 45 (and hence spanning suture 120) is withdrawn (anterior to posterior) until first, fixed anchor 135 exits implant-advancing sheath 160 and engages the ventricular side of the anterior annulus. As this occurs, first, fixed anchor 135 turns, from a position parallel to the longitudinal axis of implant-advancing sheath 160 to a position perpendicular to the axis of implant-advancing sheath 160—and hence parallel to the ventricular side of the anterior annulus. Crossing guidewire 45 is pulled until first, fixed anchor 135 seats against the ventricular side of the anterior annulus. See FIG. 35. Control line 155 can be used to help adjust the orientation of first, fixed anchor 135 if necessary or desirable.

Implant-advancing sheath 160 is then removed from the left ventricle.

At this point, the spanning implant 115 has its first, fixed anchor 135 positioned against the ventricular side of the anterior annulus and the spanning suture 120 extending through the anterior annulus, across the left atrium, through the posterior annulus and back out the left ventricle.

At any chosen point in the procedure, control line 155 can be readily removed from first, fixed anchor 135 by sliding control line 155 out of the body of first, fixed anchor 135. In the preferred embodiment shown in FIGS. 43 and 44, control line 155 can be quickly and easily removed by simply pulling on either free end of the control line.

6. Implant Sizing and Termination

The final step in the procedure is sizing and termination of spanning implant 115, preferably utilizing the tools and steps described below.

A second, sliding anchor 140 (see FIG. 33) and coaxial suture lock 145 (see FIG. 33) are provided. Second, sliding anchor 140 preferably comprises a T-bar anchor, preferably 316 stainless steel, titanium, PTFE or other material or combination of materials known for durable permanent implantation, and also preferably fitted with one or several radiopaque markers, typically tantalum, and finally coated and buffered with pledgets or a polyester cover. This second, sliding anchor 140 can be advanced coaxially over the free end 130 of spanning suture 120 so as to be brought up against the ventricular side of the posterior annulus and fixed in place, as will hereinafter be discussed.

Figure 45:
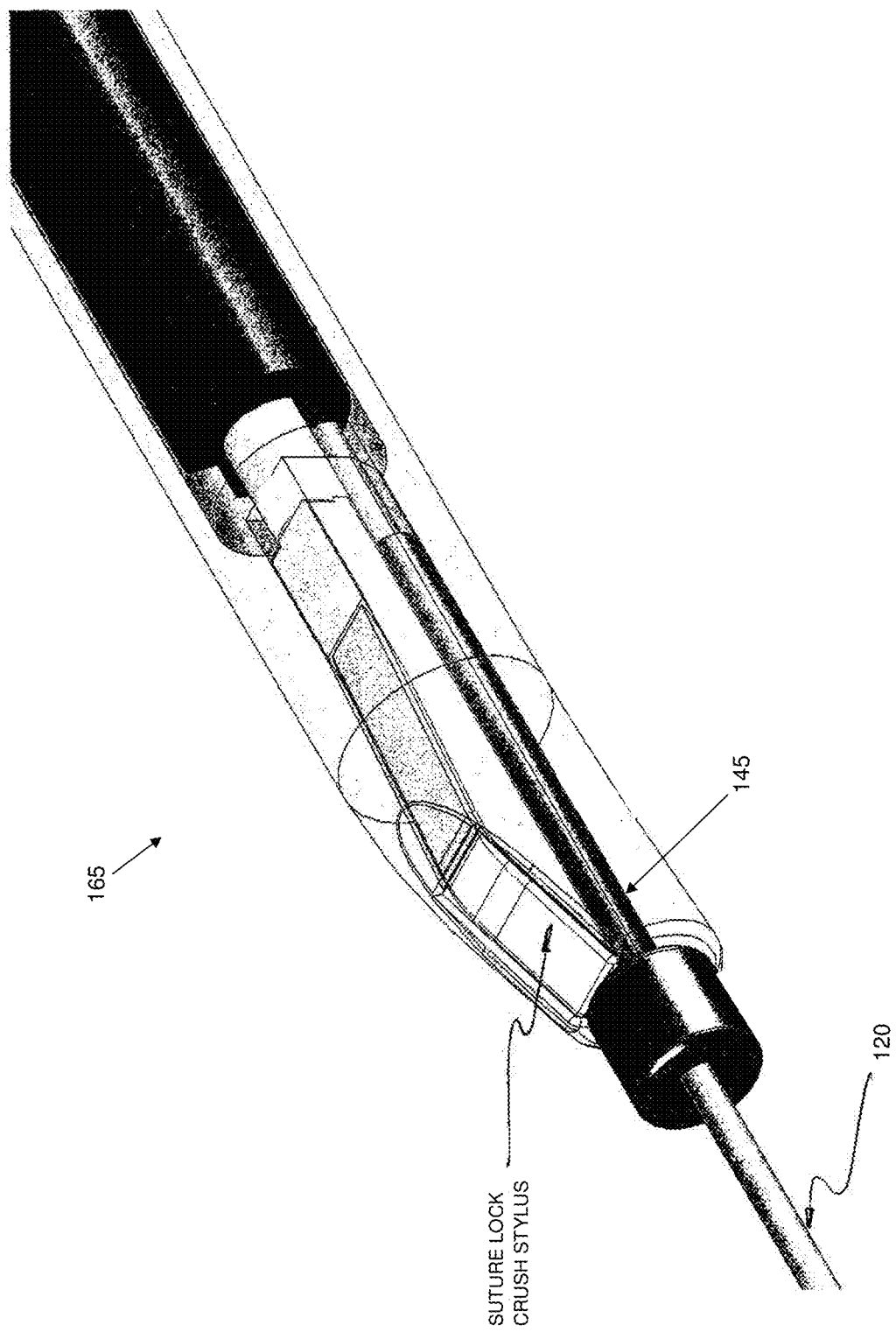
FIG. 45 is a schematic view showing one preferred form of Span-Tension-Terminate Tool" (STTT) formed in accordance with the present invention.

In one preferred form of the invention, second, sliding anchor 140 and coaxial suture lock 145 are loaded within, and applied to, spanning suture 120 by the aforementioned implant tensioning tool, such as a "Span-Tension-Terminate Tool" (STTT) 165 (see FIG. 45). More particularly, and looking now at FIG. 45, spanning suture 120 is routed coaxially through STTT 165 and coaxial suture lock 145. Coaxial suture lock 145 is fitted to the distal end of STTT 165 and maintained in position by lightly pulling on coaxial suture lock 145 so as to hold the coaxial suture lock in position in the distal end of STTT 165.

Figure 39:
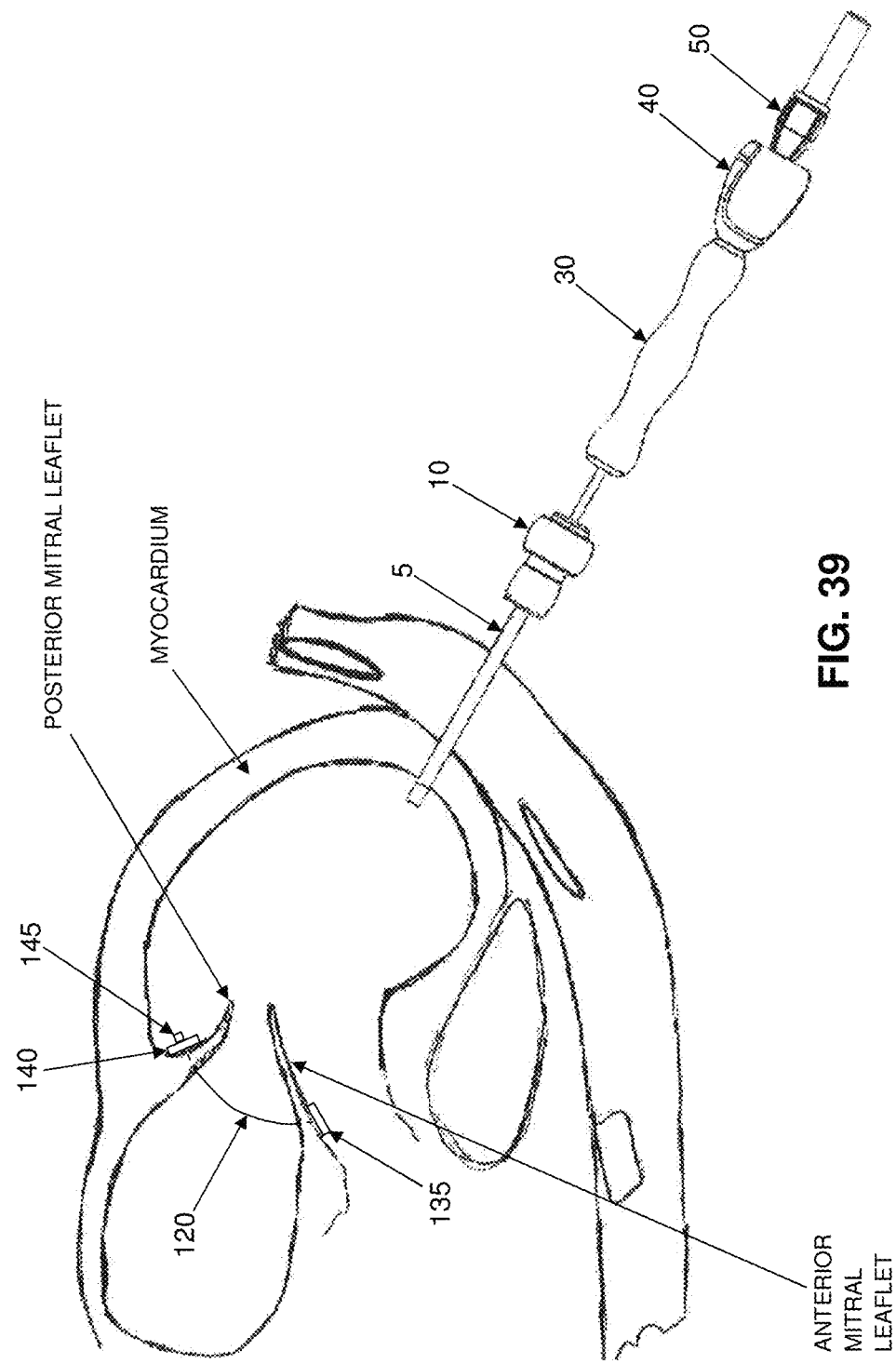

STTT 165 allows the clinician to controllably tension and then, while maintaining suture tension and without altering the optimum treatment location, terminally and permanently lock the spanning suture 120, with the spanning suture being held under tension between the first, fixed anchor 135 set on the anterior side of the annulus and the second, sliding anchor 140 set on the posterior side of the annulus (see FIG. 39), with the second, sliding anchor 140 being held in position by coaxial suture lock 145. There are various other means of achieving the same suture locking action well known in the mechanical arts, including the use of a collet-and-sleeve action or a tapered wedge action or a wedging pin forced into a constraining sleeve, etc.

STTT 165 is contained within an overall 7-9 French reinforced sheath to facilitate control and delivery of the spanning implant.

In the operative field, the free end (i.e., second end 130) of spanning suture 120 is routed through the second, sliding anchor 140, through coaxial suture lock 145 and through STTT 165 (with coaxial suture lock 145 preferably being held in STTT 165).

Figure 36:
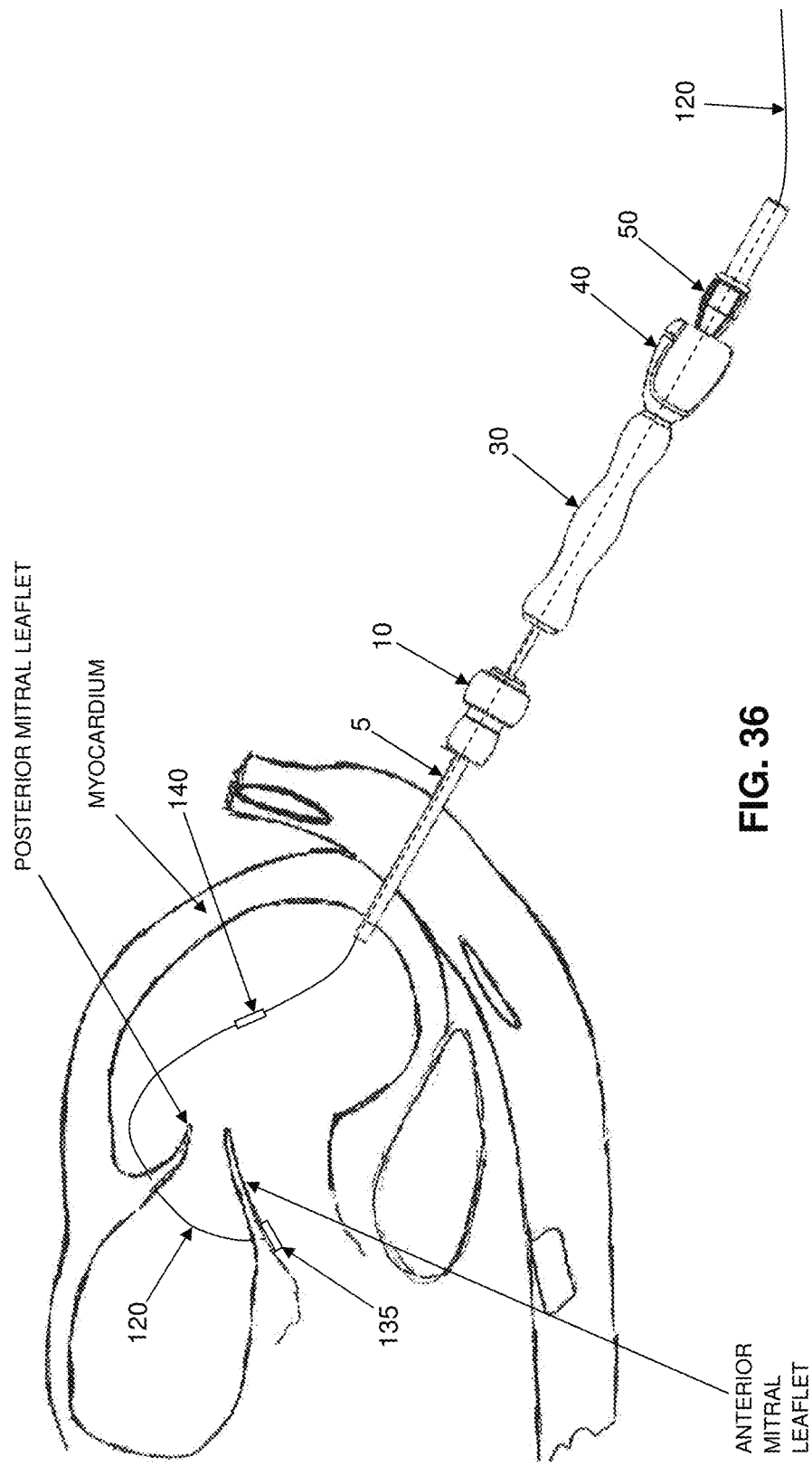
Figure 37:
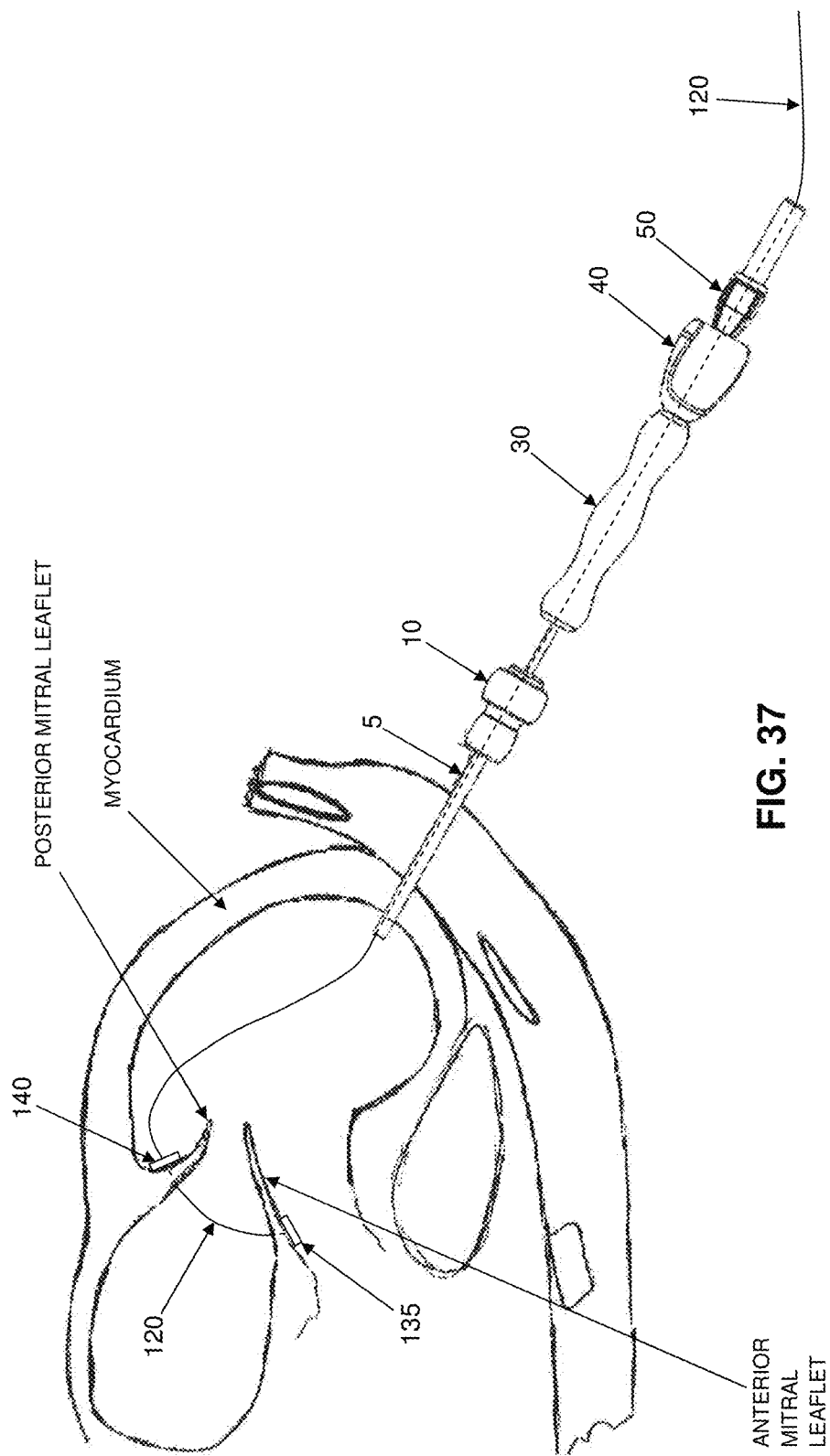

STTT 165 is advanced over spanning suture 120, pushing second, sliding anchor 140 ahead of it, until second, sliding anchor 140 reaches the ventricular side of the posterior annulus, with coaxial suture lock 145 engaging second, sliding anchor 140. See FIGS. 36 and 37.

Spanning suture 120 is then tensioned through STTT 165 to progressively decrease the anterior/posterior dimension of the mitral valve, and hence progressively reduce the mitral regurgitation of the valve. This adjustment is done in increments with observation periods in between while under real-time echo, fluoro, and EKG monitoring. If desired, STTT 165 can be provided with means for continuously measuring and displaying the tension applied to the spanning suture as the therapeutic input is applied. STTT 165 may also be provided with means for continuously measuring the length of spanning suture 120 withdrawn into STTT 165. And STTT 165 may be provided with means for withdrawing spanning suture 120 in pre-defined increments such as 1 mm, e.g., by the provision of a ratchet and pawl mechanism. Or STTT 165 may be provided with a one-way clutch to maintain tension on spanning suture 120 through the STTT, e.g., by a one-way needle-bearing clutch of the sort well-known in the medical arts. Also, STTT 165 may include a motorized withdrawal of spanning suture 120, e.g. with a small gear motor and the provision of calibrated retraction steps, again, such as 1 mm per increment.

When the desired anterior/posterior ("A/P") dimension of the mitral valve has been achieved, and hence the desired reduction of mitral regurgitation has been effected, coaxial suture lock 145 is deployed by STTT 165 by rotating a handle on the proximal end of the STTT which causes the STTT to permanently deform the coaxial suture lock 145, thus affixing a permanent diametrical lock onto spanning suture 120 in such a manner that the final treatment tension of the spanning suture is precisely secured, avoiding any alteration of the applied treatment effect. See FIG. 38.

Alternatively, other means may be used to lock coaxial suture lock 145 to spanning suture 120 (e.g., by creating an interference fit between spanning suture 120 and coaxial suture lock 145).

STTT 165 is then removed from the left ventricle coaxially over the suture. Alternatively, STTT 165 could be provided in a so-called "rapid exchange" configuration, i.e., spanning suture 120 is exited from the shaft of the STTT at a point relatively distal on the STTT, which thus allows more independent handling of the spanning suture or guidewire in the operative sterile field. STTT 165 would otherwise function as when provided in a conventional coaxial or "over-the-wire" form.

The free end of spanning suture 120 (i.e., the end proximal to coaxial suture lock 145) may then be cut proximal to the now-fixed sliding, second anchor 140. Alternatively, it may be terminated to a pledget outside the left ventricle wall, to leave a tether to the implant assembly, thereby guaranteeing that even if the spanning implant becomes loose, it will not embolize and travel in the bloodstream through the body, potentially causing injury.

Significantly, the spanning implant may be sized and terminated (i.e., spanning suture 120 tensioned and second, sliding anchor 140 set) without requiring the deformation or displacement of any intervening left ventricle anatomy (e.g., the papillary muscles, chordae tendineae, etc.).

Figure 38:
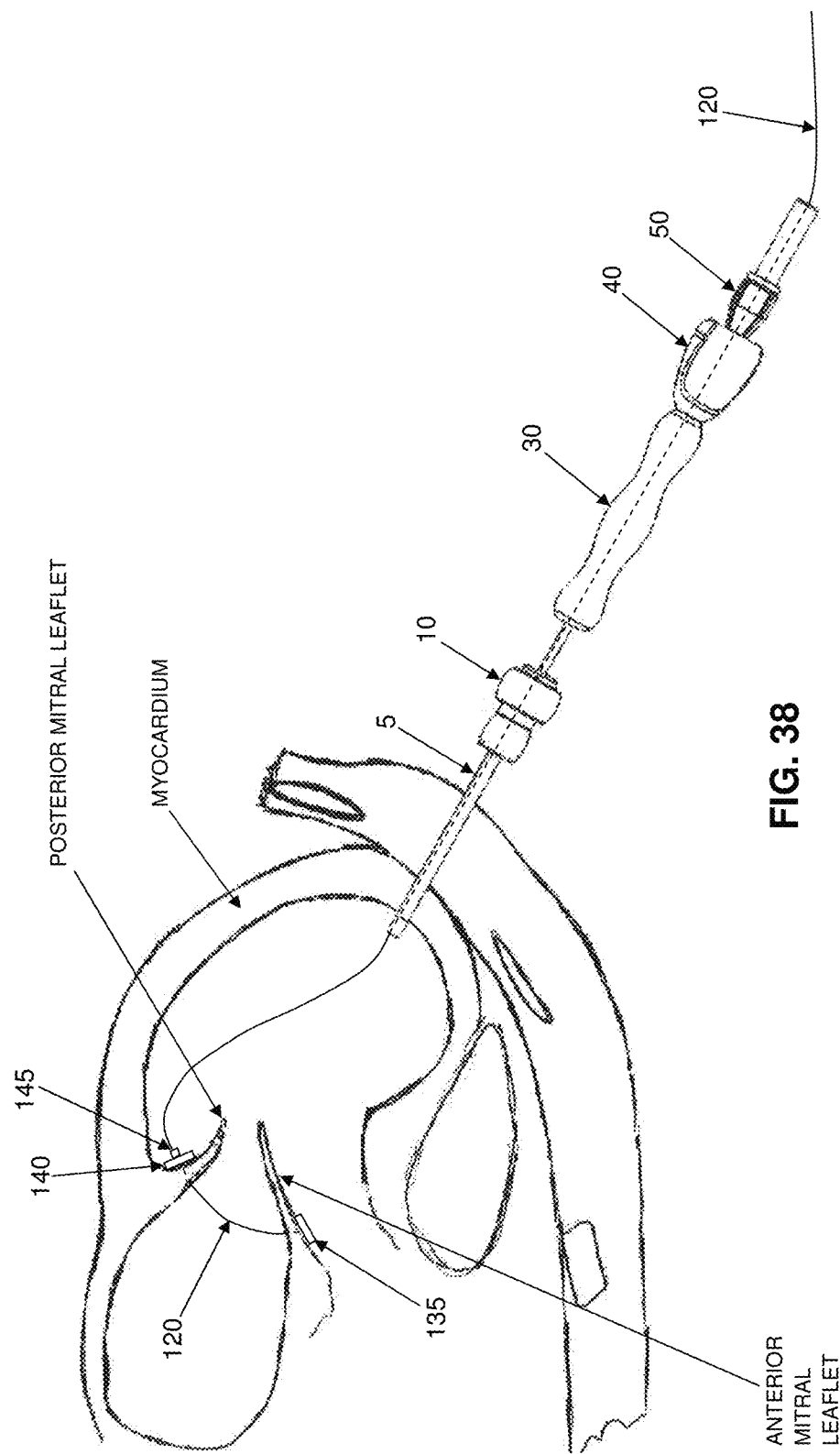

FIG. 38 shows a spanning implant 115 positioned across a mitral valve. As seen in FIG. 38, first, fixed anchor 135 is positioned against the ventricular side of the anterior annulus, spanning suture 120 extends through the anterior annulus, across the left atrium, and through the posterior annulus, where second, sliding anchor 140, secured by coaxial suture lock 145, bears against the ventricular side of the posterior annulus, whereby to hold the reconfigured mitral annulus under tension.

7. Additional Spanning Implants

Figure 40:
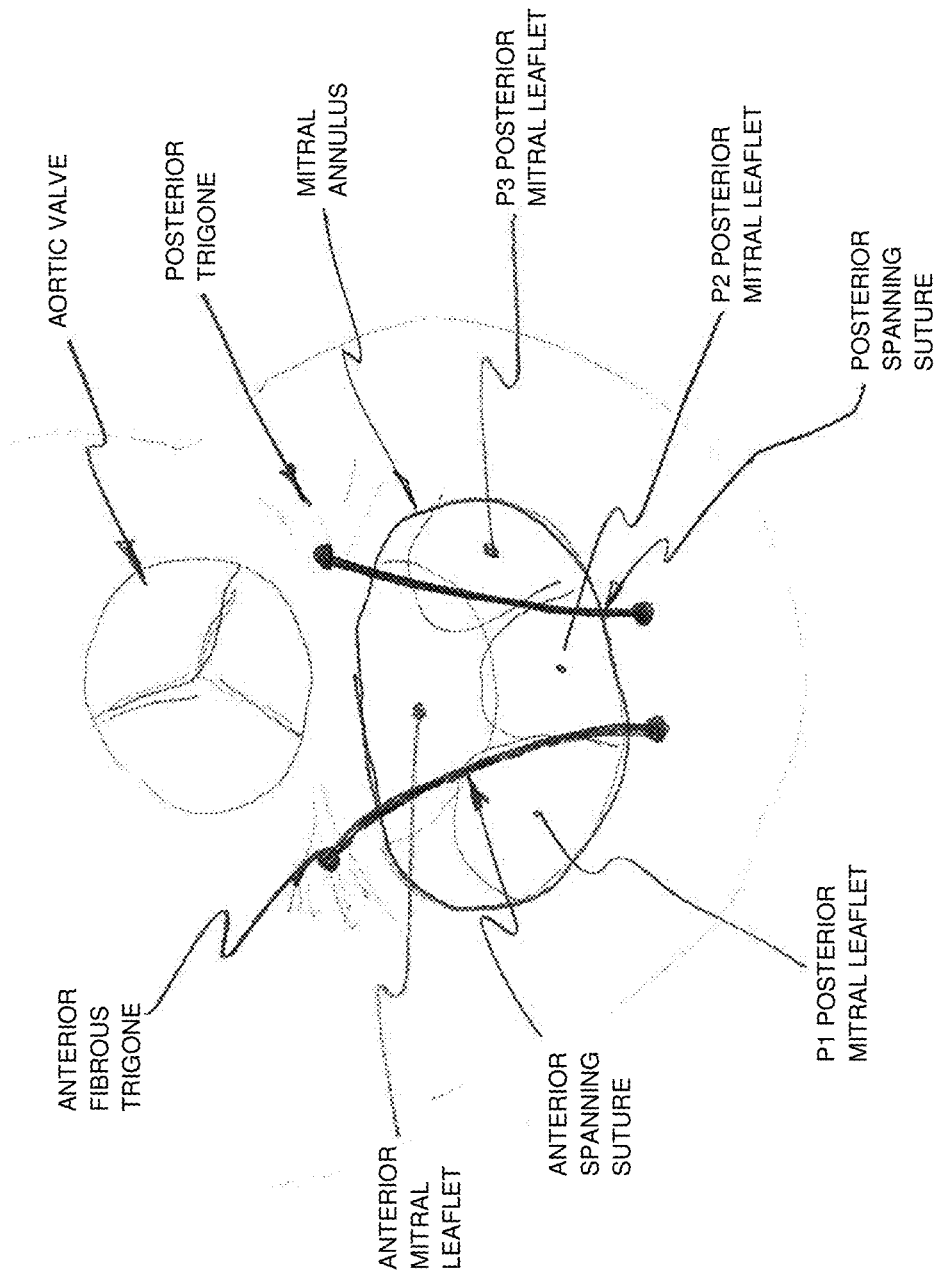
FIG. 40 is a schematic view showing multiple spanning implants deployed across the mitral valve.

Additional spanning implants may then be electively deployed across the mitral annulus as needed so as to provide correction in one or more other locations, to increase the A/P reduction as needed, and to distribute the A/P reduction forces among a greater number of spanning implants. See FIG. 40.

It should be appreciated that the sequence described above could, alternatively, be applied simultaneously to multiple spanning implants, in particular through the use of a "temporary" STTT on one spanning implant while a conventional, permanent-anchoring STTT is employed on a second spanning implant. Such an approach would provide the clinical advantage of allowing for more complete consideration of various geometric and structural changes to the valve. In a particular preferred embodiment of a multiple-spanning implant approach, one spanning implant would be placed from the posterior trigone to a position on the posterior annulus approximately at the intersection of the P2 and P3 cusps of the posterior leaflet. Similarly, a second spanning implant would be effected between the anterior trigone and a position on the posterior annulus approximately at the intersection of the P1 and P2 cusps. These two spanning implants would effect balanced control of the valve with respect to the central aortic-mitral structural axis.

To complete the procedure, the apical access sheath is removed and the apical and chest wall access closed and the patient recovered.

8. Grommets

It will be appreciated that spanning suture 120 of spanning implant 115 passes through opposing sides of the annulus, e.g., from the ventricular side of the anterior annulus into the left atrium, and from the left atrium across the posterior annulus into the left ventricle. If desired, "grommets", that is, various constructions of tissue-mediating devices, can be disposed in the annulus at the crossing points prior to passing spanning suture 120 through the annulus, with the grommets acting as protective liners to mitigate tissue erosion and trauma, and prevent suture migration or "pull through" across the annulus.

Figure 46:
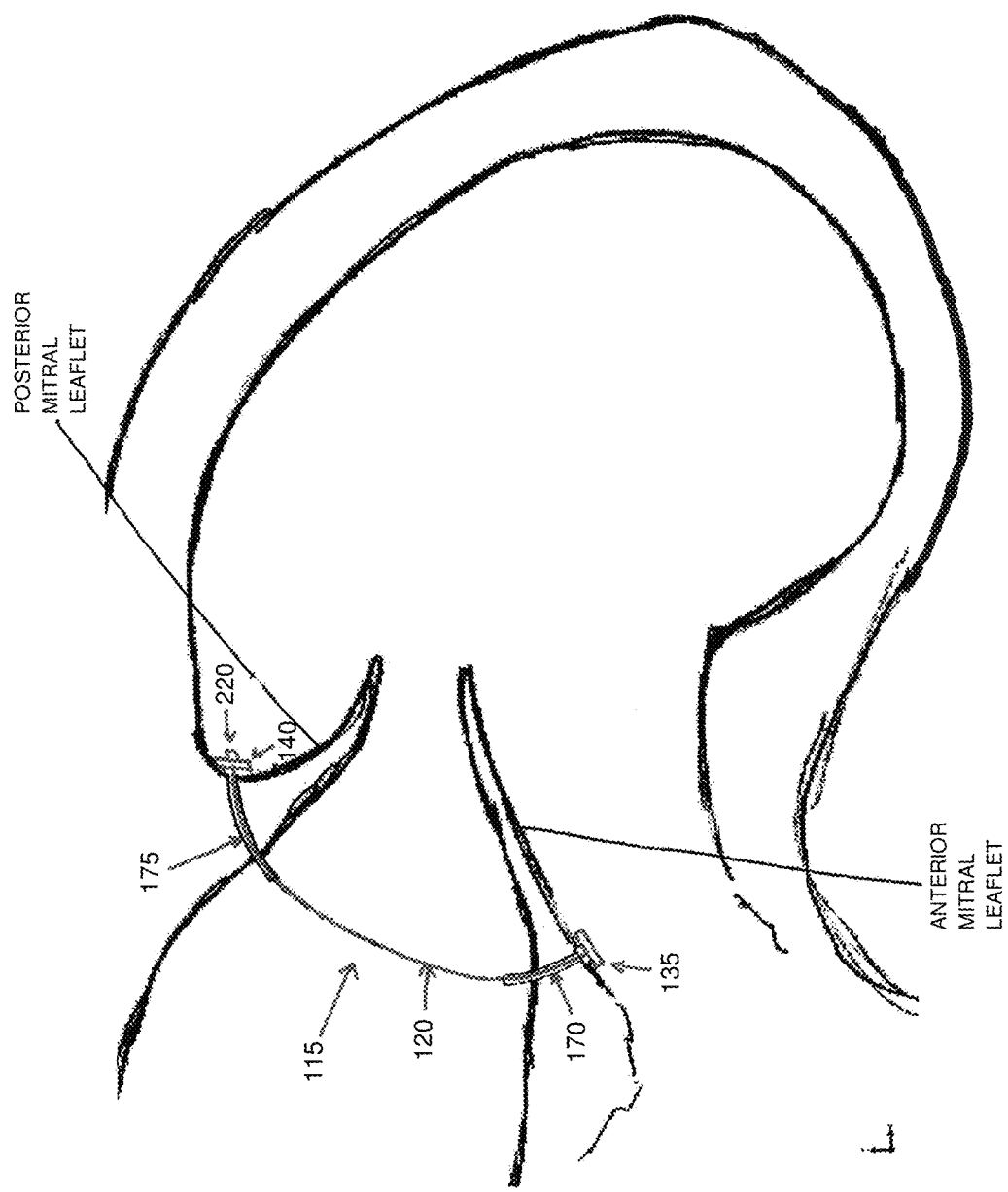
FIG. 46 is a schematic view showing a spanning implant extending across a mitral valve, wherein grommets are disposed in the mitral annulus.

In this form of the invention, after the crossing guidewire 45 has been positioned in the anatomy, and prior to routing spanning suture 120 across the anterior annulus, a tubular "tissue grommet" or dedicated pledget 170 (see FIG. 46) may be deployed across the annulus. Tissue grommet 170 may be advanced into position by loading the tissue grommet on crossing guidewire 45 and advancing the tissue grommet (e.g., with an advancing sheath) along crossing guidewire 45 so that tissue grommet 170 passes into, and spans, the anterior annulus. A corresponding tubular "tissue grommet" or dedicated pledget 175 may be deployed across the posterior annulus. Preferably the posterior tissue grommet is deployed after spanning suture 120 has been deployed, e.g., posterior grommet 175 is advanced (e.g., with an advancing sheath) over second end 130 of spanning suture 120 until the posterior tissue grommet is seated in, and spans, the posterior annulus.

The tissue grommets 170, 175 may consist of a PTFE sleeve, with an approximately 0.042 inch outer diameter, an approximately 0.014 inch inner diameter, and a flange at the ventricular end (to act as a stop during insertion of the tissue grommet into the annulus). Alternatively, the tissue grommet may have an additional cover of, or be completely formed out of, Dacron or ePTFE. In the preferred embodiment, similar tissue grommets are placed in the anterior annulus and the posterior annulus. In one preferred form of the invention, the tissue grommets 170, 175 are constructed so as to enable tissue in-growth into the surface of the grommets, thus enhancing the durability of spanning implant 115. It will also be appreciated that, after spanning implant 115 has been put in place, first, fixed anchor 135 will bear against the flange of anterior tissue grommet 170, second, sliding anchor 140 will bear against the flange of posterior tissue grommet 175, thereby ensuring that, even in the absence of tissue ingrowth, tissue grommets 170, 175 stay in place.

Figure 47:
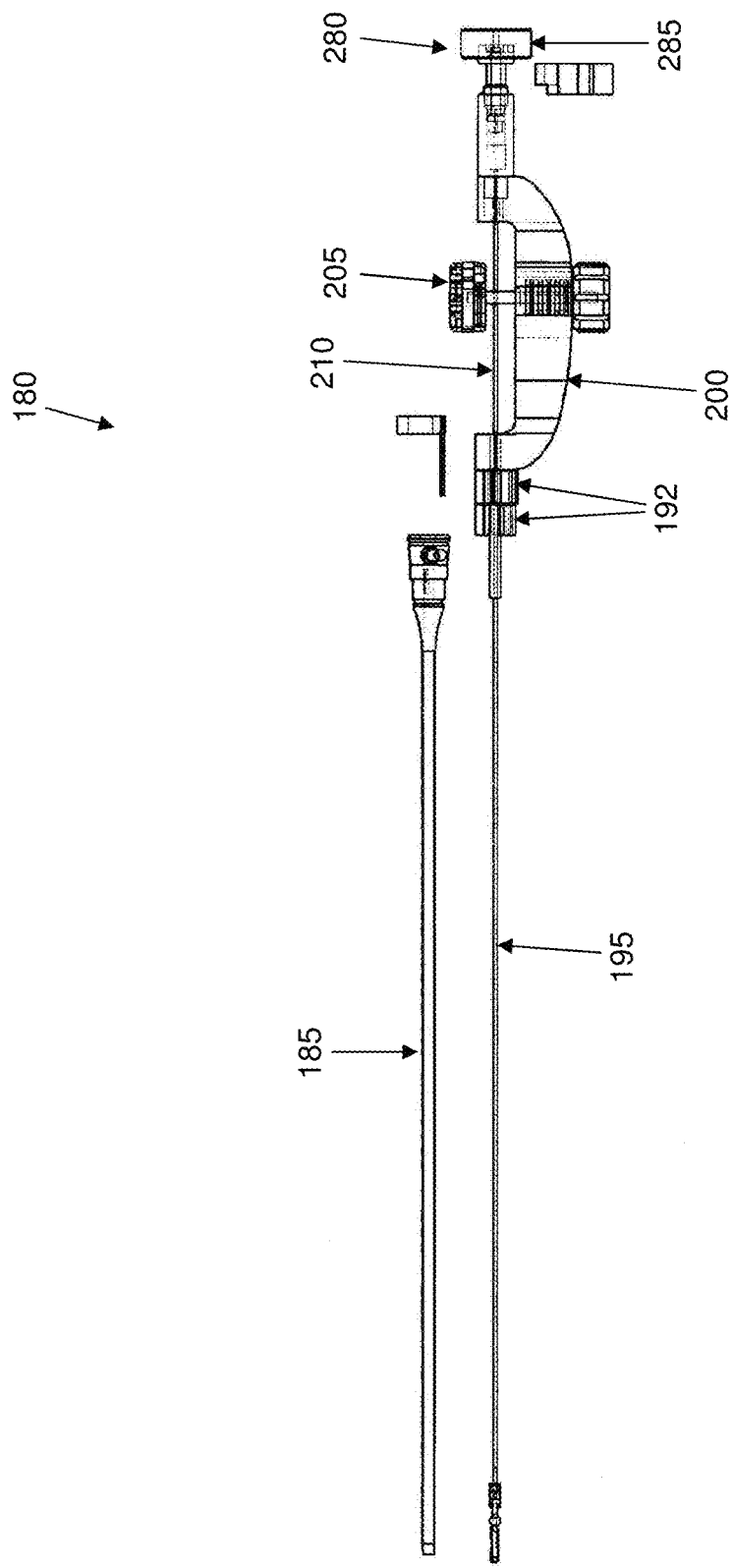
FIG. 47 is a schematic view showing another preferred form of "Span-Tension-Terminate Tool" (STTT) formed in accordance with the present invention.
Figure 48:
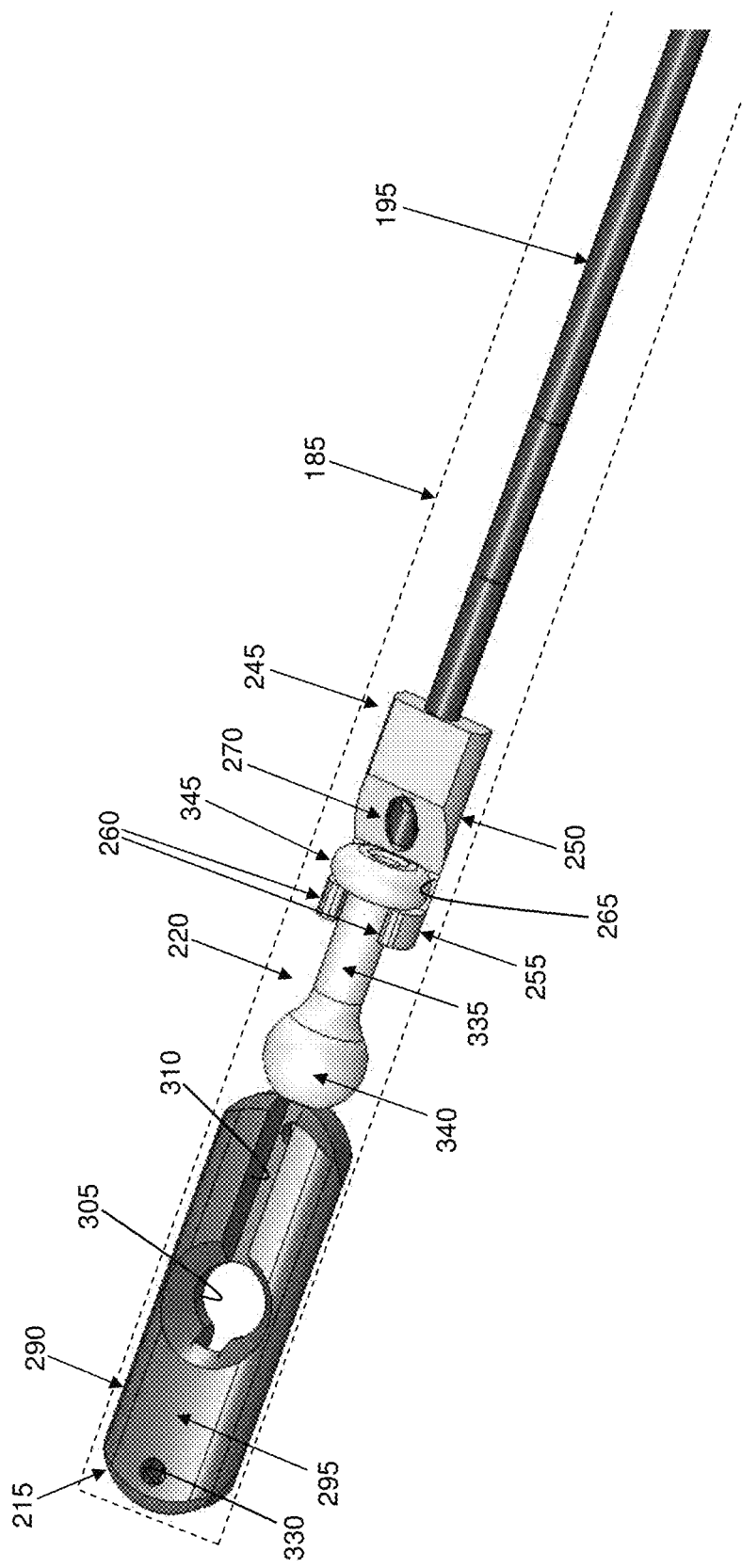
FIGS. 48 and 49 are schematic views showing a second, sliding anchor and a coaxial suture lock disposed within the STTT of FIG. 47.
Figure 49:
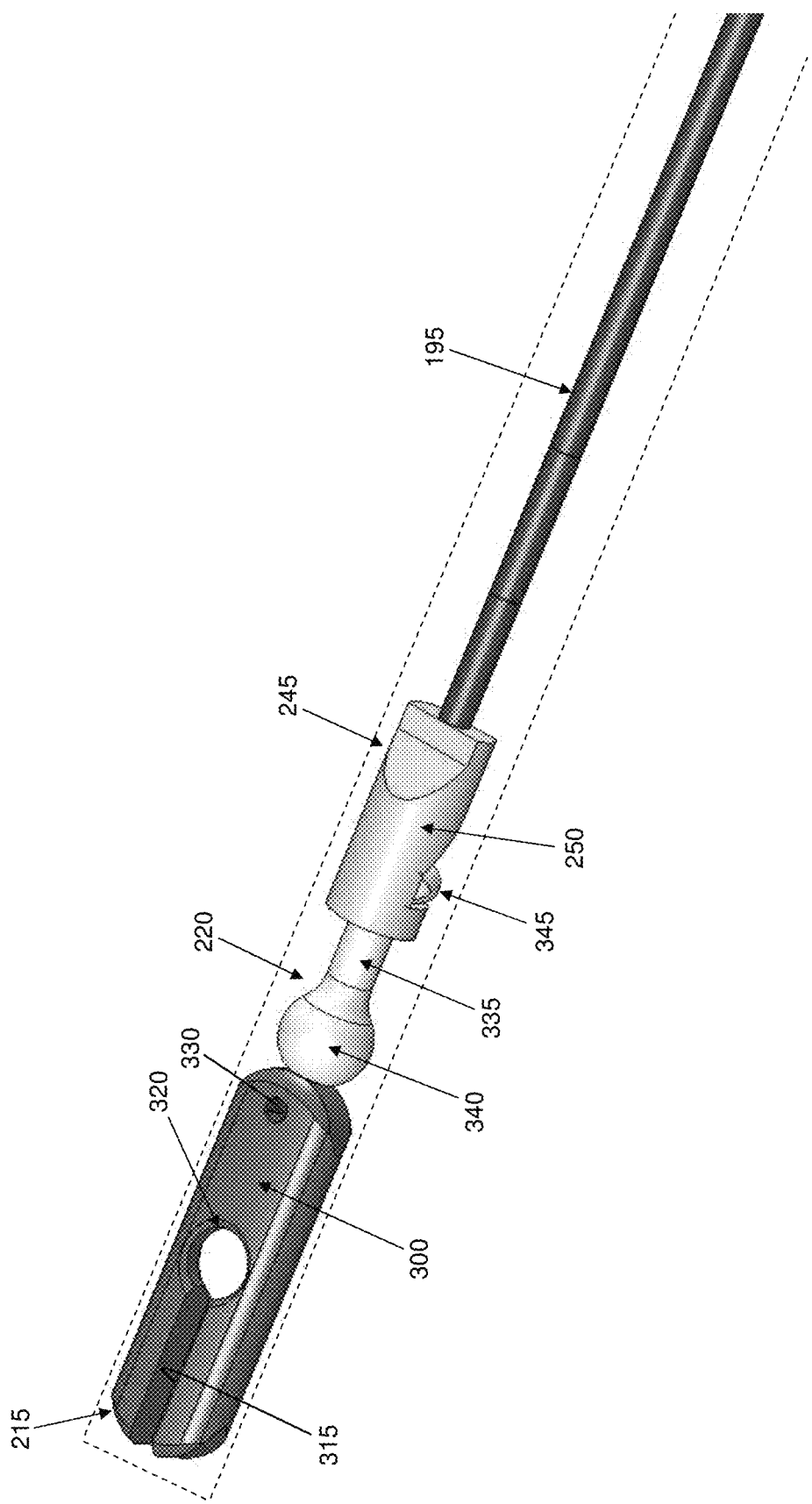
Figure 50:
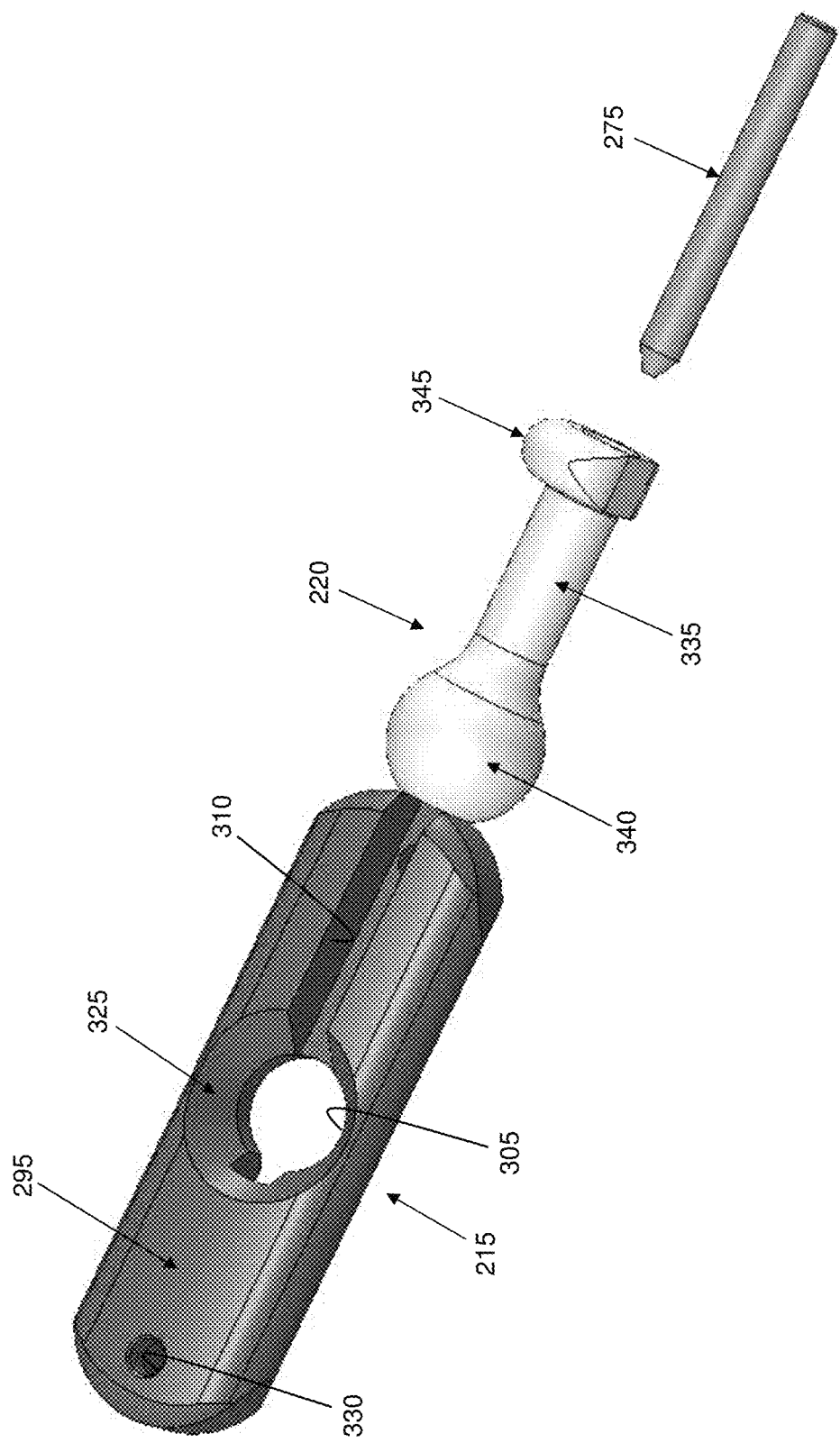
FIG. 50 is a schematic view showing further details of the second, sliding anchor and coaxial suture lock shown in FIGS. 48 and 49.
Figure 50A:
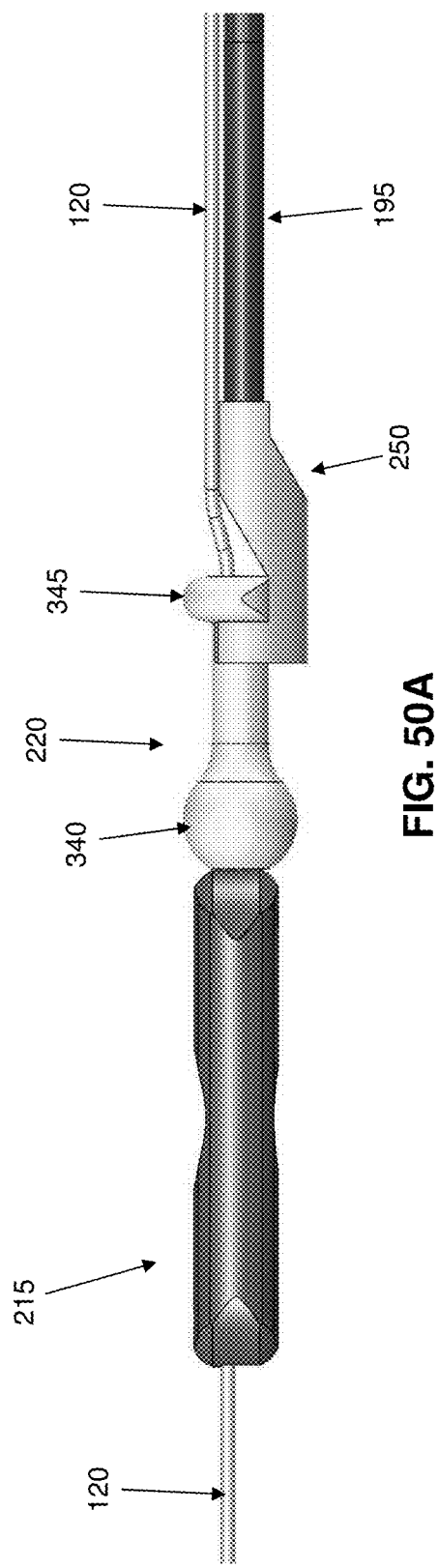
FIGS. 50A and 50B are schematic views showing the spanning suture routed through the STTT, passing through the second, sliding anchor and the coaxial suture lock.
Figure 50B:
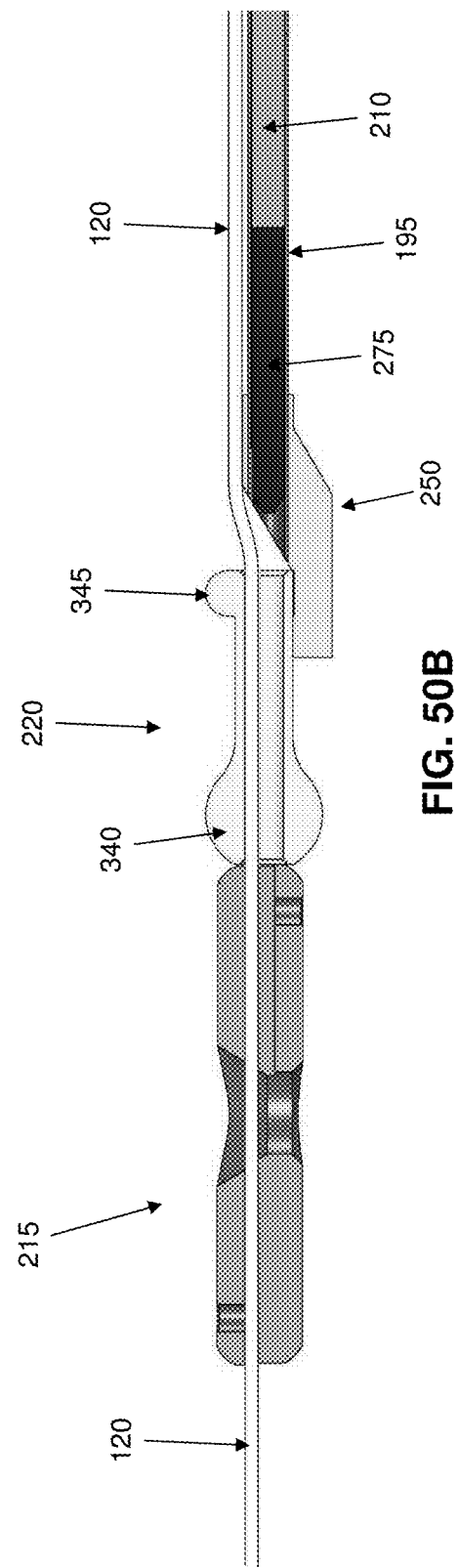
Figure 56:
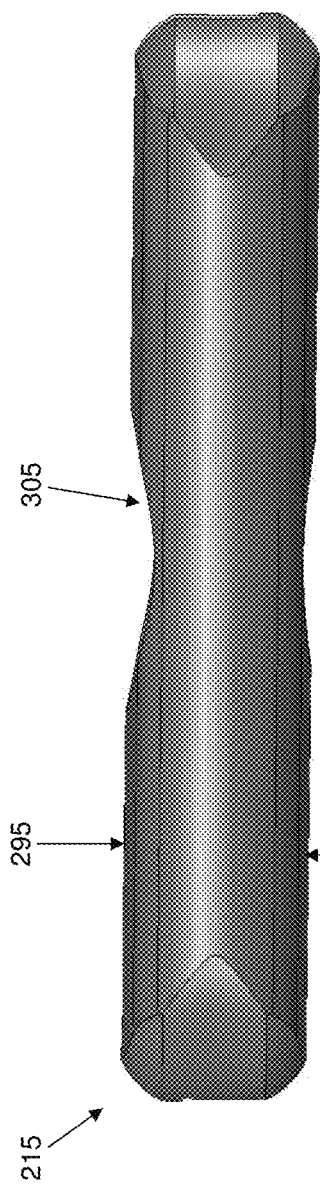
Figure 57:
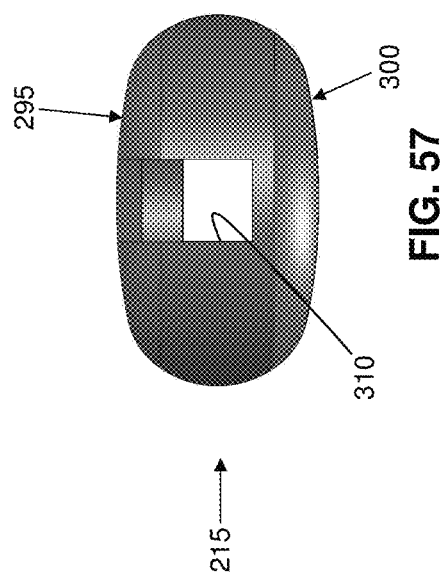

9. Alternative STTT with Alternative Sliding Second Anchor and Alternative Coaxial Suture Lock In one preferred embodiment, the implant tensioning and locking procedure is effected with a novel tool configuration referred to as the "Span-Tension-Terminate Tool" or the "STTT". The STTT allows the clinician to controllably track into the left ventricle and place the second, sliding anchor against the ventricular side of the posterior annulus, controllably tension spanning suture 120, and then terminally lock the coaxial suture lock, thus anchoring the spanning suture in position across the mitral valve. In one preferred embodiment, there is provided an STTT 180 which generally comprises a sheath 185, a hemostasis element 190, one or more removable spacers 192, a drive tube 195, a handle 200 carrying a suture tensioning mechanism 205, and a pusher 210. See FIG. 47. In one preferred embodiment, STTT 180 carries a second, sliding anchor 215 and a coaxial suture lock 220. See FIGS. 48-50. Spanning suture 120 is routed through STTT 180, passing through second, sliding anchor 215 and coaxial suture lock 220. See FIGS. 50A and 50B, which show second, sliding anchor 215 and coaxial suture lock 220 disposed within sheath 185, with spanning suture 120 routed through STTT 180 and passing through second, sliding anchor 215 and coaxial suture lock 220. See also FIGS. 50C and 50D, which are similar to FIGS. 50A and 50B, but with sheath 185 removed.

Sheath 185 preferably comprises an overall 7-11 Fr reinforced sheath to facilitate control and delivery of second, sliding anchor 215 and coaxial suture lock 220. The length of sheath 185, in conjunction with removable spacers 192, aligns the distal end of second, sliding anchor 215 with the distal end of sheath 185 so as to form a smooth end for advancing the assembly through cardiac anatomy. Sheath 185 is preferably sized so that there is slight interference fit with second, sliding anchor 215 so that second, sliding anchor 215 is retained within sheath 185 until it is deployed by the clinician.

In one preferred form of the present invention, sheath 185 comprises a form-fitting, stretchable (preferably elastomeric) sheath, preferably formed out of a polymer, making a stretch fit about second, sliding anchor 215, coaxial suture lock 220 and other elements of STTT 180 (e.g., seat 250, disposed at the end of drive tube 195, for releasably receiving coaxial suture lock 220, as hereinafter discussed). In this way, sheath 185 has the smallest possible diameter, thus facilitating atraumatic advance of STTT 180 through the left ventricle. Furthermore, by virtue of its form-fitting, stretchable construction, sheath 185 can releasably grip various elements disposed therein (e.g., second, sliding anchor 215, coaxial suture lock 220, etc.), whereby to assist in the control of such elements. With reference to FIG. 50D, position "A-A" is the fully distal position of sheath 185 (see below). The distal margin of sheath 185 stretches so as to intimately fit to the outer diameter of second, sliding anchor 215, thus, the two elements, in combination, presenting a smooth distal transition comprising the rounded end of second, sliding anchor 215 merging directly to the stretched sheath 185. Thus, the distal tip of second, sliding anchor 215 effectively forms an atraumatic "obturator tip" for sheath 185. Position "B-B" is the partially-retracted position of sheath 185 (see below), which is employed to release second, sliding anchor 215 and establish a smooth distal aspect for the system comprising the spherical distal end 340 (see below) of coaxial suture lock 220 merging with the stretched sheath 185. Thus, with second, sliding anchor 215 released from sheath 185, spherical distal end 340 of coaxial suture lock 220 effectively forms an atraumatic "obturator tip" for sheath 185. Note that in both of the aforementioned positions "A-A" and "B-B", the stretched sheath 185 is, at the same time, also serving to securely hold the D-shaped annular ring 345 of coaxial suture lock 220 (see below) in seat 250 (see below), awaiting final drive of locking pin 275 of coaxial suture lock 220 (see below). Position "C-C" is the fully retracted position of sheath 185 when coaxial suture lock 220 is released from seat 250 (see below) following the locking pin 275 being driven into position in coaxial suture lock 220 (see below).

STTT 180 is preferably fitted with a hemostasis element 190 (see FIGS. 51 and 51A) to functionally supplement the integral hemostasis in the sheath 185. Hemostasis element 190 preferably comprises a tubular section 225 having a lumen 230 formed therein and handle 235 formed thereon. Lumen 230 contains sheath 185 and is sized about 0.004" or 0.007" larger than the sheath it receives. The small clearance provides hemostasis when STTT 180 is in place without the friction associated with standard access sheath hemostasis valves. Handle 235 allows hemostasis element 190 to be readily engaged or removed by the clinician.

Spanning suture 120 is routed coaxially through STTT 180 and through a suture passage 240 formed in tubular section 225 of hemostasis element 190 and emerges in the area of handle 235.

Drive tube 195 comprises a distal end 245 carrying a seat 250 for releasably receiving coaxial suture lock 220. See FIGS. 48, 49, 52 and 53. More particularly, seat 250 comprises a fork 255 including a pair of raised tines 260 for receiving the body of coaxial suture lock 220 as will hereinafter be discussed, a transverse slot 265 for receiving the proximal end of coaxial suture lock 220 as will hereinafter be discussed and a camming surface 270 for selectively releasing coaxial suture lock 220 from seat 250 as will hereinafter be discussed. In one preferred embodiment, drive tube 195 is constructed out of stainless steel or Nitinol tubing of approximately 0.038" OD and 0.032" ID.

Drive tube 195 preferably comprises a handle 200 at its proximal end for manipulating drive tube 195.

The suture tensioning mechanism 205 is mounted to handle 200. The suture tensioning mechanism 205 receives the free end of spanning suture 120 so that tension may be selectively applied to the free end of spanning suture 120. More particularly, it is clinically desirable to provide for the controlled addition of tension to spanning suture 120 by the controlled withdrawal of spanning suture 120 out through STTT 180. It is desirable that the level of precision of suture withdrawal allow the clinician to increment suture withdrawal in steps of approximately one millimeter, or preferably less, by withdrawing the suture, and also to be able to pause, or controllably reverse, the suture withdrawal process at any time during the procedure and with the expectation that STTT 180 will stably maintain the position of spanning suture 120. In one preferred embodiment of the present invention, suture tensioning mechanism 205 is provided, and suture tensioning mechanism 205 comprises a one-way drive mechanism to allow spanning suture 120 to be controllably withdrawn by spooling the spanning suture about a shaft so as to alter the anterior-posterior dimension of the mitral valve. A preferred embodiment comprises one-way clutches mounted within handle 200. Such one-way clutches are commercially available and provide bearing and clutch functions. One or more clutches may be used. Optionally, the clutches may be mounted to handle 200 such that they may be forcibly rotated so as to provide a back-drive function to remove tension from spanning suture 120. This may be done by mounting the clutches to handle 200 with compressed O-rings or other material that provides for a limited slip function. The O-ring retention force may be set to be much greater than necessary for mitral valve dimensional correction or inadvertent handling, but less than intentional clinician manipulation to remove suture tension.

The suture tensioning mechanism 205 preferably comprises a suture tie-down which provides features to retain the free end of the spanning suture 120 during the tensioning and terminating processes. One preferred form of suture tie-down comprises a flexible element that has one or multiple slits that retain the free end of the spanning suture when the spanning suture has been slid into the slits. The flexible element may be formed from silicone, urethane, thermoplastic elastomer or other similar rubber-like materials. Each slit has a lead-in feature so that the spanning suture may be easily inserted into the slit. The spanning suture may be wound around the suture tie-down so that multiple slits are used. The flexible element may be held between two rigid disks, and they are all mounted on a single drive shaft. Alternatively, other forms of suture tie-downs may be provided, e.g., a suture cleat.

Pusher 210 is disposed within drive tube 195 and serves to selectively advance a locking pin 275 of coaxial suture lock 220 as will hereinafter be discussed. Pusher 210 is preferably constructed out of stainless steel, Nitinol, or titanium wire of, in a practical embodiment, 0.031" diameter. As will hereinafter be discussed in further detail, pusher 210 is disposed within drive tube 195, proximal to locking pin 275 of coaxial suture lock 220, and is used to selectively advance locking pin 275 into coaxial suture lock 220 so as to create a binding interference fit between coaxial suture lock 220 and spanning suture 120, whereby to fix the position of spanning suture 120 relative to second, sliding anchor 215 and thus permanently fix the length of spanning suture 120 extending across the mitral valve. In one preferred form of the invention, pusher 210 can be advanced by simple manual pushing. In another preferred form of the present invention, pusher 210 can be advanced via an advancer mechanism 280 which controllably advances pusher 210 for deployment of locking pin 275 into coaxial suture lock 220. One preferred construction for advancer mechanism 280 comprises a threaded knob 285 which is secured to pusher 210. The distal end of threaded knob 285 is received in a threaded bore in handle 200. When threaded knob 285 is rotated, the threads of threaded knob 285 engage with the threaded bore in handle 200 so as to drive threaded knob 285, and hence pusher 210, distally or proximally. When threaded knob 285 is fully advanced to its most distal position, additional distal advancement of pusher 210 is prohibited.

Figure 58:
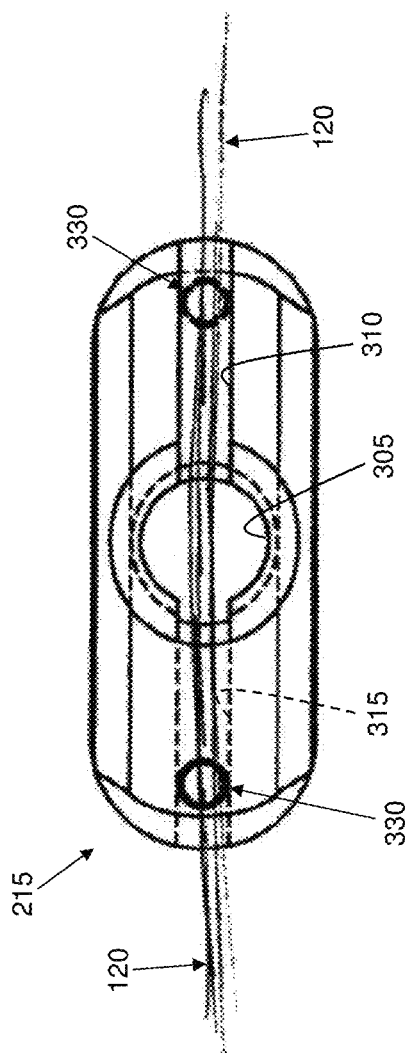
Figure 59:
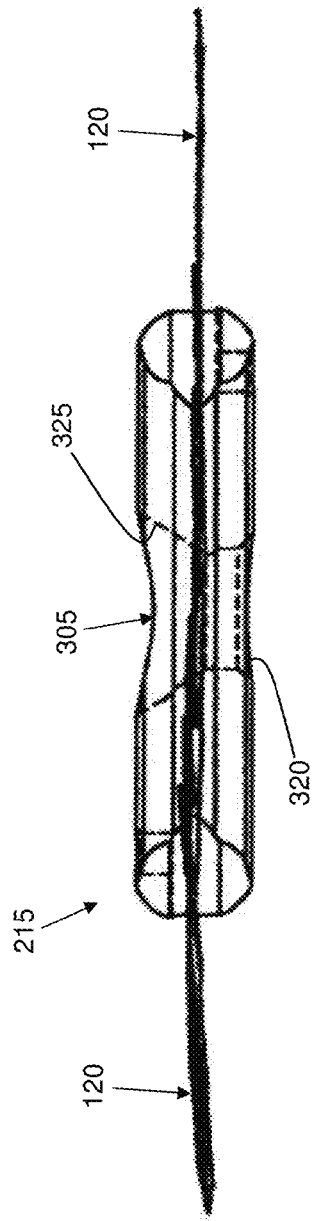

In one preferred form of the invention, second, sliding anchor 215 comprises a body 290 having a smooth and rounded profile in all three dimensions whereby to best effect both delivery and atraumatic permanent implantation. See FIGS. 48-50 and 54-59. Second, sliding anchor 215 comprises a first side 295, a second side 300 and a generally central through-hole 305 from where spanning suture 120 will ultimately emerge. In one preferred form of the invention, in order to maintain as small a crossing profile as possible during delivery through sheath 185, first side 295 comprises a proximal slot 310 extending from central through-hole 305 to the proximal end of second, sliding anchor 215, and second side 300 comprises a distal slot 315 extending from central through-hole 305 to the distal end of second, sliding anchor 215. The slots 310, 315 are deep enough, and aligned with one another, so that they "overlap" and thereby provide a continuous axial passage sufficiently large to transit spanning suture 120 through second, sliding anchor 215 without interference. See FIGS. 58 and 59. This allows second end 130 of spanning suture 120 to reside parallel and coaxial to second, sliding anchor 215 and within the anchor's profile when second, sliding anchor 215 is contained within sheath 185. Furthermore, on account of this construction, and as will hereinafter be discussed in further detail, after second, sliding anchor 215 is deployed from sheath 185, second, sliding anchor 215 may rotate away from the spanning suture so that the second, sliding anchor 215 is substantially perpendicular to the adjacent spanning suture 120. Central through-hole 305 preferably comprises chamfers on either side of the central through-hole. These chamfers may be of equivalent size or, more preferably, one chamfer may be larger and one chamfer may be smaller. By way of example but not limitation, a smaller chamfer 320 on second side 300 provides a smooth exit profile for spanning suture 120 to exit from second, sliding anchor 215. A larger chamfer 325 on first side 295 provides a seating surface for the distal end of coaxial suture lock 220. In one preferred embodiment, second, sliding anchor 215 may be provided with one or more additional through-holes 330 to allow the elective fitting of a control suture (not shown) through second, sliding anchor 215 on one or the other end (or both ends) of the anchor.

Looking next at FIGS. 48-50 and 60-63, there is shown coaxial suture lock 220. In one preferred embodiment, coaxial suture lock 220 comprises a tubular element 335 having a spherical distal end 340 and a D-shaped annular ring 345 at its proximal end. Coaxial suture lock 220 also comprises the aforementioned associated locking pin 275. Coaxial suture lock 220 and/or its associated locking pin 275 may be formed out of stainless steel, titanium, Nitinol, or similar materials suitable for permanent implantation. The spherical distal end 340 of coaxial suture lock 220 engages the proximal end of second, sliding anchor 215 when second sliding anchor 215 and coaxial suture lock 220 are disposed in sheath 185, and spherical distal end 340 seats in larger chamfer 325 of through-hole 305 of second, sliding anchor 215 when second, sliding anchor 215 is fixed on spanning suture 120. It should be appreciated that, given the complex topology of the mitral annular groove on the ventricular side of the annulus, second, sliding anchor 215 and the through-running spanning suture 120 may be disposed at a wide range of angles. The spherical distal end 340 of coaxial suture lock 220 allows a wide range of angular orientations between coaxial suture lock 220 and the larger chamfer 325 of second, sliding anchor 215 when the second, sliding anchor 215 is engaged with the tissue, without inducing undesirable chafing of the spanning suture against the exit chamfer of the second, sliding anchor. Tubular element 335 of coaxial suture lock 220 is received in fork 255 of seat 250, and D-shaped annular ring 345 at the proximal end of coaxial suture lock 220 is received in transverse slot 265, whereby to preferentially retain coaxial suture lock 220 in seat 250 prior to the release of second, sliding anchor 215 from sheath 185. Tubular element 335 of coaxial suture lock 220 has a cylindrical bore 355 which is sized to slidably receive the spanning suture when second sliding anchor 215 and coaxial suture lock 220 are disposed in sheath 185, and to fixedly receive the spanning suture and locking pin 275 when second, sliding anchor 215 is fixed on spanning suture 120. More particularly, when locking pin 275 is advanced into cylindrical bore 355 of coaxial suture lock 220, the locking pin compresses spanning suture 120 radially within the cylindrical bore 355 of tubular element 335 of the coaxial suture lock 220 and thereby forms an interference fit between spanning suture 120 and coaxial suture lock 220, whereby to fix the disposition of spanning suture 120 relative to second, sliding anchor 215. It will be appreciated that locking pin 275 may be a solid cylinder or tubular in construction. Locking pin 275 preferably has a tapered feature on its distal end to help lead-in the locking pin within coaxial suture lock 220.

In use, after spanning suture 120 has been passed through the anterior annulus and the posterior annulus, with first, fixed anchor 135 seated against the ventricular side of the anterior annulus, the free end (i.e., second end 130) of spanning suture 120 is routed through second, sliding anchor 215 and coaxial suture lock 220. Preferably this is done while second, sliding anchor 215 and coaxial suture lock 220 are loaded in STTT 180. This may be facilitated by first positioning a loading loop (not shown) through coaxial suture lock 220 and second, sliding anchor 215 so that a loading loop is disposed on the distal end of second, sliding anchor 215, with the loading loop emerging from the distal end of STTT 180. Free end 130 of spanning suture 120 is threaded through the loading loop, and the loading loop is then pulled from the proximal end until free end 130 of spanning suture 120 emerges from STTT 180.

Spanning suture 120 is then routed through hemostasis element 190. Note that the suture hemostasis provided by hemostasis element 190 has the significant advantage over a conventional hemostasis valve in that there is no friction on the proximal leg of the spanning suture so that tension of the spanning suture reflects the forces applied to the mitral valve.

STTT 180 is then advanced through apical access sheath 5 to proximate the ventricular side of the posterior annulus. Spanning suture 120 is then fixed to STTT 180 by looping the free end of the spanning suture through one or multiple slits of the suture tie-down. Spanning suture 120 is then tensioned by suture tensioning mechanism 205 of STTT 180. This progressive tensioning of spanning suture 120 progressively decreases the anterior-posterior dimension of the mitral valve, and hence progressively decreases mitral regurgitation. Distance increment markers (not shown) integrated into handle 200 of STTT 180 provide feedback to the clinician.

Figure 64:
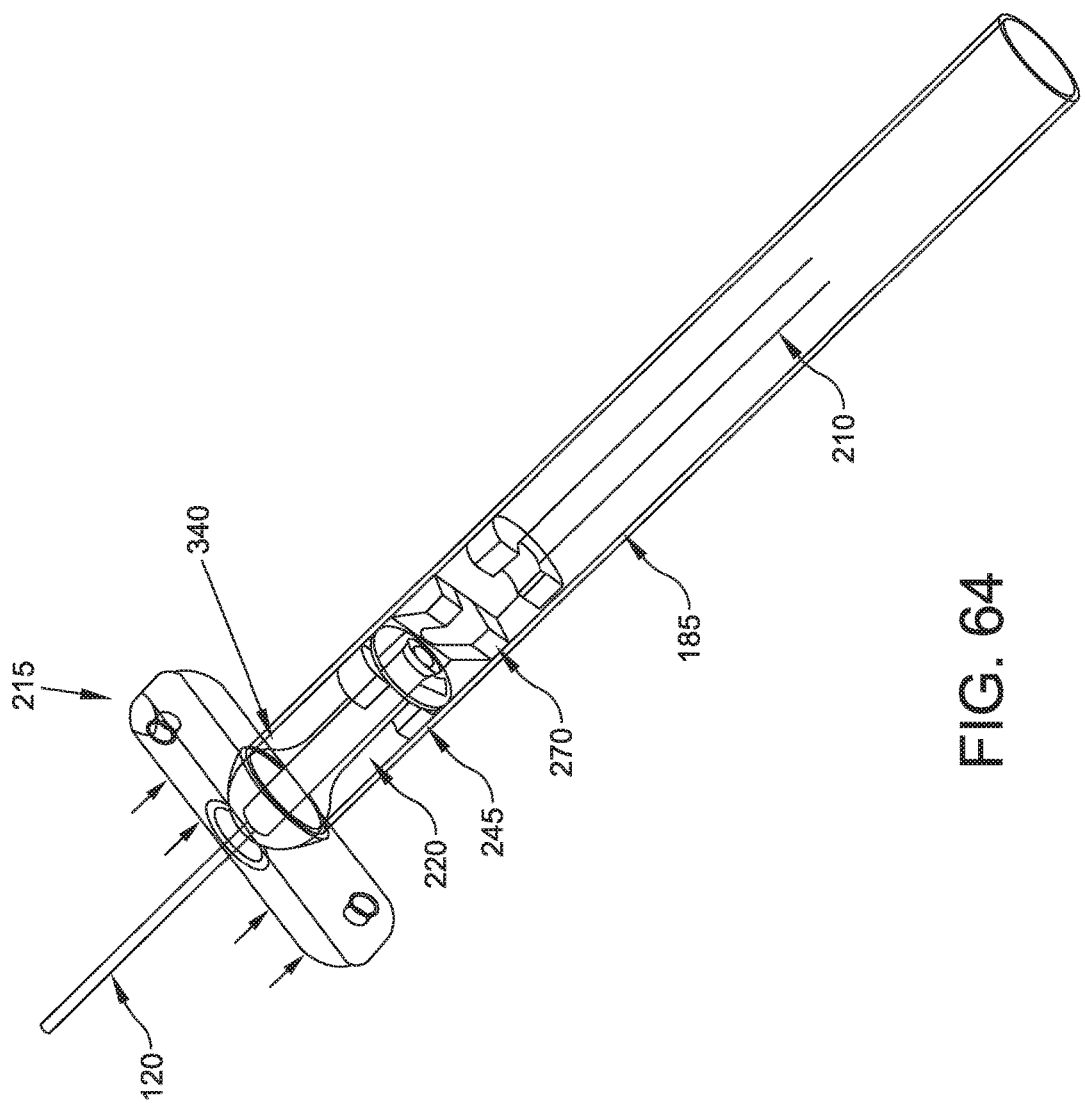
FIGS. 64-66 are schematic views showing the spanning suture locked to the second, sliding anchor of FIGS. 48 and 49 using the coaxial suture lock of FIGS. 48 and 49.
Figure 65:
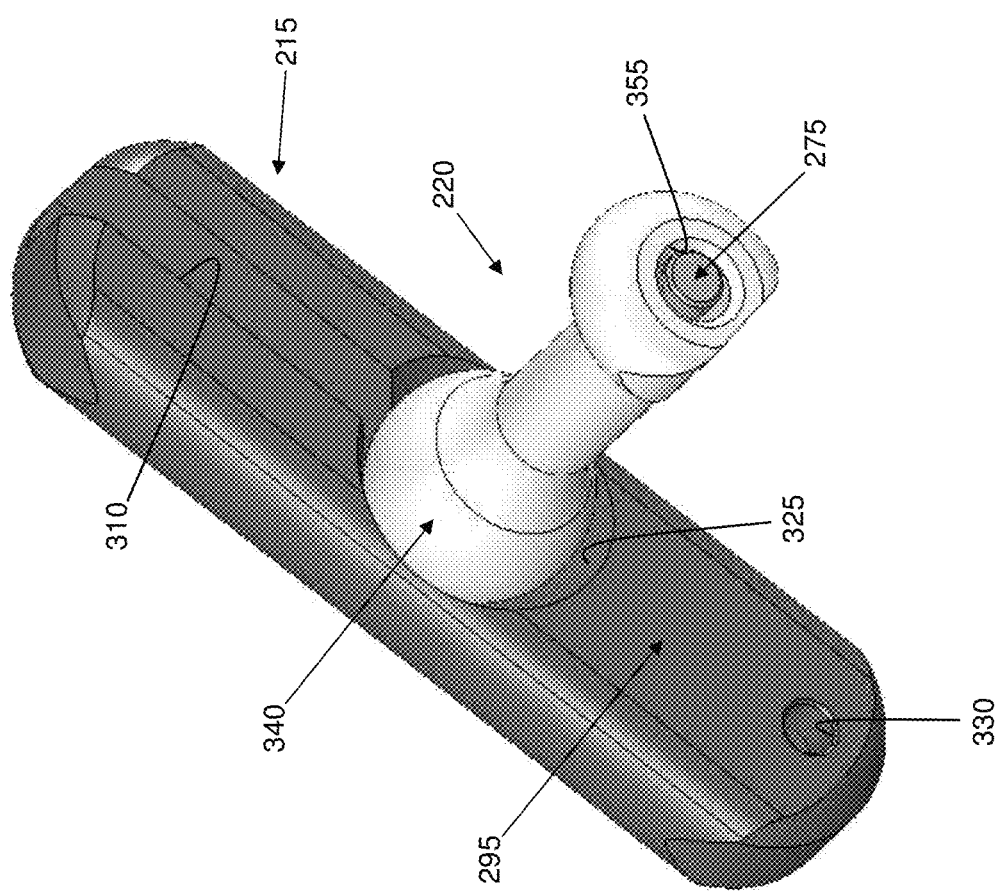
Figure 66:
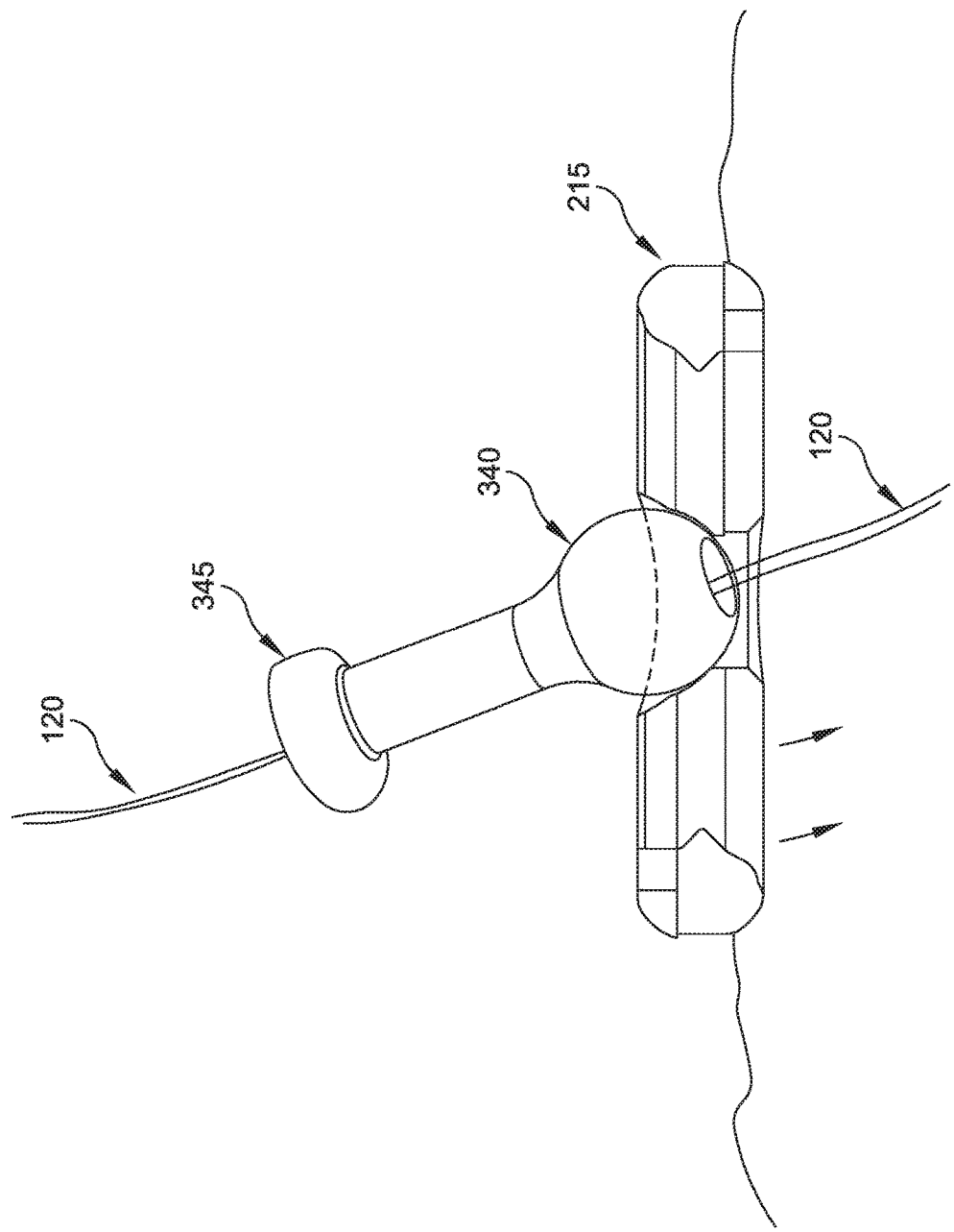

Once spanning suture 120 has been tensioned to the point where the mitral valve has been appropriately reconfigured, the one or more removable spacers 192 are removed and sheath 185 is retracted so as to free second, sliding anchor 215 from the constraint of sheath 185. With tension maintained on the free end of spanning suture 120, drive tube 195 is moved distally. As drive tube 195 is moved distally, seat 250 is moved distally, whereby to move coaxial suture lock 220 distally (note that inasmuch as the D-shaped annular ring 345 of coaxial suture lock 220 and seat 250 are held within sheath 185, coaxial suture lock 220 is bound to seat 250). This causes second, sliding anchor 215 to "tip over" into place against the ventricular side of the posterior mitral annulus, and spherical distal end 340 of coaxial suture lock 220 nestles into larger chamfer 325 of second, sliding anchor 215. See FIG. 64. Threaded knob 285 is then turned to move pusher 210 distally, which advances locking pin 275 into cylindrical bore 355, whereby to create an interference fit between locking pin 275, spanning suture 120 and coaxial suture lock 220. See FIG. 65. Coaxial suture lock 220 is then released from STTT 180 by removing one or more additional removable spacers 192 and further retracting sheath 185. This uncovers coaxial suture lock 220 and the coaxial suture lock easily swings free of fork 255 and transverse slot 265 of seat 250. If desired, pusher 210 can be moved distally slightly, causing D-shaped annular ring 345 of coaxial suture lock 220 to engage camming surface 270, whereby to assist dismounting coaxial suture lock 220 from seat 250. Note that spherical distal end 340 of coaxial suture lock 220 is able to set into larger chamfer 325 of second, sliding anchor 215 at a variety of angles so as to accommodate a wide range of patient anatomies. See FIG. 66.

Spanning suture 120 is then freed from the suture tie-down of suture tensioning mechanism 205 of STTT 180. STTT 180 may then be removed from the surgical site.

Thus it will be seen that the process of freeing second, sliding anchor 215 and coaxial suture lock 220 from STTT 180 consists of several primary functional steps. First, after STTT 180 has been tracked into position proximate to the ventricular side of the posterior annulus, sheath 185 is retracted a sufficient distance to free second, sliding anchor 215 from sheath 185. The length of sheath retraction can be controlled by various means, e.g., with the preferred construction of the present invention, by means of one or more removable spacers 192 of correct length, such that when the spacers are removed, sheath 185 can be retracted the intended distance. Second, after coaxial suture lock 220 has been secured in place against second, sliding anchor 215, sheath 185 is retracted a further sufficient distance to free coaxial suture lock 220 from seat 250, e.g., with the preferred construction of the present invention, by means of one or more additional removable spacers 192 that allow for the desired magnitude of controlled removal of sheath 185 to release coaxial suture lock 220 from seat 250.

Additional spanning implants may then be deployed across the mitral valve as required to further adjust the configuration of the mitral annulus and hence reduce mitral regurgitation.

Figure 67:
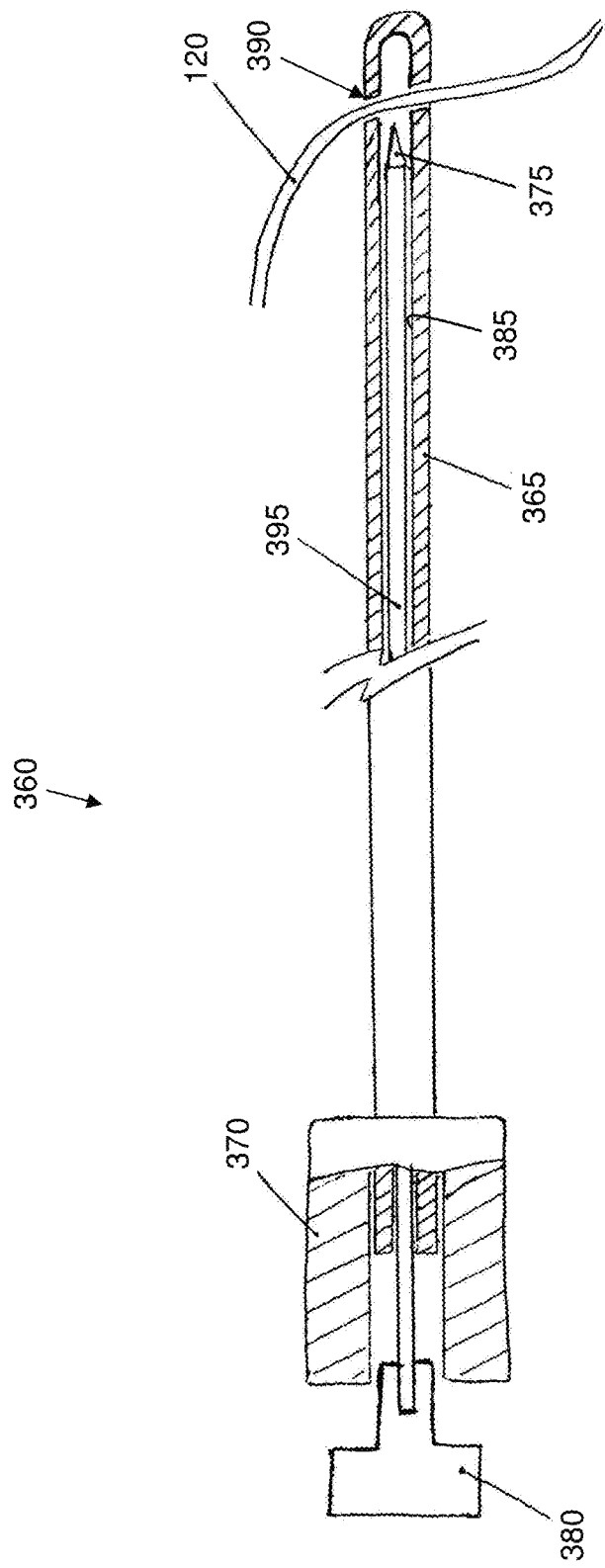
FIGS. 67 and 68 are schematic views showing various suture trimming tools formed in accordance with the present invention.

A suture trimming tool is then preferably used to cut spanning suture 120 proximal to coaxial suture lock 220. In one preferred form of the invention, and looking now at FIG. 67, a suture trimming tool 360 generally comprises an outer sheath 365 extending distally from a handle 370, and an inner cutting blade 375 extending distally from an actuator 380. Outer sheath 365 has an internal lumen 385 and is preferably approximately 6-9 Fr in size of flexible construction such as from a polymer, rubber, thermoplastic elastomer, or a combination of such materials, and may comprise a braid, coil, or other stiffening element. Outer sheath 365 comprises a side opening 390 at the distal tip though which spanning suture 120 is inserted. Side opening 390 may be a slot, diametrically-opposed holes, etc. Inner cutting blade 375 resides in the internal lumen 385 of outer sheath 365 and has its distal blade oriented perpendicular or diagonal to the axis of outer sheath 365. A long, flexible pusher section 395 connects inner cutting blade 375 to actuator 380.

If desired, outer sheath 365 of suture trimming tool 360 may be fitted with a dedicated pre-fitted accessory hemostasis device to temporarily supplement the permanently-fitted hemostasis valve in the proximal end of apical access sheath 5.

In use, spanning suture 120 is inserted through side opening 390 of suture trimming tool 360 while in the operative field. Suture trimming tool 360 is then advanced into apical access sheath 5, and the suture trimming tool is advanced down to coaxial suture lock 220. While slight tension is applied to the free end of spanning suture 120, inner cutting blade 375 is advanced and the free end of the spanning suture is cut away. The excess suture and suture trimming tool are then removed from the surgical site.

In one preferred embodiment, locking features may be provided to prevent inadvertent advance of the inner blade until the suture is ready to be cut. This may be accomplished by sliding or rotational elements or by other means.

And in one preferred embodiment, suture trimming tool 360 may include a suture retracting wire 400 movably disposed within outer sheath 365 for applying tension to spanning suture 120 during cutting.

10. Alternative First, Fixed Anchor

Figure 68:
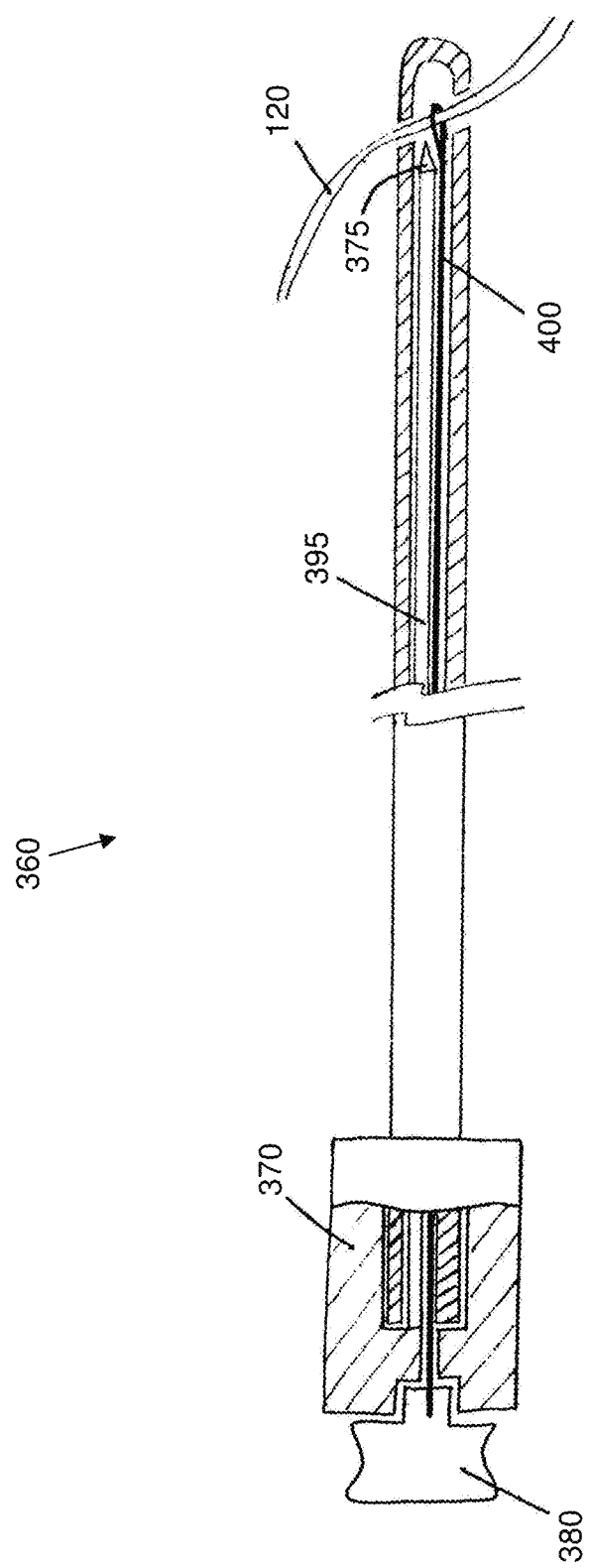
Figure 68D:
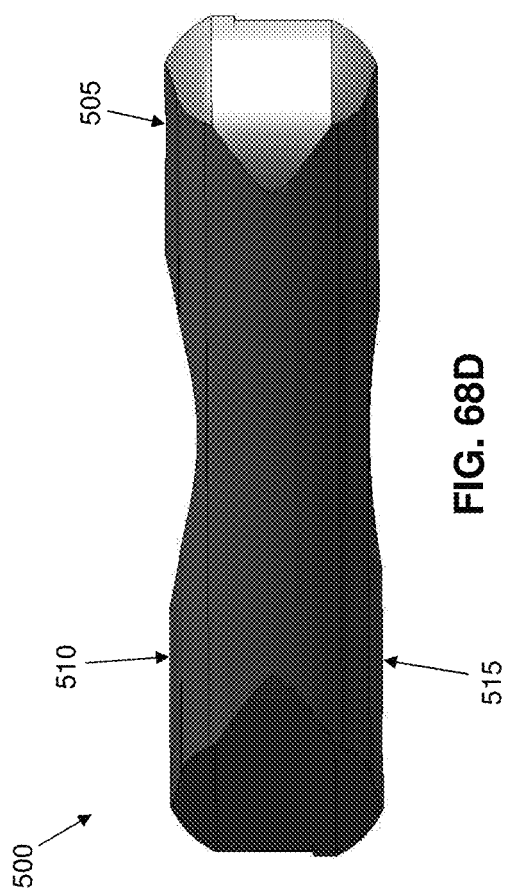
Figure 68E:
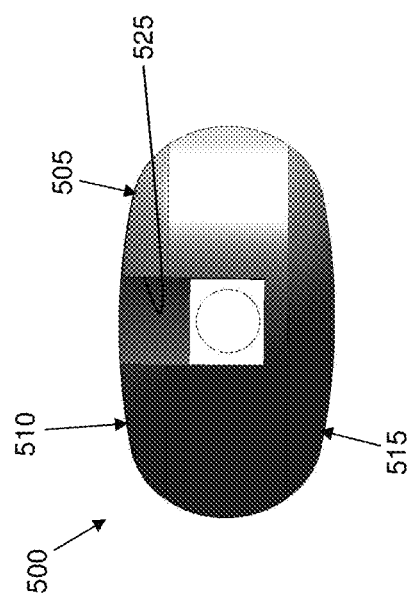
Figure 68F:
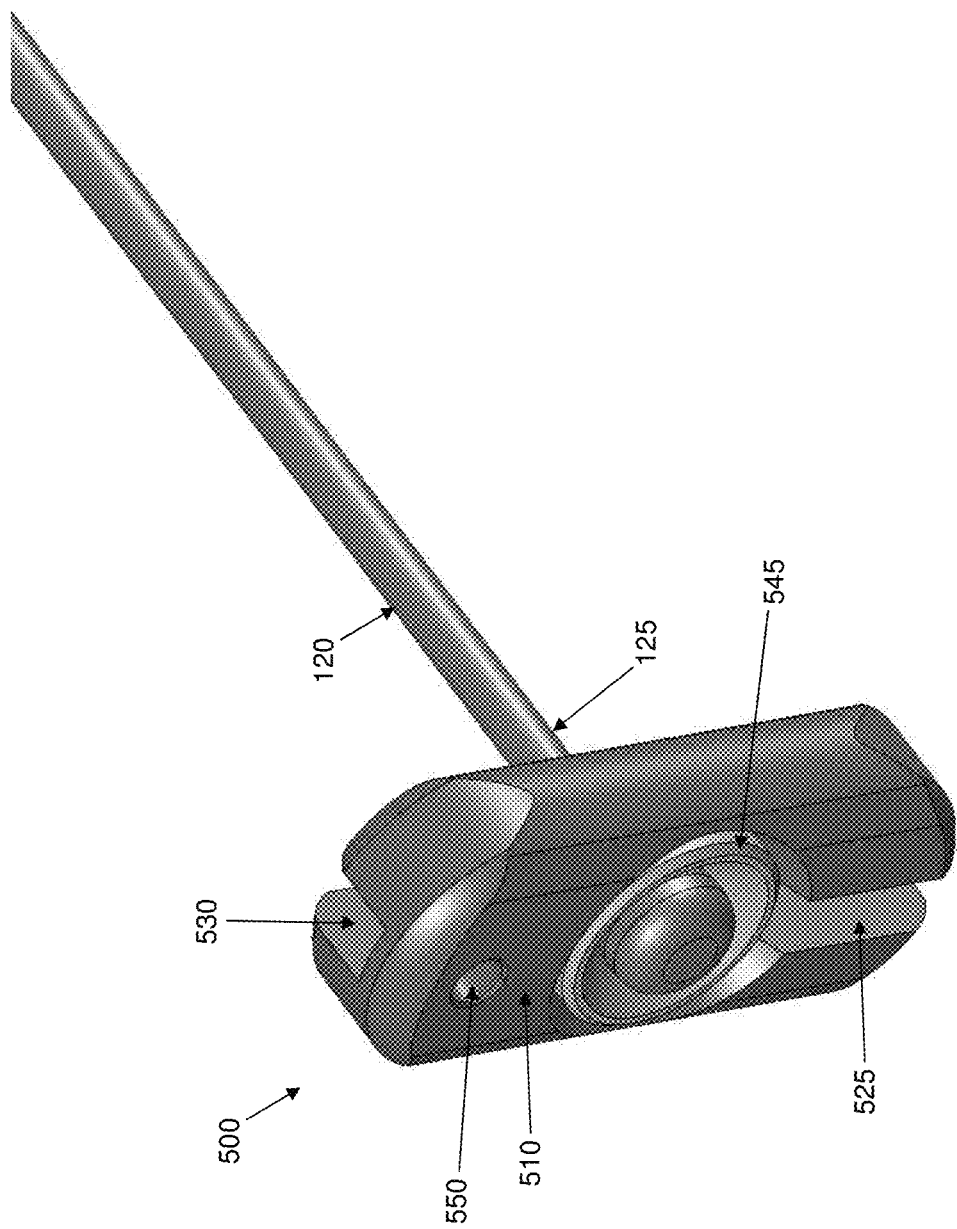
Figure 69:
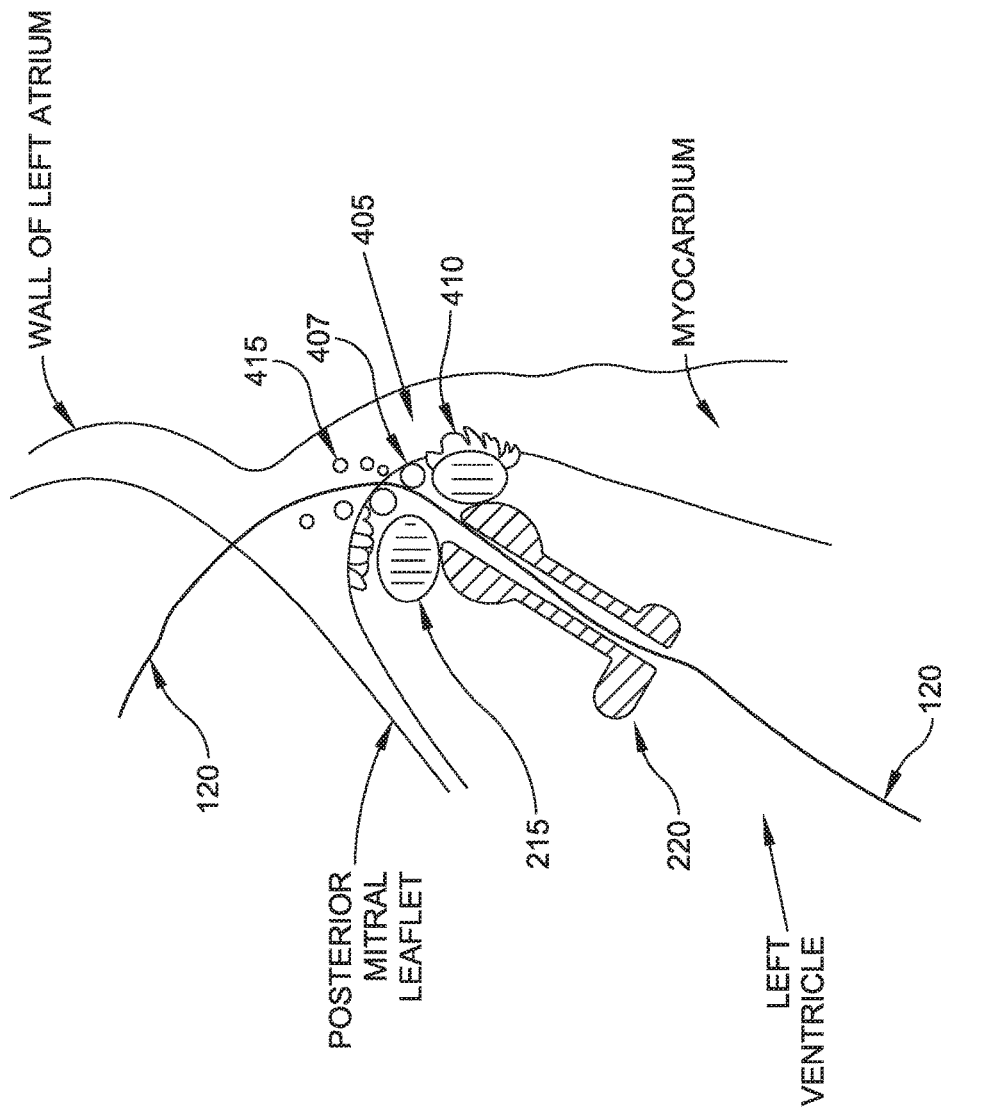
Figure 70:
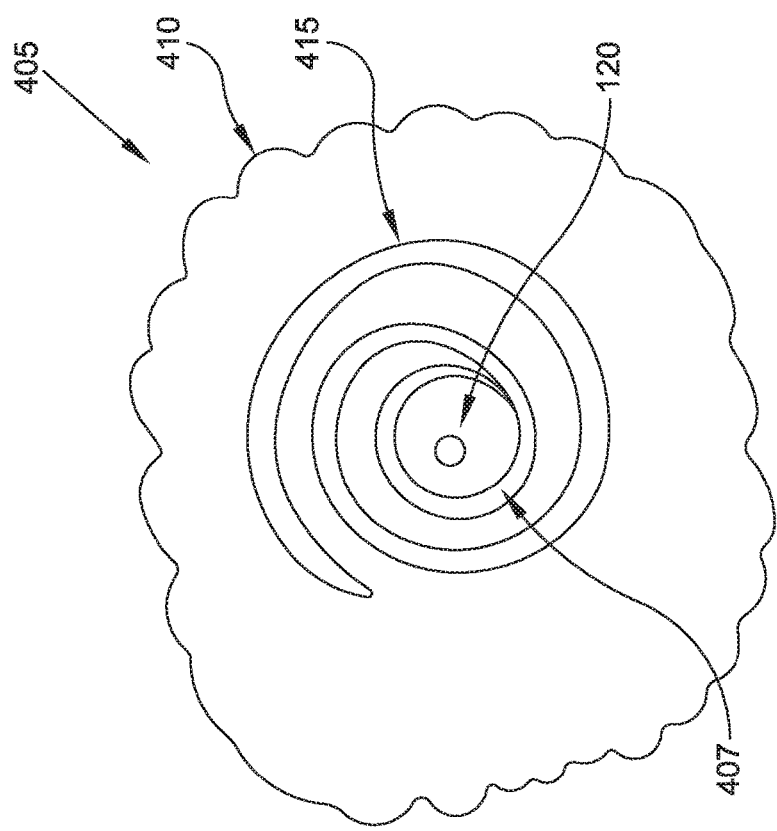

In one preferred embodiment of the present invention, the first, fixed anchor may have a configuration generally similar to that of second, sliding anchor 215. More particularly, and looking now at FIGS. 68A-68F, in one form of the invention, there is shown a first, fixed anchor 500 that comprises a body 505 having a smooth and rounded profile in all three dimensions whereby to best effect both delivery and atraumatic permanent implantation. First, fixed anchor 500 comprises a first side 510, a second side 515 and a generally central through-hole 520 through which spanning suture 120 will ultimately emerge. In one preferred form of the invention, in order to maintain as small a crossing profile as possible during delivery through a sheath, first side 510 comprises a proximal slot 525 extending from central through-hole 520 to the proximal end of first, fixed anchor 500, and second side 515 comprises a distal slot 530 extending from central through-hole 520 to the distal end of first, fixed anchor 500. The slots 525, 530 are deep enough, and aligned with one another, so that they "overlap" and thereby provide a continuous axial passage sufficiently large to transit spanning suture 120 through first, fixed anchor 500 without interference. See FIGS. 68A and 68E. This allows first end 125 of spanning suture 120 to reside parallel and coaxial to first, fixed anchor 500 and within the anchor's profile when first, fixed anchor 500 is contained within a delivery sheath. Furthermore, on account of this construction, after first, fixed anchor 500 is deployed from its delivery sheath, first, fixed anchor 500 may rotate away from the spanning suture so that the first, fixed anchor 500 is substantially perpendicular to the adjacent spanning suture 120 (see FIG. 68F). Central through-hole 520 preferably comprises chamfers on either side of the central through-hole. These chamfers may be of equivalent size or, more preferably, one chamfer may be larger and one chamfer may be smaller. By way of example but not limitation, a smaller chamfer 535 on second side 515 provides a smooth exit profile for spanning suture 120 to exit from first, fixed anchor 500 (i.e., to extend towards the ventricular side of the annulus). A larger chamfer 540 on first side 510 provides a seating surface for a cap 545 set on first end 125 of spanning suture 120. The smaller chamfer 535 minimizes the chance of the suture rubbing against the anchor, which could cause fraying and breaking of the suture. The larger chamfer 540 allows controlled contact for cap 545 at varying angular orientations, maximum contact between cap 545 and the anchor, and minimizes the distance that cap 545 protrudes into the blood stream. In one preferred embodiment, first, fixed anchor 500 may be provided with one or more additional through-holes 550 to allow the elective fitting of a control suture (not shown) through first, fixed anchor 500 on one or the other end (or both ends) of the anchor.

Depending on where first, fixed anchor 500 is set in the anatomy, it may vary in size from second, sliding anchor 215. By way of example but not limitation, first, fixed anchor 500 may be shorter or longer than second, sliding anchor 215.

11. Novel Surgical Felt Pledget

If desired, a surgical felt pledget may be disposed between the ventricular side of the mitral annulus and one or both of first, fixed anchor 135 and second, sliding anchor 140. By way of example but not limitation, where a surgical felt pledget is to be disposed between the ventricular side of the anterior mitral annulus and first, fixed anchor 135, the surgical felt pledget may be loaded onto spanning suture 120 "ahead of" first, fixed anchor 135 so that the surgical felt pledget is towed into position against the anterior mitral annulus when first, fixed anchor 135 is deployed against the anterior mitral annulus. By way of further example but not limitation, where a surgical felt pledget is to be disposed between the ventricular side of the posterior mitral annulus and second, sliding anchor 140, the surgical felt pledget may be loaded onto spanning suture 120 "ahead of" second, sliding anchor 140 so that the surgical felt pledget is pushed up into position against the anterior mitral annulus when second, sliding anchor 140 is pressed up against the posterior mitral annulus.

If desired, and looking now at FIGS. 69, 70, 70A and 71, the surgical felt pledget may comprise a novel felt pledget 405. Novel felt pledget 405 generally comprises a molding ring 407 having a felt body 410 secured thereto. A helical coil 415 is secured to molding ring 407 and projects distally therefrom. In this form of the invention, helical coil 415 can be "turned into" the mitral valve annulus, whereby to secure felt body 410 against the mitral valve annulus. By way of example but not limitation, where novel felt pledget 405 is to be disposed between the ventricular side of the anterior mitral annulus and first, fixed anchor 135, surgical felt pledget 405 may be loaded onto crossing guidewire 45 and advanced into the anterior mitral annulus. After surgical felt pledget 405 has been secured to the anterior mitral annulus, then spanning suture 120 may be used to tow first, fixed anchor 135 up against surgical felt pledget 405. By way of further example but not limitation, where a surgical felt pledget 405 is to be disposed between the ventricular side of the posterior mitral annulus and second, sliding anchor 140, surgical felt pledget 405 may be loaded onto spanning suture 120 before second, sliding anchor 140 is loaded onto spanning suture 120—in this form of the invention, surgical felt pledget 405 is pushed up spanning suture 120 and is turned into the ventricular side of the posterior mitral annulus, then, with surgical felt pledget 405 in position, second, sliding anchor 140 is loaded onto spanning suture 120 and advanced into position against the surgical felt pledget 405 before being locked onto spanning suture 120.

Figure 71:
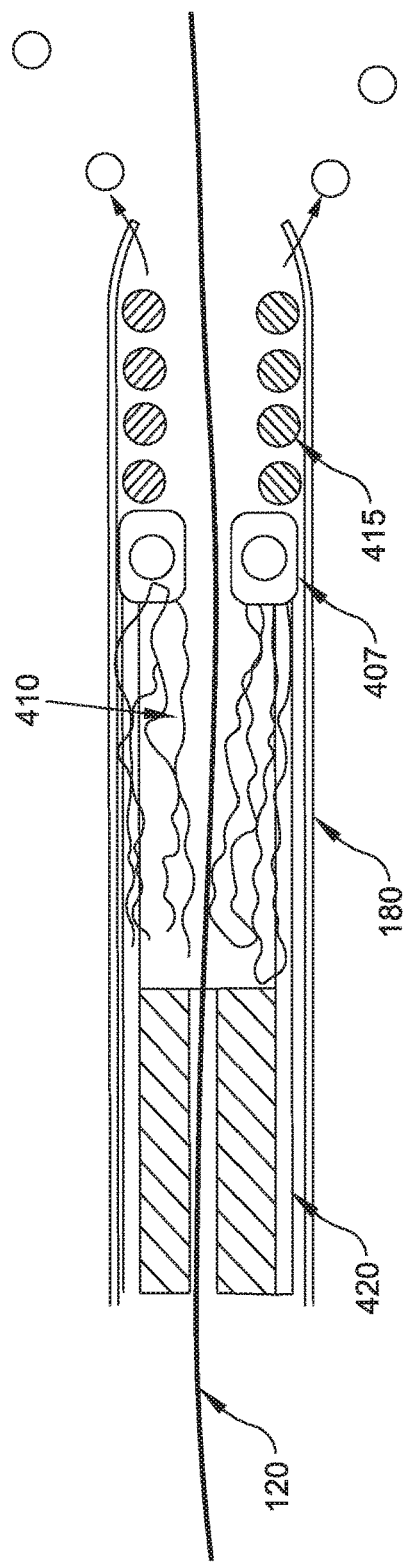

As seen in FIG. 71, where surgical felt pledget 405 is to be disposed between the ventricular side of the posterior mitral annulus and second, sliding anchor 140, surgical felt pledget 405 may be loaded into STTT 180 distal to second, sliding anchor 215, with STTT 180 including a torque driver 420 for turning helical coil 415 into the posterior mitral annulus.

12. Additional Constructions

In the foregoing disclosure, the preferred constructions of the aforementioned first, fixed anchor and the aforementioned second, sliding anchor comprise so-called T-bar anchors. However, as an alternative to T-bar anchors, a screw-in anchor, providing for central routing of the spanning suture, could be employed as a general substitute for one or both of the aforementioned first, fixed anchor and the aforementioned second, sliding anchors.

By way of example but not limitation, in one preferred form of the invention, a suture-locking anchor (preferably formed out of stainless steel or titanium) comprises a proximal component and a distal component, with the proximal component and the distal component being threaded together so as to effect locking onto the spanning suture. In this form of the invention, the proximal component and the distal component both possess a central hole for passing the spanning suture, and one or both of the proximal component and the distal component may have tines or other features to permanently lock onto the spanning suture when the aforementioned threads are fully engaged.

13. Permanently Beneficially Displacing One or Both of the Papillary Muscles

In accordance with the present invention, there is also provided a method and apparatus for permanently beneficially displacing one or both of the papillary muscles.

More particularly, in this form of the invention, a spanning procedure is performed that attaches the tip of one (or both) of the papillary muscles to either the fibrous trigones or the central fibrous body of the mitral valve so as to beneficially displace one or both of the papillary muscles. This spanning suture may be anchored to a trigone (or the central fibrous body) in a manner similar to how the annular spans are anchored to one another (see above), but in the case of anchoring the papillary muscles, the distal anchor of the spanning suture is placed on the atrial side of the mitral valve and the spanning suture is routed into the left ventricle and then on to the papillary tip. In this way, the spanning suture is anchored on the atrial side of the mitral valve, extends through the fibrous trigone or central fibrous body, extends across the left ventricle and extends through the papillary muscle. Then the same "span-tension" procedure discussed above with respect to the annular spanning procedure may be employed to precisely and sequentially reduce the length of the span between the trigone (or the central fibrous body) and the papillary tip, so as to beneficially displace the papillary tip towards the fibrous base of the heart. In this respect it will be appreciated that as the "span-tension" procedure reduces the length of the span between the trigone (or the central fibrous body) and the papillary tip, the papillary tip is displaced toward the fibrous base of the heart since the fibrous base of the heart is effectively immobile during the "span-tension" procedure. The goal of the papillary displacement procedure is to reduce excessive leaflet "tethering" due to the adverse displacement of the papillary muscles and thus the mitral leaflet which is connected to the papillary muscle via chordae. Reduction or elimination of leaflet tethering allows the leaflets to return to their normal physiologic location with increased coaptation and reduced regurgitation.

Surgeons have, for at least four decades, experimented with performing papillary displacement and tethering reduction by surgically attaching sutures to the papillary tips and routing those sutures to the fibrous base of the heart with the thought that this would increase the durability of a mitral valve repair to reduce regurgitation, especially in cases of subsequent ventricular dilation after surgery. But these prior art papillary displacement and tethering procedures require open-heart, on-bypass surgery, and the effect of the tethering reduction cannot be directly observed on a beating heart, since the conventional papillary displacement and tethering reduction procedure is performed as an "on-bypass" surgery (i.e., with the heart stopped).

Therefore, in accordance with the present invention, there is now provided a method and apparatus for effecting the papillary displacement and tethering reduction using, generally, the aforementioned spanning/tensioning tools of the present invention, and leaflet tethering is relieved prior to undertaking the annular repair in the manner discussed above. There are critical advantages to performing the papillary displacement and tethering reduction using the apparatus and method of the present invention, most particularly that the subsequent annular repair is both more effective and more durable, and less "aggressive", inasmuch as the reduction in tethering will, a priori, improve leaflet coaptation. It is well documented that overly-aggressive mitral repairs result in mitral orifice area restriction that adversely affects exercise capacity. At the same time, it is also well known that the presence of uncorrected leaflet tethering is the primary cause of recurrent mitral regurgitation following mitral repair. Thus, in accordance with the present invention, beneficial papillary displacement and tethering reduction is effected using the apparatus and method of the present invention, preferably before undertaking annular repair in the manner discussed above, whereby to provide improved leaflet coaptation. Significantly, inasmuch as the present invention allows the papillary displacement and tethering reduction to be effected on a beating heart, the tethering reduction can be directly observed as tensioning of the suture span occurs, whereby to permit the tethering reduction to be dynamically tailored while the heart is beating. It should also be appreciated that the papillary displacement and tethering reduction can be utilized independently of annulus reconfiguration, i.e., papillary displacement and tethering reduction can be effected where no annulus reconfiguration is undertaken.

One approach to the papillary displacement and tethering reduction procedure of the present invention is shown in the attached FIGS. 72-84.

Figure 72:
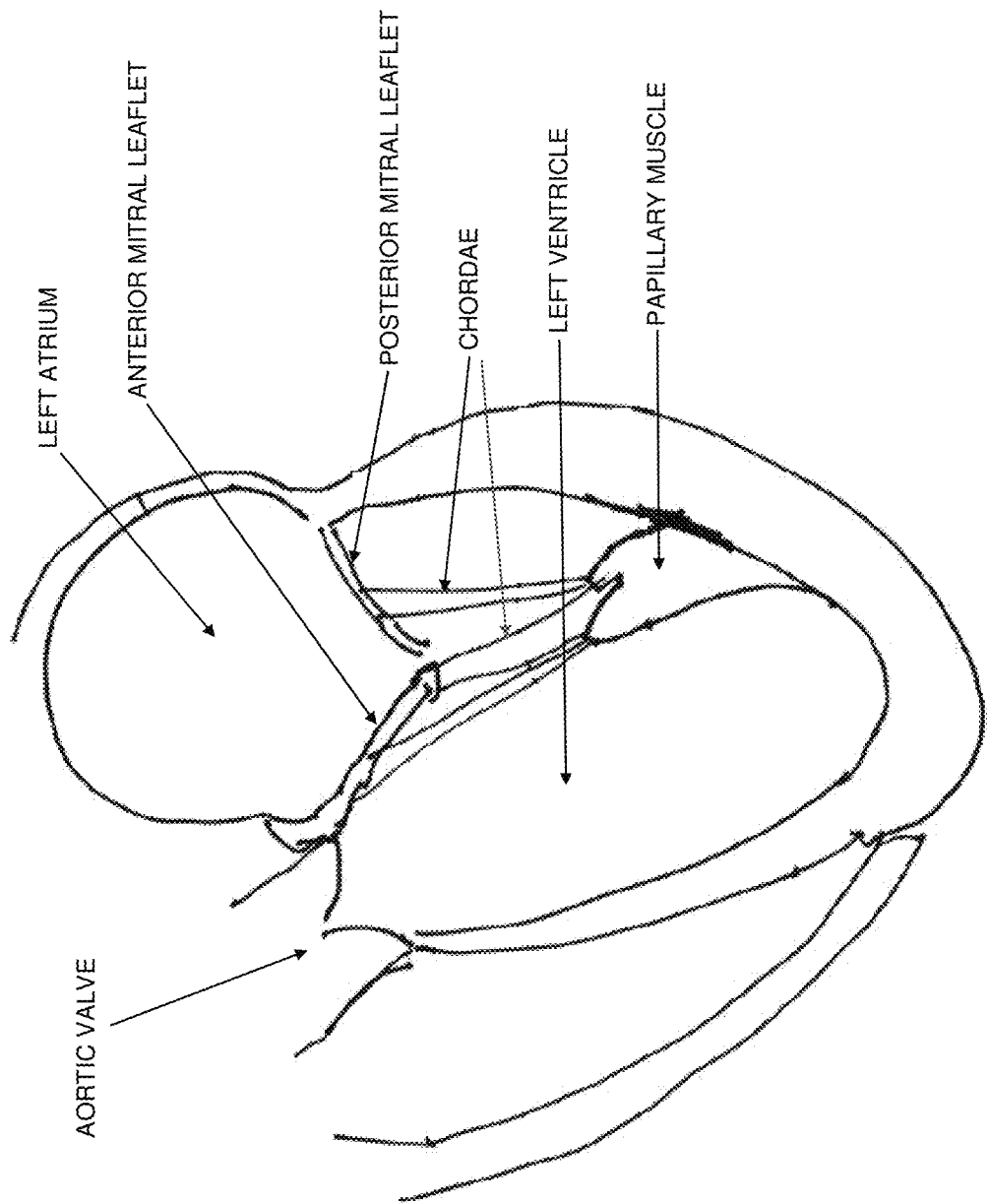

FIG. 72 shows the target anatomy, i.e., the left atrium, the left ventricle, the mitral valve, the chordae tendinae ("the chordae") and the papillary muscles.

Figure 73:
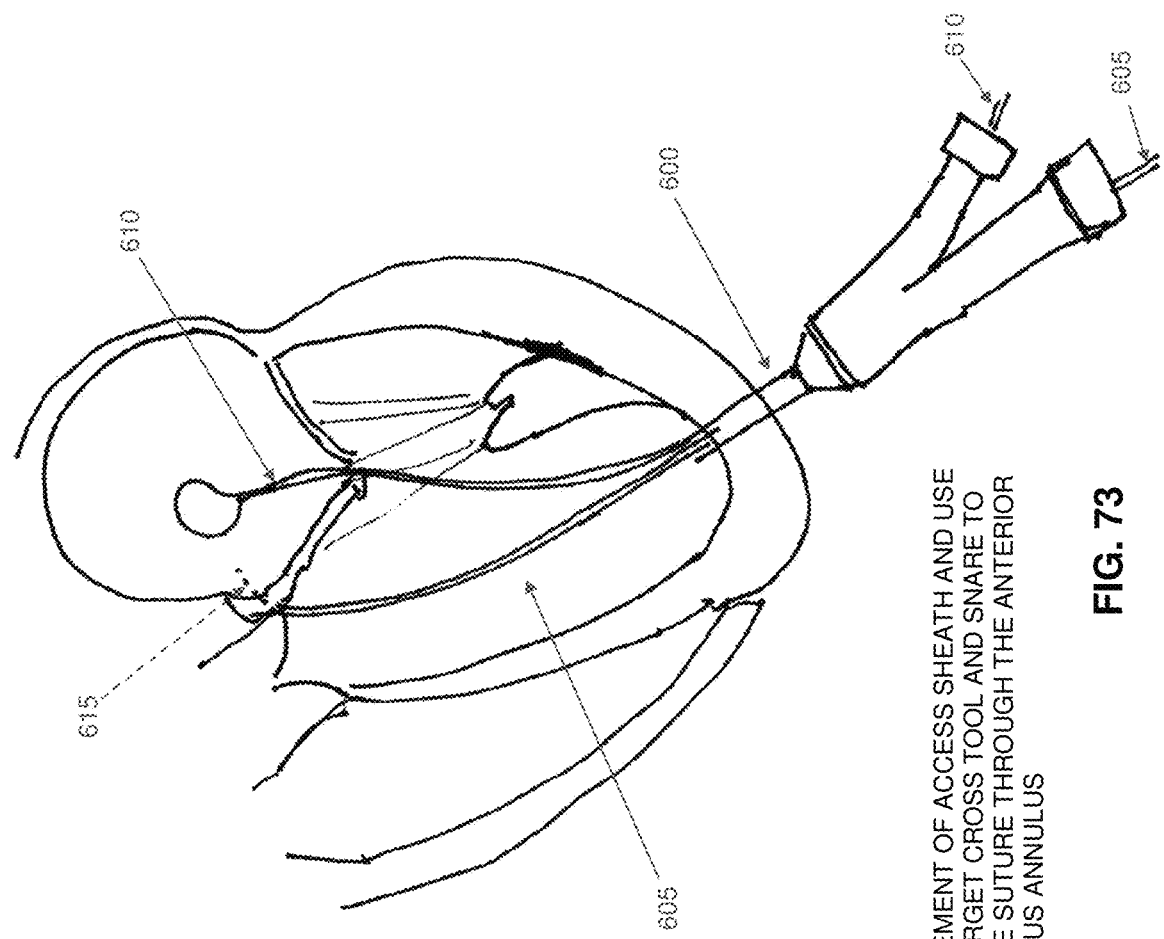

FIG. 73 shows a 2-port access sheath 600 (e.g., of the sort well known in the art) placed in the left ventricle so as to provide direct access to the anatomy. Also shown is a "target and cross tool" (also known as a "Target-Cross Tool") (TCT) 605 (e.g., of the sort disclosed above) crossing the anterior annulus of the mitral valve in a desired location, and a snare 610 (e.g., of the sort disclosed above) placed through the mitral valve leaflets and into the left atrium so as to capture a suture 615 advanced out of TCT 605 and into the left atrium. Snare 610 is used to retrieve suture 615 from TCT 605 and draw suture 615 out of the left atrium, through the mitral valve leaflets, through the left ventricle and out access sheath 600.

Figure 74:
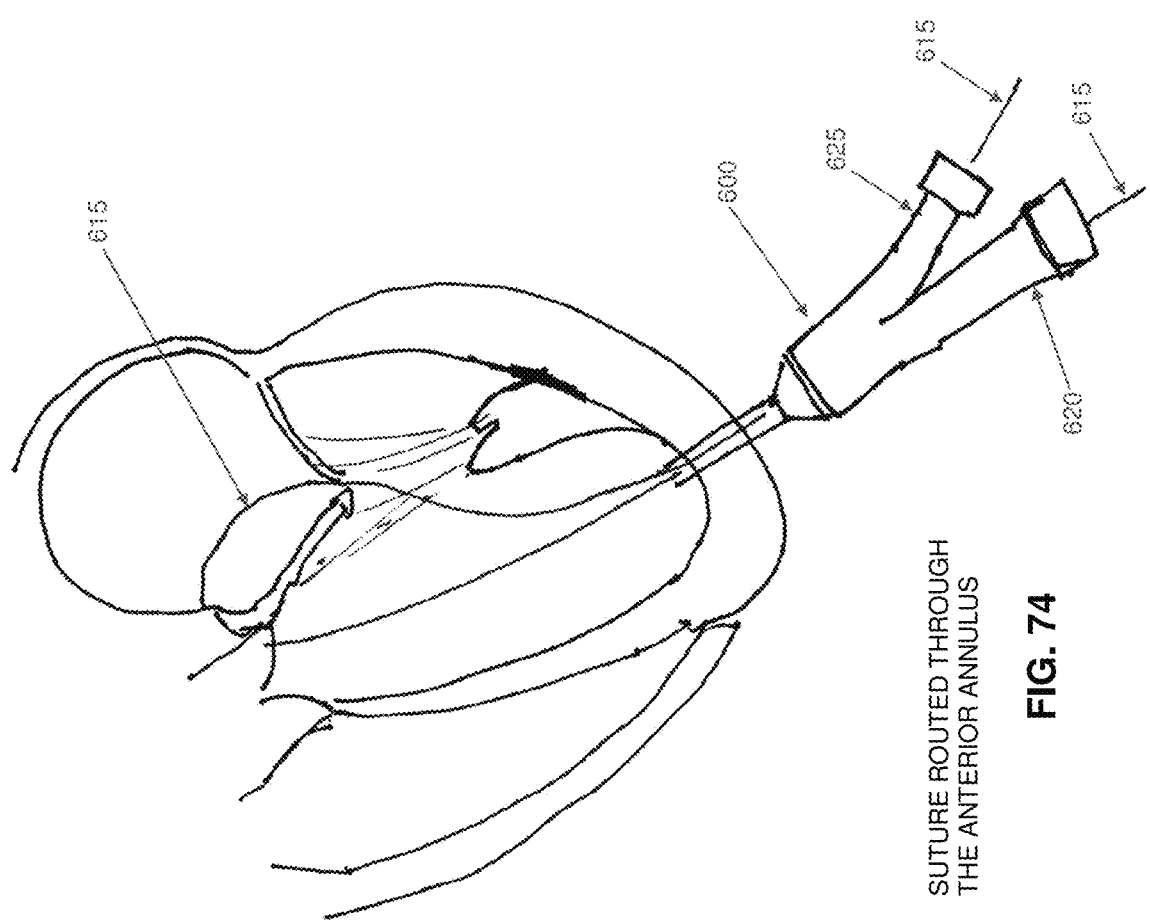

FIG. 74 shows a "clean run" of suture 615 extending into a port 620 of access sheath 600, across the left ventricle, through the anterior annulus, across the left atrium, between the valve leaflets, across the left ventricle and out a port 625 of access sheath 600.

Figure 75:
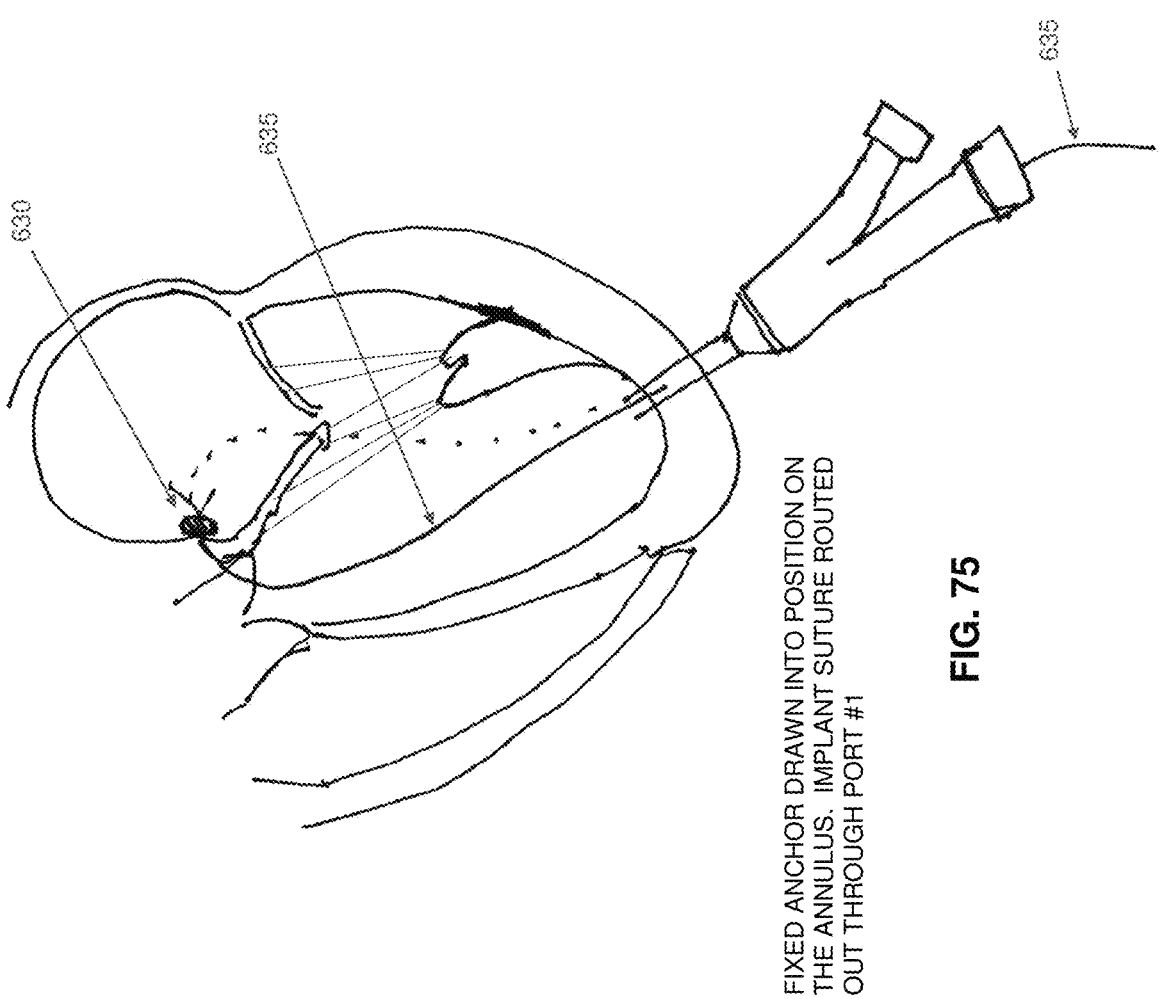

FIG. 75 shows a fixed anchor 630 (e.g., of the sort disclosed above) on the end of implant suture 635 drawn into position on the atrial side of the mitral annulus using the "tie on and draw in" technique discussed above in connection with establishing an annular span. By way of example but not limitation, implant suture 635 carrying fixed anchor 630 is secured to the portion of suture 615 emerging from port 625 of access sheath 600, and the portion of suture 615 emerging from port 620 of access sheath 600 is pulled proximally so as to "tow" implant suture 635 and fixed anchor 630 along the path followed by suture 615 until fixed anchor 630 is drawn up against the atrial side of the mitral annulus. A pledget (not shown) may be advanced over implant suture 635 ahead of anchor 630 so as to reinforce anchor seating against the atrial side of the mitral annulus.

Figure 76:
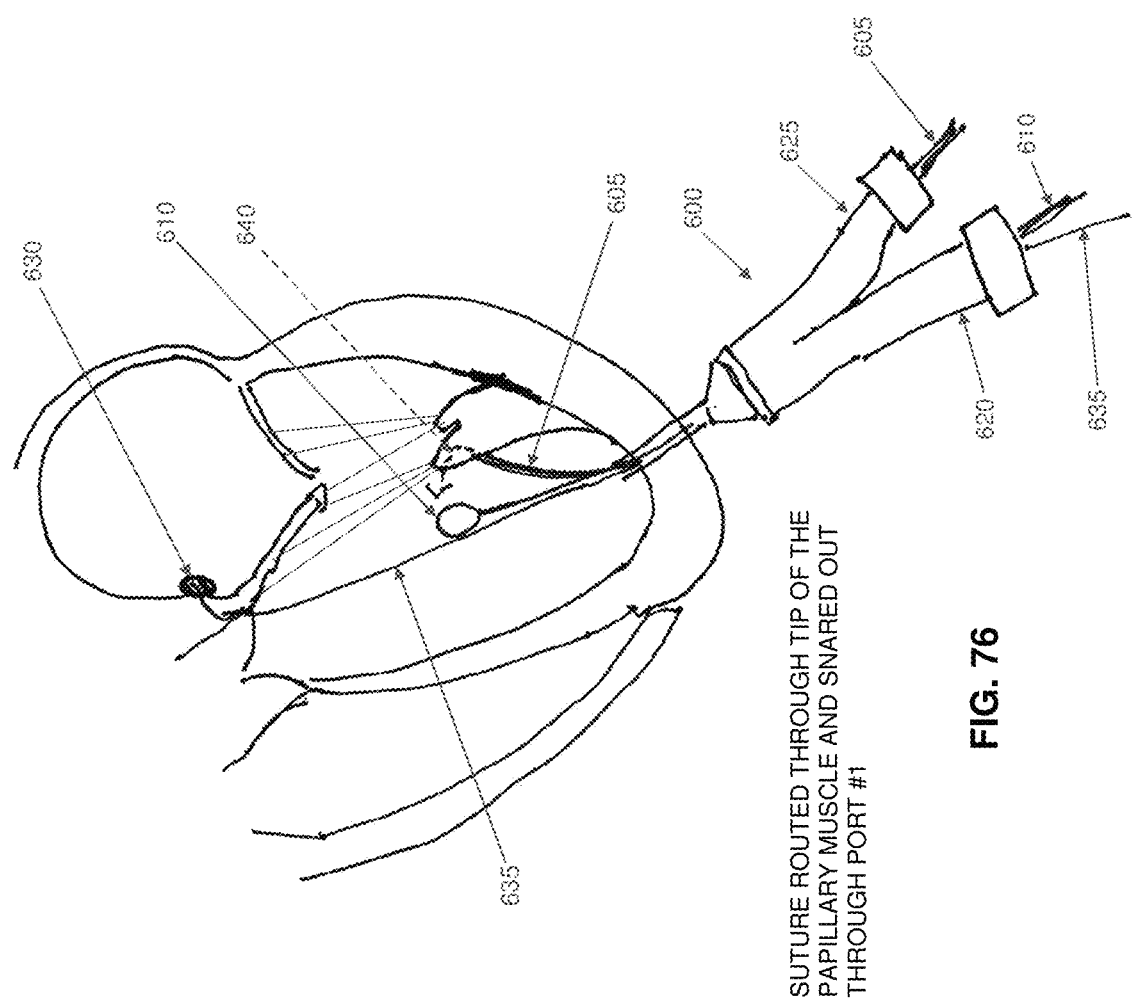

FIG. 76 shows TCT 605 and snare 610 being used to pass a routing suture 640 through the papillary muscle near the robust tip of the papillary muscle. By way of example but not limitation, TCT 605 is placed into port 625 of the 2-port access sheath 600, and snare 610 is placed into port 620 of 2-port access sheath 600, to facilitate final routing of implant suture 635 (see below).

Figure 77:
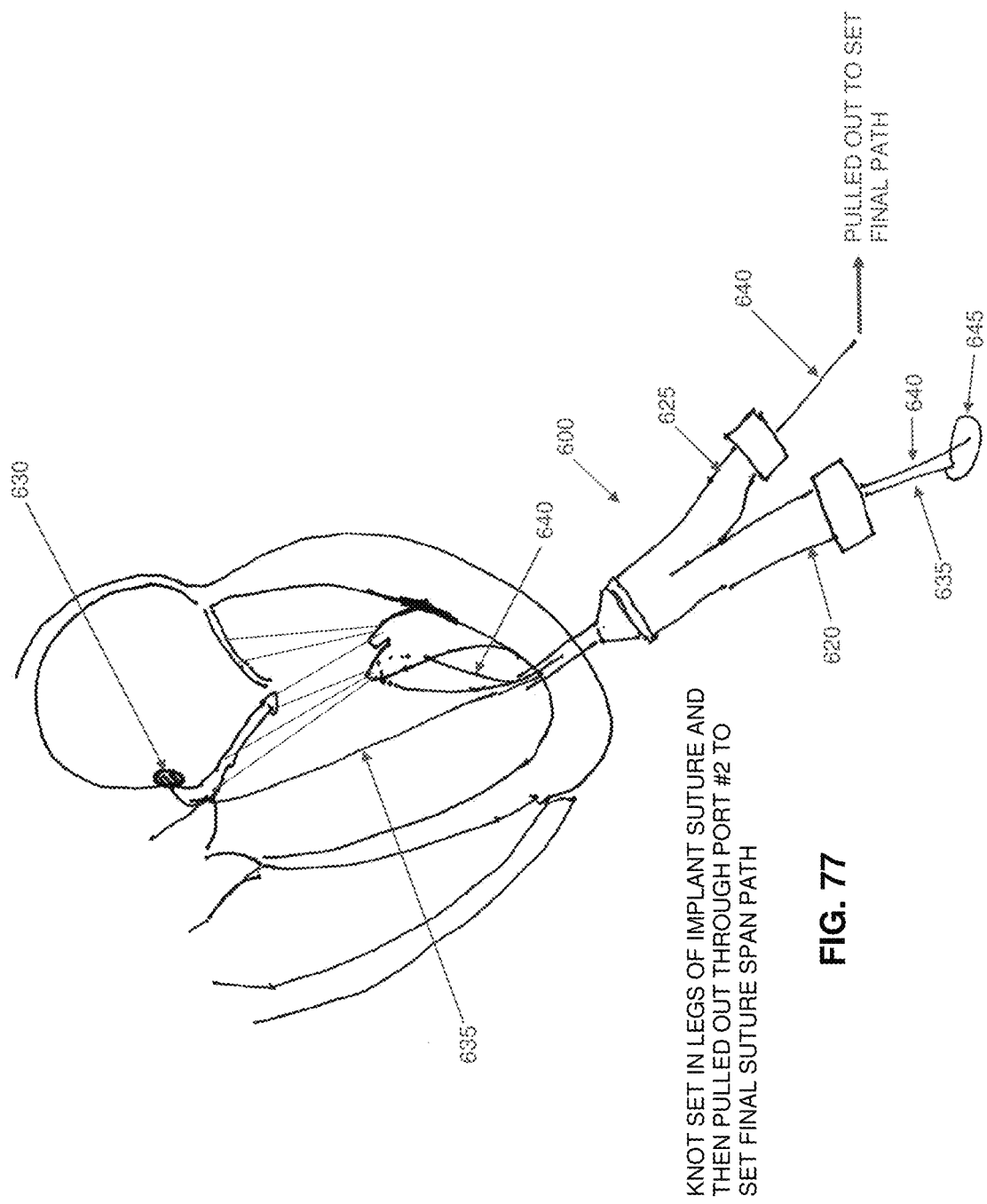

FIG. 77 shows how routing suture 640 is passed through the tip of the papillary muscle using TCT 605 and snare 610. Note that the two ends of routing suture 640 emerge from ports 620 and 625 of 2-port access sheath 600. Note also that the end of routing suture 640 emerging from port 620 of the 2-port access sheath is tied to the free end of implant suture 635 at a knot 645, and then the suture leg coming out of port 625 is pulled out so that knot 645 is drawn into the left ventricle so as to establish the final routing of implant suture 635.

Figure 78:
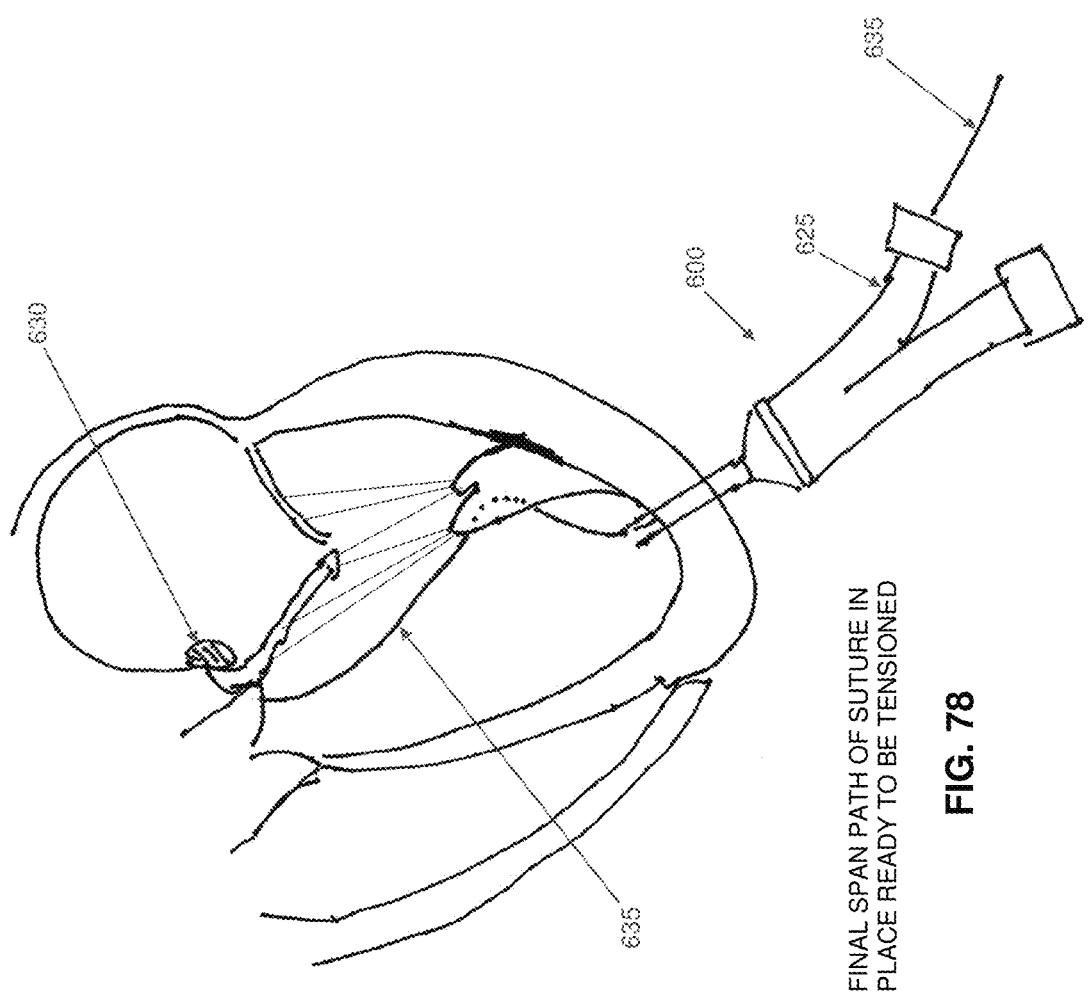

FIG. 78 shows the suture routing for a papillary displacement span of implant suture 635 in an untensioned configuration. Note that the papillary displacement span extends from atrial anchor 630, through the annulus, across the left ventricle, through the tip of the papillary muscle, further across the left atrium, and out port 625 of 2-port access sheath 600.

Figure 79:
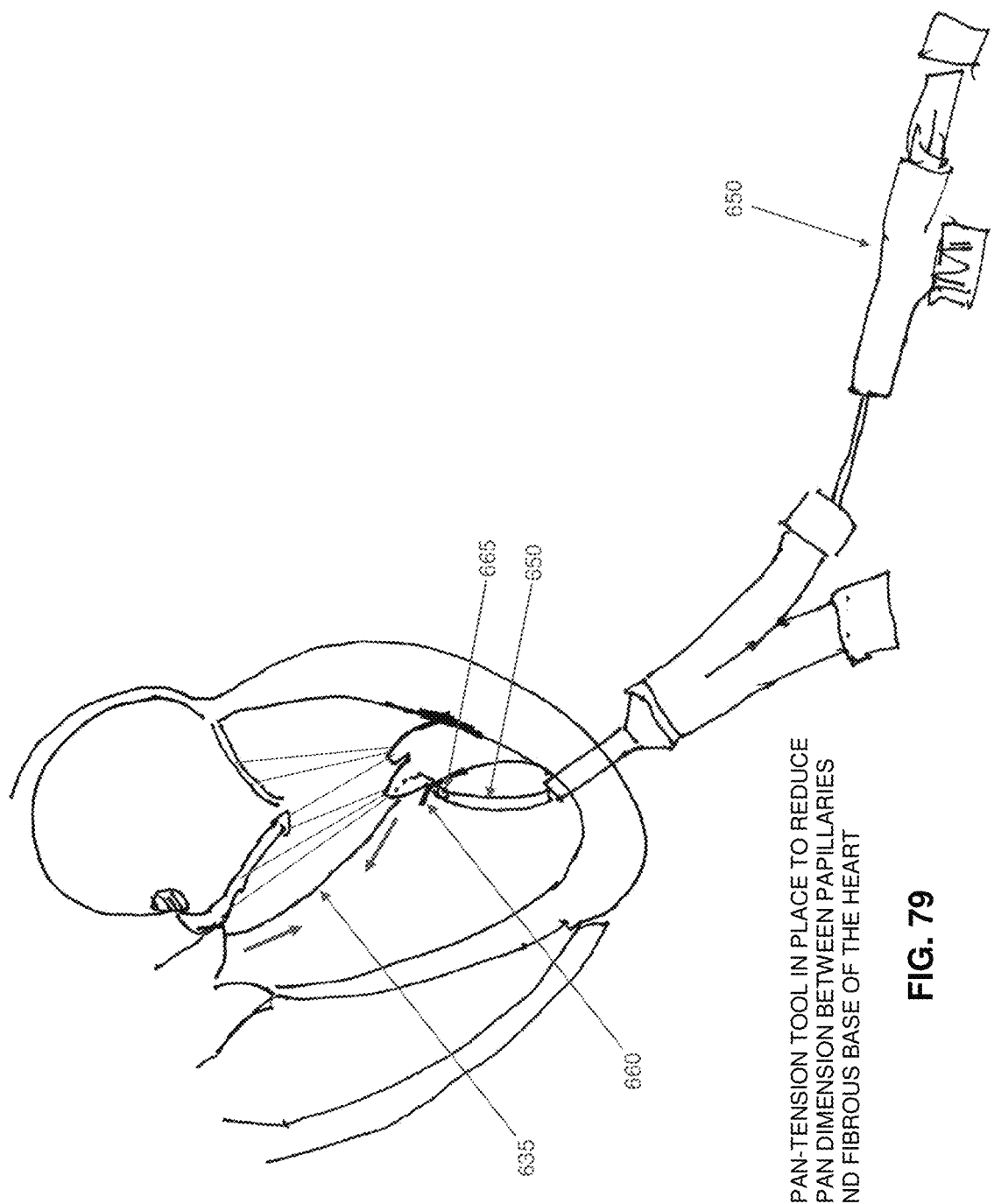

FIG. 79 shows the "Span-Tension-Terminate-Tool" (also known as the "Span-Tension-Tool") (STTT) 650 (e.g., of the sort disclosed above) routed over implant suture 635. One or more pledgets (not shown) are preferably pushed on the implant suture ahead of the sliding anchor 660 (e.g., of the sort disclosed above) to buttress the sliding anchor when the sliding anchor is placed against the papillary muscle. The tensioning capabilities of STTT 650 are used to reduce the length of the span between the trigone and the tip of the papillary muscle by tensioning implant suture 635 so as to displace the papillary muscle superiorly and septally towards the fibrous base of the heart, whereby to beneficially reduce the tension on the chordae tendinae and the mitral leaflets, and hence improve leaflet coaptation and valve closing function. When the desired degree of papillary correction is observed (e.g., by echocardiogram, effected while the heart is beating), the suture lock 665 (e.g., of the sort disclosed above) is set and deployed (e.g., in the manner discussed above with respect to annular spanning) so as to set sliding anchor 660 in position against the papillary muscle. The suture tail is trimmed in the manner discussed above using a trim tool (not shown).

Figure 80:
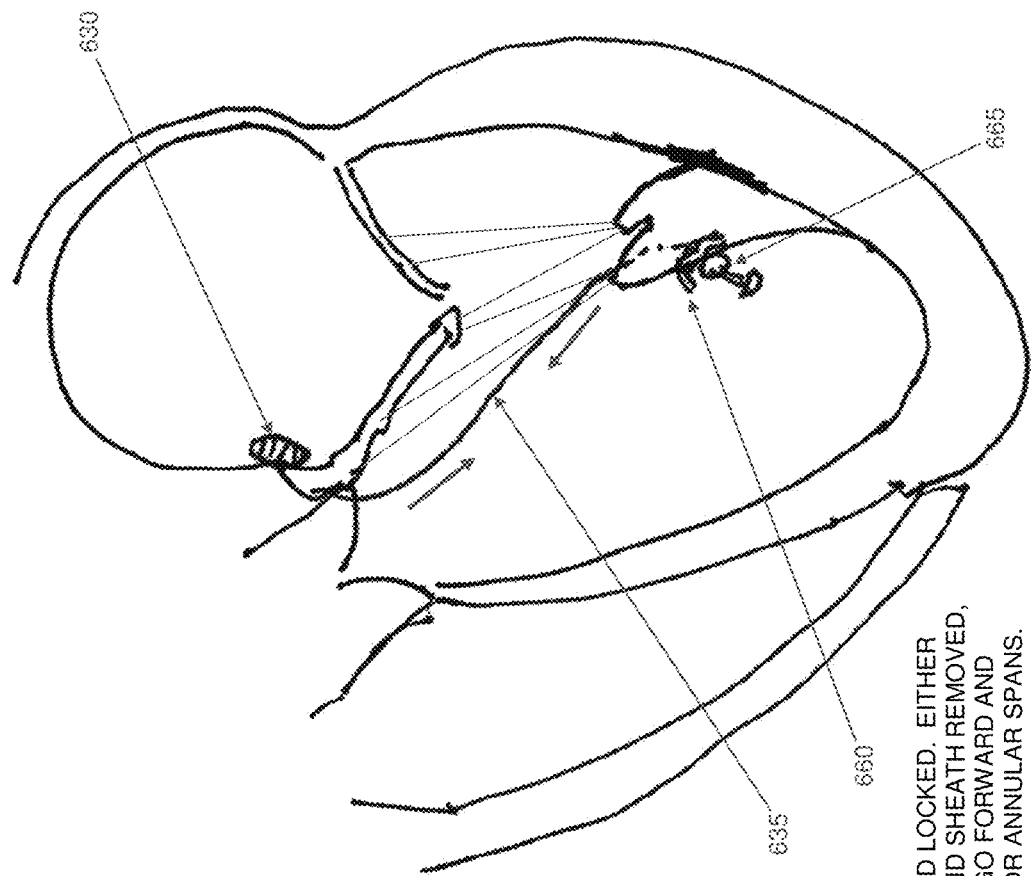

FIG. 80 shows the completed, tensioned span displacing the papillary muscle toward the fibrous base of the heart, whereby to effect beneficial papillary displacement and tethering reduction.

FIG. 81 is a cross-sectional view showing the relevant anatomy on the left side of the heart.

FIGS. 82-84 show possible preferred orientations for the papillary spans (i.e., the implant suture 635 extending between the mitral annulus and the papillary muscles). The papillary spans are shown in FIGS. 82-84 as pairs of spans (i.e., one span to each papillary muscle); however, a single papillary span to either papillary muscle may be all that is required for a particular patient for effective treatment of their leaflet tethering and associated mitral regurgitation with increased repair durability.

FIG. 82 shows papillary spans originating from the Anterior Lateral Papillary Muscle (ALPM) and Posterior Medial Papillary Muscle (PMPM) and engaging the Central Fibrous Body (CFB).

FIG. 83 shows papillary spans originating from the Anterior Lateral Papillary Muscle (ALPM) and Posterior Medial Papillary Muscle (PMPM) and each engages the diagonally-opposed trigone, for example, the Posterior Medial Papillary Muscle to the Anterior Lateral Trigone (ALT) and the Anterior Lateral Papillary Muscle to the Posterior Medial Trigone (PMT).

FIG. 84 shows papillary spans originating from the Anterior Lateral Papillary Muscle (ALPM) and Posterior Medial Papillary Muscle (PMPM) and each engages the nearby trigone, for example, the Anterior Lateral Papillary Muscle to the Anterior Lateral Trigone (ALT) and the Posterior Medial Papillary Muscle to the Posterior Medial Trigone (PMT).

It will be appreciated that in the novel method shown in FIGS. 72-84, the 2-port access sheath 600 is advanced through the apex of the heart; TCT 605 is advanced across the left ventricle and used to pass suture 615 through the anterior annulus of the mitral valve and into the left atrium; snare 610 is advanced through the left ventricle, between the leaflets of the mitral valve, into the left atrium, and used to draw suture 615 out of the left atrium, between the leaflets of the mitral valve, and into the left ventricle, etc. Furthermore, suture 615 is then used to draw implant suture 635 and fixed anchor 630 across the left ventricle, between the leaflets of the mitral valve, and into the left atrium so that implant suture 635 can pass through the anterior annulus and into the left ventricle and fixed anchor 630 can be seated against the atrial side of the mitral annulus.

It will be appreciated by those skilled in the art that, as snare 610 is advanced from the left ventricle, between the leaflets of the mitral valve and into the left atrium, and as snare 610 is retracted from the left atrium, between the leaflets of the mitral valve and into the left atrium, there arises the possibility that snare 610 may inadvertently engage the chordae. Such inadvertent engagement can damage the chordae and/or impede function of the chordae. Furthermore, it will be appreciated that as suture 615 is used to draw implant suture 635 and fixed anchor 630 across the left ventricle, between the leaflets of the mitral valve, and into the left atrium so that implant suture 635 can pass through the anterior annulus and into the left ventricle and fixed anchor 630 can be seated against the atrial side of the mitral annulus, there arises the possibility that implant suture 635 and/or fixed anchor 630 may inadvertently engage the chordae. Again, such inadvertent engagement can damage the chordae or impede function of the chordae.

To this end, and looking now at FIGS. 85-93, there is provided another novel approach for permanently beneficially displacing one or both of the papillary muscles wherein actions do not need to take place in the vicinity of the chordae.

Figure 85:
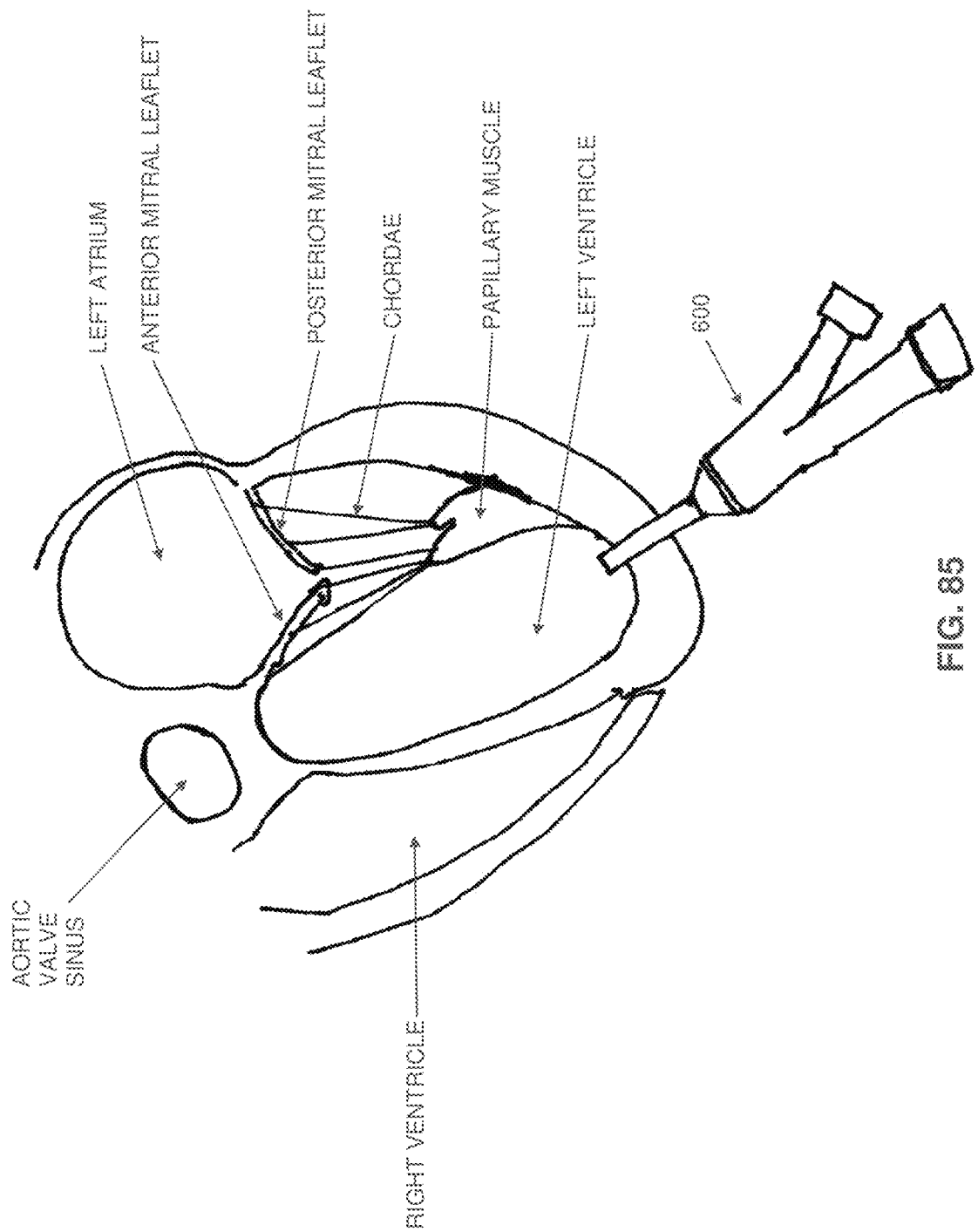
FIGS. 85-93 are schematic views showing another novel method and apparatus for permanently beneficially displacing one or both of the papillary muscles.

More particularly, FIG. 85 shows the target anatomy, i.e., the left atrium, the left ventricle, the mitral valve, the chordae tendinae ("the chordae") and the papillary muscles. FIG. 85 also shows a 2-port access sheath 600 (e.g., of the sort well known in the art) placed in the left ventricle so as to provide direct access to the anatomy (if desired, in this form of the invention, 2-port access sheath 600 may be replaced by a 1-port access sheath, a 3-port access sheath, etc.).

Figure 86:
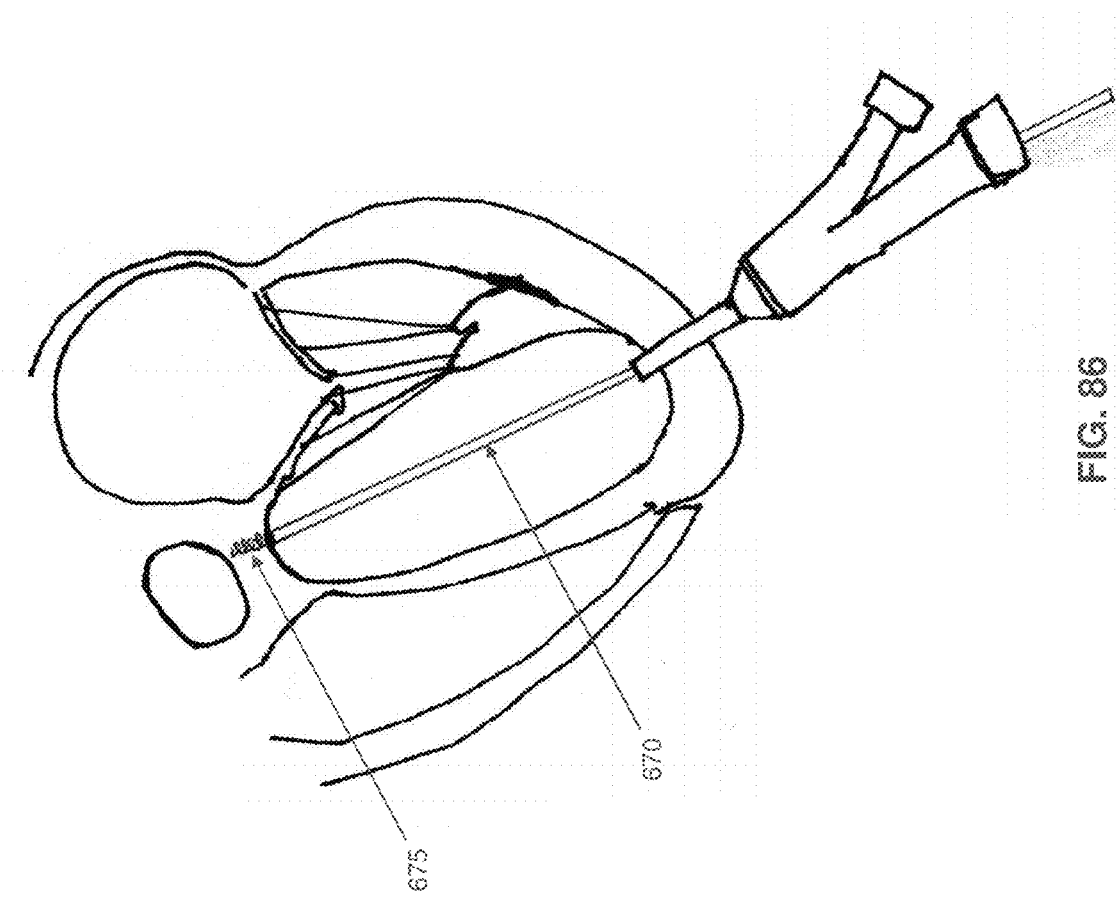

FIG. 86 shows a trigone anchor delivery tool 670 crossing the left ventricle and deploying a trigone screw anchor 675 into the fibrous trigones or the central fibrous body of the mitral valve. Trigone screw anchor 675 may be a conventional screw anchor of the sort well known in the art, e.g., it may comprise a corkscrew anchor of the sort used to anchor a pacing lead. If desired, the corkscrew anchor may be configured to provide radio frequency (RF) energy to the tissue so as to facilitate deployment of the corkscrew anchor into the fibrous trigones or the central fibrous body of the mitral valve. Trigone anchor delivery tool 670 may be a conventional anchor delivery tool of the sort well known in the art, e.g., it may comprise a cannulated sheath for turning screw anchor 675 into tissue (with the suture, see below, emanating from screw anchor 675 passing through the hollow lumen of the cannulated sheath). Note that as trigone anchor delivery tool 670 deploys trigone screw anchor 675 into the fibrous trigones or the central fibrous body of the mitral valve, trigone anchor delivery tool 670 passes directly across the left ventricle, well clear of the chordae.

Figure 87:
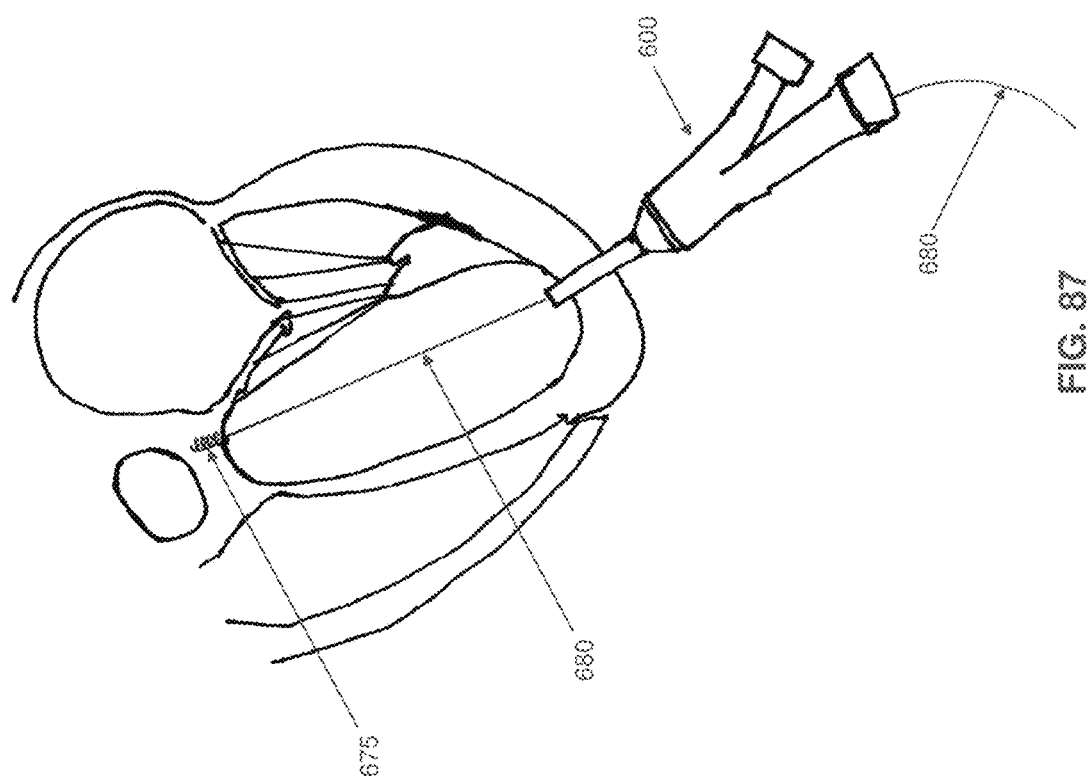

FIG. 87 shows a "clean run" of an implant suture 680 extending from trigone screw anchor 675, across the left ventricle, through 2-part access sheath 600, and out one port of the access sheath trigone. Again, note that implant suture 680 passes directly across the left ventricle, well clear of the chordae.

Figure 88:
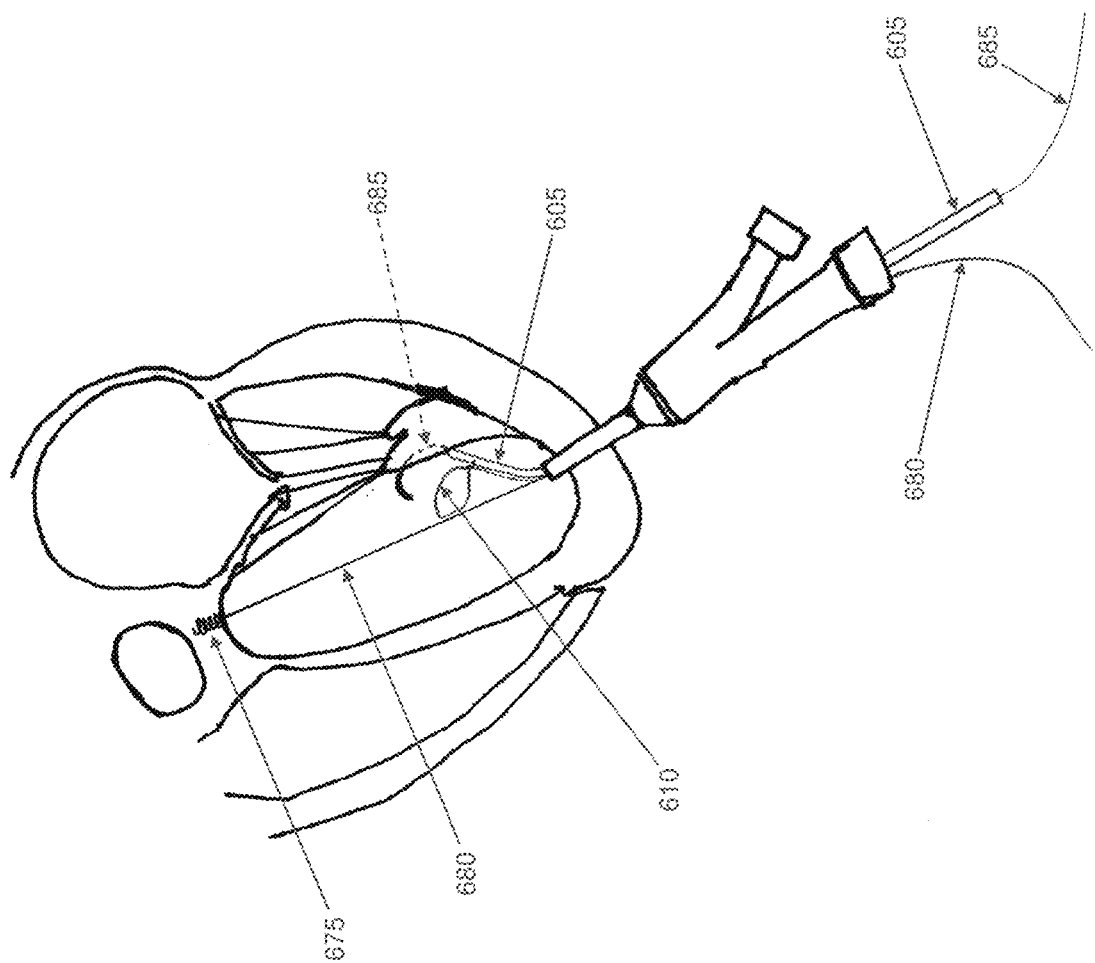

FIG. 88 show TCT 605 (e.g., of the sort disclosed above) and snare 610 (e.g., of the sort disclosed above) being prepared to pass a papillary suture 685 through the papillary muscle near the robust tip of the papillary muscle. By way of example but not limitation, TCT 605 is placed into a port of the 2-port access sheath 600 and advanced through the papillary muscle, and snare 610 is placed into a port of 2-port access sheath 600 and advanced into the left atrium, in preparation for routing of papillary suture 685 (see below). If desired, TCT 605 and snare 610 can be combined into a single device for the convenience of the surgeon.

Figure 89:
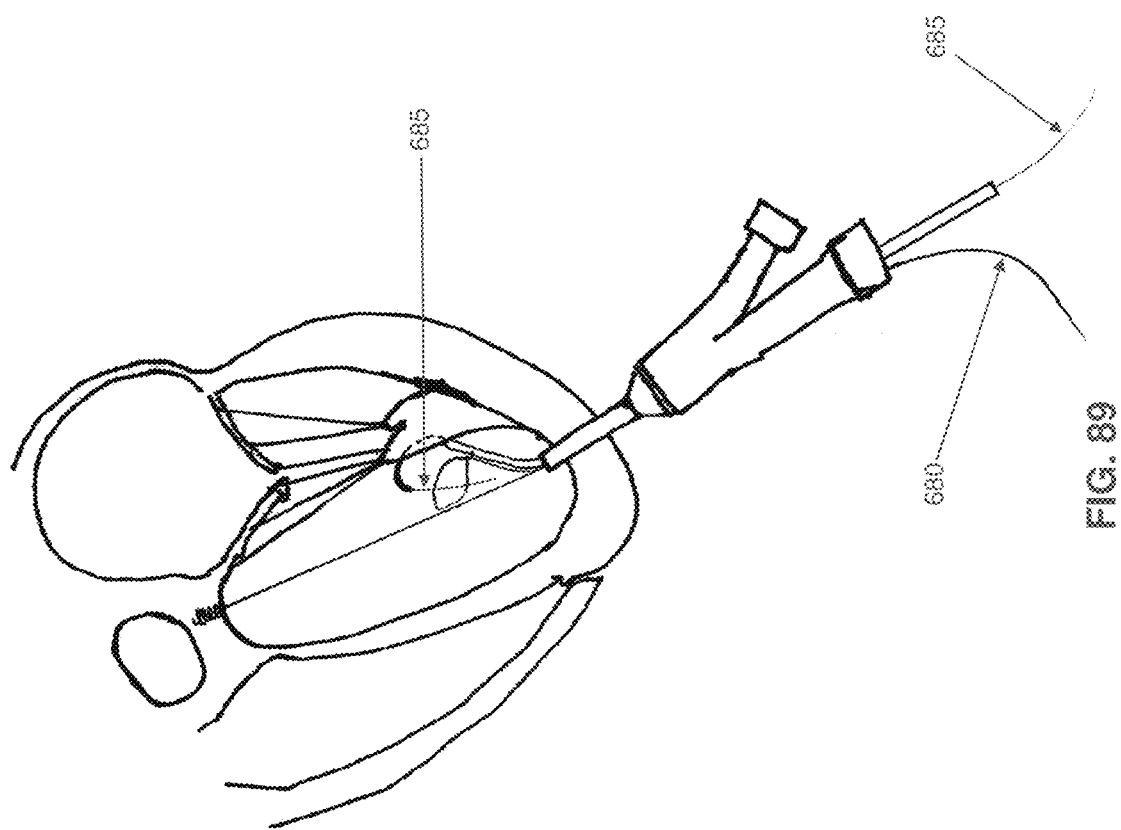
Figure 90:
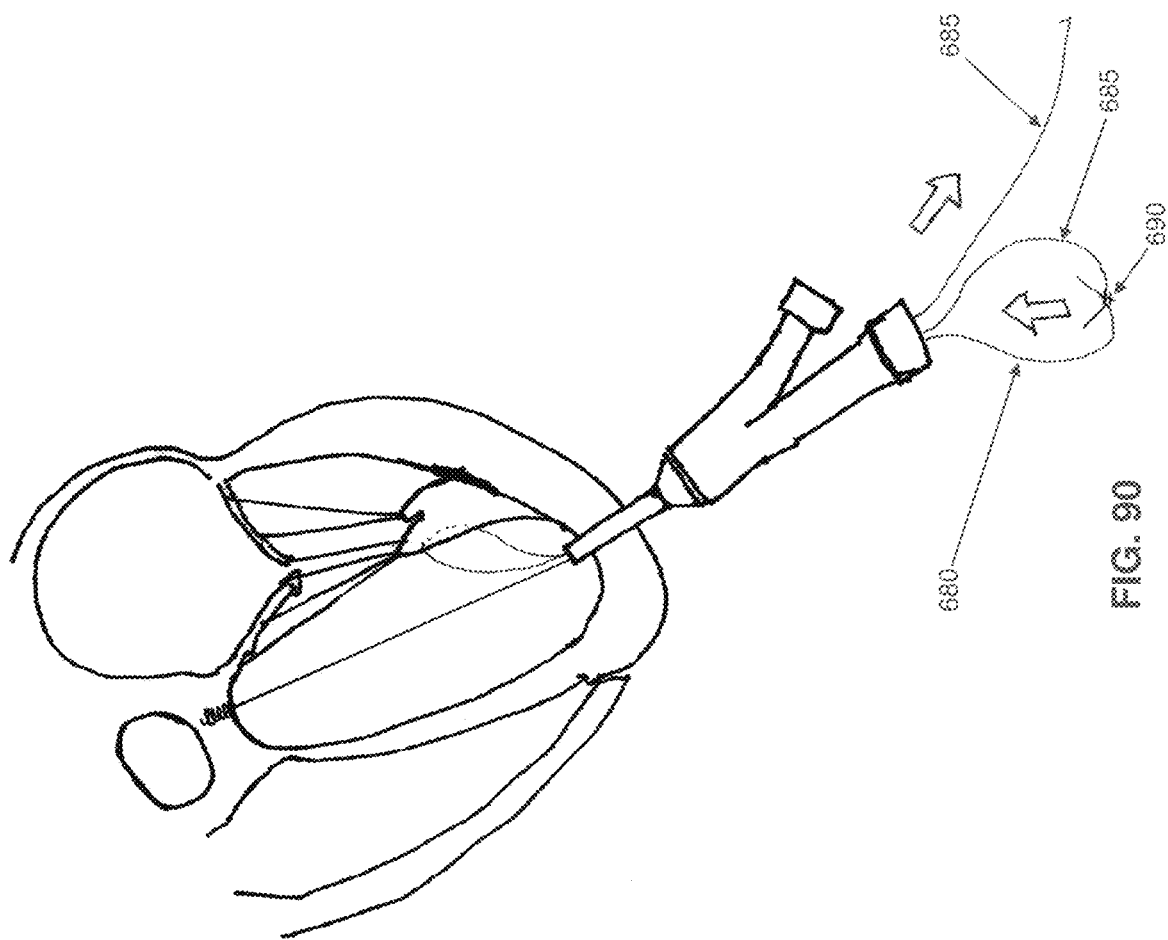

FIG. 89 shows how papillary suture 685 is passed through the tip of the papillary muscle using TCT 605 and then snared by snare 610.

Snare 610 is then used to draw the distal end of papillary suture 685 back through 2-port access sheath 600, whereupon the snared end of papillary suture 685 emerging from the 2-port access sheath is tied to implant suture 680 at a knot 690. See FIG. 90. Then the free leg of papillary suture 685 is pulled out so that knot 690 is drawn into the left ventricle so as to establish the final routing of implant suture 680.

Figure 91:
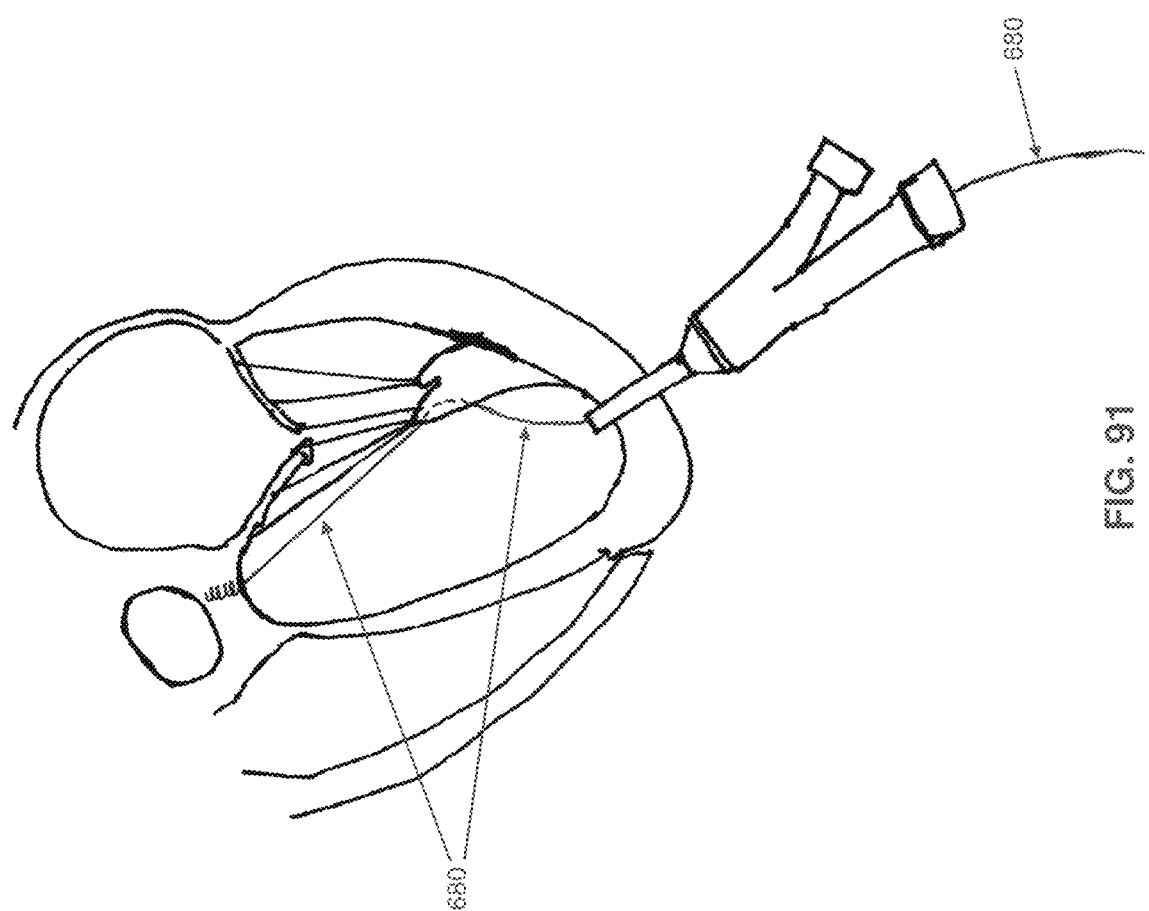

FIG. 91 shows the suture routing for a papillary displacement span of implant suture 680 in an untensioned configuration. Note that the papillary displacement span extends from trigone screw anchor 675, across the left ventricle, through the tip of the papillary muscle, further across the left atrium, and out a port of 2-port access sheath 600.

Figure 92:
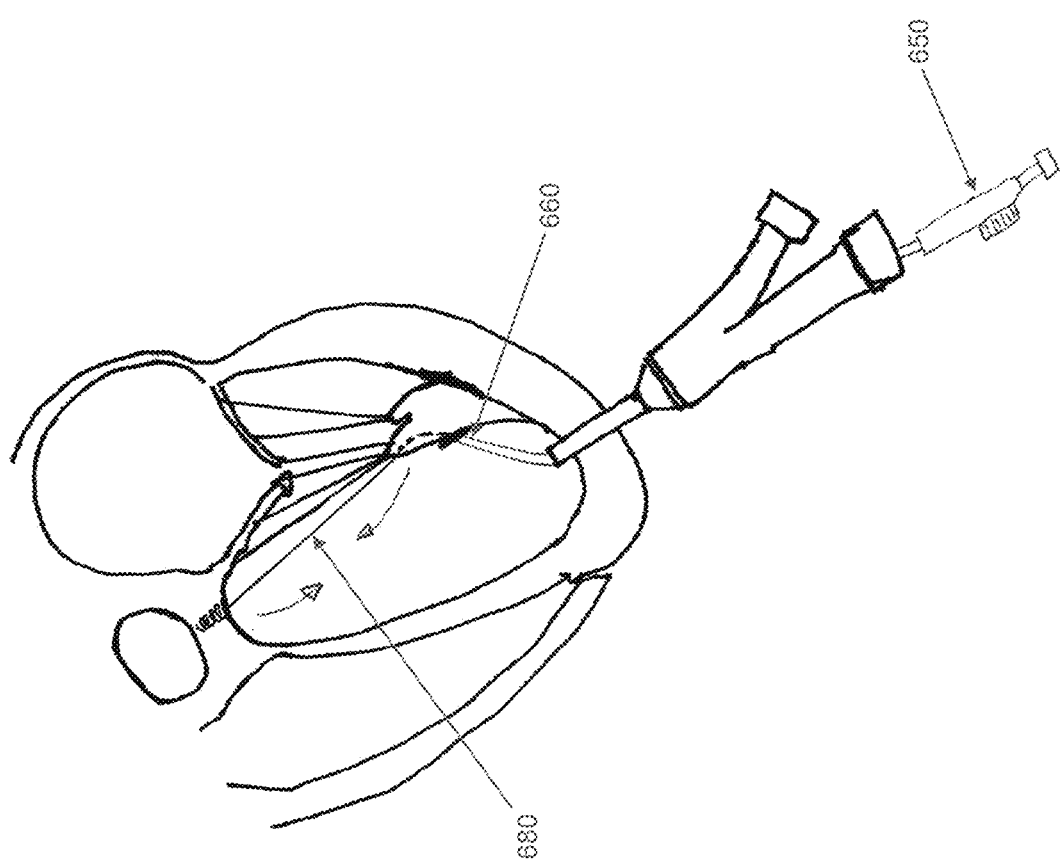

FIG. 92 shows the "Span-Tension-Terminate-Tool" (also known as the "Span-Tension-Tool") (STTT) 650 (e.g., of the sort disclosed above) routed over implant suture 680. One or more pledgets 655 are preferably pushed on the implant suture ahead of the sliding anchor 660 (e.g., of the sort disclosed above) to buttress the sliding anchor when the sliding anchor is placed against the papillary muscle. The tensioning capabilities of STTT 650 are used to reduce the length of the span between the trigone and the tip of the papillary muscle, by tensioning implant suture 680, so as to displace the papillary muscle superiorly and septally towards the fibrous base of the heart, whereby to relocate the chordae tendinae and the mitral leaflets, and hence improve leaflet coaptation and valve closing function.

When the desired degree of papillary correction is observed (e.g., by echocardiogram, effected while the heart is beating), the suture lock 665 (e.g., of the sort disclosed above) is set and deployed (e.g., in the manner discussed above with respect to annular spanning) so as to set sliding anchor 660 in position against the papillary muscle. The suture tail is trimmed in the manner discussed above using a trim tool (not shown).

Figure 93:
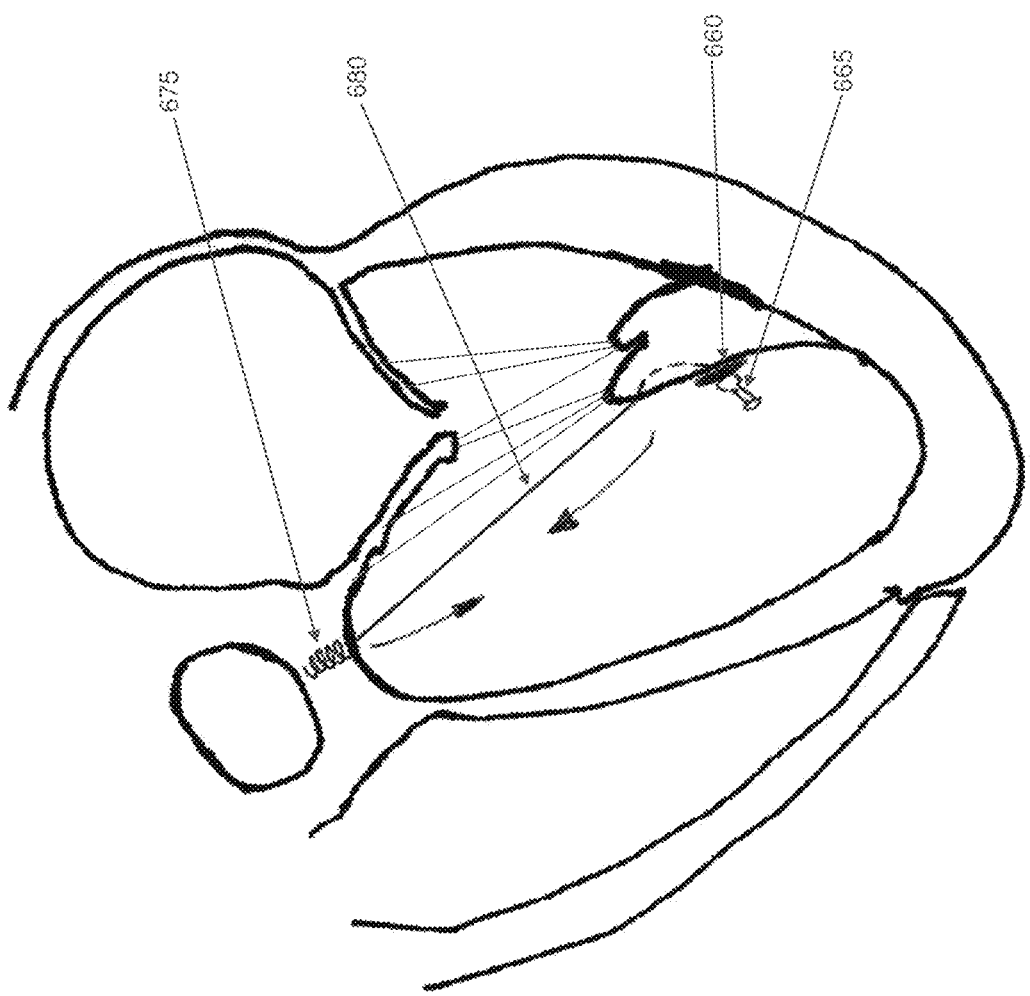

FIG. 93 shows the completed, tensioned span displacing the papillary muscle toward the fibrous base of the heart, whereby to effect papillary displacement and tethering reduction.

MODIFICATIONS

The foregoing is considered to be only illustrative of the principles of the present invention. Since numerous modifications and changes will readily occur to those skilled in the art, the present invention is not limited to the exact constructions and operation shown and described above.

While the preferred embodiment has been described, the details may be changed without departing from the spirit and scope of the present invention.

What is claimed is:

1. A method for beneficially displacing a papillary muscle, the method comprising:
    anchoring one end of an implant suture to a trigone or central fibrous body of the mitral valve;
    passing another end of the implant suture through a papillary muscle so that the implant suture extends between a trigone or central fibrous body of the mitral valve and the papillary muscle;
    tensioning the implant suture while displacing the papillary muscle toward the trigone or central fibrous body of the mitral valve; and
    securing the tensioned implant suture to the displaced papillary muscle so as to maintain the displaced papillary muscle in position relative to the trigone or central fibrous body of the mitral valve;
    wherein the foregoing steps of anchoring, passing, tensioning and securing are all effected while the heart is beating;
    wherein a fixed anchor is used to anchor one end of the implant suture to a trigone or central fibrous body of the mitral valve;
    wherein the fixed anchor is secured against the atrial side of the mitral annulus; and
    wherein the fixed anchor is secured against the atrial side of the mitral annulus by:
        passing a free end of a suture from the left ventricle, through the mitral annulus and into the left atrium;
        retrieving the free end of the suture in the left atrium and drawing the free end of the suture through the mitral leaflets, into the left ventricle and out of the heart;
        securing one end of an implant suture to the free end of the suture suture retrieved from the left atrium, wherein the implant suture has the fixed anchor secured to its other end; and
        using the suture to tow the implant suture into the left ventricle, through the mitral leaflets, through the left atrium, through the mitral annulus and through the left ventricle until the fixed anchor is seated against the atrial side of the mitral annulus.

2. A method according to claim 1 wherein a pledget is disposed between the fixed anchor and the atrial side of the mitral annulus.

3. A method for beneficially displacing a papillary muscle, the method comprising:
    anchoring one end of an implant suture to a trigone or central fibrous body of the mitral valve;
    passing another end of the implant suture through a papillary muscle so that the implant suture extends between a trigone or central fibrous body of the mitral valve and the papillary muscle;
    tensioning the implant suture while displacing the papillary muscle toward the trigone or central fibrous body of the mitral valve; and
    securing the tensioned implant suture to the displaced papillary muscle so as to maintain the displaced papillary muscle in position relative to the trigone or central fibrous body of the mitral valve;
    wherein the foregoing steps of anchoring, passing, tensioning and securing are all effected while the heart is beating;
    wherein a fixed anchor is used to anchor one end of the implant suture to a trigone or central fibrous body of the mitral valve;

wherein the fixed anchor is secured to a trigone or central fibrous body of the mitral valve; and wherein the fixed anchor comprises a screw anchor.

4. A method according to claim 3 wherein the screw anchor comprises a corkscrew anchor.

5. A method according to claim 4 wherein the corkscrew anchor is configured to provide radio frequency (RF) energy to the tissue so as to facilitate deployment of the corkscrew anchor into the fibrous trigones or the central fibrous body of the mitral valve.

6. A method for beneficially displacing a papillary muscle, the method comprising:

anchoring one end of an implant suture to a trigone or central fibrous body of the mitral valve;

passing another end of the implant suture through a papillary muscle so that the implant suture extends between a trigone or central fibrous body of the mitral valve and the papillary muscle;

tensioning the implant suture while displacing the papillary muscle toward the trigone or central fibrous body of the mitral valve; and securing the tensioned implant suture to the displaced papillary muscle so as to maintain the displaced papillary muscle in position relative to the trigone or central fibrous body of the mitral valve;

wherein the foregoing steps of anchoring, passing, tensioning and securing are all effected while the heart is beating; and wherein the step of tensioning the implant suture while displacing the papillary muscle toward the trigone or central fibrous body of the mitral valve is accomplished while observing the beating heart with echocardiogram.

7. A method for beneficially displacing a papillary muscle, the method comprising:

anchoring one end of an implant suture to a trigone or central fibrous body of the mitral valve;

passing another end of the implant suture through a papillary muscle so that the implant suture extends between a trigone or central fibrous body of the mitral valve and the papillary muscle;

tensioning the implant suture while displacing the papillary muscle toward the trigone or central fibrous body of the mitral valve; and securing the tensioned implant suture to the displaced papillary muscle so as to maintain the displaced papillary muscle in position relative to the trigone or central fibrous body of the mitral valve;

wherein the foregoing steps of anchoring, passing, tensioning and securing are all effected while the heart is beating;

wherein the step of tensioning the implant suture while displacing the papillary muscle toward the trigone or central fibrous body of the mitral valve is accomplished by:

advancing a sliding anchor over the implant suture;

advancing a cannulated tool against the sliding anchor so that the sliding anchor engages the papillary muscle and displaces the papillary muscle toward the trigone or central fibrous body of the mitral valve; and tensioning the implant suture while the cannulated tool is engaged with the sliding anchor.

8. A method according to claim 7 wherein the step of securing the tensioned implant suture to the displaced papillary muscle so as to maintain the displaced papillary muscle in position relative to the trigone or central fibrous body of the mitral valve is accomplished by:

securing a suture lock to the implant suture so as to prevent the sliding anchor from moving away from the papillary muscle.

9. A method according to claim 7 wherein a pledget is disposed between the sliding anchor and the papillary muscle.

10. A method according to claim 1 wherein one end of an implant suture is anchored to one of the anterior lateral trigone, the central fibrous body and the posterior medial trigone.

11. A method according to claim 1 wherein the implant suture is passed through one of the anterior lateral papillary muscle and the posterior medial papillary muscle.

12. A method for beneficially displacing a papillary muscle, the method comprising:

anchoring one end of an implant suture to a trigone or central fibrous body of the mitral valve;

passing another end of the implant suture through a papillary muscle so that the implant suture extends between a trigone or central fibrous body of the mitral valve and the papillary muscle;

tensioning the implant suture while displacing the papillary muscle toward the trigone or central fibrous body of the mitral valve; and securing the tensioned implant suture to the displaced papillary muscle so as to maintain the displaced papillary muscle in position relative to the trigone or central fibrous body of the mitral valve;

wherein the foregoing steps of anchoring, passing, tensioning and securing are all effected while the heart is beating;

wherein the implant suture is applied to the anterior lateral papillary muscle, and further wherein the process is repeated with a second implant suture which is applied to the posterior medial papillary muscle.

13. A method according to claim 1 comprising the additional step of reconfiguring the mitral annulus after a papillary muscle has been beneficially displaced.

* * * * *